US012624117B2

(12) United States Patent
Faustman

(10) Patent No.: US 12,624,117 B2
(45) Date of Patent: May 12, 2026

(54) ANTAGONISTIC ANTI-TUMOR NECROSIS FACTOR RECEPTOR SUPERFAMILY POLYPEPTIDES

(71) Applicant: The General Hospital Corporation, Boston, MA (US)

(72) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 326 days.

(21) Appl. No.: 17/269,315

(22) PCT Filed: Aug. 20, 2019

(86) PCT No.: PCT/US2019/047330

§ 371 (c)(1),
(2) Date: Feb. 18, 2021

(87) PCT Pub. No.: WO2020/041361

PCT Pub. Date: Feb. 27, 2020

(65) Prior Publication Data

US 2021/0340268 A1 Nov. 4, 2021

Related U.S. Application Data

(60) Provisional application No. 62/765,284, filed on Aug. 20, 2018.

(51) Int. Cl.
*C07K 16/28* (2006.01)

(52) U.S. Cl.
CPC ...... *C07K 16/2878* (2013.01); *C07K 16/2818* (2013.01); *C07K 2317/34* (2013.01); *C07K 2317/53* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,309,418 A | 1/1982 | Green | |
| 4,457,916 A | 7/1984 | Hayashi et al. | |
| 4,495,282 A | 1/1985 | Ohnishi et al. | |
| 4,677,063 A | 6/1987 | Mark et al. | |
| 4,677,064 A | 6/1987 | Mark et al. | |
| 4,681,760 A | 7/1987 | Fathman | |
| 4,791,101 A | 12/1988 | Adolf | |
| 4,816,567 A | 3/1989 | Cabilly et al. | |
| 4,879,226 A | 11/1989 | Wallace et al. | |
| 4,963,354 A | 10/1990 | Shepard et al. | |
| 4,985,241 A | 1/1991 | Zimmerman et al. | |
| 5,002,876 A | 3/1991 | Sreekrishna et al. | |
| 5,059,530 A | 10/1991 | Oshima et al. | |
| 5,139,481 A | 8/1992 | Faustman et al. | |
| 5,215,743 A | 6/1993 | Singh et al. | |

| | | | |
|---|---|---|---|
| 5,283,058 A | 2/1994 | Faustman | |
| 5,288,852 A | 2/1994 | Yamada et al. | |
| 5,370,870 A | 12/1994 | Wong | |
| 5,487,984 A | 1/1996 | Allet et al. | |
| 5,538,854 A | 7/1996 | Faustman | |
| 5,560,908 A | 10/1996 | Satoh et al. | |
| 5,593,698 A | 1/1997 | Weiner et al. | |
| 5,677,425 A | 10/1997 | Bodmer et al. | |
| 5,783,216 A | 7/1998 | Faustman | |
| 5,821,337 A | 10/1998 | Carter et al. | |
| 5,843,425 A | 12/1998 | Sachs et al. | |
| 5,843,452 A | 12/1998 | Wiedmann et al. | |
| 5,874,306 A | 2/1999 | Beattie et al. | |
| 5,919,452 A | 7/1999 | Le et al. | |
| 5,939,532 A | 8/1999 | Nakamura et al. | |
| 6,046,031 A | 4/2000 | Ni et al. | |
| 6,056,952 A | 5/2000 | Rosenberg | |
| 6,159,461 A | 12/2000 | Besmer et al. | |

(Continued)

FOREIGN PATENT DOCUMENTS

| | | |
|---|---|---|
| CN | 101084014 A | 12/2007 |
| CN | 103249742 A | 8/2013 |

(Continued)

OTHER PUBLICATIONS

Edwards et al. J Mol Biol. 2003. 334: 103-118 (Year: 2003).*
Lloyd et al. Protein Engineering, Design & Selection. 2009. 22(3): 159-168 (Year: 2009).*
Meyer et al. British Journal of Haematology. 2018. 180: 808-820. (Year: 2018).*
Vajdos et al. J Mol Biol. 2002. 320: 415-428. (Year: 2002).*
Rudikoff et al. Proc Natl Acad Sci. 1982. 79: 1979-1983 (Year: 1982).*
Bedouelle et al. FEES J. Jan. 2006;273(1):34-46 (Year: 2006).*
Wajant. Cell Death and Diff. Aug. 21, 2015. 22: 1727-1741. (Year: 2015).*
UniProt. P01834 IGKC_HUMAN. History. Jun. 20, 2018. Retrieved on Jun. 16, 2025 from <URL: https://rest.uniprot.org/unisave/P01859?format=fasta&versions=164> (Year: 2018).*

(Continued)

*Primary Examiner* — Anne M. Gussow
*Assistant Examiner* — Brianna K Swartwout
(74) *Attorney, Agent, or Firm* — Clark & Elbing LLP

(57) ABSTRACT

Described are antagonistic TNFR2 polypeptides, such as antibodies and antigen-binding fragments thereof, and the use of these polypeptides to inhibit the proliferation of regulatory T cells (T-regs) and/or myeloid-derived suppressor cells (MDSCs), to expand T effector cell populations or function, and to reduce the proliferation of, or directly kill, tumor cells, such as tumor cells that express TNFR2 antigen. The polypeptides, such as antibodies and antigen-binding fragments thereof, are TNFR2 antagonists, such as dominant TNFR2 antagonists. The polypeptides can be used to suppress the T-reg- or MDSC-mediated deactivation of tumor reactive T lymphocytes, expand populations of tumor-reactive cytotoxic T cells, and/or to directly kill TNFR2+ tumor cells. The antagonistic TNFR2 polypeptides described herein can be used to treat a wide variety of cancers and infectious diseases.

55 Claims, 13 Drawing Sheets

Specification includes a Sequence Listing.

(56) References Cited

U.S. PATENT DOCUMENTS

| | | |
|---|---|---|
| 6,165,737 A | 12/2000 | Wang et al. |
| 6,177,076 B1 | 1/2001 | Lattime et al. |
| 6,284,879 B1 | 9/2001 | Faustman |
| 6,414,218 B1 | 7/2002 | Faustman et al. |
| 6,420,139 B1 | 7/2002 | Classen |
| 6,491,908 B1 | 12/2002 | Rosenberg |
| 6,599,710 B1 | 7/2003 | Faustman |
| 6,617,171 B2 | 9/2003 | Faustman et al. |
| 6,660,487 B2 | 12/2003 | Faustman |
| 6,709,833 B2 | 3/2004 | Fukui et al. |
| 6,773,705 B1 | 8/2004 | Faustman et al. |
| 6,844,011 B1 | 1/2005 | Faustman |
| 6,866,843 B2 | 3/2005 | Habener et al. |
| 6,923,959 B2 | 8/2005 | Habener et al. |
| 6,984,380 B1 | 1/2006 | Faustman |
| 7,015,037 B1 | 3/2006 | Furcht et al. |
| 7,438,902 B2 | 10/2008 | Habener et al. |
| 7,485,293 B1 | 2/2009 | Faustman |
| 7,510,877 B2 | 3/2009 | Yilmaz et al. |
| 7,537,756 B2 | 5/2009 | Habener et al. |
| 7,582,313 B2 | 9/2009 | Faustman |
| 7,628,988 B2 | 12/2009 | Faustman |
| 8,017,392 B2 | 9/2011 | Faustman |
| 8,021,693 B2 | 9/2011 | Faustman |
| 8,173,129 B2 | 5/2012 | Faustman |
| 8,314,213 B2 | 11/2012 | Bernett et al. |
| 8,697,077 B2 | 4/2014 | Faustman |
| 9,522,181 B2 | 12/2016 | Faustman |
| 9,676,862 B2 | 6/2017 | Ellmark et al. |
| 9,821,010 B2 | 11/2017 | Faustman |
| 10,765,700 B2 | 9/2020 | Faustman |
| 10,906,982 B2 | 2/2021 | Faustman |
| 10,988,543 B2 | 4/2021 | Thompson |
| 11,844,814 B2 | 12/2023 | Faustman |
| 11,859,002 B2 | 1/2024 | Faustman |
| 12,152,082 B2 | 11/2024 | Faustman |
| 2002/0106689 A1 | 8/2002 | Faustman et al. |
| 2002/0123472 A1 | 9/2002 | Faustman |
| 2002/0187548 A1 | 12/2002 | Keller et al. |
| 2003/0005469 A1 | 1/2003 | Faustman et al. |
| 2003/0031657 A1 | 2/2003 | Habener et al. |
| 2004/0028658 A1 | 2/2004 | Faustman |
| 2004/0031066 A9 | 2/2004 | Faustman et al. |
| 2004/0229785 A1 | 11/2004 | Faustman |
| 2005/0043514 A1 | 2/2005 | Fukui et al. |
| 2005/0158288 A1 | 7/2005 | Faustman |
| 2005/0158302 A1 | 7/2005 | Faustman et al. |
| 2005/0244386 A1 | 11/2005 | Habener et al. |
| 2006/0062769 A1 | 3/2006 | Habener et al. |
| 2007/0116688 A1 | 5/2007 | Faustman |
| 2008/0102054 A1 | 5/2008 | Faustman |
| 2008/0175830 A1 | 7/2008 | Steinman et al. |
| 2008/0176796 A1 | 7/2008 | Bradley et al. |
| 2009/0028877 A1 | 1/2009 | Lida et al. |
| 2010/0068177 A1 | 3/2010 | Faustman |
| 2010/0298232 A1 | 11/2010 | Liu |
| 2011/0236374 A1 | 9/2011 | Shitara et al. |
| 2012/0066777 A1 | 3/2012 | Kawamura et al. |
| 2012/0115739 A1 | 5/2012 | Schmittling et al. |
| 2012/0196919 A1 | 8/2012 | Brown et al. |
| 2013/0064831 A1 | 3/2013 | Humphrey |
| 2014/0096274 A1 | 4/2014 | Quax et al. |
| 2014/0121123 A1 | 5/2014 | Wang et al. |
| 2015/0110794 A1 | 4/2015 | Sato et al. |
| 2015/0366909 A1 | 12/2015 | Faustman |
| 2017/0158771 A1 | 6/2017 | Glennie et al. |
| 2017/0226217 A1 | 8/2017 | Ellmark et al. |
| 2018/0044430 A1 | 2/2018 | Chiu et al. |
| 2019/0135929 A1 | 5/2019 | Faustman |
| 2019/0202925 A1 | 7/2019 | Thompson |
| 2020/0270355 A1 | 8/2020 | Faustman |
| 2021/0301028 A1 | 9/2021 | Thompson |
| 2021/0317221 A1 | 10/2021 | Faustman |
| 2022/0002423 A1 | 1/2022 | Faustman |
| 2022/0112299 A1 | 4/2022 | Faustman |
| 2023/0174659 A1 | 6/2023 | Faustman |
| 2023/0295326 A1 | 9/2023 | Faustman |
| 2023/0383003 A1 | 11/2023 | Faustman |

FOREIGN PATENT DOCUMENTS

| | | | |
|---|---|---|---|
| EP | 0612529 A2 | 8/1994 | |
| EP | 1707627 A1 | 10/2006 | |
| EP | 2295588 A1 | 3/2011 | |
| JP | 2010-531138 A | 9/2010 | |
| JP | 2013-521311 A | 6/2013 | |
| JP | 2017-511379 A | 4/2017 | |
| KR | 10-2021-0061350 A | 5/2021 | |
| WO | WO-92/04033 A1 | 3/1992 | |
| WO | WO-93/02690 A1 | 2/1993 | |
| WO | WO-94/09137 A1 | 4/1994 | |
| WO | WO-95/24914 A1 | 9/1995 | |
| WO | WO-95/25533 A1 | 9/1995 | |
| WO | WO-97/08328 A1 | 3/1997 | |
| WO | WO-97/13844 A1 | 4/1997 | |
| WO | WO-97/21802 A1 | 6/1997 | |
| WO | WO-99/53953 A2 | 10/1999 | |
| WO | WO-99/59632 A1 | 11/1999 | |
| WO | WO-00/53209 A1 | 9/2000 | |
| WO | WO-01/44472 A1 | 6/2001 | |
| WO | WO-01/91793 A1 | 12/2001 | |
| WO | WO-02/26819 A2 | 4/2002 | |
| WO | WO-2004/003164 A2 | 1/2004 | |
| WO | WO-2004022097 A1 | 3/2004 | |
| WO | WO-2005/042727 A2 | 5/2005 | |
| WO | WO-2006/038027 A2 | 4/2006 | |
| WO | WO-2006/109044 A2 | 10/2006 | |
| WO | WO-2006119107 A2 * | 11/2006 | ......... A61K 39/3955 |
| WO | WO-2008/157394 A2 | 12/2008 | |
| WO | WO-2010/124259 A1 | 10/2010 | |
| WO | WO-2011044368 A1 | 4/2011 | |
| WO | WO-2011/107989 A1 | 9/2011 | |
| WO | WO-2011109789 A2 | 9/2011 | |
| WO | WO-2012/122464 A1 | 9/2012 | |
| WO | WO-2014/015101 A1 | 1/2014 | |
| WO | WO-2014/124134 A1 | 8/2014 | |
| WO | WO-2015145360 A1 * | 10/2015 | ............. A61P 29/00 |
| WO | WO-2016/032547 A1 | 3/2016 | |
| WO | WO-2016094309 A1 * | 6/2016 | ........... A61K 31/395 |
| WO | WO-2016/187068 A1 | 11/2016 | |
| WO | WO-2017/040312 A1 | 3/2017 | |
| WO | WO-2017083525 A1 * | 5/2017 | ............. A61P 35/00 |
| WO | WO-2017/197331 A2 | 11/2017 | |
| WO | WO-2018017714 A1 * | 1/2018 | ............. A61K 38/02 |
| WO | WO-2018/064307 A2 | 4/2018 | |
| WO | WO-2018/092907 A1 | 5/2018 | |
| WO | WO-2018/115003 A2 | 6/2018 | |
| WO | WO-2019/094559 A2 | 5/2019 | |
| WO | WO-2020/041361 A1 | 2/2020 | |
| WO | WO-2020/193718 A1 | 10/2020 | |

OTHER PUBLICATIONS

UniProt. P01859 IGHG2_HUMAN. History. Jun. 20, 2018 retrieved from <URL: https://www.uniprot.org/uniprotkb/P01859/history> (Year: 2018).*

Al-Awqati et al., "Stem cells in the kidney," Kidney Int. 61(2):387-95 (2002).

Aldrich et al., "Positive selection of self- and alloreactive CD8+ T cells in Tap-1 mutant mice," Proc Natl Acad Sci USA. 91(14):6525-8 (1994).

Alison et al., "Hepatocytes from non-hepatic adult stem cells," Nature. 406(6793):257 (2000).

Allen et al., "Effect of bacillus Calmette-Guerin vaccination on new-onset type 1 diabetes," Diabetes Care. 22(10):1703-7 (1999).

Altomonte et al., "Serum levels of interleukin-1b, tumour necrosis factor-a and interleukin-2 in rheumatoid arthritis. Correlation with disease activity," Clin Rheumatol. 11(2):202-205 (1992).

Anderson et al., "Can stem cells cross lineage boundaries?," Nat Med. 7(4):393-5 (2001).

Anderson et al., "Studies on the cytophilic properties of human beta2 microglobulin," J Immunol. 114(3):997-1000 (1975).

(56)        References Cited

OTHER PUBLICATIONS

Anderson et al., "The NOD mouse: a model of immune dysregulation," Annu Rev Immunol. 23:447-485 (2005).

Aranda et al., "Analysis of intestinal lymphocytes in mouse colitis mediated by transfer of CD4+, CD45RB$^{high}$ T Cells to SCID recipients," J Immunol. 158(7):3464-3473 (1997).

Aristarkhov et al., "E2-C, a cyclin-selective ubiquitin carrier protein required for the destruction of mitotic cyclins," Proc Natl Acad Sci USA. 93(9):4294-9 (1996).

Ashton-Rickardt et al., "Evidence for a differential avidity model of T cell selection in the thymus," Cell. 76(4):651-63 (1994).

Ashton-Rickardt et al., "Peptide contributes to the specificity of positive selection of CD8+ T Cells in the thymus," Cell. 73(5):1041-9 (1993).

Atkinson et al., "The NOD mouse model of type 1 diabetes: As good as it gets?," Nat Med. 5(6):601-4 (1999).

Baeuerle et al., "NF-kappaB: Ten years after," Cell. 87(1):13-20 (1996).

Baeza et al., "Pancreatic regenerating gene overexpression in the nonobese diabetic mouse during active diabetogenesis," Diabetes. 45(1):67-70 (1996) (5 pages).

Baeza et al., "Reg protein: a potential beta-cell-specific growth factor?," Diabetes Metab. 22(4):229-34 (1996).

Baeza et al., "Specific reg II gene overexpression in the non-obese diabetic mouse pancreas during active diabetogenesis," FEBS Letters. 416(3):364-8 (1997).

Baik et al., "BCG vaccine prevents insulitis in low dose streptozotocin-induced diabetic mice," Diabetes Res Clin Pract. 46(2):91-97 (1999).

Baldwin, "The NF-kappaB and IkappaB proteins: new discoveries and insights," Annu Rev Immunol. 14:649-683 (1996).

Ban et al., "Selective death of autoreactive T Cells in human diabetes by TNF or TNF receptor 2 agonism," Proc Natl Acad Sci USA. 105(36):13644-13649 (2008).

Ban et al., "Strategic Internal Covalent Cross-Linking of TNF Produces a Stable TNF Trimer With Improved TNFR2 Signaling," Mol Cell Ther. 3:7 (2015) (6 pages).

Barres, "A new role for glia: generation of neurons!," Cell. 97(6): 667-70 (1999).

Baxter et al., "Mycobacteria precipitate an SLE-like syndrome in diabetes-prone NOD mice," Immunology. 83(2):227-231 (1994).

Beers et al., Disorders of Carbohydrate Metabolism: Diabetes Mellitus. *The Merck Manual of Diagnosis and Therapy, 17th Ed.* Merck Research Laboratories, 165-171 (1999) (5 pages).

Beg et al., "An essential role for NF-kappaB in preventing TNF-alpha-induced cell death," Science. 274(5288):782-784 (1996).

Bendelac et al., "Syngeneic transfer of autoimmune diabetes from diabetic NOD mice to healthy neonates. Requirement for both L3T4+ and Lyt-2+ T Cells," J Exp Med. 166(4):823-832 (1987).

Benkler et al., "Parkinson's disease, autoimmunity, and olfaction," Int J Neurosci. 119(12):2133-43 (2009) (Abstract only) (1 page).

Bercovici et al., "Systemic administration of agonist peptide blocks the progression of spontaneous CD8-mediated autoimmune diabetes in transgenic mice without bystander damage," J Immunol. 165(1):202-10 (2000) (10 pages).

Bernabeu et al., "Beta2-microglobulin from serum associates with MHC class I antigens on the surface of cultured cells," Nature. 308(5960):642-645 (1984) (Abstract only) (2 pages).

Bill et al., "Use of soluble MHC class II/peptide multimers to detect antigen-specific T cells in human disease," Arthritis Res. 4(4):261-265 (2002).

Bjornson et al., "Turning brain into blood: A hematopoietic fate adopted by adult neural stem cells in vivo," Science. 283(5401):534-537 (1999).

Bleumink et al., "Etanercept-induced subacute cutaneous lupus erythematosus," Rheumatology. 40(11):1317-1319 (2001).

Boches et al., "Role for the adenosine triphosphate-dependent proteolytic pathway in reticulocyte maturation," Science. 215(4535):978-980 (1982).

Brayer et al., "Alleles from chromosomes 1 and 3 of NOD mice combine to influence Sjogren's syndrome-like autoimmune exocrinopathy," J. Rheumatol. 27(8):1896-1904 (2000).

Brazelton et al., "From marrow to brain: expression of neuronal phenotypes in adult mice," Science. 290(5497):1775-1779 (2000).

Brod et al., "Ingested interferon alpha suppresses Type I diabetes in non-obese diabetic mice," Diabetologia. 41(10):1227-1232 (1998).

Brod et al., "New clinical trial in newly diagnosed type 1 diabetes," <www.diabetesstation.org/articles/brod.htm>, retrieved Jun. 19, 2001 (2 pages).

Brodbeck et al., "Genetic determination of nephrogenesis: the Pax/Eya/Six gene network," Pediatr Nephrol. 19(3):249-255 (2004) (1 page) (Abstract Only).

Bras et al., "Diabetes-prone NOD mice are resistant to *Mycobacterium avium* and the infection prevents autoimmune disease," Immunology. 389(1):20-25 (1996).

Bunting et al., "Enforced P-glycoprotein pump function in murine bone marrow cells results in expansion of side population stem cells in vitro and repopulating cells in vivo," Blood. 96(3):902-909 (2000).

Burnham et al., "Oral BCG vaccine in Crohn's disease," Gut. 20(3):229-233 (1979).

Caetano et al., "Effect of methotrexate (MTX) on NAD(P)+ dehydrogenases of Hela cells: malic enzyme, 2-oxoglutarate and isocitrate dehydrogenases," Cell Biochem Funct. 15(4):259-264 (1997).

Cairns et al., "New onset systemic lupus erythematosus in a patient receiving etanercept for rheumatoid arthritis," Ann Rheum Dis. 61(11):1031-2 (2002).

Cavallo et al., "BCG vaccine with and without nicotinamide in recent onset IDDM: a multicenter randomized trial," Second Congress of the Immunology of Diabetes Society, Canberra, Australia, Dec. 8-11, 1996. Autoimmunity. 24(Suppl. 1):18 (1996).

Cebrián et al., "MHC-I expression renders catecholaminergic neurons susceptible to T-cell-mediated degeneration," Nat Commun. 5:3633 (2014) (Abstract only) (1 page).

Charles et al., "Assessment of antibodies to double-stranded DNA induced in rheumatoid arthritis patients following treatment with infliximab, a monoclonal antibody to tumor necrosis factor alpha: findings in open-label and randomized placebo-controlled trials," Arthritis Rheum. 43(11):2383-90 (2000).

Chatenoud et al., "CD3 antibody-induced dominant self tolerance in overtly diabetic NOD mice," J Immunol. 158(6):2947-2954 (1997).

Chen et al., "Enhancement and destruction of antibody function by somatic mutation: unequal occurrence is controlled by V gene combinatorial associations," EMBO J. 14(12):2784-94 (1995).

Chen et al., "The phenotypic and functional consequences of tumour necrosis factor receptor type 2 expression on CD4(+) FoxP3(+) regulatory T cells," Immunology. 133(4):426-33 (2011).

Choi et al., "Prevention of encephalomyocarditis virus-induced diabetes by live recombinant *Mycobacterium bovis* bacillus Calmette-Guérin in susceptible mice," Diabetes. 49 (9):1459-1467 (2000).

Chopra et al., "Exogenous TNFR2 activation protects from acute GvHD via host T reg cell expansion," J Exp Med. 213(9):1881-1900 (2016) (21 pages).

Christen et al., "A dual role for TNF-alpha in type 1 diabetes: islet-specific expression abrogates the ongoing autoimmune process when induced late but not early during pathogenesis," J Immunol. 166(12):7023-32 (2001).

Cole et al., "Two ParaHox genes, SpLox and SpCdx, interact to partition the posterior endoderm in the formation of a functional gut," Development. 136(4):541-549 (2009).

Colucci et al., "Programmed cell death in the pathogenesis of murine IDDM: resistance to apoptosis induced in lymphocytes by cyclophosphamide," J Autoimmunity. 9:271-276 (1996).

Communication pursuant to Article 94(3) EPC for European Patent Application No. 14189654.8, dated Oct. 19, 2016 (5 pages).

Communication pursuant to Rules 70(2) and 70a(2) EPC for European Application No. 14748807.6, dated Aug. 2, 2016 (1 page).

Corbett et al., "Nitric oxide mediates cytokine-induced inhibition of insulin secretion by human islets of Langerhans," Proc Natl Acad Sci USA. 90(5):1731-1735 (1993).

(56) References Cited

OTHER PUBLICATIONS

Coux et al., "Enzymes catalyzing ubiquitination and proteolytic processing of the p105 precursor of nuclear factor kappaB1," J Biol Chem. 273(15):8820-8828 (1998).

Couzin, "Diabetes studies conflict on power of spleen cells," Science. 311:1694 (2006).

Creasey et al., "Biological effects of recombinant human tumor necrosis factor and its novel muteins on tumor and normal cell lines," Cancer Res. 47(1):145-9 (1987).

D'Andrea, "Add Alzheimer's disease to the list of autoimmune diseases," Med Hypotheses. 64(3):458-63 (2005) (Abstract only) (2 pages).

Darzynkiewicz et al., "Use of flow and laser scanning cytometry to study mechanisms regulating cell cycle and controlling cell death," Clinics in Laboratory Medicine. 21(4):857-873 (2001).

Dear et al., "The Hox11 gene is essential for cell survival during spleen development," Development. 121(9):2909-2915 (1995).

Declaration of Denise Faustman, M.D., Ph.D., from U.S. Appl. No. 10/851,983, dated Jul. 3, 2007 (7 pages).

Declaration of Dr. Denise Faustman from U.S. Appl. No. 10/775,487, dated Jun. 14, 2007 (13 pages).

Declaration of Dr. Denise Faustman under 37 C.F.R. § 1.132 regarding U.S. Appl. No. 10/358,664, dated May 13, 2009 (4 pages).

Diaw et al., "Structural and affinity studies of IgM polyreactive natural autoantibodies," J Immunol. 158(2):968-76 (1997).

Dieguez-Acuna et al., "Characterization of mouse spleen cells by subtractive proteomics," Mol Cell Proteomics. 4(10):1459-1470 (2005).

Dieguez-Acuna et al., "Proteomics identifies multipotent and low oncogenic risk stem cells of the spleen," Int J Biochem Cell Biol. 42(10):1651-60 (2010) (10 pages).

Dilts et al., "Autoimmune diabetes: The involvement of benign and malignant autoimmunity," J Autoimmun. 12:229-232 (1999).

Dinarello, "Interleukin-1, Interleukin-1 receptors and Interleukin-1 receptor antagonist," Intern Rev Immunol. 16:457-499 (1998).

Driscoll et al., "The proteasome (multicatalytic protease) is a component of the 1500-kDa proteolytic complex which degrades ubiquitin-conjugated proteins," J Biol Chem. 265(9):4789-4792 (1990).

Durand et al., "Mesenchymal lineage potentials of aorta-gonad-mesonephros stromal clones," Haematologica. 91(9):1172-1179 (2006).

Eglitis et al., "Hematopoietic cells differentiate into both microglia and macroglia in the brains of adult mice," Proc Natl Acad Sci USA. 94:4080-4085 (1997).

Elliott et al., "Effect of bacille Calmette-Guerin vaccination on C-peptide secretion in children newly diagnosed with IDDM," Diabetes Care. 21(10):1691-1693 (1998).

Enayati et al., "Association of anti-tumor necrosis factor therapy with the development of multiple sclerosis," J Clin Gastroenterol. 39(4): 303-6 (2005) (1 page) (Abstract only).

Engleman et al., "Treatment of NZB/NZW F1 hybrid mice with *Mycobacterium bovis* strain BCG or type II interferon preparations accelerates autoimmune disease," Arthritis Rheum. 24(11):1396-1402 (1981).

EPO Communication Enclosing Supplementary European Search Report for EP Application No. 03762242.0, dated Jun. 8, 2009 (8 pages).

EPO Communication pursuant to Article 94(3) and Rule 71(1) EPC for European Application No. 00914899.0, dated Mar. 6, 2015 (3 pages).

EPO Communication pursuant to Article 94(3) EPC for European Application No. 00914899.0, dated May 25, 2012 (9 pages).

EPO Communication pursuant to Article 94(3) EPC for European Application No. 12005556.1, dated Jul. 2, 2015 (7 pages).

EPO Communication Pursuant to Article 94(3) EPC for European Patent Application No. 11008889.5, dated Mar. 19, 2014 (4 pages).

EPO Communication Pursuant to Article 94(3) EPC for European Patent Application No. 11008889.5, dated Oct. 27, 2014 (5 pages).

EPO Communication Pursuant to Article 94(3) EPC issued in European Patent Application No. 03762242.0, dated Dec. 1, 2011 (4 pages).

EPO Communication Pursuant to Article 94(3) EPC issued in European Patent Application No. 03762242.0, dated Oct. 30, 2009 (2 pages).

EPO Communication Pursuant to Article 94(3) EPC issued in European Patent Application No. 04817543.4, dated Jan. 22, 2010 (5 pages).

EPO Communication Pursuant to Article 94(3) EPC issued in European Patent Application No. 11008889.5, dated Mar. 4, 2013 (4 pages).

EPO Communication pursuant to Rule 69 EPC for European Application No. 12005556.1, dated Oct. 7, 2014 (2 pages).

EPO Communication Pursuant to Rules 161(2) and 162 EPC for International Application No. PCT/US2014/015101, dated Oct. 15, 2015 (2 pages).

EPO Communication under Rule 71(3) EPC for European Application No. 00914899.0, dated Jun. 23, 2015 (6 pages).

EPO Invitation pursuant to Article 94(3) and Rule 71(1) EPC for European Application No. 00914899.0, dated Jun. 2, 2014 (4 pages).

EPO Summons to attend oral proceedings pursuant to Rule 115(1) EPC for European Application No. 00914899.0, dated Nov. 12, 2014 (6 pages).

EPO Summons to attend oral proceedings pursuant to Rule 115(1) EPC for European Application No. 12005556.1, dated Dec. 18, 2015 (4 pages).

Examination Report issued in Australian Patent Application No. 2003247840, dated Jan. 31, 2008 (4 pages).

Examiner's Report for Canadian Patent Application No. 2,543,745, dated Jul. 15, 2011 (4 pages).

Extended European Search Report for European Application No. 12005556.1, dated Sep. 2, 2014 (8 pages).

Extended European Search Report for European Application No. 14189654.8, dated Feb. 16, 2015 (7 pages).

Extended European Search Report for European Application No. 14748807.6, dated Jul. 15, 2016 (10 pages).

Extended European Search Report for European Application No. 17796980.5, dated Mar. 5, 2020 (12 pages).

Extended European Search Report for European Application No. 18199457.5, dated May 2, 2019 (7 pages).

Extended European Search Report for European Patent Application No. 11008889.5, dated Apr. 12, 2012 (10 pages).

Eytan et al., "ATP-dependent incorporation of 20S protease into the 26S complex that degrades proteins conjugated to ubiquitin," Proc Natl Acad Sci USA. 86:7751-7755 (1989).

Fan et al., "Generation of p50 subunit of NF-kappaB by processing of p105 through an ATP-dependent pathway," Nature. 354:395-398 (1991).

Faustman et al., "Abnormal T-lymphocyte subsets in Type I Diabetes," Diabetes. 38:1462-1468 (1989).

Faustman et al., "Linkage of faulty major histocompatibility complex class I to autoimmune diabetes," Science. 254:1756-1761 (1991).

Faustman et al., "Murine pancreatic beta-Cells express H-2K and H-2D but not la antigens," J Exp Med. 151(6):1563-1568 (1980).

Faustman et al., "Prevention of xenograft rejection by masking donor HLA class I antigens," Science. 252:1700-1702 (1991).

Faustman et al., "Stem cells in the spleen: Therapeutic potential for Sjogren's syndrome, type I diabetes, and other disorders," available in PMC Jul. 21, 2014, published in final edited form as: Int J Biochem Cell Biol. 42(10):1576-9 (2010) (8 pages).

Faustman et al., "T-lymphocyte changes linked to autoantibodies. Association of insulin autoantibodies with CD4+CD45R+ lymphocyte subpopulation in prediabetic subjects," Diabetes. 40(5):590-597 (1991).

Faustman et al., "TNF Receptor 2 and Disease: Autoimmunity and Regenerative Medicine," Front Immunol. 4:478 (2013) (8 pages).

Faustman et al., "TNF receptor 2 pathway: drug target for autoimmune diseases," Nat Rev Drug Discov. 9(6):482-93 (2010).

(56) References Cited

OTHER PUBLICATIONS

Feldman et al., "Anti-TNFalpha therapy is useful in rheumatoid arthritis and Crohn's disease: Analysis of the mechanism of action predicts utility in other diseases," Transplant Proc. 30(8):4126-4127 (1998).

Feldmann et al., "Role of cytokines in rheumatoid arthritis," Annu Rev Immunol. 14:397-440 (1996) (1 page) (Abstract only).

Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11: Abstract 578 (2002) (1 page).

Fischer et al., "A TNF receptor 2 selective agonist rescues human neurons from oxidative stress- induced cell death," PloS One. 6(11):e27621 (2011) (11 pages).

Fischer et al., "An improved flow cytometric assay for the determination of cytotoxic T lymphocyte activity," J Immunol Methods. 259:159-169 (2002).

Foulis, "C.L. Oakley lecture (1987). The pathogenesis of beta cell destruction in Type I (insulin-dependent) diabetes mellitus," J Pathol. 152(3):141-148 (1987).

Fu et al., "Antigen processing and autoimmunity: Evaluation of mRNA abundance and function of HLA-Linked genes," Ann NY Acad Sci. 842:138-155 (1998).

Fu et al., "Defective major histocompatibility complex class I expression on lymphoid cells in autoimmunity," J Clin Invest. 91:2301-2307 (1993).

Fukada et al., "Two signals are necessary for cell proliferation induced by a cytokine receptor gp130: Involvement of STAT3 in anti-apoptosis," Immunity. 5:449-460 (1996).

Gage et al., "Multipotent progenitor cells in the adult dentate gyrus," J Neurobiol. 36:249-266 (1998).

Gage, "Mammalian neural stem cells," Science. 287(5457):1433-1438 (2000).

Galaria et al., "Leukocytoclastic vasculitis due to etanercept," J Rheumatol. 27(8):2041-4 (2000) (1 page) (Abstract only).

Ganoth et al., "A multicomponent system that degrades proteins conjugated to ubiquitin. Resolution of factors and evidence for ATP-dependent complex formation," J Biol Chem. 263(25):12412-12419 (1988).

Gaur et al., "Induction of islet allotolerance in nonhuman primates," Ann NY Acad Sci. 958:199-203 (2002).

Gazda et al., "Diabetes results from a late change in the autoimmune response of NOD mice," J Autoimmun. 10(3):261-270 (1997).

Gazda et al., "Regulation of autoimmune diabetes: characteristics of non-islet-antigen specific therapies," Immunol Cell Biol. 74: 401-407 (1996).

Genestier et al., "Immunosuppressive properties of methotrexate: Apoptosis and clonal deletion of activated peripheral T Cells," J Clin Invest. 102(2):322-328 (1998).

Gerich et al., "Advances in diabetes for the millennium: Understanding insulin resistance," MedGenMed. 6(3 Suppl.):11 (2004) (9 pages).

Ghosh et al., "Activation in vitro of NF-kappaB by phosphorylation of its inhibitor IkappaB," Nature. 344(6267):678-682 (1990).

Glas et al., "The CD8+ T Cell repertoire in beta2-microglobulin-deficient mice is biased towards reactivity against self-major histocompatibility class I," J Exp Med. 179(2):661-672 (1994).

Goldberg, "Functions of the proteasome: The lysis at the end of the tunnel," Science. 268:522-523 (1995).

Goldberg, "The mechanism and functions of ATP-dependent proteases in bacterial and animal cells," Eur J Biochem. 203:9-23 (1992).

Gottlieb et al., "Cell acidification in apoptosis: Granulocyte colony-stimulating factor delays programmed cell death in neutrophils by up-regulating the vacuolar H+-ATPase," Proc Natl Acad Sci USA. 92(13):5965-5968 (1995).

Graves et al., "Lack of association between early childhood immunizations and beta-cell autoimmunity," Diabetes Care. 22:1694-7 (1999).

Grewal et al., "Local expression of transgene encoded TNFalpha in islets prevents autoimmune diabetes in nonobese diabetic (NOD) mice by preventing the development of auto-reactive islet- specific T Cells," J Exp Med. 184:1963-1974 (1996).

Grilli et al., "Neuroprotection by aspirin and sodium salicylate through blockade of NF-kappaB activation," Science. 274:1383-1385 (1996).

Gronostajski et al., "The ATP dependence of the degradation of short- and long-lived proteins in growing fibroblasts," J Biol Chem. 260(6):3344-3349 (1985).

Gueckel et al., "Mutations in the yeast proteasome beta-Type subunit Pre3 uncover position-dependent effects on proteasomal peptidase activity and in vivo function," J Biol Chem. 273(31): 19443-19452 (1998).

Gupta, "Molecular steps of tumor necrosis factor receptor-mediated apoptosis," Curr Mol Med. 1(3):317-324 (2001).

Haas et al., "Pathways of ubiquitin conjugation," FASEB J. 11:1257-1268 (1997).

Hao et al., "Effect of mycophenolate mofetil on islet allografting to chemically induced or spontaneously diabetic animals," Transplant Proc. 24(6): 2843-2844 (1992).

Harada et al., "Prevention of overt diabetes and insulitis in NOD mice by a single BCG vaccination," Diabetes Res Clin Pract. 8:85-89 (1990).

Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).

Hayashi et al., "Essential role of human leukocyte antigen-encoded proteasome subunits in NF-kappaB activation and prevention of tumor necrosis factor-alpha-induced apoptosis," J Biol Chem. 275(7):5238-5247 (2000).

Hayashi et al., "NOD mice are defective in proteasome production and activation of NF-kappaB," Mol Cell Biol. 19(12):8646-8659 (1999).

Hershko et al., "The ubiquitin system for protein degradation," Annu Rev Biochem. 61: 761-807 (1992).

Hester et al., "Studies on the cytophilic properties of human beta2-microglobulin. II. The role of histocompatibility antigens," Scand J Immunol. 9(2):125-134 (1979).

Hoffmann et al., "Large-scale in vitro expansion of polyclonal human CD4(+)CD25$^{high}$ regulatory T cells," Blood. 104(3):895-903 (2004).

Horsfall et al., "Characterization and specificity of B-cell responses in lupus induced by *Mycobacterium bovis* in NOD/Lt mice," Immunology 95(1):8-17 (1998).

Horwitz et al., "Recombinant bacillus Calmette-Guerin (BCG) vaccines expressing the *Mycobacterium tuberculosis* 30-kDa major secretory protein induce greater protective immunity against tuberculosis than conventional BCG vaccines in a highly susceptible animal model," Proc Natl Acad Sci USA. 97(25):13853-13858 (2000).

Hostikka et al., "The mouse Hoxc11 gene: genomic structure and expression pattern," Mech Dev. 70(1-2):133-145 (1998) (Abstract Only).

Hsu et al., "TRADD-TRAF2 and TRADD-FADD interactions define two distinct TNF receptor 1 signal transduction pathways," Cell. 84:299-308 (1996).

Humphreys-Beher et al., "New concepts for the development of autoimmune exocrinopathy derived from studies with the NOD mouse model," Arch Oral Biol. 44(Suppl 1):S21-S25 (1999) (Abstract Only) (2 pages).

Hyafil et al., "Dissociation and exchange of the beta2-microglobulin subunit of HLA-A and HLA-B antigens," Proc Natl Acad Sci USA. 76(11):5834-5838 (1979).

Hymowitz et al., "Toward small-molecule agonists of TNF receptors," Nat Chem Biol. 1(7):353-354 (2005).

International Preliminary Report on Patentability for International Application No. PCT/US2014/015101, issued Aug. 11, 2015 (9 pages).

International Preliminary Report on Patentability for International Application No. PCT/US2016/032547, issued Nov. 21, 2017 (16 pages).

(56) References Cited

OTHER PUBLICATIONS

International Preliminary Report on Patentability for International Application No. PCT/US2017/032513, mailed Nov. 22, 2018 (8 pages).

International Preliminary Report on Patentability for International Application No. PCT/US2018/059779, mailed May 22, 2020 (11 pages).

International Preliminary Report on Patentability for International Application No. PCT/US2019/047330, mailed Feb. 23, 2021 (7 pages).

International Search Report and Written Opinion for International Application No. PCT/US16/32547, mailed Aug. 31, 2016 (24 pages).

International Search Report and Written Opinion for International Application No. PCT/US17/32513, mailed Oct. 25, 2017 (17 pages).

International Search Report and Written Opinion for International Application No. PCT/US18/59779, mailed Apr. 18, 2019 (19 pages).

International Search Report and Written Opinion for International Application No. PCT/US2019/047330, dated Nov. 20, 2019 (15 pages).

International Search Report and Written Opinion for International Patent Application No. PCT/US14/15101, mailed Jun. 24, 2014 (14 pages).

International Search Report for International Application No. PCT/US00/06239 mailed Jul. 31, 2000 (2 pages).

International Search Report for International Application No. PCT/US2004/037998, mailed Feb. 28, 2008 (2 pages).

International Search Report for International Patent Application No. PCT/US03/20578, mailed Apr. 27, 2004 (1 page).

International Search Report for International Patent Application No. PCT/US03/36531, mailed Jul. 14, 2004 (1 page).

Jackson et al., "Hematopoietic potential of stem cells isolated from murine skeletal muscle," Proc Natl Acad Sci USA. 96(25):14482-14486 (1999).

Jacob et al., "Monoclonal anti-tumor necrosis factor antibody renders non-obese diabetic mice hypersensitive to irradiation and enhances insulitis development," Int Immunol. 4(5):611-614 (1992).

Jacob et al., "Prevention of diabetes in nonobese diabetic mice by tumor necrosis factor (TNF): Similarities between TNF-alpha and interleukin 1," Proc Natl Acad Sci USA. 87(3):968-972 (1990).

Jacob et al., "Tumour necrosis factor-alpha in murine autoimmune 'lupus' nephritis," Nature. 331(6154):356-358 (1988).

Jakubowski et al., "Phase I trial of intramuscularly administered tumor necrosis factor in patients with advanced cancer," J Clin Oncol. 7(3):298-303 (1989).

Jarrett et al., "Anti-tumor necrosis factor-alpha therapy-induced vasculitis: case series," J Rheumatol. 30(10):2287-91 (2003) (1 page) (Abstract only).

Ji et al., "Cutting Edge: The Natural Ligand for Glucocorticoid-Induced TNF Receptor-Related Protein Abrogates Regulatory T Cell Suppression," J Immunol. 172(10):5823-7 (2004).

Jiang et al., "Pluripotency of mesenchymal stem cells derived from adult marrow," Nature. 418:41-49 (2002).

Johansson et al., "Identification of a neural stem cell in the adult mammalian central nervous system," Cell. 96(1):25-34 (1999).

Juang et al., "Beneficial influence of glycemic control upon the growth and function of transplanted islets," Diabetes 43:1334-1339 (1994).

Kaijzel et al., "Functional analysis of a human tumor necrosis factor alpha (TNF-alpha) promoter polymorphism related to joint damage in rheumatoid arthritis," Mol Med. 4(11):724-733 (1998).

Kanzler et al., "Hox11 acts cell autonomously in spleen development and its absence results in altered cell fate of mesenchymal spleen precursors," Devel Biol. 234(1):231-243 (2001).

Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).

Kawasaki et al., "Prevention of type 1 diabetes: from the view point of beta cell damage," Diabetes Res Clin Pract. 66(Suppl 1):S27-32 (2004).

Kieran et al., "The DNA binding subunit of NF-kappaB is identical to factor KBF1 and homologous to the rel oncogene product," Cell. 62(5):1007-18 (1990).

Klingensmith et al., "Vaccination with BCG at diagnosis does not alter the course of IDDM," Diabetes 57th Annual Meeting and Scientific Sessions, Jun. 21-24, Boston MA. 40(Suppl 1):193A, 0744 (1997) (3 pages) (Abstract Only).

Klinkhoff, "Biological agents for rheumatoid arthritis: targeting both physical function and structural damage," Drugs. 64(12):1267-83 (2004) (Abstract only).

Koarada et al., "B Cells lacking RP105, a novel B cell antigen, in systemic lupus erythematosus," Arthritis Rheum. 42(12):2593-600 (1999).

Kodama et al., "Islet regeneration during the reversal of autoimmune diabetes in NOD mice," Science. 302(5648):1223-1227 (2003).

Kodama et al., "Regenerative medicine: A radical reappraisal of the spleen," Trends Mol Med. 11(6):271-276 (2005).

Kodama et al., "The therapeutic potential of tumor necrosis factor for autoimmune disease: A mechanistically based hypothesis," Cell Mol Life Sci. 62:1850-1862 (2005).

Kopp et al., "Inhibition of NF-kappaB by sodium salicylate and aspirin," Science. 265(5174):956-959 (1994).

Kouskoff et al., "Organ-specific disease provoked by systemic autoimmunity," Cell. 87(5):811-22 (1996) (1 page) (Abstract only).

Koyama et al., "Hox11 genes establish synovial joint organization and phylogenetic characteristics in developing mouse zeugopod skeletal elements," Development. 137(22): 3795-800 (2010) (Abstract Only).

Krause et al., "Multi-organ, multi-lineage engraftment by a single bone marrow-derived stem cell," Cell. 105(3):369-377 (2001).

Kretschmer et al., "Strong antigenic selection shaping the immunoglobulin heavy chain repertoire of B-1a lymphocytes in lambda 2(315) transgenic mice," Eur J Immunol. 32(8):2317-27 (2002).

Kuehnle et al., "The therapeutic potential of stem cells from adults," BMJ. 325(7360):372-6 (2002).

Kwon et al., "Evidence for involvement of the proteasome complex (26S) and NFkappaB in IL-1 beta-induced nitric oxide and prostaglandin production by rat islets and RINm5F Cells," Diabetes. 47(4):583-591 (1998).

Kwon et al., "Interleukin-1beta-induced nitric oxide synthase expression by rat pancreatic beta-cells: Evidence for the involvement of nuclear factor kappaB in the signaling mechanism," Endocrinology. 136(11):4790-4795 (1995).

Laakko et al., "Versatility of merocyanine 540 for the flow cytometric detection of apoptosis in human and murine cells," J Immunol Methods. 261(1-2):129-139 (2002).

Lahav-Baratz et al., "Reversible phosphorylation controls the activity of cyclosome-associated cyclin-ubiquitin ligase," Proc Natl Acad Sci USA. 92:9303-9307 (1995).

Lakey et al., "BCG immunotherapy prevents recurrence of diabetes in islet grafts transplanted into spontaneously diabetic NOD mice," Transplantation. 57(8):1213-1217 (1994).

Lammert et al., "Induction of pancreatic differentiation by signals from blood vessels," Science. 294(5542):564-567 (2001).

Lamminmaki et al., "Crystal Structure of a Recombinant Anti-Estradiol Fab Fragment in Complex With 17beta-Estradiol," J Biol Chem. 276(39):36687-94 (2001).

Lanza et al., "Transplantation of encapsulated canine islets into spontaneously diabetic BB/Wor rats without immunosuppression," Endocrinology. 131(2):637-642 (1992).

Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).

Lawrence et al., "Differential hepatocyte toxicity of recombinant Apo2L/TRAIL versions," Nat Med. 7(4):383-385 (2001).

Lewis et al., "Integrins regulate the apoptotic response to DNA damage through modulation of p53," Proc Natl Acad Sci USA. 99(6):3627-3632 (2002).

(56)     References Cited

OTHER PUBLICATIONS

Li et al., "Abnormal class I assembly and peptide presentation in the nonobese diabetic mouse," Proc Natl Acad Sci USA. 91(23):11128-11132 (1994).

Li et al., "Reduced expression of peptide-loaded HLA class I molecules on multiple sclerosis lymphocytes," Ann Neurol. 38(2):147-154 (1995).

Li et al., "Use of Donor β2-Microglobulin-Deficient Transgenic Mouse Liver Cells for Isografts, Allografts, and Xenografts," *Transplantation.* 55(4):940-946, (1993).

Lipsky et al., "Infliximab and methotrexate in the treatment of rheumatoid arthritis," N Engl J Med. 343(22):1594-1602 (2000).

Ljunggren et al., "MHC class I expression and CD8+ T cell development in TAP1/β2-microglobulin double mutant mice," Int Immunol. 7(6):975-984 (1995).

Loetscher et al., "Human tumor necrosis factor α (TNFα) mutants with exclusive specificity for the 55-kDa or 75-kDa TNF receptors," J Biol Chem. 268(35):26350-26357 (1993).

MacCallum et al., "Antibody-antigen interactions: contact analysis and binding site topography," J Mol Biol. 262(5):732-45 (1996).

Macchi et al., "Impaired apoptosis in mitogen-stimulated lymphocytes of patients with multiple sclerosis," NeuroReport. 10(25):399-402 (1999).

Mak et al., "Signaling for survival and apoptosis in the immune system," Arthritis Res. 4(Suppl 3):S243-S252 (2002).

Markiewicz et al., "Long-term T cell memory requires the surface expression of self-peptide/major histocompatibility complex molecules," Proc Natl Acad Sci USA. 95(6):3065-70 (1998).

Markmann et al., "Indefinite survival of MHC class I-deficient murine pancreatic islet allografts," Transplantation. 54(6):1085-1089 (1992).

Marriott, "TNF-α antagonists: Monoclonal antibodies, soluble receptors, thalidomide and other novel approaches," Expert Opin Invest Drugs. 6(8):1105-1108 (1997).

Matsumoto et al., "Liver organogenesis promoted by endothelial cells prior to vascular function," Science. 294:559-563 (2001).

Mayer-Proschel et al., "Isolation of lineage-restricted neuronal precursors from multipotent neuroepithelial stem cells," Neuron. 19:773-785 (1997).

McGuire et al., "An enzyme related to the high molecular weight multicatalytic proteinase, macropain, participates in a ubiquitin-mediated, ATP-stimulated proteolytic pathway in soluble extracts of BHK 21/C13 fibroblasts," Biochim Biophys Acta. 967:195-203 (1988).

McInerney et al., "Prevention of insulitis and diabetes onset by treatment with complete Freund's adjuvant in NOD mice," Diabetes. 40:715-725 (1991).

McKay, "Mammalian deconstruction for stem cell reconstruction," Nat Med. 6(7):747-748 (2000).

Mercurio et al., "p105 and p98 precursor proteins play an active role in NF-Kappa B-mediated signal transduction," Genes Dev. 7:705-718 (1993).

Mestas et al., "Of mice and not men: Differences between mouse and human immunology," J Immunol. 172:2731-2738 (2004).

Mezey et al., "Turning blood into brain: Cells bearing neuronal antigens generated in vivo from bone marrow," Science. 290:1779-1782 (2000).

Miller et al., "Both the Lyt-2+ and L3T4+ T cell subsets are required for the transfer of diabetes in nonobese diabetic mice," J Immunol. 140(1):52-8 (1988).

Mittelman et al., "A phase I pharmacokinetic study of recombinant human tumor necrosis factor administered by a 5-day continuous infusion," Invest New Drugs. 10(3):183-190 (1992).

Miyazaki et al., "Predominance of T lymphocytes in pancreatic islets and spleen of pre-diabetic non-obese diabetic (NOD) mice: A longitudinal study," Clin Exp Immunol. 60:622-630 (1985).

Moreland et al., "Etanercept therapy in rheumatoid arthritis: a randomized, controlled trial," Ann Intern Med. 130(6):478-486 (1999).

Morrison, "Stem cell potential: Can anything make anything?" Curr Biol. 11(1): R7-R9 (2001).

Murthi et al., "Novel homeobox genes are differentially expressed in placental microvascular endothelial cells compared with macrovascular cells," Placenta. 29(7):624-630 (2008) (1 page) (Abstract only).

Nomikos et al., "Combined treatment with nicotinamide and desferrioxamine prevents islet allograft destruction in NOD mice," Diabetes. 35(11):1302-1304 (1986).

Office Action for Japanese Application No. 2018-127922, mailed May 14, 2019 (3 pages).

Offield et al., "PDX-1 is required for pancreatic outgrowth and differentiation of the rostral duodenum," Development. 122(3):983-995 (1996).

Okubo et al., "Homogeneous Expansion of Human T-regulatory Cells via Tumor Necrosis Factor Receptor 2," Sci Rep. 3:3153 (11 pages).

Ono et al., "IDDM in BB rats. Enhanced MHC class I heavy-chain gene expression in pancreatic islets," Diabetes. 37:1411-1418 (1988).

Orlowski, "The multicatalytic proteinase complex, a major extralysosomal proteolytic system," Biochemistry. 29(45):10289-10297 (1990).

Osorio et al., "Beta-2 microglobulin gene disruption prolongs murine islet allograft survival in NOD mice," Transplant Proc. 26(2):752 (1994).

Palombella et al., "The ubiquitin-proteasome pathway is required for processing the NF-κB1 precursor protein and the activation of NF-κB," Cell. 78(5):773-785 (1994).

Paolillo et al., "The effect of Bacille Calmette-Guérin on the evolution of new enhancing lesions to hypointense T1 lesions in relapsing remitting MS," J Neurol. 250:247-248 (2003).

Pestano et al., "Inactivation of misselected CD8 T cells by CD8 gene methylation and cell death," Science. 284(5417):1187-91 (1999).

Petersen et al., "Bone marrow as a potential source of hepatic oval cells," Science. 284(5417):1168-70 (1999).

Pillay et al., "Antibodies in oncology," N Biotechnol. 28(5):518-529 (2011).

Pontesilli et al., "Circulating lymphocyte populations and autoantibodies in non-obese diabetic (NOD) mice: a longitudinal study," Clin Exp Immunol. 70(1):84-93 (1987).

Pozzilli, "BCG vaccine in insulin-dependent diabetes mellitus," Lancet. 349(9064):1520-1 (1997).

Prieto et al., "Apoptotic rate: A new indicator for the quantification of the incidence of apoptosis in cell cultures," Cytometry. 48(4):185-93 (2002).

Product Data Sheet for Tnf RII/TNFRSF1B Inhibition of TNP-alpha-induced Cyototoxicity and Neutralization by Human TNF RII/TNFRSF1B Antibody. Retrieved Aug. 1, 2017. R&D Systems Inc. (3 pages).

Qin et al., "BCG vaccination prevents insulin-dependent diabetes mellitus (IDDM) in NOD mice after disease acceleration with cyclophosphamide," J Autoimmun. 10:271-278 (1997).

Qin et al., "Complete Freund's adjuvant-induced T cells prevent the development and adoptive transfer of diabetes in nonobese diabetic mice," J Immunol. 150(5):2072-80 (1993).

Quintana et al., "Experimental autoimmune myasthenia gravis in naïve non-obese diabetic (NOD/LtJ) mice: Susceptibility associated with natural IgG antibodies to the acetylcholine receptor," Int Immunol. 15(1):11-16 (2003).

Raab et al., "In vitro evaluation of methotrexate and azathioprine for antipsoriatic activity," Arch Derm Res. 253(1):77-84 (1975).

Rabinovitch et al., "TNF-α down-regulates type 1 cytokines and prolongs survival of syngeneic islet grafts in nonobese diabetic mice," J Immunol. 159(12):6298-6303 (1997).

Rabinovitch et al., "Tumor necrosis factor mediates the protective effect of Freund's adjuvant against autoimmune diabetes in BB rats," J Autoimmun. 8(3):357-366 (1995).

Rajagopalan et al., "Pathogenic anti-DNA autoantibody-inducing T helper cell lines from patients with active lupus nephritis: Isolation of CD4⁻8⁻ T helper cell lines that express the γδ T-cell antigen receptor," Proc Natl Acad Sci USA. 87:7020-7024 (1990).

(56) References Cited

OTHER PUBLICATIONS

Raju et al., "Characterization and developmental expression of TIx-1, the murine homolog of HOX11," Mech Dev. 44(1):51-64 (1993).

Ramiya et al., "Reversal of insulin-dependent diabetes using islets generated in vitro from pancreatic stem cells," Nat Med. 6(3):278-282 (2000).

Rath et al., "TNF-induced signaling in apoptosis," J Clin Immunol. 19(6):350-364 (1999).

Rechsteiner, "Ubiquitin-mediated pathways for intracellular proteolysis," Annu Rev Cell Biol. 3:1-30 (1987).

Rietze et al., "Purification of a pluripotent neural stem cell from the adult mouse brain," Nature. 412(6848):736-739 (2001).

Ristori et al., "Use of Bacille Calmette-Guerin (BCG) in multiple sclerosis," Neurology. 53:1588-1589 (1999).

Roberts et al., "Developmental expression of Hox11 and specification of splenic cell fate," Am J Pathol. 146(5):1089-1101 (1995).

Roberts et al., "Hox11 controls the genesis of the spleen," Nature. 368:747-749 (1994).

Robertson et al., "Preservation of insulin mRNA levels and insulin secretion in HIT cells by avoidance of chronic exposure to high glucose concentrations," J Clin Invest. 90(2):320-325 (1992).

Robinson et al., "A novel NOD-derived murine model of primary Sjogren's Syndrome," Arthritis Rheum. 41(1):150-156 (1998).

Robinson et al., "Elevated levels of cysteine protease activity in saliva and salivary glands of the nonobese diabetic (NOD) mouse model for Sjögren Syndrome," Proc Natl Acad Sci USA. 94(11):5767-5771 (1997).

Rolfe et al., "The ubiquitin-mediated proteolytic pathway as a therapeutic area," J Mol Med. 75:5-17 (1997).

Rosenthal, "Prometheus's vulture and the stem-cell promise," N Engl J Med. 349(3):267-74 (2003).

Rudinger, "Characteristics of the amino acids as components of a peptide hormone sequence," in Peptide Hormones, Parsons, ed., University Park Press, Jun. 1976, pp. 1-7.

Ryu et al., "Reversal of established autoimmune diabetes by restoration of endogenous β cell function," J Clin Invest. 108(1):63-72 (2001).

Sadelain et al., "Prevention of type I diabetes in NOD mice by adjuvant immunotherapy," Diabetes. 39(5):583-589 (1990).

Sandborn et al., "Antitumor necrosis factor therapy for inflammatory bowel disease: a review of agents, pharmacology, clinical results, and safety," Inflamm Bowel Dis. 5(2):119-33 (1999) (Abstract only).

Sandborn, "Strategies targeting tumor necrosis factor in Crohn's disease," Acta Gastroenterol Belg. 64(2):170-2 (2001) (1 page) (Abstract only).

Santee et al., "Human tumor necrosis factor receptor p75/80 (CD120b) gene structure and promoter characterization," J Biol Chem. 271(35):21151-9 (1996).

Sarin et al., "Cytotoxic effect of TNF and lymphotoxin on T lymphoblasts," J Immunol. 155(8):3716-3718 (1995).

Satoh et al., "Inhibition of type I diabetes in BB rats with recombinant human tumor necrosis factor-α[1]," J Immunol. 145(5):1395-1399 (1990).

Satoh et al., "Recombinant human tumor necrosis factor α suppresses autoimmune diabetes in nonobese diabetic mice," J Clin Invest. 84(4):1345-1348 (1989).

Schaible, "Long term safety of infliximab," Can J Gastroenterol. 14(Suppl C):29C-32C (2000) (Abstract only).

Schatz et al., "Defective inducer T-cell function before the onset of insulin-dependent diabetes mellitus," J Autoimmun. 4(1):125-136 (1991).

Schmidt et al., "Interspecies exchange of $β_2$-microglobulin and associated MHC and differentiation antigens," Immunogenetics. 13(6):483-91 (1981).

Schuppan, "Current concepts of celiac disease pathogenesis," Gastroenterology. 119(1):234-242 (2000).

Sears et al., "NF-κB p105 processing via the ubiquitin-proteasome pathway," J Biol Chem. 273(3):1409-1419 (1998).

Sedger et al., "Poxvirus tumor necrosis factor receptor (TNFR)-like T2 proteins contain a conserved preligand assembly domain that inhibits cellular TNFR1-induced cell death," J Virol. 80(18):9300-9 (2006).

Serrano et al., "Non-HLA associations with autoimmune diseases," Autoimmun Rev. 5(3):209-214 (2006).

Serreze et al., "Th1 to Th2 cytokine shifts in nonobese diabetic mice: Sometimes an outcome, rather than the cause, of diabetes resistance elicited by immunostimulation," J Immunol. 166(2):1352-1359 (2001).

Serup et al., "Islet and stem cell transplantation for treating diabetes," BMJ. 322 (7277):29-32 (2001).

Serup, "Panning for pancreatic stem cells," Nat Genet. 25(2):134-135 (2000).

Shakoor et al., "Drug-induced systemic lupus erythematosus associated with etanercept therapy," Lancet. 359(9306):579-80 (2002) (Absract only).

Shehadeh et al., "Effect of adjuvant therapy on development of diabetes in mouse and man," Lancet. 343(8899):706-707 (1994).

Shehadeh et al., "Repeated BCG vaccination is more effective than a single dose in preventing diabetes in non-obese diabetic (NOD) mice," Isr J Med Sci. 33(11):711-715 (1997).

Shihabuddin et al., "Adult spinal cord stem cells generate neurons after transplantation in the adult dentate gyrus," J Neurosci. 20(23):8727-8735 (2000).

Shohami et al., "Dual role of tumor necrosis factor alpha in brain injury," Cytokine Growth Factor Rev. 10(2):119-130 (1999).

Silva et al., "Prevention of autoimmune diabetes through immunostimulation with Q fever complement-fixing antigen," Ann NY Acad Sci. 1005:423-430 (2003).

Singh et al., "Can progression of IDDM be prevented in newly diagnosed patients by BCG immunotherapy?" Diabetes Metab Rev. 13(4):320-321 (1997).

Slack, "Stem cells in epithelial tissues," Science. 287:1431-1433 (2000).

Song et al., "Tumor necrosis factor-related apoptosis-inducing ligand (TRAIL) is an inhibitor of autoimmune inflammation and cell cycle progression," J Exp Med. 191(7):1095-1103 (2000).

Speiser et al., "Loss of ATP-dependent proteolysis with maturation of reticulocytes and erythrocytes," J Biol Chem. 257(23):14122-14127 (1982).

Sreenan et al., "Increased β-Cell proliferation and reduced mass before diabetes onset in the nonobese diabetic mouse," Diabetes. 48(5):989-996 (1999).

Stephens et al., "Protection of NIT-1 pancreatic β-cells from immune attack by inhibition of NF-κb," J Autoimmun. 10(3):293-298 (1997).

Storms et al., "Hoechst dye efflux reveals a novel CD7+CD34; lymphoid progenitor in human umbilical cord blood," Blood. 96(6):2125-2133 (2000).

Sun et al., "MHC class I multimers," Arthritis Res. 3(5):265-269 (2001).

Supplementary Partial European Search Report for European Application No. 04817543, dated Oct. 6, 2009 (4 pages).

Swale et al., "Etanercept-induced systemic lupus erythematosus," Clin Exp Dermatol. 28(6):604-607 (2003).

Swirski et al., "Identification of splenic reservoir monocytes and their deployment to inflammatory sites," available in PMC Jan. 7, 2010, published in final edited form as: Science. 325(5940):612-616 (2009) (12 pages).

Szodoray et al., "Programmed cell death in rheumatoid arthritis peripheral blood T-cell subpopulations determined by laser scanning cytometry," Lab Invest. 83(12):1839-1848 (2003).

Tamura et al., "In vivo differentiation of stem cells in the aorta-gonad-mesonephros region of mouse embryo and adult bone marrow," Exp Hematol. 30(8):957-966 (2002) (Abstract Only).

Tartaglia et al., "The two different receptors for tumor necrosis factor mediate distinct cellular responses," Proc Natl Acad Sci USA. 88(20):9292-9296 (1991).

Tavernier et al., "Analysis of the structure-function relationship of tumour necrosis factor. Human/mouse chimeric TNF proteins: general properties and epitope analysis," J Mol Biol. 211(2):493-501 (1990).

(56)         References Cited

OTHER PUBLICATIONS

Technical Data Sheet for Purified Rat Anti-Human CD120b, BD Pharmingen™ (2011) (2 pages).

Terada et al., "Bone marrow cells adopt the phenotype of other cells by spontaneous cell fusion," Nature. 416(6880):542-545 (2002).

Thomas et al., "Demyelination during anti-tumor necrosis factor alpha therapy with infliximab for Crohn's disease," Inflamm Bowel Dis. 10(1):28-31 (2004) (Abstract only).

Toma et al., "Isolation of multipotent adult stem cells from the dermis of mammalian skin," Nat Cell Bio. 3(9):778-784 (2001).

Torrey et al., "Targeting TNFR2 With Antagonistic Antibodies Inhibits Proliferation of Ovarian Cancer Cells and Tumor-Associated Tregs," Sci Signal. 10(462):eaaf8608 (2017) (13 pages).

Totpal et al., "TNF and its receptor antibody agonist differ in mediation of cellular responses," J Immunol. 153(5):2248-2257 (1994).

Townsley et al., "Dominant-negative cyclin-selective ubiquitin carrier protein E2-C/UbcH10 blocks cells in metaphase," Proc Natl Acad Sci USA. 94(6):2362-2367 (1997).

Trad et al., "Clonal Progression during the T Cell-Dependent B Cell Antibody Response Depends on the Immunoglobulin DH Gene Segment Repertoire," Front Immunol. 5(385):1-11 (2014).

Tran et al., "Reversal of Sjögren's-like syndrome in non-obese diabetic mice," Ann Rheum Dis. 66(6):812-814 (2007).

Trowsdale et al., "Sequences encoded in the class II region of the MHC related to the 'ABC' superfamily of transporters," Nature. 348(6303):741-4 (1990).

Ulaeto et al., "A T-cell dormant state in the autoimmune process of nonobese diabetic mice treated with complete Freund's adjuvant," Proc Natl Acad Sci USA. 89(9):3927-3931 (1992).

Van der Kooy et al., "Why stem cells?," Science. 287:1439-1441 (2000).

Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).

Van Noort et al., "Cell biology of autoimmune diseases," Int Rev Cytol. 178:127-206 (1998).

Van Zee et al., "A human tumor necrosis factor (TNF) α mutant that binds exclusively to the p55 TNF receptor produces toxicity in the baboon," J Exp Med. 179(4):1185-1191 (1994).

Vermeire et al., "Autoimmunity associated with anti-tumor necrosis factor alpha treatment in Crohn's disease: a prospective cohort study," Gastroenterology. 125(1):32-9 (2003) (1 page) (Abstract only).

Vidal-Puig et al., "Tolerance to peripheral tissue is transient and maintained by tissue-specific class I expression," Transplant Proc. 26(6):3314-6 (1994).

Vogel, "Stem cell research. Studies cast doubt on plasticity of adult cells," Science. 295:1989&1991 (2002).

Von Herrath et al., "In vivo treatment with a MHC class I-restricted blocking peptide can prevent virus-induced autoimmune diabetes," J Immunol. 161:5087-5096 (1998).

Wagner, "Making and using antibodies," <www-users.med.cornell.edu/~jawagne/Antibody_Approaches.html>, accessed Aug. 8, 2016 (7 pages).

Wang et al., "Prevention of recurrence of IDDM in islet-transplanted diabetic NOD mice by adjuvant immunotherapy," Diabetes. 41:114-117 (1992).

Watt et al., "Out of Eden: stem cells and their niches," Science. 287:1427-30 (2000).

Watt et al., "Specific alternative HOX11 transcripts are expressed in paediatric neural tumours and T-cell acute lymphoblastic leukaemia," Gene. 323:89-99 (2003) (Abstract only).

Waxman et al., "Demonstration of two distinct high molecular weight proteases in rabbit reticulocytes, one of which degrades ubiquitin conjugates," J Biol Chem. 262(6):2451-2457 (1987).

Weissman, "Translating stem and progenitor cell biology to the clinic: barriers and opportunities," Science. 287:1442-1446 (2000).

Welborn et al., "A human tumor necrosis factor p75 receptor agonist stimulates in vitro T cell proliferation but does not produce inflammation or shock in the baboon," J Exp Med. 184(1):165-171 (1996).

Wellik et al., "Hox11 paralogous genes are essential for metanephric kidney induction," Genes Dev. 16:1423-1432 (2002).

Wellik, "The role of Hox11 paralogous genes in prostate development," Grant Detail. (2009) (1 page)(Abstract only).

Weringer et al., "Identification of T cell subsets and Class I and Class II antigen expression in islet grafts and pancreatic islets of diabetic BioBreeding/Worcester rats," Am J Pathol. 132(2):292-303 (1988).

Wicker et al., "Transfer of autoimmune diabetes mellitus with splenocytes from nonobese diabetic (NOD) mice," Diabetes. 35:855-860 (1986).

Willis et al., "Type 1 Diabetes in insulin-treated adult-onset diabetic subjects," Diabetes Res Clin Pract. 42:49-53 (1998).

Wilson et al., "Bone-marrow haematopoietic-stem-cell niches," Nat Rev Immunol. 6(2):93-106 (2006).

Winston, "Embryonic stem cell research: the case for . . . ," Nat Med. 7(4):396-397 (2001).

Wong et al., "Identification of an MHC class I-restricted autoantigen in Type I Diabetes by screening an organ-specific cDNA library," Nat Med. 5(9):1026-1031 (1999).

Written Opinion for International Application No. PCT/US2004/037998, mailed Feb. 28, 2008 (3 pages).

Xu et al., "MHC/peptide tetramer-based studies of T cell function," J Immunol Methods. 268(1):21-28 (2002).

Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).

Yan et al., "Reduced expression of Tap1 and Lmp2 antigen-processing genes in the nonobese diabetic (NOD) mouse due to a mutation in their shared bidirectional promoter," J Immunol. 159(6):3068-3080 (1997).

Yang et al., "Effect of tumor necrosis factor alpha on insulin-dependent diabetes mellitus in NOD Mice. I. The early development of autoimmunity and the diabetogenic process," J Exp Med. 180(3):995-1004 (1994).

Ying et al., "Changing potency by spontaneous fusion," Nature. 416(6880):545-548 (2002).

Yu et al., "Complex Interplay between Epitope Specificity and Isotype Dictates the Biological Activity of Antihuman CD40 Antibodies," Cancer Cell. 33(4):1-12 (2018) (17 pages).

Zulewski et al., "Multipotential nestin-positive stem cells isolated from adult pancreatic islets differentiate ex vivo into pancreatic endocrine, exocrine, and hepatic phenotypes," Diabetes. 50(3):521-533 (2001).

Zöller et al., "Apoptosis resistance in peripheral blood lymphocytes of alopecia areata patients," Retrieved from Science Direct, published in: J Autoimmun. 23(3):241-256 (2004) (30 pages).

Yan et al., "Construction of a synthetic phage-displayed Nanobody library with CDR3 regions randomized by trinucleotide cassettes for diagnostic applications," J Transl Med. 12:343 (2014).

Office Action for Canadian Application No. 2,985,816, dated Jun. 22, 2023 (8 pages).

Office Action for Canadian Application No. 3,109,954, dated Oct. 12, 2023 (7 pages).

Williams et al., "Phenotypic screening reveals TNFR2 as a promising target for cancer immunotherapy," Oncotarget. 7(42):68278-68291 (2016).

Extended European Search Report for European Application No. 18875602.7, dated Jul. 19, 2021 (12 pages).

International Search Report and Written Opinion for PCT/US2021/032540, mailed Oct. 29, 2021 (15 pages).

Office Action for Japanese Patent Application No. 2018-127922, mailed May 14, 2019 (5 pgs.).

Chopra et al., "Tumor necrosis factor receptor 2-dependent homeostasis of regulatory T cells as a player in TNF-induced experimental metastasis," Carcinogenesis. 34(6):1296-303 (2013).

Office Action for Japanese Patent Application No. 2020-204143, mailed Dec. 16, 2021 (6 pages).

(56) References Cited

OTHER PUBLICATIONS

Extended European Search Report for European Patent Application No. 21175520.2, dated Dec. 10, 2021 (7 pages).
Office Action for Korean Application No. 10-2018-7036235, dated Nov. 29, 2021 (11 pages).
Office Action for Chinese Patent Application No. 201780043276.X, issued Dec. 2, 2021 (17 pages).
Fischer et al., "Selective Targeting of TNF Receptors as a Novel Therapeutic Approach," Front Cell Dev Biol. 8:401 (2020) (21 pages).
"Potential New Cancer Therapy Could Target Tumors Two Ways," National Cancer Institute, <https://www.cancer.gov/news-events/cancer-currents-blog/2017/tnfr2-target-tumors>, dated Feb. 15, 2017, retrieved on Mar. 14, 2022 (6 pages).
Stevens et al., "Overcoming the challenges of topical antibody administration for improving healing outcomes: a review of recent laboratory and clinical approaches," Wound Practice Res. 25(4):188-94 (2017).
Yang et al., "Optimizing TNFR2 antagonism for immunotherapy with tumor microenvironment specificity," J Leukoc Biol. 107(6):971-80 (2020) (10 pages).
Extended European Search Report for European Patent Application No. 19852179.1, dated May 6, 2022 (9 pages).
Morris et al., "Selective Blockade of TNFR1 Improves Clinical Disease and Bronchoconstriction in Experimental RSV Infection," Viruses. 12(10):1176 (Oct. 17, 2020) (20 pages).
Yang et al., "Role of TNF-TNF Receptor 2 Signal in Regulatory T Cells and Its Therapeutic Implications," Front Immunol. 9:784 (Apr. 19, 2018) (11 pages).
Barnes et al., "Susceptibility to Burkholderia pseudomallei is associated with host immune responses involving tumor necrosis factor receptor-1 (TNFR1) and TNF receptor-2 (TNFR2)," Fems Immunol Med Microbiol. 52(3):379-88 (Feb. 22, 2008).
Liang et al., "Distinct Role of TNFR1 and TNFR2 in Protective Immunity Against Orientia tsutsugamushi Infection in Mice," Front Immunol. 13:867924 (Apr. 11, 2022) (17 pages).
English Translation of Office Action for Korean Application No. 10-2022-7020235, dated Jan. 2, 2023 (6 pages).
Examination Report for Australian Patent Application No. 2017263833, dated Jun. 1, 2023 (3 pages).
Office Action for Canadian Application No. 3,023,930, dated May 17, 2023 (6 pages).
English Translation of Notice of Reasons for Rejection for Japanese Application No. 2021-509865, mailed Aug. 8, 2023 (2 pgs).
Yagi et al., "Possible mechanism of the preventive effect of BCG against diabetes mellitus in NOD Mouse. I. Generation of suppressor macrophages in spleen cells of BCG-vaccinated mice," Cell Immunol. 138(1):130-141 (1991).

International Preliminary Report on Patentability for International Application No. PCT/US22/13273, issued Jul. 20, 2023 (8 pages).
International Search Report and Written Opinion for International Application No. PCT/US22/13273, mailed Dec. 13, 2022 (17 pages).
EPO Communication Pursuant to Article 94(3) EPC issued in European Patent Application No. 19852179.1, dated Jan. 18, 2024 (5 pages).
Qiu et al., "Engineering an anti-CD52 antibody for enhance deamidation stability," MAbs. 11(7):1266-75 (Oct. 2019).
English Translation of Office Action for Chinese Application No. 201980068984.8, mailed Mar. 1, 2024 (9 pages).
Peppel et al.: "A Tumour Necrosis Factor (TNF) Receptor IGG Heavy Chain Chimeric Protein as a Bivalent Antagonist of TNF Activity", Journal of Experimental Medicine, Rockefeller University Press, US, 174(6), Dec. 1, 1991 (Dec. 1, 1991), pp. 1483-1489.
Vanamee et al: "Structural principles of tumor necrosis factor superfamily signaling", Sci. Signal. 11, Jan. 2, 2018 (12 pages).
Naismith et al: "Crystallographic evidence for dimerization of unliganded tumor necrosis factor receptor", Journal of Biological Chemistry, American Society for Biochemistry and Molecular Biology, US, 270 (22), Jun. 2, 1995, pp. 13303-13307.
Extended European Search Report for European Application No. 23190358.4, mailed May 15, 2024 (8 pages).
Argiriadi et al., "CD40/anti-CD40 antibody complexes which illustrate agonist and antagonist structural switches," BMC Mol Cell Biol. 20(1):29 (Aug. 2019) (13 pages).
Chen et al., "TNFR2 is critical for the stabilization of the CD4+ Foxp3+ regulatory T cell phenotype in the inflammatory environment," J Immunol. 190(3):1076-84 (Feb. 2013) (Epub Dec. 2012) (11 pages).
Ferrara et al., "Recombinant renewable polyclonal antibodies," MAbs. 7(1):32-41 (2015) (10 pages).
"TNFR2 Antibodies," ThermoFisher Scientific. <https://www.thermofisher.com/antibody/primary/target/tnfr2>, accessed Jan. 10, 2025 (11 pages).
Turner et al., "Mechanism of TNFa-induced IL-1a, IL-1β and IL-6 expression in human cardiac fibroblasts: Effects of statins and thiazolidinediones," Cardiovasc Res. 76(1):81-90 (Oct. 2007) (Epub Jun. 2007).
Van der Most et al., "Tumor eradication after cyclophosphamide depends on concurrent depletion of regulatory T cells: a role for cycling TNFR2-expressing effector-suppressor T cells in limiting effective chemotherapy," Cancer Immunol Immunother. 58(8):1219-28 (Aug. 2009) (Epub Dec. 2008).
Wu et al., "An optimally designed anti-human CD40 antibody with potent B cell suppression for the treatment of autoimmune diseases," Int J Pharm. 609:121162 (Nov. 2021) (17 pages).
Sasi et al., "Breaking the 'harmony' of TNF-α signaling for cancer treatment." Oncogene, 31:4117-4127 (2012).

* cited by examiner

FIG. 1

```
           10          20          30          40          50
MAPVAVWAAL  AVGLELWAAA  HALPAQVAFT  PYAPEPGSTC  RLREYYDQTA
           60          70          80          90         100
QMCCSKCSPG  QHAKVFCTKT  SDTVCDSCED  STYTQLWNWV  PECLSCGSRC
          110         120         130         140         150
SSDQVETQAC  TREQNRICTC  RPGWYCALSK  QEGCRLCAPL  RKCRPGFGVA
          160         170         180         190         200
RPGTETSDVV  CKPCAPGTFS  NTTSSTDICR  PHQICNVVAI  PGNASMDAVC
          210         220         230         240         250
TSTSPTRSMA  PGAVHLPQPV  STRSQHTQPT  PEPSTAPSTS  FLLPMGPSPP
          260         270         280         290         300
AEGSTGDFAL  PVGLIVGVTA  LGLLIIGVVN  CVIMTQVKKK  PLCLQREAKV
          310         320         330         340         350
PHLPADKARG  TQGPEQQHLL  ITAPSSSSSS  LESSASALDR  RAPTRNQPQA
          360         370         380         390         400
PGVEASGAGE  ARASTGSSDS  SPGGHGTQVN  VTCIVNVCSS  SDHSSQCSSQ
          410         420         430         440         450
ASSTMGDTDS  SPSESPKDEQ  VPFSKEECAF  RSQLETPETL  LGSTEEKPLP
          460
LGVPDAGMKP  S
```

Murine
TNFR2
antagonist
IgG2

Human chimeric
TNFR2 antagonist
IgG2

Murine
TNFR2
antagonist
IgG2

Human chimeric
TNFR2 antagonist
IgG2 - C232S + C233S

Murine
TNFR2
antagonist
IgG2

Human chimeric
TNFR2 antagonist
IgG2 - C232S + C233S

SEQUENCE LISTING

<160> NUMBER OF SEQ ID NOS: 309

<210> SEQ ID NO 1
<211> LENGTH: 523
<212> TYPE: DNA
<213> ORGANISM: Murine

<400> SEQUENCE: 1

```
gaccaggcat cccagggtca ccatggagtt agtttgggca gcagatccag gggccagtgg      60
atagacagat gggggtgtcg ttttggctga ggagacggtg accgcggtcc ctgcgcccca     120
gacatcgaag taccagtagc tggagtaacc atcaaccctc tgtcgtgcac agtaatacat     180
ggccgtgtcc tcagacctca gactgctcat ttgcaggtac agggtgttct tggcattgtc     240
tctggagatg gtgaatcgcc ccttcacact gtctggatag taggtgtaac taccaccact     300
actaatggtt gcgacccact ccagcctctt ctccggagtc tggcgaaccc aagacatgac     360
ataactactg aaagtgaatc cagaggctgc acaggagagt ttcagggacc ctccaggctt     420
cactaagcct ccccctgact cctgcagctg cacctccgga agcctgaatt ctgcagatat     480
ccatcacact ggcggccgct cgagcatgca tctagaggcc cat                      523
```

```
<210> SEQ ID NO 2
<211> LENGTH: 123
<212> TYPE: PRT
<213> ORGANISM: Murine

<400> SEQUENCE: 2

Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Val Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Arg Val Asp Gly Tyr Ser Ser Tyr Trp Tyr Phe Asp Val
            100                 105                 110

Trp Gly Ala Gly Thr Ala Val Thr Val Ser Ser
        115                 120

<210> SEQ ID NO 3
<211> LENGTH: 508
<212> TYPE: DNA
<213> ORGANISM: Murine

<400> SEQUENCE: 3
ctccgagcgg ccgccagtgt gatggatatc tgcagaattc aggggggacat tgtgctgacc       60 cagtctccag caatcatgtc tgcatctcca ggggagaagg tcaccataac ctgcagtgcc      120
agctcaagtg tatattacat gtactggttc agcagaagc caggcacttc tcccaaactc      180
tggatttata gcacatccaa cctggcttct ggagtccctg ttcgcttcag tggcagtggc      240
tctgggacct cttactctct cacaatcagc cgaatggagg ctgaagatgc tgccacttat      300
tactgccagc aaaggaggaa ttacccgtac acgttcggag ggggaccaa gttggaaata      360 aaacgggctg atgctccacc aactgtatcc atcttccac catccagtga gcagttacct      420
gaattccagc acactggcgg ccgttactag tggatccgag ctcggtacca agcttgatgc      480
atagcttgag tattctaacg cgtcacct                                         508

<210> SEQ ID NO 4
<211> LENGTH: 108
<212> TYPE: PRT
<213> ORGANISM: Murine

<400> SEQUENCE: 4

Asp Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Tyr Tyr Met
            20                  25                  30

Tyr Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80
```

```
Asp Ala Ala Thr Tyr Tyr Cys Gln Gln Arg Arg Asn Tyr Pro Tyr Thr
            85                  90                  95

Phe Gly Gly Gly Thr Lys Leu Glu Ile Lys Arg Ala
            100                 105
```

<210> SEQ ID NO 5
<211> LENGTH: 454
<212> TYPE: DNA
<213> ORGANISM: Murine

<400> SEQUENCE: 5

```
gagcggccgc cagtgtgatg gatatctgca gaattcaggg ggacattgtg ctgacccaga      60
ctcctgcttc cttagctgta tctctggggc agagggccac catctcatgc agggccagca     120
aaagtgtcag tacatctggc tatagttata tgcactggta ccaacagaaa ccaggacagc     180
cacccaaact cctcatctat cttgcatcca acctagaatc tggggtccct gccaggttca     240
gtggcagtgg gtctgggaca gacttcaccc tcaacatcca tcctgtggag gaggaggatg     300
ctgcaaccta ttactgtcag cacagtaggg agcttcctcg gacgttcggt ggaggcacca     360
agctggaaat caaacgggct gatgctccac caactgtatc caccctgaa ttccagcaca      420 ctggcggccg ttactagtgg atccgagctc ggta                                 454
```

<210> SEQ ID NO 6
<211> LENGTH: 113
<212> TYPE: PRT
<213> ORGANISM: Murine

<400> SEQUENCE: 6

```
Asp Ile Val Leu Thr Gln Thr Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
            85                  90                  95

Glu Leu Pro Arg Thr Phe Gly Gly Gly Thr Lys Leu Glu Ile Lys Arg
            100                 105                 110

Ala
```

<210> SEQ ID NO 7
<211> LENGTH: 461
<212> TYPE: PRT
<213> ORGANISM: Homo sapiens

<400> SEQUENCE: 7

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45
```

```
Thr Ala Gln Met Cys Cys Ser Lys Cys Ser Pro Gly Gln His Ala Lys
    50              55              60

Val Phe Cys Thr Lys Thr Ser Asp Thr Val Cys Asp Ser Cys Glu Asp
65              70              75              80

Ser Thr Tyr Thr Gln Leu Trp Asn Trp Val Pro Glu Cys Leu Ser Cys
            85              90              95

Gly Ser Arg Cys Ser Ser Asp Gln Val Glu Thr Gln Ala Cys Thr Arg
            100             105             110

Glu Gln Asn Arg Ile Cys Thr Cys Arg Pro Gly Trp Tyr Cys Ala Leu
            115             120             125

Ser Lys Gln Glu Gly Cys Arg Leu Cys Ala Pro Leu Arg Lys Cys Arg
    130             135             140

Pro Gly Phe Gly Val Ala Arg Pro Gly Thr Glu Thr Ser Asp Val Val
145             150             155             160

Cys Lys Pro Cys Ala Pro Gly Thr Phe Ser Asn Thr Thr Ser Ser Thr
            165             170             175

Asp Ile Cys Arg Pro His Gln Ile Cys Asn Val Val Ala Ile Pro Gly
            180             185             190

Asn Ala Ser Met Asp Ala Val Cys Thr Ser Thr Ser Pro Thr Arg Ser
            195             200             205

Met Ala Pro Gly Ala Val His Leu Pro Gln Pro Val Ser Thr Arg Ser
    210             215             220

Gln His Thr Gln Pro Thr Pro Glu Pro Ser Thr Ala Pro Ser Thr Ser
225             230             235             240

Phe Leu Leu Pro Met Gly Pro Ser Pro Ala Glu Gly Ser Thr Gly
            245             250             255

Asp Phe Ala Leu Pro Val Gly Leu Ile Val Gly Val Thr Ala Leu Gly
            260             265             270

Leu Leu Ile Ile Gly Val Val Asn Cys Val Ile Met Thr Gln Val Lys
            275             280             285

Lys Lys Pro Leu Cys Leu Gln Arg Glu Ala Lys Val Pro His Leu Pro
    290             295             300

Ala Asp Lys Ala Arg Gly Thr Gln Gly Pro Glu Gln Gln His Leu Leu
305             310             315             320

Ile Thr Ala Pro Ser Ser Ser Ser Ser Ser Leu Glu Ser Ser Ala Ser
            325             330             335

Ala Leu Asp Arg Arg Ala Pro Thr Arg Asn Gln Pro Gln Ala Pro Gly
            340             345             350

Val Glu Ala Ser Gly Ala Gly Glu Ala Arg Ala Ser Thr Gly Ser Ser
            355             360             365

Asp Ser Ser Pro Gly Gly His Gly Thr Gln Val Asn Val Thr Cys Ile
    370             375             380

Val Asn Val Cys Ser Ser Ser Asp His Ser Ser Gln Cys Ser Ser Gln
385             390             395             400

Ala Ser Ser Thr Met Gly Asp Thr Asp Ser Ser Pro Ser Glu Ser Pro
            405             410             415

Lys Asp Glu Gln Val Pro Phe Ser Lys Glu Glu Cys Ala Phe Arg Ser
            420             425             430

Gln Leu Glu Thr Pro Glu Thr Leu Leu Gly Ser Thr Glu Glu Lys Pro
            435             440             445

Leu Pro Leu Gly Val Pro Asp Ala Gly Met Lys Pro Ser
    450             455             460
```

-continued

```
<210> SEQ ID NO 8
<211> LENGTH: 7
<212> TYPE: PRT
<213> ORGANISM: Homo sapiens

<400> SEQUENCE: 8

Asp Ser Thr Tyr Thr Gln Leu
1               5

<210> SEQ ID NO 9
<211> LENGTH: 8
<212> TYPE: PRT
<213> ORGANISM: Homo sapiens

<400> SEQUENCE: 9

Pro Glu Cys Leu Ser Cys Gly Ser
1               5

<210> SEQ ID NO 10
<211> LENGTH: 8
<212> TYPE: PRT
<213> ORGANISM: Homo sapiens

<400> SEQUENCE: 10

Arg Ile Cys Thr Cys Arg Pro Gly
1               5

<210> SEQ ID NO 11
<211> LENGTH: 8
<212> TYPE: PRT
<213> ORGANISM: Homo sapiens

<400> SEQUENCE: 11

Cys Ala Pro Leu Arg Lys Cys Arg
1               5

<210> SEQ ID NO 12
<211> LENGTH: 5
<212> TYPE: PRT
<213> ORGANISM: Homo sapiens

<400> SEQUENCE: 12

Lys Cys Ser Pro Gly
1               5

<210> SEQ ID NO 13
<211> LENGTH: 54
<212> TYPE: PRT
<213> ORGANISM: Homo sapiens

<400> SEQUENCE: 13

Cys Asp Ser Cys Glu Asp Ser Thr Tyr Thr Gln Leu Trp Asn Trp Val
1               5                   10                  15

Pro Glu Cys Leu Ser Cys Gly Ser Arg Cys Ser Ser Asp Gln Val Glu
            20                  25                  30

Thr Gln Ala Cys Thr Arg Glu Gln Asn Arg Ile Cys Thr Cys Arg Pro
        35                  40                  45

Gly Trp Tyr Cys Ala Leu
    50

<210> SEQ ID NO 14
<211> LENGTH: 17
<212> TYPE: PRT
<213> ORGANISM: Homo sapiens
```

<400> SEQUENCE: 14

Cys Asp Ser Cys Glu Asp Ser Thr Tyr Thr Gln Leu Trp Asn Trp Val
1               5               10              15

Pro

<210> SEQ ID NO 15
<211> LENGTH: 18
<212> TYPE: PRT
<213> ORGANISM: Homo sapiens

<400> SEQUENCE: 15

Leu Trp Asn Trp Val Pro Glu Cys Leu Ser Cys Gly Ser Arg Cys Ser
1               5               10              15

Ser Asp

<210> SEQ ID NO 16
<211> LENGTH: 18
<212> TYPE: PRT
<213> ORGANISM: Homo sapiens

<400> SEQUENCE: 16

Thr Arg Glu Gln Asn Arg Ile Cys Thr Cys Arg Pro Gly Trp Tyr Cys
1               5               10              15

Ala Leu

<210> SEQ ID NO 17
<211> LENGTH: 20
<212> TYPE: PRT
<213> ORGANISM: Homo sapiens

<400> SEQUENCE: 17

Lys Gln Glu Gly Cys Arg Leu Cys Ala Pro Leu Arg Lys Cys Arg Pro
1               5               10              15

Gly Phe Gly Val
            20

<210> SEQ ID NO 18
<211> LENGTH: 20
<212> TYPE: PRT
<213> ORGANISM: Homo sapiens

<400> SEQUENCE: 18

Gln Thr Ala Gln Met Cys Cys Ser Lys Cys Ser Pro Gly Gln His Ala
1               5               10              15

Lys Val Phe Cys
            20

<210> SEQ ID NO 19
<211> LENGTH: 5
<212> TYPE: PRT
<213> ORGANISM: Homo sapiens

<400> SEQUENCE: 19

Lys Cys Arg Pro Gly
1               5

<210> SEQ ID NO 20
<211> LENGTH: 8
<212> TYPE: PRT
<213> ORGANISM: Homo sapiens

<400> SEQUENCE: 20

Lys Cys Arg Pro Gly Phe Gly Val
1               5

<210> SEQ ID NO 21
<211> LENGTH: 9
<212> TYPE: PRT
<213> ORGANISM: Homo sapiens

<400> SEQUENCE: 21

Cys Lys Pro Cys Ala Pro Gly Thr Phe
1               5

<210> SEQ ID NO 22
<211> LENGTH: 41
<212> TYPE: PRT
<213> ORGANISM: Homo sapiens

<400> SEQUENCE: 22

Ala Arg Pro Gly Thr Glu Thr Ser Asp Val Val Cys Lys Pro Cys Ala
1               5                   10                  15

Pro Gly Thr Phe Ser Asn Thr Thr Ser Ser Thr Asp Ile Cys Arg Pro
            20                  25                  30

His Gln Ile Cys Asn Val Val Ala Ile
        35                  40

<210> SEQ ID NO 23
<211> LENGTH: 7
<212> TYPE: PRT
<213> ORGANISM: Murine

<400> SEQUENCE: 23

Gly Phe Thr Phe Ser Ser Tyr
1               5

<210> SEQ ID NO 24
<211> LENGTH: 6
<212> TYPE: PRT
<213> ORGANISM: Murine

<400> SEQUENCE: 24

Ser Ser Gly Gly Ser Tyr
1               5

<210> SEQ ID NO 25
<211> LENGTH: 14
<212> TYPE: PRT
<213> ORGANISM: Murine

<400> SEQUENCE: 25

Gln Arg Val Asp Gly Tyr Ser Ser Tyr Trp Tyr Phe Asp Val
1               5                   10

<210> SEQ ID NO 26
<211> LENGTH: 10
<212> TYPE: PRT
<213> ORGANISM: Murine

<400> SEQUENCE: 26

Ser Ala Ser Ser Ser Val Tyr Tyr Met Tyr
1               5                   10

<210> SEQ ID NO 27

```
<211> LENGTH: 7
<212> TYPE: PRT
<213> ORGANISM: Murine

<400> SEQUENCE: 27

Ser Thr Ser Asn Leu Ala Ser
1               5

<210> SEQ ID NO 28
<211> LENGTH: 9
<212> TYPE: PRT
<213> ORGANISM: Murine

<400> SEQUENCE: 28

Gln Gln Arg Arg Asn Tyr Pro Tyr Thr
1               5

<210> SEQ ID NO 29
<211> LENGTH: 15
<212> TYPE: PRT
<213> ORGANISM: Murine

<400> SEQUENCE: 29

Arg Ala Ser Lys Ser Val Ser Thr Ser Gly Tyr Ser Tyr Met His
1               5                   10                  15

<210> SEQ ID NO 30
<211> LENGTH: 7
<212> TYPE: PRT
<213> ORGANISM: Murine

<400> SEQUENCE: 30

Leu Ala Ser Asn Leu Glu Ser
1               5

<210> SEQ ID NO 31
<211> LENGTH: 9
<212> TYPE: PRT
<213> ORGANISM: Murine

<400> SEQUENCE: 31

Gln His Ser Arg Glu Leu Pro Arg Thr
1               5

<210> SEQ ID NO 32
<211> LENGTH: 120
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
            35                  40                  45

Ala Val Ile Ser Glu Asn Gly Ser Asp Thr Tyr Tyr Ala Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Asp Arg Gly Gly Ala Val Ser Tyr Phe Asp Val Trp Gly Gln
            100                 105                 110

Gly Thr Leu Val Thr Val Ser Ser
        115                 120

<210> SEQ ID NO 33
<211> LENGTH: 109
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105

<210> SEQ ID NO 34
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 34

Pro Glu Xaa Leu Ser Xaa Gly Ser Arg Cys Ser Gly Gly Ser Gly Gly
1               5                   10                  15

Asn Arg Ile Cys Thr Xaa Arg Pro Gly Trp Tyr
            20                  25

<210> SEQ ID NO 35
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:

<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 35

Xaa Leu Ser Xaa Gly Ser Arg Cys Ser Ser Asp Gly Gly Ser Gly Gly
1               5                   10                  15

Asn Arg Ile Cys Thr Xaa Arg Pro Gly Trp Tyr
            20                  25

<210> SEQ ID NO 36
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 36

Val Pro Glu Xaa Leu Ser Xaa Gly Ser Arg Cys Gly Gly Ser Gly Gly
1               5                   10                  15

Asn Arg Ile Cys Thr Xaa Arg Pro Gly Trp Tyr
            20                  25

<210> SEQ ID NO 37
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 37

Leu Ser Xaa Gly Ser Arg Cys Ser Ser Asp Gln Gly Gly Ser Gly Gly
1               5                   10                  15

Asn Arg Ile Cys Thr Xaa Arg Pro Gly Trp Tyr
            20                  25

<210> SEQ ID NO 38
<211> LENGTH: 27
<212> TYPE: PRT

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 38

Pro Glu Xaa Leu Ser Xaa Gly Ser Arg Cys Ser Gly Gly Ser Gly Gly
1               5                   10                  15

Cys Thr Xaa Arg Pro Gly Trp Tyr Xaa Ala Leu
            20                  25

<210> SEQ ID NO 39
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 39

Ser Xaa Gly Ser Arg Cys Ser Ser Asp Gln Val Gly Gly Ser Gly Gly
1               5                   10                  15

Asn Arg Ile Cys Thr Xaa Arg Pro Gly Trp Tyr
            20                  25

<210> SEQ ID NO 40
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
```

<223> OTHER INFORMATION: Xaa is Cys residue protected with ACM
      protecting group

<400> SEQUENCE: 40

Xaa Gly Ser Arg Cys Ser Ser Asp Gln Val Glu Gly Gly Ser Gly Gly
1               5                   10                  15

Arg Ile Cys Thr Xaa Arg Pro Gly Trp Tyr Xaa
            20                  25

<210> SEQ ID NO 41
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 41

Glu Xaa Leu Ser Xaa Gly Ser Arg Cys Ser Ser Gly Gly Ser Gly Gly
1               5                   10                  15

Cys Thr Xaa Arg Pro Gly Trp Tyr Xaa Ala Leu
            20                  25

<210> SEQ ID NO 42
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 42

Glu Gly Cys Arg Leu Xaa Ala Pro Leu Arg Lys Gly Gly Ser Gly Gly
1               5                   10                  15

Xaa Ala Pro Leu Arg Lys Cys Arg Pro Gly Phe
            20                  25

<210> SEQ ID NO 43
<211> LENGTH: 27
<212> TYPE: PRT
<213> ORGANISM: Artificial Sequence
<220> FEATURE:

```
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 43

Xaa Leu Ser Xaa Gly Ser Arg Cys Ser Ser Asp Gly Gly Ser Gly Gly
1               5                   10                  15

Cys Thr Xaa Arg Pro Gly Trp Tyr Xaa Ala Leu
            20                  25

<210> SEQ ID NO 44
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 44

Cys Ser Ser Asp Gln Val Glu Thr Gln Ala Xaa Gly Gly Ser Gly Gly
1               5                   10                  15

Arg Ile Cys Thr Xaa Arg Pro Gly Trp Tyr Xaa
            20                  25

<210> SEQ ID NO 45
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group
```

-continued

```
<400> SEQUENCE: 45

Gly Ser Arg Cys Ser Ser Asp Gln Val Glu Thr Gly Gly Ser Gly Gly
1               5                   10                  15

Arg Ile Cys Thr Xaa Arg Pro Gly Trp Tyr Xaa
            20                  25

<210> SEQ ID NO 46
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 46

Xaa Gly Ser Arg Cys Ser Ser Asp Gln Val Glu Gly Gly Ser Gly Gly
1               5                   10                  15

Asn Arg Ile Cys Thr Xaa Arg Pro Gly Trp Tyr
            20                  25

<210> SEQ ID NO 47
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 47

Gly Ser Arg Cys Ser Ser Asp Gln Val Glu Thr Gly Gly Ser Gly Gly
1               5                   10                  15

Asn Arg Ile Cys Thr Xaa Arg Pro Gly Trp Tyr
            20                  25

<210> SEQ ID NO 48
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
```

-continued

```
<222> LOCATION: (27)..(27)
<223> OTHER INFORMATION: Xaa is Cys residue protected with ACM
      protecting group

<400> SEQUENCE: 48

Pro Glu Xaa Leu Ser Xaa Gly Ser Arg Cys Ser Gly Gly Ser Gly Gly
1               5                   10                  15

Arg Ile Cys Thr Xaa Arg Pro Gly Trp Tyr Xaa
            20                  25

<210> SEQ ID NO 49
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 49

Val Pro Glu Xaa Leu Ser Xaa Gly Ser Arg Cys Gly Gly Ser Gly Gly
1               5                   10                  15

Gln Asn Arg Ile Cys Thr Xaa Arg Pro Gly Trp
            20                  25

<210> SEQ ID NO 50
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 50

Gln Glu Gly Cys Arg Leu Xaa Ala Pro Leu Arg Gly Gly Ser Gly Gly
1               5                   10                  15

Xaa Ala Pro Leu Arg Lys Cys Arg Pro Gly Phe
            20                  25

<210> SEQ ID NO 51
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
```

-continued

```
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 51

Ser Arg Cys Ser Ser Asp Gln Val Glu Thr Gln Gly Gly Ser Gly Gly
1               5                   10                  15

Arg Ile Cys Thr Xaa Arg Pro Gly Trp Tyr Xaa
            20                  25

<210> SEQ ID NO 52
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 52

Ala Leu Ser Lys Gln Glu Gly Cys Arg Leu Xaa Gly Gly Ser Gly Gly
1               5                   10                  15

Xaa Ala Pro Leu Arg Lys Cys Arg Pro Gly Phe
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 53

Gln Glu Gly Cys Arg Leu Xaa Ala Pro Leu Arg Gly Gly Ser Gly Gly
1               5                   10                  15

Pro Leu Arg Lys Cys Arg Pro Gly Phe Gly Val
            20                  25

<210> SEQ ID NO 54
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
```

<400> SEQUENCE: 54

Tyr Xaa Ala Leu Ser Lys Gln Glu Gly Cys Arg Gly Gly Ser Gly Gly
1               5                   10                  15

Ala Pro Leu Arg Lys Cys Arg Pro Gly Phe Gly
            20                  25

<210> SEQ ID NO 55
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 55

Leu Ser Xaa Gly Ser Arg Cys Ser Ser Asp Gln Gly Gly Ser Gly Gly
1               5                   10                  15

Arg Ile Cys Thr Xaa Arg Pro Gly Trp Tyr Xaa
            20                  25

<210> SEQ ID NO 56
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 56

Pro Glu Xaa Leu Ser Xaa Gly Ser Arg Cys Ser Gly Gly Ser Gly Gly
1               5                   10                  15

Gln Asn Arg Ile Cys Thr Xaa Arg Pro Gly Trp
            20                  25

<210> SEQ ID NO 57
<211> LENGTH: 27
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 57

Arg Cys Ser Ser Asp Gln Val Glu Thr Gln Ala Gly Gly Ser Gly Gly
1               5                   10                  15

Arg Ile Cys Thr Xaa Arg Pro Gly Trp Tyr Xaa
            20                  25

<210> SEQ ID NO 58
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 58

Pro Glu Xaa Leu Ser Xaa Gly Ser Arg Cys Ser Gly Gly Ser Gly Gly
1               5                   10                  15

Ile Cys Thr Xaa Arg Pro Gly Trp Tyr Xaa Ala
            20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
```

```
<223> OTHER INFORMATION: Xaa is Cys residue protected with ACM
      protecting group

<400> SEQUENCE: 59

Val Pro Glu Xaa Leu Ser Xaa Gly Ser Arg Cys Gly Gly Ser Gly Gly
1               5                   10                  15

Ile Cys Thr Xaa Arg Pro Gly Trp Tyr Xaa Ala
            20                  25

<210> SEQ ID NO 60
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 60

Ser Xaa Gly Ser Arg Cys Ser Ser Asp Gln Val Gly Gly Ser Gly Gly
1               5                   10                  15

Cys Thr Xaa Arg Pro Gly Trp Tyr Xaa Ala Leu
            20                  25

<210> SEQ ID NO 61
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 61

Trp Tyr Xaa Ala Leu Ser Lys Gln Glu Gly Cys Gly Gly Ser Gly Gly
1               5                   10                  15

Ala Pro Leu Arg Lys Cys Arg Pro Gly Phe Gly
            20                  25

<210> SEQ ID NO 62
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group
```

-continued

```
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 62

Leu Ser Lys Gln Glu Gly Cys Arg Leu Xaa Ala Gly Gly Ser Gly Gly
1               5                   10                  15

Xaa Ala Pro Leu Arg Lys Cys Arg Pro Gly Phe
            20                  25

<210> SEQ ID NO 63
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 63

Lys Gln Glu Gly Cys Arg Leu Xaa Ala Pro Leu Gly Gly Ser Gly Gly
1               5                   10                  15

Xaa Ala Pro Leu Arg Lys Cys Arg Pro Gly Phe
            20                  25

<210> SEQ ID NO 64
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 64

Leu Ser Xaa Gly Ser Arg Cys Ser Ser Asp Gln Gly Gly Ser Gly Gly
1               5                   10                  15

Cys Thr Xaa Arg Pro Gly Trp Tyr Xaa Ala Leu
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MOD_RES
<222> LOCATION: (23)..(23)
<223> OTHER INFORMATION: Xaa is Cys residue protected with ACM
      protecting group

<400> SEQUENCE: 65

Arg Cys Ser Ser Asp Gln Val Glu Thr Gln Ala Gly Gly Ser Gly Gly
1               5                   10                  15

Gln Asn Arg Ile Cys Thr Xaa Arg Pro Gly Trp
            20                  25

<210> SEQ ID NO 66
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 66

Ser Lys Gln Glu Gly Cys Arg Leu Xaa Ala Pro Gly Gly Ser Gly Gly
1               5                   10                  15

Xaa Ala Pro Leu Arg Lys Cys Arg Pro Gly Phe
            20                  25

<210> SEQ ID NO 67
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 67

Xaa Gly Ser Arg Cys Ser Ser Asp Gln Val Glu Gly Gly Ser Gly Gly
1               5                   10                  15

Gln Asn Arg Ile Cys Thr Xaa Arg Pro Gly Trp
            20                  25

<210> SEQ ID NO 68
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
```

-continued

```
<222> LOCATION: (23)..(23)
<223> OTHER INFORMATION: Xaa is Cys residue protected with ACM
      protecting group

<400> SEQUENCE: 68

Cys Ser Ser Asp Gln Val Glu Thr Gln Ala Xaa Gly Gly Ser Gly Gly
1               5                   10                  15

Gln Asn Arg Ile Cys Thr Xaa Arg Pro Gly Trp
            20                  25

<210> SEQ ID NO 69
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 69

Cys Ser Ser Asp Gln Val Glu Thr Gln Ala Xaa Gly Gly Ser Gly Gly
1               5                   10                  15

Asn Arg Ile Cys Thr Xaa Arg Pro Gly Trp Tyr
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 70

Val Pro Glu Xaa Leu Ser Xaa Gly Ser Arg Cys Gly Gly Ser Gly Gly
1               5                   10                  15

Cys Thr Xaa Arg Pro Gly Trp Tyr Xaa Ala Leu
            20                  25

<210> SEQ ID NO 71
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 71

Glu Xaa Leu Ser Xaa Gly Ser Arg Cys Ser Ser Gly Gly Ser Gly Gly
1               5                   10                  15

Gln Asn Arg Ile Cys Thr Xaa Arg Pro Gly Trp
            20                  25

<210> SEQ ID NO 72
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 72

Ser Arg Cys Ser Ser Asp Gln Val Glu Thr Gln Gly Gly Ser Gly Gly
1               5                   10                  15

Asn Arg Ile Cys Thr Xaa Arg Pro Gly Trp Tyr
            20                  25

<210> SEQ ID NO 73
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 73

Xaa Gly Ser Arg Cys Ser Ser Asp Gln Val Glu Gly Gly Ser Gly Gly
1               5                   10                  15

Cys Thr Xaa Arg Pro Gly Trp Tyr Xaa Ala Leu
            20                  25
```

```
<210> SEQ ID NO 74
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 74

Val Pro Glu Xaa Leu Ser Xaa Gly Ser Arg Cys Gly Gly Ser Gly Gly
1               5                   10                  15

Arg Ile Cys Thr Xaa Arg Pro Gly Trp Tyr Xaa
            20                  25

<210> SEQ ID NO 75
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 75

Glu Xaa Leu Ser Xaa Gly Ser Arg Cys Ser Ser Gly Gly Ser Gly Gly
1               5                   10                  15

Arg Ile Cys Thr Xaa Arg Pro Gly Trp Tyr Xaa
            20                  25

<210> SEQ ID NO 76
<211> LENGTH: 27
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MOD_RES
<222> LOCATION: (10)..(10)
<223> OTHER INFORMATION: Xaa is Cys residue protected with ACM
      protecting group

<400> SEQUENCE: 76

Leu Ser Lys Gln Glu Gly Cys Arg Leu Xaa Ala Gly Gly Ser Gly Gly
1               5                   10                  15

Arg Lys Cys Arg Pro Gly Phe Gly Val Ala Arg
            20                  25

<210> SEQ ID NO 77
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 77

Gly Ser Arg Cys Ser Ser Asp Gln Val Glu Thr Gly Gly Ser Gly Gly
1               5                   10                  15

Gln Asn Arg Ile Cys Thr Xaa Arg Pro Gly Trp
            20                  25

<210> SEQ ID NO 78
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 78

Ser Xaa Gly Ser Arg Cys Ser Ser Asp Gln Val Gly Gly Ser Gly Gly
1               5                   10                  15

Arg Ile Cys Thr Xaa Arg Pro Gly Trp Tyr Xaa
            20                  25

<210> SEQ ID NO 79
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
```

```
<222> LOCATION: (25)..(25)
<223> OTHER INFORMATION: Xaa is Cys residue protected with ACM
      protecting group

<400> SEQUENCE: 79

Gly Ser Arg Cys Ser Ser Asp Gln Val Glu Thr Gly Gly Ser Gly Gly
1               5                   10                  15

Cys Thr Xaa Arg Pro Gly Trp Tyr Xaa Ala Leu
            20                  25

<210> SEQ ID NO 80
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 80

Tyr Xaa Ala Leu Ser Lys Gln Glu Gly Cys Arg Gly Gly Ser Gly Gly
1               5                   10                  15

Arg Lys Cys Arg Pro Gly Phe Gly Val Ala Arg
            20                  25

<210> SEQ ID NO 81
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 81

Lys Gln Glu Gly Cys Arg Leu Xaa Ala Pro Leu Gly Gly Ser Gly Gly
1               5                   10                  15

Pro Leu Arg Lys Cys Arg Pro Gly Phe Gly Val
            20                  25

<210> SEQ ID NO 82
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 82

Ala Leu Ser Lys Gln Glu Gly Cys Arg Leu Xaa Gly Gly Ser Gly Gly
1               5                   10                  15

Arg Lys Cys Arg Pro Gly Phe Gly Val Ala Arg
            20                  25

<210> SEQ ID NO 83
<211> LENGTH: 27
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 83

Glu Xaa Leu Ser Xaa Gly Ser Arg Cys Ser Ser Gly Gly Ser Gly Gly
1               5                   10                  15

Ile Cys Thr Xaa Arg Pro Gly Trp Tyr Xaa Ala
            20                  25

<210> SEQ ID NO 84
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 84

Cys Ser Ser Asp Gln Val Glu Thr Gln Ala Xaa Gly Gly Ser Gly Gly
1               5                   10                  15

Ile Cys Thr Xaa Arg Pro Gly Trp Tyr Xaa Ala
            20                  25

<210> SEQ ID NO 85
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group
```

```
<400> SEQUENCE: 85

Glu Gly Cys Arg Leu Xaa Ala Pro Leu Arg Lys Gly Gly Ser Gly Gly
1               5                   10                  15

Pro Leu Arg Lys Cys Arg Pro Gly Phe Gly Val
            20                  25

<210> SEQ ID NO 86
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 86

Ala Leu Ser Lys Gln Glu Gly Cys Arg Leu Xaa Gly Gly Ser Gly Gly
1               5                   10                  15

Pro Leu Arg Lys Cys Arg Pro Gly Phe Gly Val
            20                  25

<210> SEQ ID NO 87
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 87

Xaa Ala Leu Ser Lys Gln Glu Gly Cys Arg Leu Gly Gly Ser Gly Gly
1               5                   10                  15

Arg Lys Cys Arg Pro Gly Phe Gly Val Ala Arg
            20                  25

<210> SEQ ID NO 88
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 88

Xaa Ala Leu Ser Lys Gln Glu Gly Cys Arg Leu Gly Gly Ser Gly Gly
1               5                   10                  15

Xaa Ala Pro Leu Arg Lys Cys Arg Pro Gly Phe
            20                  25

<210> SEQ ID NO 89
```

<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 89

Xaa Leu Ser Xaa Gly Ser Arg Cys Ser Ser Asp Gly Gly Ser Gly Gly
1               5                   10                  15

Arg Ile Cys Thr Xaa Arg Pro Gly Trp Tyr Xaa
            20                  25

<210> SEQ ID NO 90
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 90

Leu Ser Lys Gln Glu Gly Cys Arg Leu Xaa Ala Gly Gly Ser Gly Gly
1               5                   10                  15

Pro Leu Arg Lys Cys Arg Pro Gly Phe Gly Val
            20                  25

<210> SEQ ID NO 91
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 91

Ser Lys Gln Glu Gly Cys Arg Leu Xaa Ala Pro Gly Gly Ser Gly Gly
1               5                   10                  15

Arg Lys Cys Arg Pro Gly Phe Gly Val Ala Arg
            20                  25

<210> SEQ ID NO 92
<211> LENGTH: 27

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 92

Lys Gln Glu Gly Cys Arg Leu Xaa Ala Pro Leu Gly Gly Ser Gly Gly
1               5                   10                  15

Arg Lys Cys Arg Pro Gly Phe Gly Val Ala Arg
            20                  25

<210> SEQ ID NO 93
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 93

Gln Glu Gly Cys Arg Leu Xaa Ala Pro Leu Arg Gly Gly Ser Gly Gly
1               5                   10                  15

Arg Lys Cys Arg Pro Gly Phe Gly Val Ala Arg
            20                  25

<210> SEQ ID NO 94
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 94

Xaa Ala Leu Ser Lys Gln Glu Gly Cys Arg Leu Gly Gly Ser Gly Gly
1               5                   10                  15

Ala Pro Leu Arg Lys Cys Arg Pro Gly Phe Gly
            20                  25

<210> SEQ ID NO 95
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
```

<400> SEQUENCE: 95

Xaa Ala Leu Ser Lys Gln Glu Gly Cys Arg Leu Gly Gly Ser Gly Gly
1               5                   10                  15

Pro Leu Arg Lys Cys Arg Pro Gly Phe Gly Val
            20                  25

<210> SEQ ID NO 96
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 96

Gly Ser Arg Cys Ser Ser Asp Gln Val Glu Thr Gly Gly Ser Gly Gly
1               5                   10                  15

Ile Cys Thr Xaa Arg Pro Gly Trp Tyr Xaa Ala
            20                  25

<210> SEQ ID NO 97
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 97

Ser Arg Cys Ser Ser Asp Gln Val Glu Thr Gln Gly Gly Ser Gly Gly
1               5                   10                  15

Gln Asn Arg Ile Cys Thr Xaa Arg Pro Gly Trp
            20                  25

<210> SEQ ID NO 98
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

```
<400> SEQUENCE: 98

Xaa Gly Ser Arg Cys Ser Ser Asp Gln Val Glu Gly Gly Ser Gly Gly
1               5                   10                  15

Ile Cys Thr Xaa Arg Pro Gly Trp Tyr Xaa Ala
            20                  25

<210> SEQ ID NO 99
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 99

Glu Xaa Leu Ser Xaa Gly Ser Arg Cys Ser Ser Gly Gly Ser Gly Gly
1               5                   10                  15

Asn Arg Ile Cys Thr Xaa Arg Pro Gly Trp Tyr
            20                  25

<210> SEQ ID NO 100
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 100

Ser Arg Cys Ser Ser Asp Gln Val Glu Thr Gln Gly Gly Ser Gly Gly
1               5                   10                  15

Ile Cys Thr Xaa Arg Pro Gly Trp Tyr Xaa Ala
            20                  25

<210> SEQ ID NO 101
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 101
```

```
Tyr Xaa Ala Leu Ser Lys Gln Glu Gly Cys Arg Gly Gly Ser Gly Gly
1               5                   10                  15

Pro Leu Arg Lys Cys Arg Pro Gly Phe Gly Val
            20                  25

<210> SEQ ID NO 102
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 102

Arg Cys Ser Ser Asp Gln Val Glu Thr Gln Ala Gly Gly Ser Gly Gly
1               5                   10                  15

Ile Cys Thr Xaa Arg Pro Gly Trp Tyr Xaa Ala
            20                  25

<210> SEQ ID NO 103
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 103

Ser Lys Gln Glu Gly Cys Arg Leu Xaa Ala Pro Gly Gly Ser Gly Gly
1               5                   10                  15

Pro Leu Arg Lys Cys Arg Pro Gly Phe Gly Val
            20                  25

<210> SEQ ID NO 104
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 104

Ser Xaa Gly Ser Arg Cys Ser Ser Asp Gln Val Gly Gly Ser Gly Gly
1               5                   10                  15

Gln Asn Arg Ile Cys Thr Xaa Arg Pro Gly Trp
            20                  25
```

```
<210> SEQ ID NO 105
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 105

Glu Gly Cys Arg Leu Xaa Ala Pro Leu Arg Lys Gly Gly Ser Gly Gly
1               5                   10                  15

Arg Lys Cys Arg Pro Gly Phe Gly Val Ala Arg
            20                  25

<210> SEQ ID NO 106
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 106

Xaa Leu Ser Xaa Gly Ser Arg Cys Ser Ser Asp Gly Gly Ser Gly Gly
1               5                   10                  15

Gln Asn Arg Ile Cys Thr Xaa Arg Pro Gly Trp
            20                  25

<210> SEQ ID NO 107
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 107

Trp Tyr Xaa Ala Leu Ser Lys Gln Glu Gly Cys Gly Gly Ser Gly Gly
1               5                   10                  15

Pro Leu Arg Lys Cys Arg Pro Gly Phe Gly Val
            20                  25

<210> SEQ ID NO 108
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 108

Gln Glu Gly Cys Arg Leu Xaa Ala Pro Leu Arg Gly Gly Ser Gly Gly
1               5                   10                  15

Ala Pro Leu Arg Lys Cys Arg Pro Gly Phe Gly
            20                  25

<210> SEQ ID NO 109
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 109

Trp Tyr Xaa Ala Leu Ser Lys Gln Glu Gly Cys Gly Gly Ser Gly Gly
1               5                   10                  15

Xaa Ala Pro Leu Arg Lys Cys Arg Pro Gly Phe
            20                  25

<210> SEQ ID NO 110
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 110

Ala Leu Ser Lys Gln Glu Gly Cys Arg Leu Xaa Gly Gly Ser Gly Gly
1               5                   10                  15

Ala Pro Leu Arg Lys Cys Arg Pro Gly Phe Gly
            20                  25

<210> SEQ ID NO 111
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group
```

<400> SEQUENCE: 111

Glu Gly Cys Arg Leu Xaa Ala Pro Leu Arg Lys Gly Gly Ser Gly Gly
1               5                   10                  15

Ala Pro Leu Arg Lys Cys Arg Pro Gly Phe Gly
            20                  25

<210> SEQ ID NO 112
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 112

Tyr Xaa Ala Leu Ser Lys Gln Glu Gly Cys Arg Gly Gly Ser Gly Gly
1               5                   10                  15

Xaa Ala Pro Leu Arg Lys Cys Arg Pro Gly Phe
            20                  25

<210> SEQ ID NO 113
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 113

Leu Ser Xaa Gly Ser Arg Cys Ser Ser Asp Gln Gly Gly Ser Gly Gly
1               5                   10                  15

Gln Asn Arg Ile Cys Thr Xaa Arg Pro Gly Trp
            20                  25

<210> SEQ ID NO 114
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 114

Leu Ser Lys Gln Glu Gly Cys Arg Leu Xaa Ala Gly Gly Ser Gly Gly
1               5                   10                  15

-continued

Ala Pro Leu Arg Lys Cys Arg Pro Gly Phe Gly
            20                  25

<210> SEQ ID NO 115
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 115

Arg Cys Ser Ser Asp Gln Val Glu Thr Gln Ala Gly Gly Ser Gly Gly
1               5               10              15

Asn Arg Ile Cys Thr Xaa Arg Pro Gly Trp Tyr
            20                  25

<210> SEQ ID NO 116
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 116

Lys Gln Glu Gly Cys Arg Leu Xaa Ala Pro Leu Gly Gly Ser Gly Gly
1               5               10              15

Ala Pro Leu Arg Lys Cys Arg Pro Gly Phe Gly
            20                  25

<210> SEQ ID NO 117
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 117

Ser Lys Gln Glu Gly Cys Arg Leu Xaa Ala Pro Gly Gly Ser Gly Gly
1               5               10              15

Ala Pro Leu Arg Lys Cys Arg Pro Gly Phe Gly
            20                  25

<210> SEQ ID NO 118
<211> LENGTH: 5
<212> TYPE: PRT
<213> ORGANISM: Murine

<400> SEQUENCE: 118

Ala Asp Ala Ala Pro
1               5

<210> SEQ ID NO 119

-continued

```
<211> LENGTH: 5
<212> TYPE: PRT
<213> ORGANISM: Homo sapiens

<400> SEQUENCE: 119

Thr Val Ala Ala Pro
1               5

<210> SEQ ID NO 120
<211> LENGTH: 11
<212> TYPE: PRT
<213> ORGANISM: Murine

<400> SEQUENCE: 120

Ala Asp Ala Ala Pro Thr Val Ser Ile Phe Pro
1               5                   10

<210> SEQ ID NO 121
<211> LENGTH: 12
<212> TYPE: PRT
<213> ORGANISM: Homo sapiens

<400> SEQUENCE: 121

Thr Val Ala Ala Pro Ser Val Phe Ile Phe Pro Pro
1               5                   10

<210> SEQ ID NO 122
<211> LENGTH: 6
<212> TYPE: PRT
<213> ORGANISM: Homo sapiens

<400> SEQUENCE: 122

Gln Pro Lys Ala Ala Pro
1               5

<210> SEQ ID NO 123
<211> LENGTH: 13
<212> TYPE: PRT
<213> ORGANISM: Homo sapiens

<400> SEQUENCE: 123

Gln Pro Lys Ala Ala Pro Ser Val Thr Leu Phe Pro Pro
1               5                   10

<210> SEQ ID NO 124
<211> LENGTH: 5
<212> TYPE: PRT
<213> ORGANISM: Artificial Sequence
<220> FEATURE:
<223> OTHER INFORMATION: Synthetic Construct

<400> SEQUENCE: 124

Gly Gly Ser Gly Gly
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic Construct

<400> SEQUENCE: 125

Gly Gly Ser Gly Gly Gly Gly Ser Gly
1               5
```

```
<210> SEQ ID NO 126
<211> LENGTH: 13
<212> TYPE: PRT
<213> ORGANISM: Artificial Sequence
<220> FEATURE:
<223> OTHER INFORMATION: Synthetic Construct

<400> SEQUENCE: 126

Gly Gly Ser Gly Gly Gly Gly Ser Gly Gly Gly Gly Ser
1               5                   10

<210> SEQ ID NO 127
<211> LENGTH: 6
<212> TYPE: PRT
<213> ORGANISM: Murine

<400> SEQUENCE: 127

Ala Lys Thr Thr Ala Pro
1               5

<210> SEQ ID NO 128
<211> LENGTH: 6
<212> TYPE: PRT
<213> ORGANISM: Homo sapiens

<400> SEQUENCE: 128

Ala Ser Thr Lys Gly Pro
1               5

<210> SEQ ID NO 129
<211> LENGTH: 13
<212> TYPE: PRT
<213> ORGANISM: Murine

<400> SEQUENCE: 129

Ala Lys Thr Thr Ala Pro Ser Val Tyr Pro Leu Ala Pro
1               5                   10

<210> SEQ ID NO 130
<211> LENGTH: 13
<212> TYPE: PRT
<213> ORGANISM: Homo sapiens

<400> SEQUENCE: 130

Ala Ser Thr Lys Gly Pro Ser Val Phe Pro Leu Ala Pro
1               5                   10

<210> SEQ ID NO 131
<211> LENGTH: 6
<212> TYPE: PRT
<213> ORGANISM: Artificial Sequence
<220> FEATURE:
<223> OTHER INFORMATION: Synthetic Construct

<400> SEQUENCE: 131

Gly Gly Gly Gly Ser Gly
1               5

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 132

Gly Gly Gly Gly Ser Gly Gly Gly Gly Ser
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Synthetic Construct

<400> SEQUENCE: 133

Gly Gly Gly Gly Ser Gly Gly Gly Gly Ser Gly Gly Gly Gly
1               5                   10

<210> SEQ ID NO 134
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 134

Ser Arg Cys Ser Ser Asp Gln Val Glu Thr Gln Gly Gly Ser Gly Gly
1               5                   10                  15

Thr Arg Glu Gln Asn Arg Ile Cys Thr Xaa Arg
            20                  25

<210> SEQ ID NO 135
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 135

Arg Cys Ser Ser Asp Gln Val Glu Thr Gln Ala Gly Gly Ser Gly Gly
1               5                   10                  15

Thr Arg Glu Gln Asn Arg Ile Cys Thr Xaa Arg
            20                  25

<210> SEQ ID NO 136
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group
```

-continued

```
<400> SEQUENCE: 136

Cys Ser Ser Asp Gln Val Glu Thr Gln Ala Xaa Gly Gly Ser Gly Gly
1               5                   10                  15

Thr Arg Glu Gln Asn Arg Ile Cys Thr Xaa Arg
            20                  25

<210> SEQ ID NO 137
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 137

Val Pro Glu Xaa Leu Ser Xaa Gly Ser Arg Cys Gly Gly Ser Gly Gly
1               5                   10                  15

Arg Glu Gln Asn Arg Ile Cys Thr Xaa Arg Pro
            20                  25

<210> SEQ ID NO 138
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 138

Pro Glu Xaa Leu Ser Xaa Gly Ser Arg Cys Ser Gly Gly Ser Gly Gly
1               5                   10                  15

Arg Glu Gln Asn Arg Ile Cys Thr Xaa Arg Pro
            20                  25

<210> SEQ ID NO 139
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 139

Glu Xaa Leu Ser Xaa Gly Ser Arg Cys Ser Ser Gly Gly Ser Gly Gly
1               5                   10                  15

Arg Glu Gln Asn Arg Ile Cys Thr Xaa Arg Pro
            20                  25

<210> SEQ ID NO 140
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 140

Xaa Leu Ser Xaa Gly Ser Arg Cys Ser Ser Asp Gly Gly Ser Gly Gly
1               5                   10                  15

Arg Glu Gln Asn Arg Ile Cys Thr Xaa Arg Pro
            20                  25

<210> SEQ ID NO 141
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 141

Leu Ser Xaa Gly Ser Arg Cys Ser Ser Asp Gln Gly Gly Ser Gly Gly
1               5                   10                  15

Arg Glu Gln Asn Arg Ile Cys Thr Xaa Arg Pro
            20                  25
```

<210> SEQ ID NO 142
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 142

Ser Xaa Gly Ser Arg Cys Ser Ser Asp Gln Val Gly Gly Ser Gly Gly
1               5                   10                  15

Arg Glu Gln Asn Arg Ile Cys Thr Xaa Arg Pro
            20                  25

<210> SEQ ID NO 143
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 143

Xaa Gly Ser Arg Cys Ser Ser Asp Gln Val Glu Gly Gly Ser Gly Gly
1               5                   10                  15

Arg Glu Gln Asn Arg Ile Cys Thr Xaa Arg Pro
            20                  25

<210> SEQ ID NO 144
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 144

Gly Ser Arg Cys Ser Ser Asp Gln Val Glu Thr Gly Gly Ser Gly Gly
1               5                   10                  15

Arg Glu Gln Asn Arg Ile Cys Thr Xaa Arg Pro
            20                  25

<210> SEQ ID NO 145
<211> LENGTH: 27
<212> TYPE: PRT
<213> ORGANISM: Artificial Sequence
<220> FEATURE:

<223> OTHER INFORMATION: Synthetic Construct
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 145

Ser Arg Cys Ser Ser Asp Gln Val Glu Thr Gln Gly Gly Ser Gly Gly
1               5                   10                  15

Arg Glu Gln Asn Arg Ile Cys Thr Xaa Arg Pro
            20                  25

<210> SEQ ID NO 146
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 146

Arg Cys Ser Ser Asp Gln Val Glu Thr Gln Ala Gly Gly Ser Gly Gly
1               5                   10                  15

Arg Glu Gln Asn Arg Ile Cys Thr Xaa Arg Pro
            20                  25

<210> SEQ ID NO 147
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 147

Cys Ser Ser Asp Gln Val Glu Thr Gln Ala Xaa Gly Gly Ser Gly Gly
1               5                   10                  15

Arg Glu Gln Asn Arg Ile Cys Thr Xaa Arg Pro
            20                  25

<210> SEQ ID NO 148
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group

```
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 148

Val Pro Glu Xaa Leu Ser Xaa Gly Ser Arg Cys Gly Gly Ser Gly Gly
1               5                   10                  15

Glu Gln Asn Arg Ile Cys Thr Xaa Arg Pro Gly
            20                  25

<210> SEQ ID NO 149
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 149

Pro Glu Xaa Leu Ser Xaa Gly Ser Arg Cys Ser Gly Gly Ser Gly Gly
1               5                   10                  15

Glu Gln Asn Arg Ile Cys Thr Xaa Arg Pro Gly
            20                  25

<210> SEQ ID NO 150
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 150

Glu Xaa Leu Ser Xaa Gly Ser Arg Cys Ser Ser Gly Gly Ser Gly Gly
1               5                   10                  15

Glu Gln Asn Arg Ile Cys Thr Xaa Arg Pro Gly
            20                  25

<210> SEQ ID NO 151
<211> LENGTH: 27
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 151

Xaa Leu Ser Xaa Gly Ser Arg Cys Ser Ser Asp Gly Gly Ser Gly Gly
1               5                   10                  15

Glu Gln Asn Arg Ile Cys Thr Xaa Arg Pro Gly
            20                  25

<210> SEQ ID NO 152
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 152

Leu Ser Xaa Gly Ser Arg Cys Ser Ser Asp Gln Gly Gly Ser Gly Gly
1               5                   10                  15

Glu Gln Asn Arg Ile Cys Thr Xaa Arg Pro Gly
            20                  25

<210> SEQ ID NO 153
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 153

Ser Xaa Gly Ser Arg Cys Ser Ser Asp Gln Val Gly Gly Ser Gly Gly
1               5                   10                  15

Glu Gln Asn Arg Ile Cys Thr Xaa Arg Pro Gly
            20                  25
```

-continued

```
<210> SEQ ID NO 154
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 154

Xaa Gly Ser Arg Cys Ser Ser Asp Gln Val Glu Gly Gly Ser Gly Gly
1               5                   10                  15

Glu Gln Asn Arg Ile Cys Thr Xaa Arg Pro Gly
            20                  25

<210> SEQ ID NO 155
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 155

Gly Ser Arg Cys Ser Ser Asp Gln Val Glu Thr Gly Gly Ser Gly Gly
1               5                   10                  15

Glu Gln Asn Arg Ile Cys Thr Xaa Arg Pro Gly
            20                  25

<210> SEQ ID NO 156
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 156

Ser Arg Cys Ser Ser Asp Gln Val Glu Thr Gln Gly Gly Ser Gly Gly
1               5                   10                  15

Glu Gln Asn Arg Ile Cys Thr Xaa Arg Pro Gly
            20                  25

<210> SEQ ID NO 157
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
```

<223> OTHER INFORMATION: Xaa is Cys residue protected with ACM
      protecting group

<400> SEQUENCE: 157

Arg Cys Ser Ser Asp Gln Val Glu Thr Gln Ala Gly Gly Ser Gly Gly
1               5                   10                  15

Glu Gln Asn Arg Ile Cys Thr Xaa Arg Pro Gly
            20                  25

<210> SEQ ID NO 158
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (24)..(24)
<223> OTHER INFORMATION: Xaa is Cys residue protected with ACM
      protecting group

<400> SEQUENCE: 158

Cys Ser Ser Asp Gln Val Glu Thr Gln Ala Xaa Gly Gly Ser Gly Gly
1               5                   10                  15

Glu Gln Asn Arg Ile Cys Thr Xaa Arg Pro Gly
            20                  25

<210> SEQ ID NO 159
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 159

Val Pro Glu Xaa Leu Ser Xaa Gly Ser Arg Cys Gly Gly Ser Gly Gly
1               5                   10                  15

Gln Asn Arg Ile Cys Thr Xaa Arg Pro Gly Trp
            20                  25

<210> SEQ ID NO 160
<211> LENGTH: 27
<212> TYPE: PRT
<213> ORGANISM: Artificial Sequence
<220> FEATURE:
<223> OTHER INFORMATION: Xaa is Cys residue protected with ACM
      protecting group
<220> FEATURE:
<221> NAME/KEY: MOD_RES
<222> LOCATION: (3)..(3)

```
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 160

Pro Glu Xaa Leu Ser Xaa Gly Ser Arg Cys Ser Gly Gly Ser Gly Gly
1               5                   10                  15

Gln Asn Arg Ile Cys Thr Xaa Arg Pro Gly Trp
            20                  25

<210> SEQ ID NO 161
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 161

Glu Xaa Leu Ser Xaa Gly Ser Arg Cys Ser Ser Gly Gly Ser Gly Gly
1               5                   10                  15

Gln Asn Arg Ile Cys Thr Xaa Arg Pro Gly Trp
            20                  25

<210> SEQ ID NO 162
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 162

Xaa Leu Ser Xaa Gly Ser Arg Cys Ser Ser Asp Gly Gly Ser Gly Gly
1               5                   10                  15
```

```
Gln Asn Arg Ile Cys Thr Xaa Arg Pro Gly Trp
            20                  25

<210> SEQ ID NO 163
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 163

Leu Ser Xaa Gly Ser Arg Cys Ser Ser Asp Gln Gly Gly Ser Gly Gly
1               5                   10                  15

Gln Asn Arg Ile Cys Thr Xaa Arg Pro Gly Trp
            20                  25

<210> SEQ ID NO 164
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 164

Ser Xaa Gly Ser Arg Cys Ser Ser Asp Gln Val Gly Gly Ser Gly Gly
1               5                   10                  15

Gln Asn Arg Ile Cys Thr Xaa Arg Pro Gly Trp
            20                  25

<210> SEQ ID NO 165
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 165

Xaa Gly Ser Arg Cys Ser Ser Asp Gln Val Glu Gly Gly Ser Gly Gly
1               5                   10                  15
```

```
Gln Asn Arg Ile Cys Thr Xaa Arg Pro Gly Trp
        20                  25

<210> SEQ ID NO 166
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 166

Gly Ser Arg Cys Ser Ser Asp Gln Val Glu Thr Gly Gly Ser Gly Gly
1               5                   10                  15

Gln Asn Arg Ile Cys Thr Xaa Arg Pro Gly Trp
        20                  25

<210> SEQ ID NO 167
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 167

Ser Arg Cys Ser Ser Asp Gln Val Glu Thr Gln Gly Gly Ser Gly Gly
1               5                   10                  15

Gln Asn Arg Ile Cys Thr Xaa Arg Pro Gly Trp
        20                  25

<210> SEQ ID NO 168
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (23)..(23)
<223> OTHER INFORMATION: Xaa is Cys residue protected with ACM
      protecting group

<400> SEQUENCE: 168

Arg Cys Ser Ser Asp Gln Val Glu Thr Gln Ala Gly Gly Ser Gly Gly
1               5                   10                  15

Gln Asn Arg Ile Cys Thr Xaa Arg Pro Gly Trp
        20                  25

<210> SEQ ID NO 169
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
```

```
<221> NAME/KEY: MOD_RES
<222> LOCATION: (23)..(23)
<223> OTHER INFORMATION: Xaa is Cys residue protected with ACM
      protecting group

<400> SEQUENCE: 169

Cys Ser Ser Asp Gln Val Glu Thr Gln Ala Xaa Gly Gly Ser Gly Gly
1               5                   10                  15

Gln Asn Arg Ile Cys Thr Xaa Arg Pro Gly Trp
            20                  25

<210> SEQ ID NO 170
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 170

Val Pro Glu Xaa Leu Ser Xaa Gly Ser Arg Cys Gly Gly Ser Gly Gly
1               5                   10                  15

Asn Arg Ile Cys Thr Xaa Arg Pro Gly Trp Tyr
            20                  25

<210> SEQ ID NO 171
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 171

Pro Glu Xaa Leu Ser Xaa Gly Ser Arg Cys Ser Gly Gly Ser Gly Gly
1               5                   10                  15

Asn Arg Ile Cys Thr Xaa Arg Pro Gly Trp Tyr
            20                  25

<210> SEQ ID NO 172
<211> LENGTH: 27
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 172

Glu Xaa Leu Ser Xaa Gly Ser Arg Cys Ser Ser Gly Gly Ser Gly Gly
1               5                   10                  15

Asn Arg Ile Cys Thr Xaa Arg Pro Gly Trp Tyr
            20                  25

<210> SEQ ID NO 173
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 173

Xaa Leu Ser Xaa Gly Ser Arg Cys Ser Ser Asp Gly Gly Ser Gly Gly
1               5                   10                  15

Asn Arg Ile Cys Thr Xaa Arg Pro Gly Trp Tyr
            20                  25

<210> SEQ ID NO 174
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group
```

-continued

<400> SEQUENCE: 174

Leu Ser Xaa Gly Ser Arg Cys Ser Ser Asp Gln Gly Gly Ser Gly Gly
1               5                   10                  15

Asn Arg Ile Cys Thr Xaa Arg Pro Gly Trp Tyr
            20                  25

<210> SEQ ID NO 175
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 175

Ser Xaa Gly Ser Arg Cys Ser Ser Asp Gln Val Gly Gly Ser Gly Gly
1               5                   10                  15

Asn Arg Ile Cys Thr Xaa Arg Pro Gly Trp Tyr
            20                  25

<210> SEQ ID NO 176
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 176

Xaa Gly Ser Arg Cys Ser Ser Asp Gln Val Glu Gly Gly Ser Gly Gly
1               5                   10                  15

Asn Arg Ile Cys Thr Xaa Arg Pro Gly Trp Tyr
            20                  25

<210> SEQ ID NO 177
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 177

Gly Ser Arg Cys Ser Ser Asp Gln Val Glu Thr Gly Gly Ser Gly Gly
1               5                   10                  15

```
Asn Arg Ile Cys Thr Xaa Arg Pro Gly Trp Tyr
            20              25

<210> SEQ ID NO 178
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 178

Ser Arg Cys Ser Ser Asp Gln Val Glu Thr Gln Gly Gly Ser Gly Gly
1               5                   10                  15

Asn Arg Ile Cys Thr Xaa Arg Pro Gly Trp Tyr
            20              25

<210> SEQ ID NO 179
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 179

Arg Cys Ser Ser Asp Gln Val Glu Thr Gln Ala Gly Gly Ser Gly Gly
1               5                   10                  15

Asn Arg Ile Cys Thr Xaa Arg Pro Gly Trp Tyr
            20              25

<210> SEQ ID NO 180
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (22)..(22)
<223> OTHER INFORMATION: Xaa is Cys residue protected with ACM
      protecting group

<400> SEQUENCE: 180

Cys Ser Ser Asp Gln Val Glu Thr Gln Ala Xaa Gly Gly Ser Gly Gly
1               5                   10                  15

Asn Arg Ile Cys Thr Xaa Arg Pro Gly Trp Tyr
            20              25

<210> SEQ ID NO 181
<211> LENGTH: 27
<212> TYPE: PRT
<213> ORGANISM: Artificial Sequence
<220> FEATURE:
<223> OTHER INFORMATION: Synthetic Construct
<220> FEATURE:
```

-continued

```
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 181

Val Pro Glu Xaa Leu Ser Xaa Gly Ser Arg Cys Gly Gly Ser Gly Gly
1               5                   10                  15

Arg Ile Cys Thr Xaa Arg Pro Gly Trp Tyr Xaa
            20                  25

<210> SEQ ID NO 182
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 182

Pro Glu Xaa Leu Ser Xaa Gly Ser Arg Cys Ser Gly Gly Ser Gly Gly
1               5                   10                  15

Arg Ile Cys Thr Xaa Arg Pro Gly Trp Tyr Xaa
            20                  25

<210> SEQ ID NO 183
<211> LENGTH: 27
<212> TYPE: PRT
<213> ORGANISM: Artificial Sequence
<220> FEATURE:
<223> OTHER INFORMATION: Xaa is Cys residue protected with ACM
      protecting group
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
```

```
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 183

Glu Xaa Leu Ser Xaa Gly Ser Arg Cys Ser Ser Gly Gly Ser Gly Gly
1               5                   10                  15

Arg Ile Cys Thr Xaa Arg Pro Gly Trp Tyr Xaa
            20                  25

<210> SEQ ID NO 184
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 184

Xaa Leu Ser Xaa Gly Ser Arg Cys Ser Ser Asp Gly Gly Ser Gly Gly
1               5                   10                  15

Arg Ile Cys Thr Xaa Arg Pro Gly Trp Tyr Xaa
            20                  25

<210> SEQ ID NO 185
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
```

```
<222> LOCATION: (27)..(27)
<223> OTHER INFORMATION: Xaa is Cys residue protected with ACM
      protecting group

<400> SEQUENCE: 185

Leu Ser Xaa Gly Ser Arg Cys Ser Ser Asp Gln Gly Gly Ser Gly Gly
1               5                   10                  15

Arg Ile Cys Thr Xaa Arg Pro Gly Trp Tyr Xaa
            20                  25

<210> SEQ ID NO 186
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 186

Ser Xaa Gly Ser Arg Cys Ser Ser Asp Gln Val Gly Gly Ser Gly Gly
1               5                   10                  15

Arg Ile Cys Thr Xaa Arg Pro Gly Trp Tyr Xaa
            20                  25

<210> SEQ ID NO 187
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 187

Xaa Gly Ser Arg Cys Ser Ser Asp Gln Val Glu Gly Gly Ser Gly Gly
1               5                   10                  15

Arg Ile Cys Thr Xaa Arg Pro Gly Trp Tyr Xaa
            20                  25

<210> SEQ ID NO 188
<211> LENGTH: 27
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 188

Gly Ser Arg Cys Ser Ser Asp Gln Val Glu Thr Gly Gly Ser Gly Gly
1               5                   10                  15

Arg Ile Cys Thr Xaa Arg Pro Gly Trp Tyr Xaa
            20                  25

<210> SEQ ID NO 189
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 189

Ser Arg Cys Ser Ser Asp Gln Val Glu Thr Gln Gly Gly Ser Gly Gly
1               5                   10                  15

Arg Ile Cys Thr Xaa Arg Pro Gly Trp Tyr Xaa
            20                  25

<210> SEQ ID NO 190
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 190

Arg Cys Ser Ser Asp Gln Val Glu Thr Gln Ala Gly Gly Ser Gly Gly
1               5                   10                  15

Arg Ile Cys Thr Xaa Arg Pro Gly Trp Tyr Xaa
            20                  25

<210> SEQ ID NO 191
<211> LENGTH: 27
<212> TYPE: PRT
<213> ORGANISM: Artificial Sequence
<220> FEATURE:
```

-continued

```
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (21)..(21)
<223> OTHER INFORMATION: Xaa is Cys residue protected with ACM
      protecting group
<220> FEATURE:
<221> NAME/KEY: MOD_RES
<222> LOCATION: (27)..(27)
<223> OTHER INFORMATION: Xaa is Cys residue protected with ACM
      protecting group

<400> SEQUENCE: 191

Cys Ser Ser Asp Gln Val Glu Thr Gln Ala Xaa Gly Gly Ser Gly Gly
1               5                   10                  15

Arg Ile Cys Thr Xaa Arg Pro Gly Trp Tyr Xaa
            20                  25

<210> SEQ ID NO 192
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 192

Val Pro Glu Xaa Leu Ser Xaa Gly Ser Arg Cys Gly Gly Ser Gly Gly
1               5                   10                  15

Ile Cys Thr Xaa Arg Pro Gly Trp Tyr Xaa Ala
            20                  25

<210> SEQ ID NO 193
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
```

```
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 193

Pro Glu Xaa Leu Ser Xaa Gly Ser Arg Cys Ser Gly Gly Ser Gly Gly
1               5                   10                  15

Ile Cys Thr Xaa Arg Pro Gly Trp Tyr Xaa Ala
            20                  25

<210> SEQ ID NO 194
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 194

Glu Xaa Leu Ser Xaa Gly Ser Arg Cys Ser Ser Gly Gly Ser Gly Gly
1               5                   10                  15

Ile Cys Thr Xaa Arg Pro Gly Trp Tyr Xaa Ala
            20                  25

<210> SEQ ID NO 195
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group
```

-continued

```
<400> SEQUENCE: 195

Xaa Gly Ser Arg Cys Ser Ser Asp Gln Val Glu Gly Gly Ser Gly Gly
1               5                   10                  15

Ile Cys Thr Xaa Arg Pro Gly Trp Tyr Xaa Ala
            20                  25

<210> SEQ ID NO 196
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 196

Gly Ser Arg Cys Ser Ser Asp Gln Val Glu Thr Gly Gly Ser Gly Gly
1               5                   10                  15

Ile Cys Thr Xaa Arg Pro Gly Trp Tyr Xaa Ala
            20                  25

<210> SEQ ID NO 197
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 197

Ser Arg Cys Ser Ser Asp Gln Val Glu Thr Gln Gly Gly Ser Gly Gly
1               5                   10                  15

Ile Cys Thr Xaa Arg Pro Gly Trp Tyr Xaa Ala
            20                  25

<210> SEQ ID NO 198
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group
```

```
<400> SEQUENCE: 198

Arg Cys Ser Ser Asp Gln Val Glu Thr Gln Ala Gly Gly Ser Gly Gly
1               5                   10                  15

Ile Cys Thr Xaa Arg Pro Gly Trp Tyr Xaa Ala
            20                  25

<210> SEQ ID NO 199
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (20)..(20)
<223> OTHER INFORMATION: Xaa is Cys residue protected with ACM
      protecting group
<220> FEATURE:
<221> NAME/KEY: MOD_RES
<222> LOCATION: (26)..(26)
<223> OTHER INFORMATION: Xaa is Cys residue protected with ACM
      protecting group

<400> SEQUENCE: 199

Cys Ser Ser Asp Gln Val Glu Thr Gln Ala Xaa Gly Gly Ser Gly Gly
1               5                   10                  15

Ile Cys Thr Xaa Arg Pro Gly Trp Tyr Xaa Ala
            20                  25

<210> SEQ ID NO 200
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 200

Val Pro Glu Xaa Leu Ser Xaa Gly Ser Arg Cys Gly Gly Ser Gly Gly
1               5                   10                  15

Cys Thr Xaa Arg Pro Gly Trp Tyr Xaa Ala Leu
            20                  25

<210> SEQ ID NO 201
<211> LENGTH: 27
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 201

Pro Glu Xaa Leu Ser Xaa Gly Ser Arg Cys Ser Gly Gly Ser Gly Gly
1               5                   10                  15

Cys Thr Xaa Arg Pro Gly Trp Tyr Xaa Ala Leu
            20                  25

<210> SEQ ID NO 202
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (5)..(5)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 202

Glu Xaa Leu Ser Xaa Gly Ser Arg Cys Ser Ser Gly Gly Ser Gly Gly
1               5                   10                  15

Cys Thr Xaa Arg Pro Gly Trp Tyr Xaa Ala Leu
            20                  25

<210> SEQ ID NO 203
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (4)..(4)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 203

Xaa Leu Ser Xaa Gly Ser Arg Cys Ser Ser Asp Gly Gly Ser Gly Gly
1               5                   10                  15

Cys Thr Xaa Arg Pro Gly Trp Tyr Xaa Ala Leu
            20                  25

<210> SEQ ID NO 204
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 204

Leu Ser Xaa Gly Ser Arg Cys Ser Ser Asp Gln Gly Gly Ser Gly Gly
1               5                   10                  15

Cys Thr Xaa Arg Pro Gly Trp Tyr Xaa Ala Leu
            20                  25

<210> SEQ ID NO 205
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
```

-continued

```
<222> LOCATION: (25)..(25)
<223> OTHER INFORMATION: Xaa is Cys residue protected with ACM
      protecting group

<400> SEQUENCE: 205

Ser Xaa Gly Ser Arg Cys Ser Ser Asp Gln Val Gly Gly Ser Gly Gly
1               5                   10                  15

Cys Thr Xaa Arg Pro Gly Trp Tyr Xaa Ala Leu
            20                  25

<210> SEQ ID NO 206
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 206

Xaa Gly Ser Arg Cys Ser Ser Asp Gln Val Glu Gly Gly Ser Gly Gly
1               5                   10                  15

Cys Thr Xaa Arg Pro Gly Trp Tyr Xaa Ala Leu
            20                  25

<210> SEQ ID NO 207
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 207

Gly Ser Arg Cys Ser Ser Asp Gln Val Glu Thr Gly Gly Ser Gly Gly
1               5                   10                  15

Cys Thr Xaa Arg Pro Gly Trp Tyr Xaa Ala Leu
            20                  25

<210> SEQ ID NO 208
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
```

```
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 208

Ser Arg Cys Ser Ser Asp Gln Val Glu Thr Gln Gly Gly Ser Gly Gly
1               5                   10                  15

Cys Thr Xaa Arg Pro Gly Trp Tyr Xaa Ala Leu
            20                  25

<210> SEQ ID NO 209
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 209

Arg Cys Ser Ser Asp Gln Val Glu Thr Gln Ala Gly Gly Ser Gly Gly
1               5                   10                  15

Cys Thr Xaa Arg Pro Gly Trp Tyr Xaa Ala Leu
            20                  25

<210> SEQ ID NO 210
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (19)..(19)
<223> OTHER INFORMATION: Xaa is Cys residue protected with ACM
      protecting group
<220> FEATURE:
<221> NAME/KEY: MOD_RES
<222> LOCATION: (25)..(25)
<223> OTHER INFORMATION: Xaa is Cys residue protected with ACM
      protecting group

<400> SEQUENCE: 210

Cys Ser Ser Asp Gln Val Glu Thr Gln Ala Xaa Gly Gly Ser Gly Gly
1               5                   10                  15

Cys Thr Xaa Arg Pro Gly Trp Tyr Xaa Ala Leu
            20                  25

<210> SEQ ID NO 211
<211> LENGTH: 27
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 211

Xaa Thr Arg Glu Gln Asn Arg Ile Xaa Thr Cys Gly Gly Ser Gly Gly
1               5                   10                  15

Arg Pro Gly Trp Tyr Cys Ala Leu Ser Lys Gln
            20                  25

<210> SEQ ID NO 212
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 212

Thr Arg Glu Gln Asn Arg Ile Xaa Thr Cys Arg Gly Gly Ser Gly Gly
1               5                   10                  15

Arg Pro Gly Trp Tyr Cys Ala Leu Ser Lys Gln
            20                  25

<210> SEQ ID NO 213
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 213

Arg Glu Gln Asn Arg Ile Xaa Thr Cys Arg Pro Gly Gly Ser Gly Gly
1               5                   10                  15

Arg Pro Gly Trp Tyr Cys Ala Leu Ser Lys Gln
            20                  25

<210> SEQ ID NO 214
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 214

Glu Gln Asn Arg Ile Xaa Thr Cys Arg Pro Gly Gly Gly Ser Gly Gly
1               5                   10                  15
```

```
Arg Pro Gly Trp Tyr Cys Ala Leu Ser Lys Gln
            20                  25

<210> SEQ ID NO 215
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Cys residue protected with ACM
      protecting group

<400> SEQUENCE: 215

Gln Asn Arg Ile Xaa Thr Cys Arg Pro Gly Trp Gly Gly Ser Gly Gly
1               5                  10                  15

Arg Pro Gly Trp Tyr Cys Ala Leu Ser Lys Gln
            20                  25

<210> SEQ ID NO 216
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 216

Asn Arg Ile Xaa Thr Cys Arg Pro Gly Trp Tyr Gly Gly Ser Gly Gly
1               5                  10                  15

Arg Pro Gly Trp Tyr Cys Ala Leu Ser Lys Gln
            20                  25

<210> SEQ ID NO 217
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group
```

<400> SEQUENCE: 217

Trp Tyr Xaa Ala Leu Ser Lys Gln Glu Gly Cys Gly Gly Ser Gly Gly
1               5                   10                  15

Xaa Ala Pro Leu Arg Lys Cys Arg Pro Gly Phe
            20                  25

<210> SEQ ID NO 218
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 218

Tyr Xaa Ala Leu Ser Lys Gln Glu Gly Cys Arg Gly Gly Ser Gly Gly
1               5                   10                  15

Xaa Ala Pro Leu Arg Lys Cys Arg Pro Gly Phe
            20                  25

<210> SEQ ID NO 219
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 219

Xaa Ala Leu Ser Lys Gln Glu Gly Cys Arg Leu Gly Gly Ser Gly Gly
1               5                   10                  15

Xaa Ala Pro Leu Arg Lys Cys Arg Pro Gly Phe
            20                  25

<210> SEQ ID NO 220
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group -continued

```
<400> SEQUENCE: 220

Ala Leu Ser Lys Gln Glu Gly Cys Arg Leu Xaa Gly Gly Ser Gly Gly
1               5                   10                  15

Xaa Ala Pro Leu Arg Lys Cys Arg Pro Gly Phe
            20                  25

<210> SEQ ID NO 221
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 221

Leu Ser Lys Gln Glu Gly Cys Arg Leu Xaa Ala Gly Gly Ser Gly Gly
1               5                   10                  15

Xaa Ala Pro Leu Arg Lys Cys Arg Pro Gly Phe
            20                  25

<210> SEQ ID NO 222
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 222

Ser Lys Gln Glu Gly Cys Arg Leu Xaa Ala Pro Gly Gly Ser Gly Gly
1               5                   10                  15

Xaa Ala Pro Leu Arg Lys Cys Arg Pro Gly Phe
            20                  25

<210> SEQ ID NO 223
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group
```

<400> SEQUENCE: 223

Lys Gln Glu Gly Cys Arg Leu Xaa Ala Pro Leu Gly Gly Ser Gly Gly
1               5                   10                  15

Xaa Ala Pro Leu Arg Lys Cys Arg Pro Gly Phe
            20                  25

<210> SEQ ID NO 224
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 224

Gln Glu Gly Cys Arg Leu Xaa Ala Pro Leu Arg Gly Gly Ser Gly Gly
1               5                   10                  15

Xaa Ala Pro Leu Arg Lys Cys Arg Pro Gly Phe
            20                  25

<210> SEQ ID NO 225
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group
<220> FEATURE:
<221> NAME/KEY: MOD_RES
<222> LOCATION: (17)..(17)
<223> OTHER INFORMATION: Xaa is Cys residue protected with ACM
      protecting group

<400> SEQUENCE: 225

Glu Gly Cys Arg Leu Xaa Ala Pro Leu Arg Lys Gly Gly Ser Gly Gly
1               5                   10                  15

Xaa Ala Pro Leu Arg Lys Cys Arg Pro Gly Phe
            20                  25

<210> SEQ ID NO 226
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 226

Trp Tyr Xaa Ala Leu Ser Lys Gln Glu Gly Cys Gly Gly Ser Gly Gly
1               5                   10                  15

```
Ala Pro Leu Arg Lys Cys Arg Pro Gly Phe Gly
            20              25

<210> SEQ ID NO 227
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 227

Tyr Xaa Ala Leu Ser Lys Gln Glu Gly Cys Arg Gly Gly Ser Gly Gly
1               5                   10                  15

Ala Pro Leu Arg Lys Cys Arg Pro Gly Phe Gly
            20              25

<210> SEQ ID NO 228
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 228

Xaa Ala Leu Ser Lys Gln Glu Gly Cys Arg Leu Gly Gly Ser Gly Gly
1               5                   10                  15

Ala Pro Leu Arg Lys Cys Arg Pro Gly Phe Gly
            20              25

<210> SEQ ID NO 229
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 229

Ala Leu Ser Lys Gln Glu Gly Cys Arg Leu Xaa Gly Gly Ser Gly Gly
1               5                   10                  15

Ala Pro Leu Arg Lys Cys Arg Pro Gly Phe Gly
            20              25

<210> SEQ ID NO 230
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group
```

-continued

```
<400> SEQUENCE: 230

Leu Ser Lys Gln Glu Gly Cys Arg Leu Xaa Ala Gly Gly Ser Gly Gly
1               5                   10                  15

Ala Pro Leu Arg Lys Cys Arg Pro Gly Phe Gly
            20                  25

<210> SEQ ID NO 231
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 231

Ser Lys Gln Glu Gly Cys Arg Leu Xaa Ala Pro Gly Gly Ser Gly Gly
1               5                   10                  15

Ala Pro Leu Arg Lys Cys Arg Pro Gly Phe Gly
            20                  25

<210> SEQ ID NO 232
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 232

Lys Gln Glu Gly Cys Arg Leu Xaa Ala Pro Leu Gly Gly Ser Gly Gly
1               5                   10                  15

Ala Pro Leu Arg Lys Cys Arg Pro Gly Phe Gly
            20                  25

<210> SEQ ID NO 233
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 233

Gln Glu Gly Cys Arg Leu Xaa Ala Pro Leu Arg Gly Gly Ser Gly Gly
1               5                   10                  15

Ala Pro Leu Arg Lys Cys Arg Pro Gly Phe Gly
            20                  25

<210> SEQ ID NO 234
<211> LENGTH: 27
<212> TYPE: PRT
<213> ORGANISM: Artificial Sequence
<220> FEATURE:
<223> OTHER INFORMATION: Synthetic Construct
<220> FEATURE:
```

<221> NAME/KEY: MOD_RES
<222> LOCATION: (6)..(6)
<223> OTHER INFORMATION: Xaa is Cys residue protected with ACM
      protecting group

<400> SEQUENCE: 234

Glu Gly Cys Arg Leu Xaa Ala Pro Leu Arg Lys Gly Gly Ser Gly Gly
1               5                   10                  15

Ala Pro Leu Arg Lys Cys Arg Pro Gly Phe Gly
            20                  25

<210> SEQ ID NO 235
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 235

Trp Tyr Xaa Ala Leu Ser Lys Gln Glu Gly Cys Gly Gly Ser Gly Gly
1               5                   10                  15

Pro Leu Arg Lys Cys Arg Pro Gly Phe Gly Val
            20                  25

<210> SEQ ID NO 236
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 236

Tyr Xaa Ala Leu Ser Lys Gln Glu Gly Cys Arg Gly Gly Ser Gly Gly
1               5                   10                  15

Pro Leu Arg Lys Cys Arg Pro Gly Phe Gly Val
            20                  25

<210> SEQ ID NO 237
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 237

Xaa Ala Leu Ser Lys Gln Glu Gly Cys Arg Leu Gly Gly Ser Gly Gly
1               5                   10                  15

Pro Leu Arg Lys Cys Arg Pro Gly Phe Gly Val
            20                  25

<210> SEQ ID NO 238
<211> LENGTH: 27

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 238

Ala Leu Ser Lys Gln Glu Gly Cys Arg Leu Xaa Gly Gly Ser Gly Gly
1               5                   10                  15

Pro Leu Arg Lys Cys Arg Pro Gly Phe Gly Val
            20                  25

<210> SEQ ID NO 239
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 239

Leu Ser Lys Gln Glu Gly Cys Arg Leu Xaa Ala Gly Gly Ser Gly Gly
1               5                   10                  15

Pro Leu Arg Lys Cys Arg Pro Gly Phe Gly Val
            20                  25

<210> SEQ ID NO 240
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 240

Ser Lys Gln Glu Gly Cys Arg Leu Xaa Ala Pro Gly Gly Ser Gly Gly
1               5                   10                  15

Pro Leu Arg Lys Cys Arg Pro Gly Phe Gly Val
            20                  25

<210> SEQ ID NO 241
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group
```

<400> SEQUENCE: 241

Lys Gln Glu Gly Cys Arg Leu Xaa Ala Pro Leu Gly Gly Ser Gly Gly
1               5                   10                  15

Pro Leu Arg Lys Cys Arg Pro Gly Phe Gly Val
            20                  25

<210> SEQ ID NO 242
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 242

Gln Glu Gly Cys Arg Leu Xaa Ala Pro Leu Arg Gly Gly Ser Gly Gly
1               5                   10                  15

Pro Leu Arg Lys Cys Arg Pro Gly Phe Gly Val
            20                  25

<210> SEQ ID NO 243
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 243

Glu Gly Cys Arg Leu Xaa Ala Pro Leu Arg Lys Gly Gly Ser Gly Gly
1               5                   10                  15

Pro Leu Arg Lys Cys Arg Pro Gly Phe Gly Val
            20                  25

<210> SEQ ID NO 244
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Cys residue protected with ACM
      protecting group

<400> SEQUENCE: 244

Trp Tyr Xaa Ala Leu Ser Lys Gln Glu Gly Cys Gly Gly Ser Gly Gly
1               5                   10                  15

Leu Arg Lys Cys Arg Pro Gly Phe Gly Val Ala
            20                  25

<210> SEQ ID NO 245
<211> LENGTH: 27
<212> TYPE: PRT
<213> ORGANISM: Artificial Sequence
<220> FEATURE:
<223> OTHER INFORMATION: Synthetic Construct

```
<220> FEATURE:
<221> NAME/KEY: MOD_RES
<222> LOCATION: (2)..(2)
<223> OTHER INFORMATION: Xaa is Cys residue protected with ACM
      protecting group

<400> SEQUENCE: 245

Tyr Xaa Ala Leu Ser Lys Gln Glu Gly Cys Arg Gly Gly Ser Gly Gly
1               5                   10                  15

Arg Lys Cys Arg Pro Gly Phe Gly Val Ala Arg
            20                  25

<210> SEQ ID NO 246
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Cys residue protected with ACM
      protecting group

<400> SEQUENCE: 246

Xaa Ala Leu Ser Lys Gln Glu Gly Cys Arg Leu Gly Gly Ser Gly Gly
1               5                   10                  15

Arg Lys Cys Arg Pro Gly Phe Gly Val Ala Arg
            20                  25

<210> SEQ ID NO 247
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (11)..(11)
<223> OTHER INFORMATION: Xaa is Cys residue protected with ACM
      protecting group

<400> SEQUENCE: 247

Ala Leu Ser Lys Gln Glu Gly Cys Arg Leu Xaa Gly Gly Ser Gly Gly
1               5                   10                  15

Arg Lys Cys Arg Pro Gly Phe Gly Val Ala Arg
            20                  25

<210> SEQ ID NO 248
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (10)..(10)
<223> OTHER INFORMATION: Xaa is Cys residue protected with ACM
      protecting group

<400> SEQUENCE: 248

Leu Ser Lys Gln Glu Gly Cys Arg Leu Xaa Ala Gly Gly Ser Gly Gly
1               5                   10                  15

Arg Lys Cys Arg Pro Gly Phe Gly Val Ala Arg
            20                  25

<210> SEQ ID NO 249
```

```
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Cys residue protected with ACM
      protecting group

<400> SEQUENCE: 249

Ser Lys Gln Glu Gly Cys Arg Leu Xaa Ala Pro Gly Gly Ser Gly Gly
1               5                   10                  15

Arg Lys Cys Arg Pro Gly Phe Gly Val Ala Arg
            20                  25

<210> SEQ ID NO 250
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Cys residue protected with ACM
      protecting group

<400> SEQUENCE: 250

Lys Gln Glu Gly Cys Arg Leu Xaa Ala Pro Leu Gly Gly Ser Gly Gly
1               5                   10                  15

Arg Lys Cys Arg Pro Gly Phe Gly Val Ala Arg
            20                  25

<210> SEQ ID NO 251
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Cys residue protected with ACM
      protecting group

<400> SEQUENCE: 251

Gln Glu Gly Cys Arg Leu Xaa Ala Pro Leu Arg Gly Gly Ser Gly Gly
1               5                   10                  15

Arg Lys Cys Arg Pro Gly Phe Gly Val Ala Arg
            20                  25

<210> SEQ ID NO 252
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Cys residue protected with ACM
      protecting group

<400> SEQUENCE: 252

Glu Gly Cys Arg Leu Xaa Ala Pro Leu Arg Lys Gly Gly Ser Gly Gly
1               5                   10                  15
```

-continued

```
Arg Lys Cys Arg Pro Gly Phe Gly Val Ala Arg
            20                  25

<210> SEQ ID NO 253
<211> LENGTH: 20
<212> TYPE: PRT
<213> ORGANISM: Homo sapiens

<400> SEQUENCE: 253

Arg Glu Gln Asn Arg Ile Cys Thr Cys Arg Pro Gly Trp Tyr Cys Ala
1               5                   10                  15

Leu Ser Lys Gln
            20

<210> SEQ ID NO 254
<211> LENGTH: 20
<212> TYPE: PRT
<213> ORGANISM: Homo sapiens

<400> SEQUENCE: 254

Cys Arg Pro Gly Trp Tyr Cys Ala Leu Ser Lys Gln Glu Gly Cys Arg
1               5                   10                  15

Leu Cys Ala Pro
            20

<210> SEQ ID NO 255
<211> LENGTH: 20
<212> TYPE: PRT
<213> ORGANISM: Homo sapiens

<400> SEQUENCE: 255

Leu Ser Lys Gln Glu Gly Cys Arg Leu Cys Ala Pro Leu Arg Lys Cys
1               5                   10                  15

Arg Pro Gly Phe
            20

<210> SEQ ID NO 256
<211> LENGTH: 20
<212> TYPE: PRT
<213> ORGANISM: Homo sapiens

<400> SEQUENCE: 256

Leu Cys Ala Pro Leu Arg Lys Cys Arg Pro Gly Phe Gly Val Ala Arg
1               5                   10                  15

Pro Gly Thr Glu
            20

<210> SEQ ID NO 257
<211> LENGTH: 8
<212> TYPE: PRT
<213> ORGANISM: Murine
<220> FEATURE:
<221> NAME/KEY: MISC_FEATURE
<222> LOCATION: (8)..(8)
<223> OTHER INFORMATION: Xaa is Leu or Ile

<400> SEQUENCE: 257

Gly Tyr Thr Phe Thr Asp Tyr Xaa
1               5

<210> SEQ ID NO 258
<211> LENGTH: 8
<212> TYPE: PRT
<213> ORGANISM: Murine
```

<400> SEQUENCE: 258

Val Asp Pro Glu Tyr Gly Ser Thr
1               5

<210> SEQ ID NO 259
<211> LENGTH: 14
<212> TYPE: PRT
<213> ORGANISM: Murine

<400> SEQUENCE: 259

Ala Arg Asp Asp Gly Ser Tyr Ser Pro Phe Asp Tyr Trp Gly
1               5                   10

<210> SEQ ID NO 260
<211> LENGTH: 6
<212> TYPE: PRT
<213> ORGANISM: Murine

<400> SEQUENCE: 260

Gln Asn Ile Asn Lys Tyr
1               5

<210> SEQ ID NO 261
<211> LENGTH: 9
<212> TYPE: PRT
<213> ORGANISM: Murine
<220> FEATURE:
<221> NAME/KEY: MISC_FEATURE
<222> LOCATION: (8)..(8)
<223> OTHER INFORMATION: Xaa is Leu or Ile

<400> SEQUENCE: 261

Cys Leu Gln Tyr Val Asn Leu Xaa Thr
1               5

<210> SEQ ID NO 262
<211> LENGTH: 4
<212> TYPE: PRT
<213> ORGANISM: Murine

<400> SEQUENCE: 262

Leu Leu Ile Arg
1

<210> SEQ ID NO 263
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Gly or Ala
<220> FEATURE:
<221> NAME/KEY: MISC_FEATURE
<222> LOCATION: (5)..(5)
<223> OTHER INFORMATION: Xaa is Asn, Gln, Ser, or Thr

<400> SEQUENCE: 263

Ser Ser Gly Xaa Xaa Tyr
1               5

<210> SEQ ID NO 264
<211> LENGTH: 8
<212> TYPE: PRT

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Gly or Ala
<220> FEATURE:
<221> NAME/KEY: MISC_FEATURE
<222> LOCATION: (7)..(7)
<223> OTHER INFORMATION: Xaa is Asn, Gln, Ser, or Thr

<400> SEQUENCE: 264

Val Asp Pro Glu Tyr Xaa Xaa Thr
1               5

<210> SEQ ID NO 265
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Arg, Lys, or His
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (7)..(7)
<223> OTHER INFORMATION: Xaa is Asn, Gln, Ser, or Thr
<220> FEATURE:
<221> NAME/KEY: MISC_FEATURE
<222> LOCATION: (9)..(9)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (12)..(12)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (13)..(13)
<223> OTHER INFORMATION: Xaa is Asp or Glu
<220> FEATURE:
<221> NAME/KEY: MISC_FEATURE
<222> LOCATION: (14)..(14)
<223> OTHER INFORMATION: Xaa is Ala, Val, Leu, Ile, Pro, Met, Trp, Phe,
      or Tyr

<400> SEQUENCE: 265

Gln Xaa Val Xaa Xaa Tyr Xaa Ser Xaa Trp Tyr Xaa Xaa Xaa
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Lys, Arg, or His
<220> FEATURE:
<221> NAME/KEY: MISC_FEATURE
<222> LOCATION: (4)..(4)
```

```
<223> OTHER INFORMATION: Xaa is Asp or Glu
<220> FEATURE:
<221> NAME/KEY: MISC_FEATURE
<222> LOCATION: (5)..(5)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Asn, Gln, Ser, or Thr
<220> FEATURE:
<221> NAME/KEY: MISC_FEATURE
<222> LOCATION: (7)..(7)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (10)..(10)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (11)..(11)
<223> OTHER INFORMATION: Xaa is Asp or Glu
<220> FEATURE:
<221> NAME/KEY: MISC_FEATURE
<222> LOCATION: (12)..(12)
<223> OTHER INFORMATION: Xaa is Ala, Val, Leu, Ile, Pro, Met, Trp, Phe,
      or Tyr

<400> SEQUENCE: 266

Ala Xaa Asp Xaa Xaa Xaa Xaa Ser Pro Xaa Xaa Xaa Trp Gly
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is Ala, Val, Leu, Ile, Pro, Met, Trp, Phe,
      or Tyr

<400> SEQUENCE: 267

Ser Ala Ser Ser Ser Val Tyr Tyr Met Xaa
1               5                   10

<210> SEQ ID NO 268
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Ala, Val, Leu, Ile, Pro, Met, Trp, Phe,
      or Tyr

<400> SEQUENCE: 268

Gln Asn Ile Asn Lys Xaa
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (7)..(7)
<223> OTHER INFORMATION: Xaa is Asn, Gln, Ser, or Thr

<400> SEQUENCE: 269

Ser Thr Ser Asn Leu Ala Xaa
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (9)..(9)
<223> OTHER INFORMATION: Xaa is Asn, Gln, Ser, or Thr

<400> SEQUENCE: 270

Gln Gln Arg Arg Asn Xaa Pro Tyr Xaa
1               5

<210> SEQ ID NO 271
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Ala, Val, Leu, Ile, Pro, Met, Trp, Phe,
      or Tyr
<220> FEATURE:
<221> NAME/KEY: MISC_FEATURE
<222> LOCATION: (8)..(8)
<223> OTHER INFORMATION: Xaa is Leu or Ile
<220> FEATURE:
<221> NAME/KEY: MISC_FEATURE
<222> LOCATION: (9)..(9)
<223> OTHER INFORMATION: Xaa is Asn, Gln, Ser, or Thr

<400> SEQUENCE: 271

Cys Leu Gln Xaa Val Asn Leu Xaa Xaa
1               5

<210> SEQ ID NO 272
<211> LENGTH: 9
<212> TYPE: PRT
<213> ORGANISM: Murine

<400> SEQUENCE: 272

Cys Leu Gln Tyr Val Asn Leu Leu Thr
1               5

<210> SEQ ID NO 273
<211> LENGTH: 9
<212> TYPE: PRT
<213> ORGANISM: Murine

<400> SEQUENCE: 273

Cys Leu Gln Tyr Val Asn Leu Ile Thr
1               5
```

```
<210> SEQ ID NO 274
<211> LENGTH: 8
<212> TYPE: PRT
<213> ORGANISM: Murine

<400> SEQUENCE: 274

Gly Tyr Thr Phe Thr Asp Tyr Leu
1               5

<210> SEQ ID NO 275
<211> LENGTH: 8
<212> TYPE: PRT
<213> ORGANISM: Murine

<400> SEQUENCE: 275

Gly Tyr Thr Phe Thr Asp Tyr Ile
1               5

<210> SEQ ID NO 276
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid

<400> SEQUENCE: 276

Gly Xaa Thr Phe Xaa Xaa Tyr
1               5

<210> SEQ ID NO 277
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid

<400> SEQUENCE: 277

Gly Xaa Thr Phe Xaa Xaa Tyr Xaa
1               5

<210> SEQ ID NO 278
<211> LENGTH: 14
<212> TYPE: PRT
```

-continued

<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid

<400> SEQUENCE: 278

Xaa Arg Xaa Asp Gly Xaa Ser Xaa Tyr Xaa Xaa Phe Asp Xaa
1               5                   10

<210> SEQ ID NO 279
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid

<400> SEQUENCE: 279

Xaa Arg Xaa Asp Gly Ser Tyr Xaa Xaa Phe Asp Xaa Xaa Xaa
1               5                   10

-continued

```
<210> SEQ ID NO 280
<211> LENGTH: 459
<212> TYPE: PRT
<213> ORGANISM: Bos taurus

<400> SEQUENCE: 280

Met Ala Pro Thr Ala Phe Trp Ala Ala Leu Ala Val Gly Leu Gln Phe
1               5                   10                  15

Trp Ala Ala Gly Arg Ala Val Pro Ala Gln Ala Val Phe Thr Pro Tyr
            20                  25                  30

Ile Pro Glu Pro Gly Ser Ser Cys Arg Gln Gln Glu Tyr Tyr Asn Gln
        35                  40                  45

Lys Ile Gln Met Cys Cys Ser Lys Cys Pro Pro Gly Tyr Arg Val Gln
    50                  55                  60

Ser Leu Cys Asn Met Thr Leu Asp Thr Ile Cys Ala Ser Cys Glu Ser
65                  70                  75                  80

Ser Thr Tyr Thr Gln Leu Trp Asn Leu Val Thr Ala Cys Phe Ser Cys
                85                  90                  95

Asn Ser Arg Cys Ser Ser Asp Gln Val Glu Thr Gln Ala Cys Thr Thr
            100                 105                 110

Lys Gln Asn Arg Ile Cys Thr Cys Lys Pro Gly Trp Tyr Cys Thr Leu
        115                 120                 125

Gly Arg Gln Glu Gly Cys Arg Leu Cys Val Ala Leu Arg Lys Cys Gly
    130                 135                 140

Pro Gly Phe Gly Val Ala Lys Pro Gly Thr Ala Thr Thr Asn Val Ile
145                 150                 155                 160

Cys Ala Pro Cys Gly Pro Gly Thr Phe Ser Asp Thr Thr Ser Tyr Thr
                165                 170                 175

Asp Thr Cys Lys Pro His Arg Asn Cys Ser Ser Val Ala Ile Pro Gly
            180                 185                 190

Thr Ala Ser Thr Asp Ala Val Cys Thr Ser Val Leu Pro Thr Arg Lys
        195                 200                 205

Val Ala Arg Gly Pro Ala Thr Thr Arg Ser Gln His Met Glu Pro Thr
    210                 215                 220

Leu Gly Pro Ser Thr Ala Pro Ser Thr Phe Phe Leu Leu Pro Lys Val
225                 230                 235                 240

Pro Ser Pro Pro Ser Ser Pro Val Glu Gln Pro Asn Thr Gly Asn Ile
                245                 250                 255

Ser Leu Pro Ile Glu Leu Ile Val Gly Val Thr Ala Leu Gly Leu Leu
            260                 265                 270

Leu Ile Val Val Val Asn Cys Val Ile Met Thr Gln Lys Lys Lys Lys
        275                 280                 285

Pro Phe Cys Leu Gln Gly Asp Ala Lys Val Pro His Leu Pro Ala Asn
    290                 295                 300

Lys Ala Gln Gly Ala Pro Gly Pro Glu Gln Gln His Leu Leu Thr Thr
305                 310                 315                 320

Ala Pro Ser Ser Ser Ser Ser Ser Leu Glu Ser Ser Thr Ser Ser Thr
                325                 330                 335

Asp Lys Arg Ala Pro Thr Arg Ser Gln Leu Gln Ser Pro Gly Val Glu
            340                 345                 350

Lys Ala Ser Thr Ser Gly Glu Ala Gln Thr Gly Cys Ser Ser Ser Glu
        355                 360                 365

Ala Ser Ser Gly Gly His Gly Thr Gln Val Asn Val Thr Cys Ile Val
    370                 375                 380
```

Asn Val Cys Ser Gly Pro Asp His Ser Ser Gln Cys Pro Ser Gln Ala
385                 390             395             400

Gly Ser Thr Arg Asp Thr Asp Ala Ser Thr Pro Asn Ser Pro Lys Glu
                405             410             415

Glu Gln Val Pro Phe Ser Lys Glu Glu Arg Pro Phe Gln Ser Gln Pro
            420             425             430

Gly Ala Pro Glu Thr Leu Leu Gln Gly Leu Glu Glu Lys Pro Leu Pro
        435             440             445

Leu Gly Val Pro Asp Ala Gly Met Lys Pro Ser
    450             455

<210> SEQ ID NO 281
<211> LENGTH: 458
<212> TYPE: PRT
<213> ORGANISM: Bison bison

<400> SEQUENCE: 281

Met Ala Pro Thr Ala Phe Trp Ala Ala Leu Ala Val Gly Leu Gln Phe
1               5               10              15

Trp Ala Ala Gly Arg Ala Val Pro Ala Gln Ala Val Phe Thr Pro Tyr
                20              25              30

Ile Pro Glu Pro Gly Ser Ser Cys Arg Gln Gln Glu Tyr Tyr Asn His
            35              40              45

Lys Ile Gln Met Cys Cys Ser Lys Cys Pro Pro Gly Tyr Arg Val Gln
    50              55              60

Ser Leu Cys Asn Thr Thr Leu Asp Thr Ile Cys Ala Ser Cys Glu Ser
65              70              75              80

Ser Thr Tyr Thr Gln Leu Trp Asn Leu Val Thr Ala Cys Phe Ser Cys
                85              90              95

Asn Ser Arg Cys Ser Ser Asp Gln Val Glu Thr Gln Ala Cys Thr Thr
            100             105             110

Lys Gln Asn Arg Ile Cys Thr Cys Lys Pro Gly Trp Tyr Cys Thr Leu
        115             120             125

Gly Arg Gln Glu Gly Cys Arg Leu Cys Val Ala Leu Arg Lys Cys Gly
    130             135             140

Pro Gly Phe Gly Val Ala Lys Pro Gly Thr Ala Thr Thr Asn Val Ile
145             150             155             160

Cys Ala Pro Cys Gly Pro Gly Thr Phe Ser Asp Thr Thr Ser Tyr Thr
                165             170             175

Asp Thr Cys Lys Pro His Arg Asn Cys Ser Ser Val Ala Ile Pro Gly
            180             185             190

Thr Ala Ser Thr Asp Ala Val Cys Thr Ser Val Leu Pro Thr Arg Lys
        195             200             205

Val Ala Arg Gly Pro Ala Thr Thr Arg Ser Gln His Met Glu Pro Thr
    210             215             220

Leu Gly Pro Ser Thr Ala Pro Ser Thr Phe Phe Leu Leu Pro Lys Val
225             230             235             240

Pro Ser Pro Pro Ser Ser Pro Val Glu Gln Pro Asn Ala Gly Asn Ile
                245             250             255

Ser Leu Pro Ile Glu Leu Ile Val Gly Val Thr Ala Leu Gly Leu Leu
            260             265             270

Leu Ile Val Val Val Asn Cys Val Ile Met Thr Gln Lys Lys Lys Lys
        275             280             285

Pro Phe Cys Leu Gln Gly Asp Ala Lys Val Pro His Leu Pro Ala Asn
    290             295             300

-continued

```
Lys Ala Gln Gly Ala Pro Gly Pro Glu Gln Gln His Leu Leu Thr Thr
305                 310             315                 320

Ala Pro Ser Ser Ser Ser Ser Ser Leu Glu Ser Ser Thr Ser Ser Thr
                325             330             335

Asp Lys Arg Ala Pro Thr Arg Ser Gln Leu Gln Ser Pro Gly Val Glu
            340             345             350

Ala Asn Thr Ser Gly Glu Ala Gln Thr Gly Cys Ser Ser Ser Glu Ala
            355             360             365

Ser Ser Gly Gly His Gly Thr Gln Val Asn Val Thr Cys Ile Val Asn
    370             375             380

Val Cys Ser Gly Pro Asp His Ser Ser Gln Cys Pro Ser Gln Ala Gly
385             390             395                 400

Ser Thr Arg Asp Thr Asp Ala Ser Thr Pro Asn Ser Pro Lys Glu Glu
            405             410             415

Gln Val Pro Phe Ser Lys Glu Glu Arg Pro Phe Gln Ser Gln Pro Gly
            420             425             430

Ala Pro Glu Thr Leu Leu Gln Gly Leu Glu Glu Lys Pro Leu Pro Leu
            435             440             445

Gly Val Pro Asp Ala Gly Met Lys Pro Ser
    450             455
```

```
<210> SEQ ID NO 282
<211> LENGTH: 474
<212> TYPE: PRT
<213> ORGANISM: Mus musculus

<400> SEQUENCE: 282
```

```
Met Ala Pro Ala Ala Leu Trp Val Ala Leu Val Phe Glu Leu Gln Leu
1               5               10              15

Trp Ala Thr Gly His Thr Val Pro Ala Gln Val Val Leu Thr Pro Tyr
            20              25              30

Lys Pro Glu Pro Gly Tyr Glu Cys Gln Ile Ser Gln Glu Tyr Tyr Asp
        35              40              45

Arg Lys Ala Gln Met Cys Cys Ala Lys Cys Pro Pro Gly Gln Tyr Val
    50              55              60

Lys His Phe Cys Asn Lys Thr Ser Asp Thr Val Cys Ala Asp Cys Glu
65              70              75              80

Ala Ser Met Tyr Thr Gln Val Trp Asn Gln Phe Arg Thr Cys Leu Ser
            85              90              95

Cys Ser Ser Ser Cys Thr Thr Asp Gln Val Glu Ile Arg Ala Cys Thr
            100             105             110

Lys Gln Gln Asn Arg Val Cys Ala Cys Glu Ala Gly Arg Tyr Cys Ala
        115             120             125

Leu Lys Thr His Ser Gly Ser Cys Arg Gln Cys Met Arg Leu Ser Lys
    130             135             140

Cys Gly Pro Gly Phe Gly Val Ala Ser Ser Arg Ala Pro Asn Gly Asn
145             150             155             160

Val Leu Cys Lys Ala Cys Ala Pro Gly Thr Phe Ser Asp Thr Thr Ser
            165             170             175

Ser Thr Asp Val Cys Arg Pro His Arg Ile Cys Ser Ile Leu Ala Ile
            180             185             190

Pro Gly Asn Ala Ser Thr Asp Ala Val Cys Ala Pro Glu Ser Pro Thr
    195             200             205
```

```
Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly Ile Ser Leu Pro Ile Gly Leu Ile Val Gly Val Thr Ser Leu
                260                 265                 270

Gly Leu Leu Met Leu Gly Leu Val Asn Cys Ile Ile Leu Val Gln Arg
        275                 280                 285

Lys Lys Lys Pro Ser Cys Leu Gln Arg Asp Ala Lys Val Pro His Val
    290                 295                 300

Pro Asp Glu Lys Ser Gln Asp Ala Val Gly Leu Glu Gln Gln His Leu
305                 310                 315                 320

Leu Thr Thr Ala Pro Ser Ser Ser Ser Ser Ser Leu Glu Ser Ser Ala
                325                 330                 335

Ser Ala Gly Asp Arg Arg Ala Pro Pro Gly Gly His Pro Gln Ala Arg
                340                 345                 350

Val Met Ala Glu Ala Gln Gly Phe Gln Glu Ala Arg Ala Ser Ser Arg
                355                 360                 365

Ile Ser Asp Ser Ser His Gly Ser His Gly Thr His Val Asn Val Thr
    370                 375                 380

Cys Ile Val Asn Val Cys Ser Ser Ser Asp His Ser Ser Gln Cys Ser
385                 390                 395                 400

Ser Gln Ala Ser Ala Thr Val Gly Asp Pro Asp Ala Lys Pro Ser Ala
                405                 410                 415

Ser Pro Lys Asp Glu Gln Val Pro Phe Ser Gln Glu Glu Cys Pro Ser
                420                 425                 430

Gln Ser Pro Cys Glu Thr Thr Glu Thr Leu Gln Ser His Glu Lys Pro
        435                 440                 445

Leu Pro Leu Gly Val Pro Asp Met Gly Met Lys Pro Ser Gln Ala Gly
    450                 455                 460

Trp Phe Asp Gln Ile Ala Val Lys Val Ala
465                 470

<210> SEQ ID NO 283
<211> LENGTH: 474
<212> TYPE: PRT
<213> ORGANISM: Rattus norvegicus

<400> SEQUENCE: 283

Met Ala Pro Ala Ala Leu Trp Val Ala Leu Val Val Glu Leu Gln Leu
1                 5                   10                  15

Trp Ala Thr Gly His Thr Val Pro Ala Lys Val Val Leu Thr Pro Tyr
                20                  25                  30

Lys Pro Glu Pro Gly Asn Gln Cys Gln Ile Ser Gln Glu Tyr Tyr Asp
        35                  40                  45

Lys Lys Ala Gln Met Cys Cys Ala Lys Cys Pro Pro Gly Gln Tyr Ala
    50                  55                  60

Lys His Phe Cys Asn Lys Thr Ser Asp Thr Val Cys Ala Asp Cys Ala
65                  70                  75                  80

Ala Gly Met Phe Thr Gln Val Trp Asn His Leu His Thr Cys Leu Ser
                85                  90                  95
```

```
Cys Ser Ser Ser Cys Ser Asp Asp Gln Val Glu Thr His Asn Cys Thr
            100                 105                 110

Lys Lys Gln Asn Arg Val Cys Ala Cys Asn Ala Asp Ser Tyr Cys Ala
            115                 120                 125

Leu Lys Leu His Ser Gly Asn Cys Arg Gln Cys Met Lys Leu Ser Lys
    130                 135                 140

Cys Gly Pro Gly Phe Gly Val Ala Arg Ser Arg Thr Ser Asn Gly Asn
145                 150                 155                 160

Val Ile Cys Ser Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Ser Glu Ser Pro Thr
            195                 200                 205

Pro Ser Ala Val Pro Arg Thr Ile Tyr Val Ser Gln Pro Glu Pro Thr
    210                 215                 220

Arg Ser Gln Pro Met Asp Gln Glu Pro Gly Pro Ser Gln Thr Pro His
225                 230                 235                 240

Ile Pro Val Ser Leu Gly Ser Thr Pro Ile Ile Glu Pro Ser Ile Thr
                245                 250                 255

Gly Gly Ile Ser Leu Pro Ile Gly Leu Ile Val Gly Leu Thr Thr Leu
            260                 265                 270

Gly Leu Leu Met Leu Gly Leu Ala Asn Cys Phe Ile Leu Val Gln Arg
    275                 280                 285

Lys Lys Lys Pro Ser Cys Leu Gln Arg Glu Thr Met Val Pro His Leu
    290                 295                 300

Pro Asp Asp Lys Ser Gln Asp Ala Ile Gly Leu Glu Gln Gln His Leu
305                 310                 315                 320

Leu Thr Thr Ala Pro Ser Ser Ser Ser Ser Ser Leu Glu Ser Ser Ala
                325                 330                 335

Ser Ala Gly Asp Arg Arg Ala Pro Pro Gly Gly His Pro Gln Ala Arg
            340                 345                 350

Val Thr Ala Glu Ala Gln Gly Ser Gln Glu Ala Cys Ala Gly Ser Arg
            355                 360                 365

Ser Ser Asp Ser Ser His Gly Ser His Gly Thr His Val Asn Val Thr
    370                 375                 380

Cys Ile Val Asn Val Cys Ser Ser Ser Asp His Ser Ser Gln Cys Ser
385                 390                 395                 400

Ser Gln Ala Ser Thr Thr Val Gly Asp Pro Asp Ala Asn Pro Ser Gly
                405                 410                 415

Ser Pro Lys Asp Glu Gln Val Pro Phe Ser Gln Glu Glu Cys Pro Ser
            420                 425                 430

Gln Ser Gln Trp Glu Thr Thr Glu Thr Leu Gln Asn His Asp Lys Pro
            435                 440                 445

Phe Pro Leu Gly Val Pro Asp Val Gly Met Lys Pro Asn Gln Pro Gly
    450                 455                 460

Trp Tyr Asp Gln Ile Ala Val Lys Val Pro
465                 470
```

<210> SEQ ID NO 284
<211> LENGTH: 14
<212> TYPE: PRT
<213> ORGANISM: Artificial Sequence
<220> FEATURE:

<223> OTHER INFORMATION: Synthetic Construct

<400> SEQUENCE: 284

Ala Arg Asp Asp Gly Ser Tyr Ser Pro Phe Asp Tyr Phe Gly
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Synthetic Construct

<400> SEQUENCE: 285

Leu Arg Lys Cys Arg Pro Gly Phe Gly Val Ala
1               5                   10

<210> SEQ ID NO 286
<211> LENGTH: 13
<212> TYPE: PRT
<213> ORGANISM: Artificial Sequence
<220> FEATURE:
<223> OTHER INFORMATION: Synthetic Construct

<400> SEQUENCE: 286

Val Val Cys Lys Pro Cys Ala Pro Gly Thr Phe Ser Asn
1               5                   10

<210> SEQ ID NO 287
<211> LENGTH: 5
<212> TYPE: PRT
<213> ORGANISM: Bison bison

<400> SEQUENCE: 287

Lys Cys Gly Pro Gly
1               5

<210> SEQ ID NO 288
<211> LENGTH: 11
<212> TYPE: PRT
<213> ORGANISM: Homo sapiens

<400> SEQUENCE: 288

Ser Ser Thr Asp Ile Cys Arg Pro His Gln Ile
1               5                   10

<210> SEQ ID NO 289
<211> LENGTH: 15
<212> TYPE: PRT
<213> ORGANISM: Homo sapiens

<400> SEQUENCE: 289

Cys Ala Leu Ser Lys Gln Glu Gly Cys Arg Leu Cys Ala Pro Leu
1               5                   10                  15

<210> SEQ ID NO 290
<211> LENGTH: 10
<212> TYPE: PRT
<213> ORGANISM: Homo sapiens

<400> SEQUENCE: 290

Thr Ser Asp Val Val Cys Lys Pro Cys Ala
1               5                   10

<210> SEQ ID NO 291

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 291

Glu Arg Lys Ser Ser Val Glu Cys Pro Pro Cys Pro
1               5                   10

<210> SEQ ID NO 292
<211> LENGTH: 12
<212> TYPE: PRT
<213> ORGANISM: Homo sapiens

<400> SEQUENCE: 292

Glu Arg Lys Cys Cys Val Glu Cys Pro Pro Cys Pro
1               5                   10

<210> SEQ ID NO 293
<211> LENGTH: 8
<212> TYPE: PRT
<213> ORGANISM: Artificial Sequence
<220> FEATURE:
<223> OTHER INFORMATION: Synthetic Construct

<400> SEQUENCE: 293

Gly Tyr Thr Phe Thr Asp Val Ile
1               5

<210> SEQ ID NO 294
<211> LENGTH: 8
<212> TYPE: PRT
<213> ORGANISM: Artificial Sequence
<220> FEATURE:
<223> OTHER INFORMATION: Synthetic Construct

<400> SEQUENCE: 294

Gly Tyr Thr Phe Thr Asp Tyr Ser
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Tyr or Phe
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid or absent

<400> SEQUENCE: 295

Gly Xaa Thr Phe Xaa Xaa Tyr Xaa
1               5

<210> SEQ ID NO 296
```

-continued

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 296

Ala Arg Asp Asp Gly Ser Tyr Ser Pro Phe Asp Tyr
1               5                   10

<210> SEQ ID NO 297
<211> LENGTH: 233
<212> TYPE: PRT
<213> ORGANISM: Artificial Sequence
<220> FEATURE:
<223> OTHER INFORMATION: Synthetic Construct

<400> SEQUENCE: 297

Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Val Thr Cys Gln Ala Ser Gln Asn
        35                  40                  45

Ile Asn Lys Tyr Ile Ala Trp Tyr Gln Gln Lys Pro Gly Lys Ala Pro
    50                  55                  60

Lys Leu Leu Ile His Tyr Thr Ser Thr Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Thr Tyr Tyr Cys Leu Gln Tyr Val
            100                 105                 110

Asn Leu Ile Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 298
<211> LENGTH: 233
<212> TYPE: PRT
<213> ORGANISM: Artificial Sequence
<220> FEATURE:
<223> OTHER INFORMATION: Synthetic Construct

<400> SEQUENCE: 298

Met Val Ser Ser Ala Gln Phe Leu Gly Leu Leu Leu Leu Cys Phe Gln
1               5                   10                  15
```

```
Gly Thr Arg Cys Asp Ile Gln Met Thr Gln Ser Pro Ser Ser Leu Ser
        20                  25                  30

Ala Ser Val Gly Asp Arg Val Thr Ile Thr Cys Gln Ala Ser Gln Asn
        35                  40                  45

Ile Asn Lys Tyr Ile Ala Trp Tyr Gln Gln Lys Pro Gly Lys Ala Pro
    50                  55                  60

Lys Leu Leu Leu Tyr Tyr Thr Ser Thr Leu Glu Ser Gly Val Pro Ser
65                  70                  75                  80

Arg Phe Ser Gly Ser Gly Ser Gly Thr Asp Tyr Thr Leu Thr Ile Ser
            85                  90                  95

Ser Leu Gln Pro Glu Asp Phe Ala Thr Tyr Tyr Cys Leu Gln Tyr Val
            100                 105                 110

Asn Leu Ile Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 299
<211> LENGTH: 233
<212> TYPE: PRT
<213> ORGANISM: Artificial Sequence
<220> FEATURE:
<223> OTHER INFORMATION: Synthetic Construct

<400> SEQUENCE: 299

Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
        20                  25                  30

Ala Ser Val Gly Asp Arg Val Thr Ile Thr Cys Gln Ala Ser Gln Asn
        35                  40                  45

Ile Asn Lys Tyr Ile Ala Trp Tyr Gln Gln Lys Pro Gly Lys Val Pro
    50                  55                  60

Thr Leu Leu Ile Phe Tyr Thr Ser Thr Leu Glu Ser Gly Val Pro Ser
65                  70                  75                  80

Arg Phe Ser Gly Ser Gly Ser Gly Thr Asp Phe Thr Leu Thr Ile Ser
            85                  90                  95

Ser Leu Gln Ser Glu Asp Val Ala Thr Tyr Phe Cys Leu Gln Tyr Val
            100                 105                 110

Asn Leu Ile Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
        130                 135                 140
```

```
Lys Ser Gly Thr Ala Ser Val Val Cys Leu Leu Asn Asn Phe Tyr Pro
145             150             155             160

Arg Glu Ala Lys Val Gln Trp Lys Val Asp Asn Ala Leu Gln Ser Gly
            165             170             175

Asn Ser Gln Glu Ser Val Thr Glu Gln Asp Ser Lys Asp Ser Thr Tyr
            180             185             190

Ser Leu Ser Ser Thr Leu Thr Leu Ser Lys Ala Asp Tyr Glu Lys His
        195             200             205

Lys Val Tyr Ala Cys Glu Val Thr His Gln Gly Leu Ser Ser Pro Val
    210             215             220

Thr Lys Ser Phe Asn Arg Gly Glu Cys
225             230
```

```
<210> SEQ ID NO 300
<211> LENGTH: 233
<212> TYPE: PRT
<213> ORGANISM: Artificial Sequence
<220> FEATURE:
<223> OTHER INFORMATION: Synthetic Construct

<400> SEQUENCE: 300
```

```
Met Val Ser Ser Ala Gln Phe Leu Gly Leu Leu Leu Leu Cys Phe Gln
1               5               10              15

Gly Thr Arg Cys Asp Ile Gln Met Thr Gln Ser Pro Ser Ser Leu Ser
            20              25              30

Ala Ser Ile Gly Asp Arg Val Thr Ile Thr Cys Gln Ala Ser Gln Asn
        35              40              45

Ile Asn Lys Tyr Ile Ala Trp Tyr Gln Gln Lys Pro Gly Lys Ala Pro
    50              55              60

Lys Leu Leu Ile Tyr Tyr Thr Ser Thr Leu Glu Ser Gly Val Pro Ser
65              70              75              80

Arg Phe Ser Gly Ser Gly Ser Gly Thr Asp Phe Thr Phe Thr Ile Ser
            85              90              95

Ser Leu Gln Pro Glu Asp Ile Gly Thr Tyr Tyr Cys Leu Gln Tyr Val
            100             105             110

Asn Leu Ile Thr Phe Gly Gln Gly Thr Arg Leu Glu Ile Lys Arg Thr
        115             120             125

Val Ala Ala Pro Ser Val Phe Ile Phe Pro Pro Ser Asp Glu Gln Leu
    130             135             140

Lys Ser Gly Thr Ala Ser Val Val Cys Leu Leu Asn Asn Phe Tyr Pro
145             150             155             160

Arg Glu Ala Lys Val Gln Trp Lys Val Asp Asn Ala Leu Gln Ser Gly
            165             170             175

Asn Ser Gln Glu Ser Val Thr Glu Gln Asp Ser Lys Asp Ser Thr Tyr
            180             185             190

Ser Leu Ser Ser Thr Leu Thr Leu Ser Lys Ala Asp Tyr Glu Lys His
        195             200             205

Lys Val Tyr Ala Cys Glu Val Thr His Gln Gly Leu Ser Ser Pro Val
    210             215             220

Thr Lys Ser Phe Asn Arg Gly Glu Cys
225             230
```

```
<210> SEQ ID NO 301
<211> LENGTH: 233
<212> TYPE: PRT
<213> ORGANISM: Artificial Sequence
<220> FEATURE:
```

<223> OTHER INFORMATION: Synthetic Construct

<400> SEQUENCE: 301

```
Met Val Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asn
        35                  40                  45

Ile Asn Lys Tyr Ile Ala Trp Tyr Gln Gln Lys Pro Gly Lys Ala Pro
    50                  55                  60

Lys Leu Leu Ile Tyr Tyr Thr Ser Thr Leu Glu Ser Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Leu Gln Tyr Val
            100                 105                 110

Asn Leu Ile Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 302
<211> LENGTH: 464
<212> TYPE: PRT
<213> ORGANISM: Artificial Sequence
<220> FEATURE:
<223> OTHER INFORMATION: Synthetic Construct

<400> SEQUENCE: 302

```
Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Leu Met His Trp Val Arg Gln Ala Pro Gly Gln Gly Leu
    50                  55                  60

Glu Trp Ile Gly Trp Val Asp Pro Glu Tyr Gly Ser Thr Asp Tyr Ala
65                  70                  75                  80

Glu Lys Phe Lys Lys Trp Val Thr Val Thr Arg Asp Thr Ser Ile Ser
                85                  90                  95

Thr Ala Tyr Met Glu Leu Ser Arg Leu Thr Ser Asp Asp Thr Ala Val
            100                 105                 110
```

-continued

```
Tyr Tyr Cys Ala Arg Asp Asp Gly Ser Tyr Ser Pro Phe Asp Tyr Trp
        115                 120                 125

Gly Gln Gly Thr Met Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Ser
225                 230                 235                 240

Ser Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
                340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460
```

```
<210> SEQ ID NO 303
<211> LENGTH: 464
<212> TYPE: PRT
<213> ORGANISM: Artificial Sequence
<220> FEATURE:
<223> OTHER INFORMATION: Synthetic Construct

<400> SEQUENCE: 303

Met Gly Trp Thr Leu Val Phe Leu Phe Leu Leu Ser Val Thr Ala Gly
1               5                   10                  15
```

-continued

```
Val His Ser Glu Val Gln Leu Val Gln Ser Gly Ala Glu Val Lys Lys
        20              25              30

Pro Gly Ala Ser Val Lys Val Ser Cys Lys Ala Ser Gly Tyr Thr Phe
        35              40              45

Thr Asp Tyr Leu Met His Trp Val Arg Gln Ala Pro Gly Gln Gly Leu
        50              55              60

Glu Trp Met Gly Trp Val Asp Pro Glu Tyr Gly Ser Thr Asp Tyr Ala
65              70              75              80

Glu Lys Phe Lys Lys Arg Val Thr Met Thr Arg Asp Thr Ser Thr Ser
                85              90              95

Thr Phe Tyr Met Glu Leu Ser Ser Leu Arg Ser Asp Asp Thr Ala Val
                100             105             110

Tyr Phe Cys Ala Arg Asp Asp Gly Ser Tyr Ser Pro Phe Asp Tyr Trp
                115             120             125

Gly Gln Gly Thr Leu Val Thr Val Ser Ser Ala Ser Thr Lys Gly Pro
        130             135             140

Ser Val Phe Pro Leu Ala Pro Cys Ser Arg Ser Thr Ser Glu Ser Thr
145             150             155             160

Ala Ala Leu Gly Cys Leu Val Lys Asp Tyr Phe Pro Glu Pro Val Thr
                165             170             175

Val Ser Trp Asn Ser Gly Ala Leu Thr Ser Gly Val His Thr Phe Pro
                180             185             190

Ala Val Leu Gln Ser Ser Gly Leu Tyr Ser Leu Ser Ser Val Val Thr
                195             200             205

Val Pro Ser Ser Asn Phe Gly Thr Gln Thr Tyr Thr Cys Asn Val Asp
        210             215             220

His Lys Pro Ser Asn Thr Lys Val Asp Lys Thr Val Glu Arg Lys Ser
225             230             235             240

Ser Val Glu Cys Pro Pro Cys Pro Ala Pro Pro Val Ala Gly Pro Ser
                245             250             255

Val Phe Leu Phe Pro Pro Lys Pro Lys Asp Thr Leu Met Ile Ser Arg
                260             265             270

Thr Pro Glu Val Thr Cys Val Val Val Asp Val Ser His Glu Asp Pro
        275             280             285

Glu Val Gln Phe Asn Trp Tyr Val Asp Gly Val Glu Val His Asn Ala
        290             295             300

Lys Thr Lys Pro Arg Glu Glu Gln Phe Asn Ser Thr Phe Arg Val Val
305             310             315             320

Ser Val Leu Thr Val Val His Gln Asp Trp Leu Asn Gly Lys Glu Tyr
                325             330             335

Lys Cys Lys Val Ser Asn Lys Gly Leu Pro Ala Pro Ile Glu Lys Thr
                340             345             350

Ile Ser Lys Thr Lys Gly Gln Pro Arg Glu Pro Gln Val Tyr Thr Leu
        355             360             365

Pro Pro Ser Arg Glu Glu Met Thr Lys Asn Gln Val Ser Leu Thr Cys
        370             375             380

Leu Val Lys Gly Phe Tyr Pro Ser Asp Ile Ala Val Glu Trp Glu Ser
385             390             395             400

Asn Gly Gln Pro Glu Asn Asn Tyr Lys Thr Thr Pro Pro Met Leu Asp
                405             410             415

Ser Asp Gly Ser Phe Phe Leu Tyr Ser Lys Leu Thr Val Asp Lys Ser
        420             425             430
```

```
Arg Trp Gln Gln Gly Asn Val Phe Ser Cys Ser Val Met His Glu Ala
        435             440             445

Leu His Asn His Tyr Thr Gln Lys Ser Leu Ser Leu Ser Pro Gly Lys
    450             455             460

<210> SEQ ID NO 304
<211> LENGTH: 464
<212> TYPE: PRT
<213> ORGANISM: Artificial Sequence
<220> FEATURE:
<223> OTHER INFORMATION: Synthetic Construct

<400> SEQUENCE: 304

Met Gly Trp Thr Leu Val Phe Leu Phe Leu Leu Ser Val Thr Ala Gly
1               5               10              15

Val His Ser Glu Val Gln Leu Val Glu Ser Gly Ala Glu Val Lys Lys
            20              25              30

Pro Gly Ala Ser Val Lys Val Ser Cys Lys Ala Ser Gly Tyr Thr Phe
        35              40              45

Thr Asp Tyr Leu Met His Trp Val Arg Gln Ala Pro Gly Gln Gly Leu
    50              55              60

Glu Trp Met Gly Trp Val Asp Pro Glu Tyr Gly Ser Thr Asp Tyr Ala
65              70              75              80

Glu Lys Phe Lys Lys Arg Val Thr Met Thr Arg Asp Thr Ser Ile Ser
            85              90              95

Thr Ala Tyr Met Glu Leu Asn Arg Leu Thr Ser Asp Asp Thr Ala Val
            100             105             110

Tyr Phe Cys Ala Arg Asp Asp Gly Ser Tyr Ser Pro Phe Asp Tyr Trp
            115             120             125

Gly Gln Gly Thr Leu Val Thr Val Ser Ser Ala Ser Thr Lys Gly Pro
    130             135             140

Ser Val Phe Pro Leu Ala Pro Cys Ser Arg Ser Thr Ser Glu Ser Thr
145             150             155             160

Ala Ala Leu Gly Cys Leu Val Lys Asp Tyr Phe Pro Glu Pro Val Thr
            165             170             175

Val Ser Trp Asn Ser Gly Ala Leu Thr Ser Gly Val His Thr Phe Pro
            180             185             190

Ala Val Leu Gln Ser Ser Gly Leu Tyr Ser Leu Ser Ser Val Val Thr
            195             200             205

Val Pro Ser Ser Asn Phe Gly Thr Gln Thr Tyr Thr Cys Asn Val Asp
    210             215             220

His Lys Pro Ser Asn Thr Lys Val Asp Lys Thr Val Glu Arg Lys Ser
225             230             235             240

Ser Val Glu Cys Pro Pro Cys Pro Ala Pro Pro Val Ala Gly Pro Ser
            245             250             255

Val Phe Leu Phe Pro Pro Lys Pro Lys Asp Thr Leu Met Ile Ser Arg
            260             265             270

Thr Pro Glu Val Thr Cys Val Val Val Asp Val Ser His Glu Asp Pro
            275             280             285

Glu Val Gln Phe Asn Trp Tyr Val Asp Gly Val Glu Val His Asn Ala
    290             295             300

Lys Thr Lys Pro Arg Glu Glu Gln Phe Asn Ser Thr Phe Arg Val Val
305             310             315             320

Ser Val Leu Thr Val Val His Gln Asp Trp Leu Asn Gly Lys Glu Tyr
            325             330             335
```

-continued

Lys Cys Lys Val Ser Asn Lys Gly Leu Pro Ala Pro Ile Glu Lys Thr
             340                 345                 350

Ile Ser Lys Thr Lys Gly Gln Pro Arg Glu Pro Gln Val Tyr Thr Leu
         355                 360                 365

Pro Pro Ser Arg Glu Glu Met Thr Lys Asn Gln Val Ser Leu Thr Cys
     370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                 405                 410                 415

Ser Asp Gly Ser Phe Phe Leu Tyr Ser Lys Leu Thr Val Asp Lys Ser
             420                 425                 430

Arg Trp Gln Gln Gly Asn Val Phe Ser Cys Ser Val Met His Glu Ala
         435                 440                 445

Leu His Asn His Tyr Thr Gln Lys Ser Leu Ser Leu Ser Pro Gly Lys
     450                 455                 460

<210> SEQ ID NO 305
<211> LENGTH: 464
<212> TYPE: PRT
<213> ORGANISM: Artificial Sequence
<220> FEATURE:
<223> OTHER INFORMATION: Synthetic Construct

<400> SEQUENCE: 305

Met Gly Trp Thr Leu Val Phe Leu Phe Leu Leu Ser Val Thr Ala Gly
1               5                   10                  15

Val His Ser Gln Val Gln Leu Val Gln Ser Gly Thr Glu Val Thr Lys
                 20                  25                  30

Pro Gly Ala Ser Val Lys Val Ser Cys Lys Ala Ser Gly Tyr Thr Phe
             35                  40                  45

Thr Asp Tyr Leu Met His Trp Val Arg Gln Ala Pro Gly Gln Gly Leu
     50                  55                  60

Glu Trp Leu Gly Trp Val Asp Pro Glu Tyr Gly Ser Thr Asp Tyr Ala
65                  70                  75                  80

Glu Lys Phe Lys Lys Arg Val Thr Met Thr Arg Asp Thr Ser Thr Asn
                 85                  90                  95

Thr Val Tyr Met Glu Leu Thr Ser Leu Arg Ser Glu Asp Thr Ala Ile
                 100                 105                 110

Tyr Tyr Cys Ala Arg Asp Asp Gly Ser Tyr Ser Pro Phe Asp Tyr Trp
             115                 120                 125

Gly Gln Gly Thr Leu Val Thr Val Ser Ser Ala Ser Thr Lys Gly Pro
     130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                 165                 170                 175

Val Ser Trp Asn Ser Gly Ala Leu Thr Ser Gly Val His Thr Phe Pro
                 180                 185                 190

Ala Val Leu Gln Ser Ser Gly Leu Tyr Ser Leu Ser Ser Val Val Thr
             195                 200                 205

Val Pro Ser Ser Asn Phe Gly Thr Gln Thr Tyr Thr Cys Asn Val Asp
     210                 215                 220

His Lys Pro Ser Asn Thr Lys Val Asp Lys Thr Val Glu Arg Lys Ser
225                 230                 235                 240

-continued

```
Ser Val Glu Cys Pro Pro Cys Pro Ala Pro Pro Val Ala Gly Pro Ser
            245             250             255

Val Phe Leu Phe Pro Pro Lys Pro Lys Asp Thr Leu Met Ile Ser Arg
            260             265             270

Thr Pro Glu Val Thr Cys Val Val Val Asp Val Ser His Glu Asp Pro
            275             280             285

Glu Val Gln Phe Asn Trp Tyr Val Asp Gly Val Glu Val His Asn Ala
    290             295             300

Lys Thr Lys Pro Arg Glu Glu Gln Phe Asn Ser Thr Phe Arg Val Val
305             310             315             320

Ser Val Leu Thr Val Val His Gln Asp Trp Leu Asn Gly Lys Glu Tyr
            325             330             335

Lys Cys Lys Val Ser Asn Lys Gly Leu Pro Ala Pro Ile Glu Lys Thr
            340             345             350

Ile Ser Lys Thr Lys Gly Gln Pro Arg Glu Pro Gln Val Tyr Thr Leu
            355             360             365

Pro Pro Ser Arg Glu Glu Met Thr Lys Asn Gln Val Ser Leu Thr Cys
    370             375             380

Leu Val Lys Gly Phe Tyr Pro Ser Asp Ile Ala Val Glu Trp Glu Ser
385             390             395             400

Asn Gly Gln Pro Glu Asn Asn Tyr Lys Thr Thr Pro Pro Met Leu Asp
            405             410             415

Ser Asp Gly Ser Phe Phe Leu Tyr Ser Lys Leu Thr Val Asp Lys Ser
            420             425             430

Arg Trp Gln Gln Gly Asn Val Phe Ser Cys Ser Val Met His Glu Ala
            435             440             445

Leu His Asn His Tyr Thr Gln Lys Ser Leu Ser Leu Ser Pro Gly Lys
    450             455             460
```

```
<210> SEQ ID NO 306
<211> LENGTH: 464
<212> TYPE: PRT
<213> ORGANISM: Artificial Sequence
<220> FEATURE:
<223> OTHER INFORMATION: Synthetic Construct

<400> SEQUENCE: 306

Met Gly Trp Thr Leu Val Phe Leu Phe Leu Leu Ser Val Thr Ala Gly
1               5               10              15

Val His Ser Glu Val Gln Leu Val Gln Ser Gly Ala Glu Val Lys Lys
            20              25              30

Pro Gly Ala Thr Val Lys Ile Ser Cys Lys Val Ser Gly Tyr Thr Phe
            35              40              45

Thr Asp Tyr Leu Met His Trp Val Gln Gln Ala Pro Gly Lys Gly Leu
    50              55              60

Glu Trp Met Gly Trp Val Asp Pro Glu Tyr Gly Ser Thr Asp Tyr Ala
65              70              75              80

Glu Lys Phe Lys Lys Arg Val Thr Ile Thr Ala Asp Thr Ser Thr Asp
            85              90              95

Thr Ala Tyr Met Glu Leu Ser Ser Leu Arg Ser Glu Asp Thr Ala Val
            100             105             110

Tyr Tyr Cys Ala Arg Asp Asp Gly Ser Tyr Ser Pro Phe Asp Tyr Trp
            115             120             125

Gly Gln Gly Val Met Val Thr Val Ser Ser Ala Ser Thr Lys Gly Pro
    130             135             140
```

-continued

```
Ser Val Phe Pro Leu Ala Pro Cys Ser Arg Ser Thr Ser Glu Ser Thr
145             150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Asn Phe Gly Thr Gln Thr Tyr Thr Cys Asn Val Asp
210                 215                 220

His Lys Pro Ser Asn Thr Lys Val Asp Lys Thr Val Glu Arg Lys Ser
225                 230                 235                 240

Ser Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
                275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305             310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
                340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 307
<211> LENGTH: 40
<212> TYPE: PRT
<213> ORGANISM: Homo sapiens

<400> SEQUENCE: 307

Arg Pro Gly Thr Glu Thr Ser Asp Val Val Cys Lys Pro Cys Ala Pro
1               5                   10                  15

Gly Thr Phe Ser Asn Thr Thr Ser Ser Thr Asp Ile Cys Arg Pro His
            20                  25                  30

Gln Ile Cys Asn Val Val Ala Ile
        35                  40

<210> SEQ ID NO 308
```

-continued

```
<211> LENGTH: 54
<212> TYPE: PRT
<213> ORGANISM: Homo sapiens

<400> SEQUENCE: 308

Cys Asp Ser Cys Glu Asp Ser Thr Tyr Thr Gln Leu Trp Asn Trp Val
1               5                   10                  15

Pro Glu Cys Leu Ser Cys Gly Ser Arg Cys Ser Ser Asp Gln Val Glu
            20                  25                  30

Thr Gln Ala Cys Thr Arg Glu Gln Asn Arg Ile Cys Thr Cys Arg Pro
        35                  40                  45

Gly Trp Tyr Cys Ala Leu
    50

<210> SEQ ID NO 309
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa is Gln or Ala
<220> FEATURE:
<221> NAME/KEY: VARIANT
<222> LOCATION: (3)..(3)
<223> OTHER INFORMATION: Xaa is Val or Asp
<220> FEATURE:
<221> NAME/KEY: VARIANT
<222> LOCATION: (6)..(6)
<223> OTHER INFORMATION: Xaa is Tyr or absent
<220> FEATURE:
<221> NAME/KEY: VARIANT
<222> LOCATION: (8)..(8)
<223> OTHER INFORMATION: Xaa is Ser or absent
<220> FEATURE:
<221> NAME/KEY: VARIANT
<222> LOCATION: (10)..(10)
<223> OTHER INFORMATION: Xaa is Trp or Ser
<220> FEATURE:
<221> NAME/KEY: VARIANT
<222> LOCATION: (11)..(11)
<223> OTHER INFORMATION: Xaa is Tyr or Pro
<220> FEATURE:
<221> NAME/KEY: VARIANT
<222> LOCATION: (14)..(14)
<223> OTHER INFORMATION: Xaa is Val or Tyr
<220> FEATURE:
<221> NAME/KEY: VARIANT
<222> LOCATION: (15)..(15)
<223> OTHER INFORMATION: Xaa is Trp or Phe or absent
<220> FEATURE:
<221> NAME/KEY: VARIANT
<222> LOCATION: (16)..(16)
<223> OTHER INFORMATION: Xaa is Gly or absent

<400> SEQUENCE: 309

Xaa Arg Xaa Asp Gly Xaa Ser Xaa Tyr Xaa Xaa Phe Asp Xaa Xaa Xaa
1               5                   10                  15
```

ANTAGONISTIC ANTI-TUMOR NECROSIS FACTOR RECEPTOR SUPERFAMILY POLYPEPTIDES

SEQUENCE LISTING

This application contains a Sequence Listing which has been submitted electronically in ASCII file format and is hereby incorporated by reference in its entirety. Said ASCII copy, created on Jan. 23, 2024, is named 00786-583002_Sequence_Listing_1_23_24_ST25 and is 195,185 bytes in size.

BACKGROUND OF THE INVENTION

The use of naturally-occurring and genetically engineered T lymphocytes is a prominent paradigm for ameliorating various human pathologies. For instance, while traditional therapeutic platforms for the treatment of cancer include surgical removal of tumor mass, radiation therapy, and administration of chemotherapeutics (Shewach, Chem. Rev., 109:2859-2861, 2009), the last decade has witnessed a resurgence in the application of adoptive immunotherapy to cancer treatment regimens. With the advent of chimeric antigen receptor (CAR-T) therapy, new methods have emerged for the infusion of autologous and allogeneic tumor-reactive T cells to patients (June, *J. Clin. Invest.,* 117:1466-1476, 2007). CAR-T therapies harness the resources of the adaptive immune response in order to promote cancer cell cytotoxicity and eradicate tumor material. A common motif in adoptive immunotherapy is the use of T cells that exhibit the ability to selectively potentiate cytotoxicity in cells that display distinct tumor antigens. Examples of this technique include the administration of tumor-infiltrating lymphocytes (Dudley et al., *J. Immunother.,* 26:332-342, 2003), as well as autologous or allogeneic T cells that have been genetically re-engineered so as to exhibit reactivity with a tumor-specific antigen (Yee et al., *PNAS.,* 99:16168-16173, 2002).

Despite the promise of T lymphocyte-based cancer immunotherapy, the development of this therapeutic platform has been hindered by the natural propensity of the immune system to suppress immune attacks mounted on self cells. Cancer cells express class I major histocompatibility complex (MHC) proteins that distinguish these cells from foreign cells. In order to prevent cell fratricide, regulatory T cells (T-reg cells) have evolved that suppress the activity of T cells that exhibit reactivity against "self" MHC antigens. T-reg cells represent a heterogeneous class of T cells that can be distinguished based on their unique surface protein presentation. The most well-understood populations of T-reg cells include CD4+, CD25+, FoxP3+ T-reg cells and CD17+ T-reg cells. The precise mechanisms by which these cells suppress autoreactive T cells is the subject of ongoing investigations, though it has been shown that certain classes of T-reg cells inhibit production of the proliferation-inducing cytokine IL-2 in target T cells and may additionally sequester IL-2 from autoreactive cells by virtue of the affinity of CD25 (a subdomain of the IL-2 receptor) for IL-2 (Josefowicz et al., Ann. Rev. Immun., 30:531-564, 2012).

Although T-reg cells play an important role in maintaining peripheral tolerance, the same biochemical features that underlie the ability of these cells to modulate autoreactive T cell activity also serve to undermine adoptive immunotherapy and the natural immune response by suppressing the activity of tumor-reactive T lymphocytes. The development of chemical modulators of T-reg cell activity has been the subject of many pharmacological investigations, as access to an agent capable of inhibiting T-reg-mediated T cell suppression could vastly improve the scope and efficacy of adoptive cancer immunotherapy, as well as improve the ability of the immune system to eradicate pathogenic organisms that give rise to infectious diseases.

There is a need for improved therapies for treating cell proliferation disorders, such as cancer, and a wide array of infectious diseases.

SUMMARY OF THE INVENTION

Described herein are antagonistic tumor necrosis factor receptor superfamily polypeptides, such as single-chain polypeptides, antibodies, antigen-binding fragments thereof, and constructs. For instance, featured are antagonistic tumor necrosis factor receptor 2 (TNFR2)-binding polypeptides, such as single-chain polypeptides, antibodies, antigen-binding fragments thereof, and constructs. Human TNFR2 contains four cysteine-rich domains (CRDs): CRD1 (amino acid residues 48-76 of SEQ ID NO: 7), CRD2 (amino acid residues 78-120 of SEQ ID NO: 7), CRD3 (amino acid residues 121-162 of SEQ ID NO: 7), and CRD4 (amino acid residues 162-202 of SEQ ID NO: 7). Antagonistic TNFR2 polypeptides described herein include those that bind one or more epitopes within CRD3 of TNFR2 and/or one or more epitopes within CRD4 of TNFR2, such as those that bind TNFR2 exclusively within one or more epitopes of CRD3 and/or one or more epitopes of CRD4 without binding TNFR2 within CRD1 and/or CRD2.

The antagonistic TNFR2 polypeptides described herein include IgG2 isotype antibodies and antigen-binding fragments thereof that specifically bind TNFR2 at one or more of the epitopes detailed above. The present disclosure in based, in part, on the surprising discovery that antibodies and antigen-binding fragments thereof exhibit markedly superior TNFR2 antagonist properties when these molecules are in the form of an IgG2 isotype relative to other antibody isotypes. The antagonistic TNFR2 polypeptides described herein also include those with at least two TNFR2 binding sites (e.g., antigen-binding sites, in which TNFR2 is the "antigen"), in which the binding sites are spatially separated from one another by about 133 Å or more, as it has presently been discovered that such polypeptides exhibit unexpectedly superior TNFR2 antagonist effects relative to polypeptides that specifically bind TNFR2 at one or more of the epitopes described above, but that contain TNFR2-binding sites (e.g., antigen-binding sites) separated from one another by fewer than about 133 Å, such as IgG1 antibodies and antigen-binding fragments thereof that contain antigen-binding sites separated from one another by about 117 Å and IgG3 antibodies and antigen-binding fragments thereof that contain antigen-binding sites separated from one another by 125 Å.

Also featured are anti-TNFR2 polypeptides that adopt a single disulfide-bonded isoform and pharmaceutical compositions containing the same. For example, pharmaceutical compositions of the disclosure include those containing an antagonist TNFR2-binding polypeptide in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform. Antagonistic TNFR2-binding polypeptides that adopt a human IgG2-A isoform exhibit substantially superior TNFR2 antagonist effects relative to TNFR2-binding polypeptides that adopt other human IgG2 isoforms, such as the IgG2-B, IgG2-A/B$_1$, and IgG2-A/B$_2$.

Thus, TNFR2 polypeptides that adopt a single disulfide-bonded isoform can be prepared as pharmaceutical compositions and administered in methods of treatment described herein to promote robust TNFR2 antagonistic effects.

Antagonistic TNFR2 polypeptides of the present disclosure exhibit one or more beneficial biological properties, such as the ability to inhibit the proliferation of, and/or to promote the death of, regulator T cells (T-reg cells) and/or myeloid-derived suppressor cells (MDSCs). Antagonistic TNFR2 polypeptides can be used to inhibit the proliferation of, and/or promote the death of, TNFR2- and oncogene-expressing cancer cells. Additionally, or alternatively, antagonistic TNFR2 polypeptides can be administered to promote the reciprocal expansion of T effector cells, such as cytotoxic CD8+ T cells. This may occur, for instance, by the attenuation of T-reg cell proliferation and activity or by the direct expansion of T effector cells, such as cytotoxic CD8+ T cells. Therefore, the designation of TNFR2 polypeptides as antagonists refers to their capacity to attenuate the proliferation and activity of T-reg cells, MDSCs, and/or TNFR2-expressing cancer cells and, for clarity, does not indicate antagonism of the T effector cell response. The polypeptides (e.g., single-chain polypeptides, antibodies, antigen-binding fragments thereof, and constructs thereof) described herein can be used for the treatment of a variety of pathologies, including cancers and infectious diseases.

In one aspect, the disclosure features polypeptides, such as single-chain polypeptides, antibodies, antigen-binding fragments thereof, and constructs thereof, that specifically bind human tumor necrosis factor receptor 2 (TNFR2) at an epitope within cysteine-rich domain (CRD) 3 (CRD3) and/or CRD4 and that do not specifically bind TNFR2 at an epitope defined by one or more amino acids within CRD1, in which the polypeptide:

(a) contains a human IgG2 hinge region that lacks a cysteine residue at positions 232 and/or 233 of the amino acid sequence of the IgG2 hinge region; and/or (b) contains antigen-binding sites separated from one another by a distance of at least about 133 Å.

Exemplary antagonistic TNFR2 polypeptides of the disclosure (e.g., antibodies and antigen-binding fragments thereof) that exhibit the foregoing characteristics are described in Table 1 below. Table 1 provides a description of various antagonistic TNFR2 antibodies and antigen-binding fragments thereof as defined by their heavy chain and light chain amino acid sequences. Antagonistic TNFR2 antibodies and antigen-binding fragments thereof of the disclosure include those having a heavy chain and/or light chain as shown as Table 1, as well as antibodies and antigen-binding fragments thereof that contain a heavy chain and/or light chain having at least 85% sequence identity (e.g., at least 85%, 86%, 87%, 88%, 89%, 90%, 91%, 92%, 93%, 94%, 95%, 96%, 97%, 98%, 99%, 99.9%, or 100% sequence identity) to a heavy chain and/or light chain shown in Table 1. Complementarity-determining regions are shown in bold.

TABLE 1

Exemplary Antagonistic TNFR2 antibodies of the disclosure

| Antibody No. | Light Chain Amino Acid Sequence | Heavy Chain Amino Acid Sequence |
|---|---|---|
| 1 | MVSSAQFLGLLLLCFQGTR CDIQMTQSPSSLSASVGDR VTVTCQASQNINKYIAWYQ QKPGKAPKLLIHYTSTLESG VPSRFSGSGSGTDFTLTISS LQAEDVATYYCLQYVNLITF GGGTKVEIKRTVAAPSVFIF PPSDEQLKSGTASVVCLLN NFYPREAKVQWKVDNALQS GNSQESVTEQDSKDSTYSL SSTLTLSKADYEKHKVYACE VTHQGLSSPVTKSFNRGEC (SEQ ID NO: 297) | MGWTLVFLFLLSVTAGVHSQVQLVQSGAE VKKPGASVKVSCKASGYTFTDYLMHWVRQ APGQGLEWIGWVDPEYGSTDYAEKFKK WVTVTRDTSISTAYMELSRLTSDDTAVYYC ARDDGSYSPFDYWGQGTMVTVSSASTKG PSVFPLAPCSRSTSESTAALGCLVKDYFPE PVTVSWNSGALTSGVHTFPAVLQSSGLYSL SSVVTVPSSNFGTQTYTCNVDHKPSNTKV DKTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIE KTISKTKGQPREPQVYTLPPSREEMTKNQV SLTCLVKGFYPSDIAVEWESNGQPENNYKT TPPMLDSDGSFFLYSKLTVDKSRWQQGN VFSCSVMHEALHNHYTQKSLSLSPGK (SEQ ID NO: 302) |
| 2 | MVSSAQFLGLLLLCFQGTR CDIQMTQSPSSLSASVGDR VTVTCQASQNINKYIAWYQ QKPGKAPKLLIHYTSTLESG VPSRFSGSGSGTDFTLTISS LQAEDVATYYCLQYVNLITF GGGTKVEIRTVAAPSVFIF PPSDEQLKSGTASVVCLLN NFYPREAKVQWKVDNALQS GNSQESVTEQDSKDSTYSL SSTLTLSKADYEKHKVYACE VTHQGLSSPVTKSFNRGEC (SEQ ID NO: 297) | MGWTLVFLFLLSVTAGVHSEVQLVQSGAE VKKPGASVKVSCKASGYTFTDYLMHWVRQ APGQGLEWMGWVDPEYGSTDYAEKFK KRVTMTRDTSTSTFYMELSSLRSDDT AVYFCARDDGSYSPFDYWGQGTLVTVSSA STKGPSVFPLAPCSRSTSESTAALGCLVKD YFPEPVTVSWNSGALTSGVHTFPAVLQSS GLYSLSSVVTVPSSNFGTQTYTCNVDHKPS NTKVDKTVERKSSVECPPCPAPPVAGPSV FLFPPKPKDTLMISRTPEVTCVVVDVSHED PEVQFNWYVDGVEVHNAKTKPREEQFNST FRVVSVLTVVHQDWLNGKEYKCKVSNKGL PAPIEKTISKTKGQPREPQVYTLPPSREEMT KNQVSLTCLVKGFYPSDIAVEWESNGQPE NNYKTTPPMLDSDGSFFLYSKLTVDKSRW QQGNVFSCSVMHEALHNHYTQKSLSLSPG K (SEQ ID NO: 303) |
| 3 | MVSSAQFLGLLLLCFQGTR CDIQMTQSPSSLSASVGDR | MGWTLVFLFLLSVTAGVHSEVQLVESGAEV KKPGASVKVSCKASGYTFTDYLMHWVRQA |

TABLE 1-continued

| Exemplary Antagonistic TNFR2 antibodies of the disclosure | | |
|---|---|---|
| Antibody No. | Light Chain Amino Acid Sequence | Heavy Chain Amino Acid Sequence |
| | VTVTCQASQNINKYIAWYQ QKPGKAPKLLIHYTSTLESG VPSRFSGSGSGTDFTLTISS LQAEDVATYYCLQYVNLITF GGGTKVEIKRTVAAPSVFIF PPSDEQLKSGTASVVCLLN NFYPREAKVQWKVDNALQS GNSQESVTEQDSKDSTYSL SSTLTLSKADYEKHKVYACE VTHQGLSSPVTKSFNRGEC (SEQ ID NO: 297) | PGQGLEWMGWVDPEYGSTDYAEKFKK RVTMTRDTSISTAYMELNRLTSDDTAVYFC ARDDGSYSPFDYWQGTLVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNV FSCSVMHEALHNHYTQKSLSLSPGK (SEQ ID NO: 304) |
| 4 | MVSSAQFLGLLLLCFQGTR CDIQMTQSPSSLSASVGDR VTVTCQASQNINKYIAWYQ QKPGKAPKLLIHYTSTLESG VPSRFSGSGSGTDFTLTISS LQAEDVATYYCLQYVNLITF GGGTKVEIKRTVAAPSVFIF PPSDEQLKSGTASVVCLLN NFYPREAKVQWKVDNALQS GNSQESVTEQDSKDSTYSL SSTLTLSKADYEKHKVYACE VTHQGLSSPVTKSFNRGEC (SEQ ID NO: 297) | MGWTLVFLFLLSVTAGVHSQVQLVQSGTE VTKPGASVKVSCKASGYTFTDYLMHWVRQ APGQGLEWLGWVDPEYGSTDYAEKFKKR VTMTRDTSTNTVYMELTSLRSEDTAIYYCA RDDGSYSPFDYWGQGTLVTVSSASTKGPS VFPLAPCSRSTSESTAALGCLVKDYFPEPV TVSWNSGALTSGVHTFPAVLQSSGLYSLSS VVTVPSSNFGTQTYTCNVDHKPSNTKVDK TVERKSSVECPPCPAPPVAGPSVFLFPPKP KDTLMISRTPEVTCVVVDVSHEDPEVQFN WYVDGVEVHNAKTKPREEQFNSTFRVVSV LTVVHQDWLNGKEYKCKVSNKGLPAPIEKT ISKTKGQPREPQVYTLPPSREEMTKNQVSL TCLVKGFYPSDIAVEWESNGQPENNYKTTP PMLDSDGSFFLYSKLTVDKSRWQQGNVFS CSVMHEALHNHYTQKSLSLSPGK (SEQ ID NO: 305) |
| 5 | MVSSAQFLGLLLLCFQGTR CDIQMTQSPSSLSASVGDR VTVTCQASQNINKYIAWYQ QKPGKAPKLLIHYTSTLESG VPSRFSGSGSGTDFTLTISS LQAEDVATYYCLQYVNLITF GGGTKVEIKRTVAAPSVFIF PPSDEQLKSGTASVVCLLN NFYPREAKVQWKVDNALQS GNSQESVTEQDSKDSTYSL SSTLTLSKADYEKHKVYACE VTHQGLSSPVTKSFNRGEC (SEQ ID NO: 297) | MGWTLVFLFLLSVTAGVHSEVQLVQSGAE VKKPGATVKISCKVSGYTFTDYLMHWVQQ APGKGLEWMGWVDPEYGSTDYAEKFKKR VTITADTSTDTAYMELSSLRSEDTAVYYCA RDDGSYSPFDYWQGVMVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNVF SCSVMHEALHNHYTQKSLSLSPGK (SEQ ID NO: 306) |
| 6 | MVSSAQFLGLLLLCFQGTR CDIQMTQSPSSLSASVGDR VTITCQASQNINKYIAWYQQ KPGKAPKLLLYYTSTLESGV PSRFSGSGSGTDYTLTISSL QPEDFATYYCLQYVNLITFG GGTKVEIKRTVAAPSVFIFPP SDEQLKSGTASVVCLLNNF YPREAKVQWKVDNALQSG NSQESVTEQDSKDSTYSLS STLTLSKADYEKHKVYACEV THQGLSSPVTKSFNRGEC (SEQ ID NO: 298) | MGWTLVFLFLLSVTAGVHSQVQLVQSGAE VKKPGASVKVSCKASGYTFTDYLMHWVRQ APGQGLEWIGWVDPEYGSTDYAEKFKK WVTVTRDTSISTAYMELSRLTSDDTAVYYC ARDDGSYSPFDYWGQGTMVTVSSASTKG PSVFPLAPCSRSTSESTAALGCLVKDYFPE PVTVSWNSGALTSGVHTFPAVLQSSGLYSL SSVVTVPSSNFGTQTYTCNVDHKPSNTKV DKTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIE KTISKTKGQPREPQVYTLPPSREEMTKNQV SLTCLVKGFYPSDIAVEWESNGQPENNYKT TPPMLDSDGSFFLYSKLTVDKSRWQQGN VFSCSVMHEALHNHYTQKSLSLSPGK (SEQ ID NO: 302) |
| 7 | MVSSAQFLGLLLLCFQGTR CDIQMTQSPSSLSASVGDR VTITCQASQNINKYIAWYQQ KPGKAPKLLLYYTSTLESGV PSRFSGSGSGTDYTLTISSL | MGWTLVFLFLLSVTAGVHSEVQLVQSGAE VKKPGASVKVSCKASGYTFTDYLMHWVRQ APGQGLEWMGWVDPEYGSTDYAEKFK KRVTMTRDTSTSTFYMELSSLRSDDT AVYFCARDDGSYSPFDYWGQGTLVTVSSA |

TABLE 1-continued

| Exemplary Antagonistic TNFR2 antibodies of the disclosure | | |
| --- | --- | --- |
| Antibody No. | Light Chain Amino Acid Sequence | Heavy Chain Amino Acid Sequence |
| | QPEDFATYYCLQYVNLITFG GGTKVEIKRTVAAPSVFIFPP SDEQLKSGTASVVCLLNNF YPREAKVQWKVDNALQSG NSQESVTEQDSKDSTYSLS STLTLSKADYEKHKVYACEV THQGLSSPVTKSFNRGEC (SEQ ID NO: 298) | STKGPSVFPLAPCSRSTSESTAALGCLVKD YFPEPVTVSWNSGALTSGVHTFPAVLQSS GLYSLSSVVTVPSSNFGTQTYTCNVDHKPS NTKVDKTVERKSSVECPPCPAPPVAGPSV FLFPPKPKDTLMISRTPEVTCVVVDVSHED PEVQFNWYVDGVEVHNAKTKPREEQFNST FRVVSVLTVVHQDWLNGKEYKCKVSNKGL PAPIEKTISKTKGQPREPQVYTLPPSREEMT KNQVSLTCLVKGFYPSDIAVEWESNGQPE NNYKTTPPMLDSDGSFFLYSKLTVDKSRW QQGNVFSCSVMHEALHNHYTQKSLSLSPG K (SEQ ID NO: 303) |
| 8 | MVSSAQFLGLLLLCFQGTR CDIQMTQSPSSLSASVGDR VTITCQASQNINKYIAWYQQ KPGKAPKLLLYYTSTLESGV PSRFSGSGSGTDYTLTISSL QPEDFATYYCLQYVNLITFG GGTKVEIKRTVAAPSVFIFPP SDEQLKSGTASVVCLLNNF YPREAKVQWKVDNALQSG NSQESVTEQDSKDSTYSLS STLTLSKADYEKHKVYACEV THQGLSSPVTKSFNRGEC (SEQ ID NO: 298) | MGWTLVFLFLLSVTAGVHSEVQLVESGAEV KKPGASVKVSCKASGYTFTDYLMHWVRQA PGQGLEWMGWVDPEYGSTDYAEKFKK RVTMTRDTSISTAYMELNRLTSDDTAVYFC ARDDGSYSPFDYWGQGTLVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNV FSCSVMHEALHNHYTQKSLSLSPGK (SEQ ID NO: 304) |
| 9 | MVSSAQFLGLLLLCFQGTR CDIQMTQSPSSLSASVGDR VTITCQASQNINKYIAWYQQ KPGKAPKLLLYYTSTLESGV PSRFSGSGSGTDYTLTISSL QPEDFATYYCLQYVNLITFG GGTKVEIKRTVAAPSVFIFPP SDEQLKSGTASVVCLLNNF YPREAKVQWKVDNALQSG NSQESVTEQDSKDSTYSLS STLTLSKADYEKHKVYACEV THQGLSSPVTKSFNRGEC (SEQ ID NO: 298) | MGWTLVFLFLLSVTAGVHSQVQLVQSGTE VTKPGASVKVSCKASGYTFTDYLMHWVRQ APGQGLEWLGWVDPEYGSTDYAEKFKKR VTMTRDTSTNTVYMELTSLRSEDTAIYYCA RDDGSYSPFDYWGQGTLVTVSSASTKGPS VFPLAPCSRSTSESTAALGCLVKDYFPEPV TVSWNSGALTSGVHTFPAVLQSSGLYSLSS VVTVPSSNFGTQTYTCNVDHKPSNTKVDK TVERKSSVECPPCPAPPVAGPSVFLFPPKP KDTLMISRTPEVTCVVVDVSHEDPEVQFN WYVDGVEVHNAKTKPREEQFNSTFRVVSV LTVVHQDWLNGKEYKCKVSNKGLPAPIEKT ISKTKGQPREPQVYTLPPSREEMTKNQVSL TCLVKGFYPSDIAVEWESNGQPENNYKTTP PMLDSDGSFFLYSKLTVDKSRWQQGNVFS CSVMHEALHNHYTQKSLSLSPGK (SEQ ID NO: 305) |
| 10 | MVSSAQFLGLLLLCFQGTR CDIQMTQSPSSLSASVGDR VTITCQASQNINKYIAWYQQ KPGKAPKLLLYYTSTLESGV PSRFSGSGSGTDYTLTISSL QPEDFATYYCLQYVNLITFG GGTKVEIKRTVAAPSVFIFPP SDEQLKSGTASVVCLLNNF YPREAKVQWKVDNALQSG NSQESVTEQDSKDSTYSLS STLTLSKADYEKHKVYACEV THQGLSSPVTKSFNRGEC (SEQ ID NO: 298) | MGWTLVFLFLLSVTAGVHSEVQLVQSGAE VKKPGATVKISCKVSGYTFTDYLMHWVQQ APGKGLEWMGWVDPEYGSTDYAEKFKKR VTITADTSTDTAYMELSSLRSEDTAVYYCA RDDGSYSPFDYWGQGVMVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNVF SCSVMHEALHNHYTQKSLSLSPGK (SEQ ID NO: 306) |
| 11 | MVSSAQFLGLLLLCFQGTR CDIQMTQSPSSLSASVGDR VTITCQASQNINKYIAWYQQ KPGKVPTLLIFYTSTLESGVP SRFSGSGSGTDFTLTISSLQ SEDVATYFCLQYVNLITFGG GTKVEIKRTVAAPSVFIFPS | MGWTLVFLFLLSVTAGVHSQVQLVQSGAE VKKPGASVKVSCKASGYTFTDYLMHWVRQ APGQGLEWIGWVDPEYGSTDYAEKFKK WVTVTRDTSISTAYMELSRLTSDDTAVYYC ARDDGSYSPFDYWGQGTMVTVSSASTKG PSVFPLAPCSRSTSESTAALGCLVKDYFPE PVTVSWNSGALTSGVHTFPAVLQSSGLYSL |

TABLE 1-continued

| Antibody No. | Light Chain Amino Acid Sequence | Heavy Chain Amino Acid Sequence |
|---|---|---|
| | DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 299) | SSVVTVPSSNFGTQTYTCNVDHKPSNTKV DKTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIE KTISKTKGQPREPQVYTLPPSREEMTKNQV SLTCLVKGFYPSDIAVEWESNGQPENNYKT TPPMLDSDGSFFLYSKLTVDKSRWQQGN VFSCSVMHEALHNHYTQKSLSLSPGK (SEQ ID NO: 302) |
| 12 | MVSSAQFLGLLLLCFQGTR CDIQMTQSPSSLSASVGDR VTITCQASQNINKYIAWYQQ KPGKVPTLLIFYTSTLESGVP SRFSGSGSGTDFTLTISSLQ SEDVATYFCLQYVNLITFGG GTKVEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 299) | MGWTLVFLFLLSVTAGVHSEVQLVQSGAE VKKPGASVKVSCKASGYTFTDYLMHWVRQ APGQGLEWMGWVDPEYGSTDYAEKFK KRVTMTRDTSTSTFYMELSSLRSDDT AVYFCARDDGSYSPFDYWGQGTLVTVSSA STKGPSVFPLAPCSRSTSESTAALGCLVKD YFPEPVTVSWNSGALTSGVHTFPAVLQSS GLYSLSSVVTVPSSNFGTQTYTCNVDHKPS NTKVDKTVERKSSVECPPCPAPPVAGPSV FLFPPKPKDTLMISRTPEVTCVVVDVSHED PEVQFNWYVDGVEVHNAKTKPREEQFNST FRVVSVLTVVHQDWLNGKEYKCKVSNKGL PAPIEKTISKTKGQPREPQVYTLPPSREEMT KNQVSLTCLVKGFYPSDIAVEWESNGQPE NNYKTTPPMLDSDGSFFLYSKLTVDKSRW QQGNVFSCSVMHEALHNHYTQKSLSLSPG K (SEQ ID NO: 303) |
| 13 | MVSSAQFLGLLLLCFQGTR CDIQMTQSPSSLSASVGDR VTITCQASQNINKYIAWYQQ KPGKVPTLLIFYTSTLESGVP SRFSGSGSGTDFTLTISSLQ SEDVATYFCLQYVNLITFGG GTKVEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 299) | MGWTLVFLFLLSVTAGVHSEVQLVESGAEV KKPGASVKVSCKASGYTFTDYLMHWVRQA PGQGLEWMGWVDPEYGSTDYAEKFKK RVTMTRDTSISTAYMELNRLTSDDTAVYFC ARDDGSYSPFDYWGQGTLVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNV FSCSVMHEALHNHYTQKSLSLSPGK (SEQ ID NO: 304) |
| 14 | MVSSAQFLGLLLLCFQGTR CDIQMTQSPSSLSASVGDR VTITCQASQNINKYIAWYQQ KPGKVPTLLIFYTSTLESGVP SRFSGSGSGTDFTLTISSLQ SEDVATYFCLQYVNLITFGG GTKVEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 299) | MGWTLVFLFLLSVTAGVHSQVQLVQSGTE VTKPGASVKVSCKASGYTFTDYLMHWVRQ APGQGLEWLGWVDPEYGSTDYAEKFKKR VTMTRDTSTNTVYMELTSLRSEDTAIYYCA RDDGSYSPFDYWGQGTLVTVSSASTKGPS VFPLAPCSRSTSESTAALGCLVKDYFPEPV TVSWNSGALTSGVHTFPAVLQSSGLYSLSS VVTVPSSNFGTQTYTCNVDHKPSNTKVDK TVERKSSVECPPCPAPPVAGPSVFLFPPKP KDTLMISRTPEVTCVVVDVSHEDPEVQFN WYVDGVEVHNAKTKPREEQFNSTFRVVSV LTVVHQDWLNGKEYKCKVSNKGLPAPIEKT ISKTKGQPREPQVYTLPPSREEMTKNQVSL TCLVKGFYPSDIAVEWESNGQPENNYKTTP PMLDSDGSFFLYSKLTVDKSRWQQGNVFS CSVMHEALHNHYTQKSLSLSPGK (SEQ ID NO: 305) |
| 15 | MVSSAQFLGLLLLCFQGTR CDIQMTQSPSSLSASVGDR VTITCQASQNINKYIAWYQQ KPGKVPTLLIFYTSTLESGVP SRFSGSGSGTDFTLTISSLQ SEDVATYFCLQYVNLITFGG GTKVEIKRTVAAPSVFIFPPS DEQLKSGTASVVCLLNNFY PREAKVQWKVDNALQSGN | MGWTLVFLFLLSVTAGVHSEVQLVQSGAE VKKPGATVKISCKVSGYTFTDYLMHWVQQ APGKGLEWMGWVDPEYGSTDYAEKFKKR VTITADTSTDTAYMELSSLRSEDTAVYYCA RDDGSYSPFDYWGQGVMVTVSSASTKGP SVFPLAPCSRSTSESTAALGCLVKDYFPEP VTVSWNSGALTSGVHTFPAVLQSSGLYSL SVVTVPSSNFGTQTYTCNVDHKPSNTKVD KTVERKSSVECPPCPAPPVAGPSVFLFPP |

TABLE 1-continued

| Exemplary Antagonistic TNFR2 antibodies of the disclosure | | |
| --- | --- | --- |
| Antibody No. | Light Chain Amino Acid Sequence | Heavy Chain Amino Acid Sequence |
| | SQESVTEQDSKDSTYSLSS TLTLSKADYEKHKVYACEVT HQGLSSPVTKSFNRGEC (SEQ ID NO: 299) | KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNVF SCSVMHEALHNHYTQKSLSLSPGK (SEQ ID NO: 306) |
| 16 | MVSSAQFLGLLLLCFQGTR CDIQMTQSPSSLSASIGDRV TITCQASQNINKYIAWYQQK PGKAPKLLIYYTSTLESGVP SRFSGSGSGTDFTFTISSLQ PEDIGTYYCLQYVNLITFGQ GTRLEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 300) | MGWTLVFLFLLSVTAGVHSQVQLVQSGAE VKKPGASVKVSCKASGYTFTDYLMHWVRQ APGQGLEWIGWVDPEYGSTDYAEKFKK WVTVTRDTSISTAYMELSRLTSDDTAVYYC ARDDGSYSPFDYWGQGTMVTVSSASTKG PSVFPLAPCSRSTSESTAALGCLVKDYFPE PVTVSWNSGALTSGVHTFPAVLQSSGLYSL SSVVTVPSSNFGTQTYTCNVDHKPSNTKV DKTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIE KTISKTKGQPREPQVYTLPPSREEMTKNQV SLTCLVKGFYPSDIAVEWESNGQPENNYKT TPPMLDSDGSFFLYSKLTVDKSRWQQGN VFSCSVMHEALHNHYTQKSLSLSPGK (SEQ ID NO: 302) |
| 17 | MVSSAQFLGLLLLCFQGTR CDIQMTQSPSSLSASIGDRV TITCQASQNINKYIAWYQQK PGKAPKLLIYYTSTLESGVP SRFSGSGSGTDFTFTISSLQ PEDIGTYYCLQYVNLITFGQ GTRLEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 300) | MGWTLVFLFLLSVTAGVHSEVQLVQSGAE VKKPGASVKVSCKASGYTFTDYLMHWVRQ APGQGLEWMGWVDPEYGSTDYAEKFK KRVTMTRDTSTSTFYMELSSLRSDDT AVYFCARDDGSYSPFDYWGQGTLVTVSSA STKGPSVFPLAPCSRSTSESTAALGCLVKD YFPEPVTVSWNSGALTSGVHTFPAVLQSS GLYSLSSVVTVPSSNFGTQTYTCNVDHKPS NTKVDKTVERKSSVECPPCPAPPVAGPSV FLFPPPKPKDTLMISRTPEVTCVVVDVSHED PEVQFNWYVDGVEVHNAKTKPREEQFNST FRVVSVLTVVHQDWLNGKEYKCKVSNKGL PAPIEKTISKTKGQPREPQVYTLPPSREEMT KNQVSLTCLVKGFYPSDIAVEWESNGQPE NNYKTTPPMLDSDGSFFLYSKLTVDKSRW QQGNVFSCSVMHEALHNHYTQKSLSLSPG K (SEQ ID NO: 303) |
| 18 | MVSSAQFLGLLLLCFQGTR CDIQMTQSPSSLSASIGDRV TITCQASQNINKYIAWYQQK PGKAPKLLIYYTSTLESGVP SRFSGSGSGTDFTFTISSLQ PEDIGTYYCLQYVNLITFGQ GTRLEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 300) | MGWTLVFLFLLSVTAGVHSEVQLVESGAEV KKPGASVKVSCKASGYTFTDYLMHWVRQA PGQGLEWMGWVDPEYGSTDYAEKFKK RVTMTRDTSISTAYMELNRLTSDDTAVYFC ARDDGSYSPFDYWGQGTLVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNV FSCSVMHEALHNHYTQKSLSLSPGK (SEQ ID NO: 304) |
| 19 | MVSSAQFLGLLLLCFQGTR CDIQMTQSPSSLSASIGDRV TITCQASQNINKYIAWYQQK PGKAPKLLIYYTSTLESGVP SRFSGSGSGTDFTFTISSLQ PEDIGTYYCLQYVNLITFGQ GTRLEIKRTVAAPSVFIFPPS DEQLKSGTASVVCLLNNFY PREAKVQWKVDNALQSGN SQESVTEQDSKDSTYSLSS TLTLSKADYEKHKVYACEVT | MGWTLVFLFLLSVTAGVHSQVQLVQSGTE VTKPGASVKVSCKASGYTFTDYLMHWVRQ APGQGLEWLGWVDPEYGSTDYAEKFKKR VTMTRDTSTNTVYMELTSLRSEDTAIYYCA RDDGSYSPFDYWGQGTLVTVSSASTKGPS VFPLAPCSRSTSESTAALGCLVKDYFPEPV TVSWNSGALTSGVHTFPAVLQSSGLYSLSS VVTVPSSNFGTQTYTCNVDHKPSNTKVDK TVERKSSVECPPCPAPPVAGPSVFLFPPKP KDTLMISRTPEVTCVVVDVSHEDPEVQFN WYVDGVEVHNAKTKPREEQFNSTFRVVSV |

TABLE 1-continued

| | Exemplary Antagonistic TNFR2 antibodies of the disclosure | |
|---|---|---|
| Antibody No. | Light Chain Amino Acid Sequence | Heavy Chain Amino Acid Sequence |
| | HQGLSSPVTKSFNRGEC (SEQ ID NO: 300) | LTVVHQDWLNGKEYKCKVSNKGLPAPIEKT ISKTKGQPREPQVYTLPPSREEMTKNQVSL TCLVKGFYPSDIAVEWESNGQPENNYKTTP PMLDSDGSFFLYSKLTVDKSRWQQGNVFS CSVMHEALHNHYTQKSLSLSPGK (SEQ ID NO: 305) |
| 20 | MVSSAQFLGLLLLCFQGTR CDIQMTQSPSSLSASIGDRV TITCQASQNINKYIAWYQQK PGKAPKLLIYYTSTLESGVP SRFSGSGSGTDFTFTISSLQ PEDIGTYYCLQYVNLITFGQ GTRLEIKRTVAAPSVFIFPPS DEQLKSGTASVVCLLNNFY PREAKVQWKVDNALQSGN SQESVTEQDSKDSTYSLSS TLTLSKADYEKHKVYACEVT HQGLSSPVTKSFNRGEC (SEQ ID NO: 300) | MGWTLVFLFLLSVTAGVHSEVQLVQSGAE VKKPGATVKISCKVSGYTFTDYLMHWVQQ APGKGLEWMGWVDPEYGSTDYAEKFKKR VTITADTSTDTAYMELSSLRSEDTAVYYCA RDDGSYSPFDYWGQGVMVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNVF SCSVMHEALHNHYTQKSLSLSPGK (SEQ ID NO: 306) |
| 21 | MVSSAQFLGLLLLCFQGTR CDIQMTQSPSSLSASVGDR VTITCQASQNINKYIAWYQQ KPGKAPKLLIYYTSTLESGV PSRFSGSGSGTDFTFTISSL QPEDIATYYCLQYVNLITFG AGTKLELKRTVAAPSVFIFP PSDEQLKSGTASVVCLLNN FYPREAKVQWKVDNALQSG NSQESVTEQDSKDSTYSLS STLTLSKADYEKHKVYACEV THQGLSSPVTKSFNRGEC (SEQ ID NO: 301) | MGWTLVFLFLLSVTAGVHSQVQLVQSGAE VKKPGASVKVSCKASGYTFTDYLMHWVRQ APGQGLEWIGWVDPEYGSTDYAEKFKK WVTVTRDTSISTAYMELSRLTSDDTAVYYC ARDDGSYSPFDYWGQGTMVTVSSASTKG PSVFPLAPCSRSTSESTAALGCLVKDYFPE PVTVSWNSGALTSGVHTFPAVLQSSGLYSL SSVVTVPSSNFGTQTYTCNVDHKPSNTKV DKTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIE KTISKTKGQPREPQVYTLPPSREEMTKNQV SLTCLVKGFYPSDIAVEWESNGQPENNYKT TPPMLDSDGSFFLYSKLTVDKSRWQQGN VFSCSVMHEALHNHYTQKSLSLSPGK (SEQ ID NO: 302) |
| 22 | MVSSAQFLGLLLLCFQGTR CDIQMTQSPSSLSASVGDR VTITCQASQNINKYIAWYQQ KPGKAPKLLIYYTSTLESGV PSRFSGSGSGTDFTFTISSL QPEDIATYYCLQYVNLITFG AGTKLELKRTVAAPSVFIFP PSDEQLKSGTASVVCLLNN FYPREAKVQWKVDNALQSG NSQESVTEQDSKDSTYSLS STLTLSKADYEKHKVYACEV THQGLSSPVTKSFNRGEC (SEQ ID NO: 301) | MGWTLVFLFLLSVTAGVHSEVQLVQSGAE VKKPGASVKVSCKASGYTFTDYLMHWVRQ APGQGLEWMGWVDPEYGSTDYAEKFK KRVTMTRDTSTSTFYMELSSLRSDDT AVYFCARDDGSYSPFDYWGQGTLVTVSSA STKGPSVFPLAPCSRSTSESTAALGCLVKD YFPEPVTVSWNSGALTSGVHTFPAVLQSS GLYSLSSVVTVPSSNFGTQTYTCNVDHKPS NTKVDKTVERKSSVECPPCPAPPVAGPSV FLFPPPKPKDTLMISRTPEVTCVVVDVSHED PEVQFNWYVDGVEVHNAKTKPREEQFNST FRVVSVLTVVHQDWLNGKEYKCKVSNKGL PAPIEKTISKTKGQPREPQVYTLPPSREEMT KNQVSLTCLVKGFYPSDIAVEWESNGQPE NNYKTTPPMLDSDGSFFLYSKLTVDKSRW QQGNVFSCSVMHEALHNHYTQKSLSLSPG K (SEQ ID NO: 303) |
| 23 | MVSSAQFLGLLLLCFQGTR CDIQMTQSPSSLSASVGDR VTITCQASQNINKYIAWYQQ KPGKAPKLLIYYTSTLESGV PSRFSGSGSGTDFTFTISSL QPEDIATYYCLQYVNLITFG AGTKLELKRTVAAPSVFIFP PSDEQLKSGTASVVCLLNN FYPREAKVQWKVDNALQSG NSQESVTEQDSKDSTYSLS STLTLSKADYEKHKVYACEV THQGLSSPVTKSFNRGEC (SEQ ID NO: 301) | MGWTLVFLFLLSVTAGVHSEVQLVESGAEV KKPGASVKVSCKASGYTFTDYLMHWVRQA PGQGLEWMGWVDPEYGSTDYAEKFKK RVTMTRDTSISTAYMELNRLTSDDTAVYFC ARDDGSYSPFDYWGQGTLVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS |

TABLE 1-continued

Exemplary Antagonistic TNFR2 antibodies of the disclosure

| Antibody No. | Light Chain Amino Acid Sequence | Heavy Chain Amino Acid Sequence |
|---|---|---|
| | | LTCLVKGFYPSDIAVEWESNGQPENNYKTT PPMLDSDGSFFLYSKLTVDKSRWQQGNV FSCSVMHEALHNHYTQKSLSLSPGK (SEQ ID NO: 304) |
| 24 | MVSSAQFLGLLLLCFQGTR CDIQMTQSPSSLSASVGDR VTITCQASQNINKYIAWYQQ KPGKAPKLLIYYTSTLESGV PSRFSGSGSGTDFTFTISSL QPEDIATYYCLQYVNLITFG AGTKLELKRTVAAPSVFIFP PSDEQLKSGTASVVCLLNN FYPREAKVQWKVDNALQSG NSQESVTEQDSKDSTYSLS STLTLSKADYEKHKVYACEV THQGLSSPVTKSFNRGEC (SEQ ID NO: 301) | MGWTLVFLFLLSVTAGVHSQVQLVQSGTE VTKPGASVKVSCKASGYTFTDYLMHWVRQ APGQGLEWLGWVDPEYGSTDYAEKFKKR VTMTRDTSTNTVYMELTSLRSEDTAIYYCA RDDGSYSPFDYWGQGTLVTVSSASTKGPS VFPLAPCSRSTSESTAALGCLVKDYFPEPV TVSWNSGALTSGVHTFPAVLQSSGLYSLSS VVTVPSSNFGTQTYTCNVDHKPSNTKVDK TVERKSSVECPPCPAPPVAGPSVFLFPPKP KDTLMISRTPEVTCVVVDVSHEDPEVQFN WYVDGVEVHNAKTKPREEQFNSTFRVVSV LTVVHQDWLNGKEYKCKVSNKGLPAPIEKT ISKTKGQPREPQVYTLPPSREEMTKNQVSL TCLVKGFYPSDIAVEWESNGQPENNYKTTP PMLDSDGSFFLYSKLTVDKSRWQQGNVFS CSVMHEALHNHYTQKSLSLSPGK (SEQ ID NO: 305) |
| 25 | MVSSAQFLGLLLLCFQGTR CDIQMTQSPSSLSASVGDR VTITCQASQNINKYIAWYQQ KPGKAPKLLIYYTSTLESGV PSRFSGSGSGTDFTFTISSL QPEDIATYYCLQYVNLITFG AGTKLELKRTVAAPSVFIFP PSDEQLKSGTASVVCLLNN FYPREAKVQWKVDNALQSG NSQESVTEQDSKDSTYSLS STLTLSKADYEKHKVYACEV THQGLSSPVTKSFNRGEC (SEQ ID NO: 301) | MGWTLVFLFLLSVTAGVHSEVQLVQSGAE VKKPGATVKISCKVSGYTFTDYLMHWVQQ APGKGLEWMGWVDPEYGSTDYAEKFKKR VTITADTSTDTAYMELSSLRSEDTAVYYCA RDDGSYSPFDYWGQGVMVTVSSASTKGP SVFPLAPCSRSTSESTAALGCLVKDYFPEP VTVSWNSGALTSGVHTFPAVLQSSGLYSLS SVVTVPSSNFGTQTYTCNVDHKPSNTKVD KTVERKSSVECPPCPAPPVAGPSVFLFPP KPKDTLMISRTPEVTCVVVDVSHEDPEVQF NWYVDGVEVHNAKTKPREEQFNSTFRVVS VLTVVHQDWLNGKEYKCKVSNKGLPAPIEK TISKTKGQPREPQVYTLPPSREEMTKNQVS LTCLVKGFYPSDIAVEWESNGQPENNYKTT PPMLDSDGSFFLYSKLTVDKSRWQQGNVF SCSVMHEALHNHYTQKSLSLSPGK (SEQ ID NO: 306) |

For example, in some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 302. In some embodiments, the antagonistic TNFR2 antibody or antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 302. In some embodiments, the antagonistic TNFR2 antibody or antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 302. In some embodiments, the antagonistic TNFR2 antibody or antigen-binding fragment thereof contains a heavy chain having the amino acid sequence of SEQ ID NO: 302.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 303. In some embodiments, the antagonistic TNFR2 antibody or antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 303. In some embodiments, the antagonistic TNFR2 antibody or antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 303. In some embodiments, the antagonistic TNFR2 antibody or antigen-binding fragment thereof contains a heavy chain having the amino acid sequence of SEQ ID NO: 303.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 304. In some embodiments, the antagonistic TNFR2 antibody or antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 304. In some embodiments, the antagonistic TNFR2 antibody or antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 304. In some embodiments, the antagonistic TNFR2 antibody or antigen-binding fragment thereof contains a heavy chain having the amino acid sequence of SEQ ID NO: 304.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 305. In some embodiments, the antagonistic TNFR2 antibody or antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 305. In some embodiments, the antagonistic TNFR2 antibody or antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 305. In some embodiments, the antagonistic TNFR2 antibody or antigen-binding fragment thereof contains a heavy chain having the amino acid sequence of SEQ ID NO: 305.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 306. In some embodiments, the antagonistic TNFR2 antibody or antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 306. In some embodiments, the antagonistic TNFR2 antibody or antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 306. In some embodiments, the antagonistic TNFR2 antibody or antigen-binding fragment thereof contains a heavy chain having the amino acid sequence of SEQ ID NO: 306.

In some embodiments, the disclosure features an antagonistic TNFR2 antibody or antigen-binding fragment thereof containing a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody or antigen-binding fragment thereof contains a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody or antigen-binding fragment thereof contains a light chain having an amino acid sequence that is at least 95% identical (e.g., at least 95%, 96%, 97%, 98%, 99%, 99.9%, or 100% identical) to the amino acid sequence of SEQ ID NO: 297. In some embodiments, the antagonistic TNFR2 antibody or antigen-binding fragment thereof contains a light chain having the amino acid sequence of SEQ ID NO: 297.

In some embodiments, the disclosure features an antagonistic TNFR2 antibody or antigen-binding fragment thereof containing a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody or antigen-binding fragment thereof contains a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody or antigen-binding fragment thereof contains a light chain having an amino acid sequence that is at least 95% identical (e.g., at least 95%, 96%, 97%, 98%, 99%, 99.9%, or 100% identical) to the amino acid sequence of SEQ ID NO: 298. In some embodiments, the antagonistic TNFR2 antibody or antigen-binding fragment thereof contains a light chain having the amino acid sequence of SEQ ID NO: 298.

In some embodiments, the disclosure features an antagonistic TNFR2 antibody or antigen-binding fragment thereof containing a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody or antigen-binding fragment thereof contains a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody or antigen-binding fragment thereof contains a light chain having an amino acid sequence that is at least 95% identical (e.g., at least 95%, 96%, 97%, 98%, 99%, 99.9%, or 100% identical) to the amino acid sequence of SEQ ID NO: 299. In some embodiments, the antagonistic TNFR2 antibody or antigen-binding fragment thereof contains a light chain having the amino acid sequence of SEQ ID NO: 299.

In some embodiments, the disclosure features an antagonistic TNFR2 antibody or antigen-binding fragment thereof containing a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody or antigen-binding fragment thereof contains a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody or antigen-binding fragment thereof contains a light chain having an amino acid sequence that is at least 95% identical (e.g., at least 95%, 96%, 97%, 98%, 99%, 99.9%, or 100% identical) to the amino acid sequence of SEQ ID NO: 300. In some embodiments, the antagonistic TNFR2 antibody or antigen-binding fragment thereof contains a light chain having the amino acid sequence of SEQ ID NO: 300.

In some embodiments, the disclosure features an antagonistic TNFR2 antibody or antigen-binding fragment thereof containing a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody or antigen-binding fragment thereof contains a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody or antigen-binding fragment thereof contains a light chain having an amino acid sequence that is at least 95% identical (e.g., at least 95%, 96%, 97%, 98%, 99%, 99.9%, or 100% identical) to the amino acid sequence of SEQ ID NO: 301. In some embodiments, the antagonistic TNFR2 antibody or antigen-binding fragment thereof contains a light chain having the amino acid sequence of SEQ ID NO: 301.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 302 and a light chain having an amino acid sequence that is at least 95% identical (e.g., at least 95%, 96%, 97%, 98%, 99%, 99.9/0, or 100/0 identical) to the amino acid sequence of SEQ ID NO: 297. In some embodiments, the antagonistic TNFR2 antibody of antigen-binding fragment thereof contains a heavy chain having the amino acid sequence of SEQ ID NO: 302 and a light chain having the amino acid sequence of SEQ ID NO: 297.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 302 and a light chain having an amino acid sequence that is at least 95% identical (e.g., at least 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having the amino acid sequence of SEQ ID NO: 302 and a light chain having the amino acid sequence of SEQ ID NO: 298.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 302 and a light chain having an amino acid sequence that is at least 95% identical (e.g., at least 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having the amino acid sequence of SEQ ID NO: 302 and a light chain having the amino acid sequence of SEQ ID NO: 299.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 302 and a light chain having an amino acid sequence that is at least 95% identical (e.g., at least 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having the amino acid sequence of SEQ ID NO: 302 and a light chain having the amino acid sequence of SEQ ID NO: 300.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 302 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 302 and a light chain having an amino acid sequence that is at least 95% identical (e.g., at least 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having the amino acid sequence of SEQ ID NO: 302 and a light chain having the amino acid sequence of SEQ ID NO: 301.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 303 and a light chain having an amino acid sequence that is at least 95% identical (e.g., at least 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having the amino acid sequence of SEQ ID NO: 303 and a light chain having the amino acid sequence of SEQ ID NO: 297.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 303 and a light chain having an amino acid sequence that is at least 95% identical (e.g., at least 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having the amino acid sequence of SEQ ID NO: 303 and a light chain having the amino acid sequence of SEQ ID NO: 298.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 303 and a light chain having an amino acid sequence that is at least 95% identical (e.g., at least 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having the amino acid sequence of SEQ ID NO: 303 and a light chain having the amino acid sequence of SEQ ID NO: 299.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 303 and a light chain having an amino acid sequence that is at least 95% identical (e.g., at least 95%, 96%, 97%, 98%, 99%, 99.9/0, or 100/0 identical) to the amino acid sequence of SEQ ID NO: 300. In some embodiments, the antagonistic TNFR2 antibody of antigen-binding fragment thereof contains a heavy chain having the amino acid sequence of SEQ ID NO: 303 and a light chain having the amino acid sequence of SEQ ID NO: 300.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 303 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 303 and a light chain having an amino acid sequence that is at least 95% identical (e.g., at least 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having the amino acid sequence of SEQ ID NO: 303 and a light chain having the amino acid sequence of SEQ ID NO: 301.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 304 and a light chain having an amino acid sequence that is at least 95% identical (e.g., at least 95%, 96%, 97%, 98%, 99%, 99.9/0, or 100/0 identical) to the amino acid sequence of SEQ ID NO: 297. In some embodiments, the antagonistic TNFR2 antibody of antigen-binding fragment thereof contains a heavy chain having the amino acid sequence of SEQ ID NO: 304 and a light chain having the amino acid sequence of SEQ ID NO: 297.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 304 and a light chain having an amino acid sequence that is at least 95% identical (e.g., at least 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having the amino acid sequence of SEQ ID NO: 304 and a light chain having the amino acid sequence of SEQ ID NO: 298.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 304 and a light chain having an amino acid sequence that is at least 95% identical (e.g., at least 95%, 96%, 97%, 98%, 99%, 99.9/0, or 100/0 identical) to the amino acid sequence of SEQ ID NO: 299. In some embodiments, the antagonistic TNFR2 antibody of antigen-binding fragment thereof contains a heavy chain having the amino acid sequence of SEQ ID NO: 304 and a light chain having the amino acid sequence of SEQ ID NO: 299.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 304 and a light chain having an amino acid sequence that is at least 95% identical (e.g., at least 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having the amino acid sequence of SEQ ID NO: 304 and a light chain having the amino acid sequence of SEQ ID NO: 300.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 304 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 304 and a light chain having an amino acid sequence that is at least 95% identical (e.g., at least 95%, 96%, 97%, 98%, 99%, 99.9/0, or 100/0 identical) to the amino acid sequence of SEQ ID NO: 301. In some embodiments, the antagonistic TNFR2 antibody of antigen-binding fragment thereof contains a heavy chain having the amino acid sequence of SEQ ID NO: 304 and a light chain having the amino acid sequence of SEQ ID NO: 301.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 305 and a light chain having an amino acid sequence that is at least 95% identical (e.g., at least 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having the amino acid sequence of SEQ ID NO: 305 and a light chain having the amino acid sequence of SEQ ID NO: 297.

In some embodiments, the disclosure features an antagonistic TNFR2 antibody or antigen-binding fragment thereof containing heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 305 and a light chain having an amino acid sequence that is at least 95% identical (e.g., at least 95%, 96%, 97%, 98%, 99%, 99.9/0, or 100/0 identical) to the amino acid sequence of SEQ ID NO: 298. In some embodiments, the antagonistic TNFR2 antibody of antigen-binding fragment thereof contains a heavy chain having the amino acid sequence of SEQ ID NO: 305 and a light chain having the amino acid sequence of SEQ ID NO: 298.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 305 and a light chain having an amino acid sequence that is at least 95% identical (e.g., at least 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having the amino acid sequence of SEQ ID NO: 305 and a light chain having the amino acid sequence of SEQ ID NO: 299.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 305 and a light chain having an amino acid sequence that is at least 95% identical (e.g., at least 95%, 96%, 97%, 98%, 99%, 99.9/0, or 100/0 identical) to the amino acid sequence of SEQ ID NO: 300. In some embodiments, the antagonistic TNFR2 antibody of antigen-binding fragment thereof contains a heavy chain having the amino acid sequence of SEQ ID NO: 305 and a light chain having the amino acid sequence of SEQ ID NO: 300.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 305 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 305 and a light chain having an amino acid sequence that is at least 95% identical (e.g., at least 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having the amino acid sequence of SEQ ID NO: 305 and a light chain having the amino acid sequence of SEQ ID NO: 301.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 297. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 306 and a light chain having an amino acid sequence that is at least 95% identical (e.g., at least 95%, 96%, 97%, 98%, 99%, 99.9/0, or 100/0 identical) to the amino acid sequence of SEQ ID NO: 297. In some embodiments, the antagonistic TNFR2 antibody of antigen-binding fragment thereof contains a heavy chain having the amino acid sequence of SEQ ID NO: 306 and a light chain having the amino acid sequence of SEQ ID NO: 297.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 306 and a light chain having an amino acid sequence that is at least 95% identical (e.g., at least 95%, 96%, 97%, 98%, 99%, 99.9%, or 100% identical) to the amino acid sequence of SEQ ID NO: 298. In some embodiments, the antagonistic TNFR2 antibody of antigen-binding fragment thereof contains a heavy chain having the amino acid sequence of SEQ ID NO: 306 and a light chain having the amino acid sequence of SEQ ID NO: 298.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 299. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 306 and a light chain having an amino acid sequence that is at least 95% identical (e.g., at least 95%, 96%, 97%, 98%, 99%, 99.9/0, or 100/0 identical) to the amino acid sequence of SEQ ID NO: 299. In some embodiments, the antagonistic TNFR2 antibody of antigen-binding fragment thereof contains a heavy chain having the amino acid sequence of SEQ ID NO: 306 and a light chain having the amino acid sequence of SEQ ID NO: 299.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 306 and a light chain having an amino acid sequence that is at least 95% identical (e.g., at least 95%, 96%, 97%, 98%, 99%, 99.9%, or 100% identical) to the amino acid sequence of SEQ ID NO: 300. In some embodiments, the antagonistic TNFR2 antibody of antigen-binding fragment thereof contains a heavy chain having the amino acid sequence of SEQ ID NO: 306 and a light chain having the amino acid sequence of SEQ ID NO: 300.

In some embodiments, the disclosure features an antagonistic TNFR2 antibody or antigen-binding fragment thereof containing a heavy chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 306 and a light chain having an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 301. In some embodiments, the antagonistic TNFR2 antibody of antigen-binding fragment thereof contains a heavy chain having an amino acid sequence that is at least 95% identical (e.g., at least 95%, 96%, 97%, 98%, 99%, 99.9%, or 100% identical) to the amino acid sequence of SEQ ID NO: 306 and a light chain having an amino acid sequence that is at least 95% identical (e.g., at least 95%, 96%, 97%, 98%, 99%, 99.9/0, or 100/0 identical) to the amino acid sequence of SEQ ID NO: 301. In some embodiments, the antagonistic TNFR2 antibody of antigen-binding fragment thereof contains a heavy chain having the amino acid sequence of SEQ ID NO: 306 and a light chain having the amino acid sequence of SEQ ID NO: 301.

In some embodiments of the disclosure, the polypeptides, such as single-chain polypeptides, antibodies, antigen-binding fragments thereof, and constructs thereof, contain a human IgG2 hinge region that lacks a cysteine residue at positions 232 and/or 233 of the amino acid sequence of the IgG2 hinge region. For example, the polypeptide (e.g., a single-chain polypeptide, antibody, antigen-binding fragment thereof, or construct thereof) may contain a human IgG2 hinge region having an amino acid other than cysteine, such as a serine residue, at positions 232 and/or 233 of the amino acid sequence of the IgG2 hinge region.

The polypeptide (e.g., a single-chain polypeptide, antibody, antigen-binding fragment thereof, or construct thereof) may contain, for example, a human IgG2 hinge region having an amino acid substitution or deletion at one or both of cysteine residues 232 and 233. The amino acid substitution may be a conservative amino acid substitution, such as a C232S and/or C233S amino acid substitution.

In some embodiments, the IgG2 hinge region has an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 291, e.g., provided that the IgG2 hinge region contains serine residues at one or both of positions 232 and 233 of the IgG2 hinge amino acid sequence. The IgG2 hinge region may have, for example, an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 291, e.g., provided that the IgG2 hinge region contains serine residues at positions 232 and 233 of the IgG2 hinge amino acid sequence. In some embodiments, the IgG2 hinge region has an amino acid sequence that is at least 95% identical (e.g., at least 95%, 96%, 97%, 98%, 99%, 99.9%, or 100% identical) to the amino acid sequence of SEQ ID NO: 291, e.g., provided that the IgG2 hinge region contains serine residues at positions 232 and 233 of the IgG2 hinge amino acid sequence.

The polypeptide (e.g., a single-chain polypeptide, antibody, antigen-binding fragment thereof, or construct thereof) may contain antigen-binding sites that are separated from one another by a distance of at least about 133 Å (e.g., by a distance of from about 133 Å to about 160 Å, such as a distance of about 133 Å, 134 Å, 135 Å, 136 Å, 137 Å, 138 Å, 139 Å, 140 Å, 141 Å, 142 Å, 143 Å, 144 Å, 145 Å, 146 Å, 147 Å, 148 Å, 149 Å, 150 Å, 151 Å, 152 Å, 153 Å, 154 Å, 155 Å, 156 Å, 157 Å, 158 Å, 159 Å, or 160 Å). In some embodiments, the antigen-binding sites are separated from one another by a distance of at least about 134 Å (e.g., by a distance of from about 134 Å to about 160 Å, such as a distance of about 134 Å, 135 Å, 136 Å, 137 Å, 138 Å, 139 Å, 140 Å, 141 Å, 142 Å, 143 Å, 144 Å, 145 Å, 146 Å, 147 Å, 148 Å, 149 Å, 150 Å, 151 Å, 152 Å, 153 Å, 154 Å, 155 Å, 156 Å, 157 Å, 158 Å, 159 Å, or 160 Å). In some embodiments, the antigen-binding sites are separated from one another by a distance of at least about 139 Å (e.g., by a distance of from about 139 Å to about 160 Å, such as a distance of about 139 Å, 140 Å, 141 Å, 142 Å, 143 Å, 144 Å, 145 Å, 146 Å, 147 Å, 148 Å, 149 Å, 150 Å, 151 Å, 152 Å, 153 Å, 154 Å, 155 Å, 156 Å, 157 Å, 158 Å, 159 Å, or 160 Å). In some embodiments, the antigen-binding sites are separated from one another by a distance of at least about 150 Å (e.g., by a distance of from about 150 Å to about 160 Å, such as a distance of about 150 Å, 151 Å, 152 Å, 153 Å, 154 Å, 155 Å, 156 Å, 157 Å, 158 Å, 159 Å, or 160 Å).

For example, the polypeptide (e.g., a single-chain polypeptide, antibody, antigen-binding fragment thereof, or construct thereof) may contain antigen-binding sites that are separated from one another by a distance of from about 133 Å to about 150 Å, such as by a distance of about 133 Å, 134 Å, 135 Å, 136 Å, 137 Å, 138 Å, 139 Å, 140 Å, 141 Å, 142 Å, 143 Å, 144 Å, 145 Å, 146 Å, 147 Å, 148 Å, 149 Å, or 150 Å. In some embodiments, the antigen-binding are separated from one another by a distance of from about 133 Å to about 145 Å, such as by a distance of about 133 Å, 134 Å, 135 Å, 136 Å, 137 Å, 138 Å, 139 Å, 140 Å, 141 Å, 142 Å, 143 Å, 144 Å, or 145 Å. In some embodiments, the antigen-binding are separated from one another by a distance of from about 133 Å to about 139 Å, such as by a distance of about 133 Å, 134 Å, 135 Å, 136 Å, 137 Å, 138 Å, or 139 Å. In some embodiments, the antigen-binding are separated from one another by a distance of from about 134 Å to about 139 Å, such as by a distance of about 134 Å, 135 Å, 136 Å, 137 Å, 138 Å, or 139 Å.

The polypeptide (e.g., a single-chain polypeptide, antibody, antigen-binding fragment thereof, or construct thereof) may contain a complementarity-determining region (CDR) heavy chain 1 (CDR1) having the amino acid sequence GJTF(J)$_2$Y (SEQ ID NO: 276) or GJTF(J)$_2$YJ (SEQ ID NO: 277), in which each J is independently a naturally occurring amino acid. In some embodiments, the polypeptide (e.g., a single-chain polypeptide, antibody, antigen-binding fragment thereof, or construct thereof) further contains:

(a) a CDR-H2 having the amino acid sequence $(J)_3GSJ$ or $(J)_5GSJ$;

(b) a CDR-H3 having the amino acid sequence JRJDGJSJY$(J)_2$FDJ (SEQ ID NO: 278) or JRJDGSY $(J)_2$FD$(J)_3$ (SEQ ID NO: 279);

(c) a CDR-L1 having the amino acid sequence $(J)_9Y$ or $(J)_5Y$;

(d) a CDR-L2 having the amino acid sequence $(J)_6S$ or $(J)_2S$; and/or (e) a CDR-L3 having the amino acid sequence $(J)_5Y(J)_2T$ or $(J)_3Y(J)_4T$, in which each J is independently a naturally occurring amino acid.

The polypeptide (e.g., a single-chain polypeptide, antibody, antigen-binding fragment thereof, or construct thereof) may contain a CDR-H1 having the amino acid sequence $Z^4FZ^3Z^5SSZ^5$ or $Z^4YZ^3Z^5TDZ^5X$;

In which each $Z^3$ is independently an amino acid including a polar, uncharged side-chain at physiological pH;

each $Z^4$ is independently a glycine or alanine;

each $Z^5$ is independently an amino acid including a hydrophobic side-chain; and each X is independently leucine or isoleucine.

In some embodiments, the polypeptide (e.g., a single-chain polypeptide, antibody, antigen-binding fragment thereof, or construct thereof) further contains:

(a) a CDR-H2 having the amino acid sequence $SSGZ^4Z^3Y$ (SEQ ID NO: 263) or $VDPEYZ^4Z^3T$ (SEQ ID NO: 264);

(b) a CDR-H3 having the amino acid sequence $QZ^1VZ^2Z^4YZ^3SZ^5WYZ^5Z^2Z^5$ (SEQ ID NO: 265) or $AZ^1DZ^2Z^4Z^3Z^5SPZ^5Z^2Z^5WG$ (SEQ ID NO: 266);

(c) a CDR-L1 having the amino acid sequence $SASSSVYYMZ^5$ (SEQ ID NO: 267) or $QNINKZ^5$ (SEQ ID NO: 268);

(d) a CDR-L2 having the amino acid sequence $STSNLAZ^3$ (SEQ ID NO: 269), $TYZ^3$, or $YTZ^3$; and/or (e) a CDR-L3 having the amino acid sequence $QQRRNZ^5PYZ^3$ (SEQ ID NO: 270) or $CLQZ^5VNLXZ^3$ (SEQ ID NO: 271);

in which each $Z^1$ is independently an amino acid including a cationic side-chain at physiological pH;

each $Z^2$ is independently an amino acid including an anionic side-chain at physiological pH;

each $Z^3$ is independently an amino acid including a polar, uncharged side-chain at physiological pH;

each $Z^4$ is independently a glycine or alanine;

each $Z^5$ is independently an amino acid including a hydrophobic side-chain; and each X is independently leucine or isoleucine.

The polypeptide (e.g., a single-chain polypeptide, antibody, antigen-binding fragment thereof, or construct thereof) may contain a CDR-H1 having the amino acid sequence GFTFSSY (SEQ ID NO: 23), GYTFTDYX (SEQ ID NO: 257), or an amino acid sequence having up to two amino acid substitutions (e.g., conservative amino acid substitutions) relative to these sequences, in which each X is independently leucine or isoleucine, optionally in which the amino acid substitutions are conservative amino acid substitutions. In some embodiments, the polypeptide (e.g., a single-chain polypeptide, antibody, antigen-binding fragment thereof, or construct thereof) further contains:

(a) a CDR-H2 having the amino acid sequence SSGGSY (SEQ ID NO: 24), VDPEYGST (SEQ ID NO: 258), or an amino acid sequence having up to two amino acid substitutions (e.g., conservative amino acid substitutions) relative to these sequences;

(b) a CDR-H3 having the amino acid sequence QRVDGYSSYWYFDV (SEQ ID NO: 25), ARDDG-SYSPFDYWG (SEQ ID NO: 259), ARDDGSYS-PFDY (SEQ ID NO: 296), or an amino acid sequence having up to two amino acid substitutions (e.g., conservative amino acid substitutions) relative to these sequences;

(c) a CDR-L1 having the amino acid sequence SASSSVYYMY (SEQ ID NO: 26), QNINKY (SEQ ID NO: 260), or an amino acid sequence having up to two amino acid substitutions (e.g., conservative amino acid substitutions) relative to these sequences;

(d) a CDR-L2 having the amino acid sequence STSNLAS (SEQ ID NO: 27), TYS, YTS, or an amino acid sequence having up to two amino acid substitutions (e.g., conservative amino acid substitutions) relative to SEQ ID NO: 27; and/or (e) a CDR-L3 having the amino acid sequence QQRRNY-PYT (SEQ ID NO: 28), CLQYVNLXT (SEQ ID NO: 261), or an amino acid sequence having up to two amino acid substitutions (e.g., conservative amino acid substitutions) relative to these sequences.

In some embodiments, the polypeptide (e.g., a single-chain polypeptide, antibody, antigen-binding fragment thereof, or construct thereof) contains a heavy chain including one or more of the following CDRs:

(a) a CDR-H1 having the amino acid sequence GFTFSSY (SEQ ID NO: 23);

(b) a CDR-H2 having the amino acid sequence SSGGSY (SEQ ID NO: 24); and (c) a CDR-H3 having the amino acid sequence QRVDGYSSYWYFDV (SEQ ID NO: 25).

The polypeptide (e.g., a single-chain polypeptide, antibody, antigen-binding fragment thereof, or construct thereof) may contain, for example, a heavy chain having one or more of the following CDRs:

(a) a CDR-H1 having the amino acid sequence GYTFTDYX (SEQ ID NO: 257);

(b) a CDR-H2 having the amino acid sequence VDPEYGST (SEQ ID NO: 258); and (c) a CDR-H3 having the amino acid sequence ARDDG-SYSPFDYWG (SEQ ID NO: 259);

in which each X is independently leucine or isoleucine.

In some embodiments, the CDR-H1 has the amino acid sequence GYTFTDYL (SEQ ID NO: 274). In some embodiments, the CDR-H1 has the amino acid sequence GYTFTDYI (SEQ ID NO: 275). In some embodiments, the CDR-H1 has the amino acid sequence GYTFTDVI (SEQ ID NO: 293). In some embodiments, the CDR-H1 has the amino acid sequence GYTFTDYS (SEQ ID NO: 294).

Additionally or alternatively, the polypeptide (e.g., a single-chain polypeptide, antibody, antigen-binding fragment thereof, or construct thereof) may contain, for example, a light chain having one or more of the following CDRs:

(a) a CDR-L1 having the amino acid sequence SASSSVYYMY (SEQ ID NO: 26);

(b) a CDR-L2 having the amino acid sequence STSNLAS (SEQ ID NO: 27); and (c) a CDR-L3 having the amino acid sequence QQRRNY-PYT (SEQ ID NO: 28).

In some embodiments, the antibody or antigen-binding fragment thereof contains a light chain having one or more of the following CDRs:

(a) a CDR-L1 having the amino acid sequence QNINKY (SEQ ID NO: 260);

(b) a CDR-L2 having the amino acid sequence TYS or YTS; and (c) a CDR-L3 having the amino acid sequence CLQYVNLXT (SEQ ID NO: 261);

in which each X is independently leucine or isoleucine.

In some embodiments, the CDR-L2 has the amino acid sequence TYS. In some embodiments, the CDR-L2 has the amino acid sequence YTS. The CDR-L3 may have the amino acid sequence CLQYVNLLT (SEQ ID NO: 272). In some embodiments, the CDR-L3 has the amino acid sequence CLQYVNLIT (SEQ ID NO: 273).

The polypeptide (e.g., a single-chain polypeptide, antibody, antigen-binding fragment thereof, or construct thereof) may contain three heavy chain CDRs, including:

(a) a CDR-H1 having the amino acid sequence GFTFSSY (SEQ ID NO: 23);

(b) a CDR-H2 having the amino acid sequence SSGGSY (SEQ ID NO: 24); and (c) a CDR-H3 having the amino acid sequence QRVDGYSSYWYFDV (SEQ ID NO: 25);

and may further contain three light chain CDRs, including:

(d) a CDR-L1 having the amino acid sequence SASSSVYYMY (SEQ ID NO: 26);

(e) a CDR-L2 having the amino acid sequence STSNLAS (SEQ ID NO: 27); and (f) a CDR-L3 having the amino acid sequence QQRRNY-PYT (SEQ ID NO: 28).

In some embodiments, polypeptide (e.g., single-chain polypeptides, antibody, antigen-binding fragment thereof, or construct thereof) contains three heavy chain CDRs, including:

(a) a CDR-H1 having the amino acid sequence GYTFTDYX (SEQ ID NO: 257), such as GYTFTDYL (SEQ ID NO: 274) or GYTFTDYI (SEQ ID NO: 275);

(b) a CDR-H2 having the amino acid sequence VDPEYGST (SEQ ID NO: 258); and (c) a CDR-H3 having the amino acid sequence ARDDG-SYSPFDYWG (SEQ ID NO: 259);

and further contains three light chain CDRs, including:

(d) a CDR-L1 having the amino acid sequence QNINKY (SEQ ID NO: 260);

(e) a CDR-L2 having the amino acid sequence TYS or YTS; and (f) a CDR-L3 having the amino acid sequence CLQYVNLXT (SEQ ID NO: 261), such as CLQYVNLLT (SEQ ID NO: 272) or CLQYVNLIT (SEQ ID NO: 273);

in which each X is independently leucine or isoleucine.

In some embodiments, the polypeptide (e.g., a single-chain polypeptide, antibody, antigen-binding fragment thereof, or construct thereof) includes a framework region having the amino acid sequence LLIR (SEQ ID NO: 262) bound to the N-terminus of the CDR-L2 and/or a framework region having the amino acid sequence TLE bound to the C-terminus of the CDR-L2.

The polypeptide (e.g., a single-chain polypeptide, antibody, antigen-binding fragment thereof, or construct thereof) may have a heavy chain variable domain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 2. In some embodiments, the heavy chain variable domain has an amino acid sequence that is at least 90% identical (e.g., at least 90%, 91%, 92%, 93%, 94%, 95%, 96%, 97%, 98%, 99%, 99.9%, or 100% identical) to the amino acid sequence of SEQ ID NO: 2. In some embodiments, the heavy chain variable domain has an amino acid sequence that is at least 95% identical (e.g., at least 95%, 96%, 97%, 98%, 99%, 99.9%, or 100% identical) to the amino acid sequence of SEQ ID NO: 2.

Additionally or alternatively, the polypeptide (e.g., a single-chain polypeptide, antibody, antigen-binding fragment thereof, or construct thereof) may have a light chain variable domain having an amino acid sequence that is at least 85% identical (e.g., at least 85%, 86%, 87%, 88%, 89%, 90%, 91%, 92%, 93%, 94%, 95%, 96%, 97%, 98%, 99%, 99.9%, or 100% identical) to the amino acid sequence of SEQ ID NO: 4. In some embodiments, the light chain variable domain has an amino acid sequence that is at least 90% identical (e.g., at least 90%, 91%, 92%, 93%, 94%, 95%, 96%, 97%, 98%, 99%, 99.9%, or 100% % identical) to the amino acid sequence of SEQ ID NO: 4. In some embodiments, the light chain variable domain has an amino acid sequence that is at least 95% identical (e.g., at least 95%, 96%, 97%, 98%, 99%, 99.9%, or 100% identical) to the amino acid sequence of SEQ ID NO: 4.

In some embodiments, the polypeptide (e.g., a single-chain polypeptide, antibody, antigen-binding fragment thereof, or construct thereof) specifically binds to a peptide having the amino acid sequence of any one of SEQ ID NOs: 11, 19, 20, and 34-117 with a $K_D$ of less than about 100 nM (e.g., with a $K_D$ of from about 10 pM to about 99 nM, such as a $K_D$ of from about 20 pM to about 80 nM, from about 30 pM to about 70 nM, from about 40 pM to about 60 nM, from about 50 pM to about 50 nM, from about 60 pM to about 40 nM, from about 70 pM to about 30 nM, from about 80 pM to about 20 nM, from about 90 pM to about 10 nM, or from about 100 pM to about 1 nM) and does not specifically bind a peptide containing amino acids 56-60 (KCSPG, SEQ ID NO: 12) of SEQ ID NO: 7. The polypeptide (e.g., a single-chain polypeptide, antibody, antigen-binding fragment thereof, or construct thereof) may bind the peptide having the amino acid sequence of any one of SEQ ID NOs: 11, 19, 20, and 34-117 with a $K_D$, e.g., of about 1 pM, 5 pM, 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM, 100 pM, 105 pM, 110 pM, 115 pM, 120 pM, 125 pM, 130 pM, 135 pM, 140 pM, 145 pM, 150 pM, 155 pM, 160 pM, 165 pM, 170 pM, 175 pM, 180 pM, 185 pM, 190 pM, 195 pM, 200 pM, 205 pM, 210 pM, 215 pM, 220 pM, 225 pM, 230 pM, 235 pM, 240 pM, 245 pM, 250 pM, 255 pM, 260 pM, 265 pM, 270 pM, 275 pM, 280 pM, 285 pM, 290 pM, 295 pM, 300 pM, 305 pM, 310 pM, 315 pM, 320 pM, 325 pM, 330 pM, 335 pM, 340 pM, 345 pM, 350 pM, 355 pM, 360 pM, 365 pM, 370 pM, 375 pM, 380 pM, 385 pM, 390 pM, 395 pM, 400 pM, 405 pM, 410 pM, 415 pM, 420 pM, 425 pM, 430 pM, 435 pM, 440 pM, 445 pM, 450 pM, 455 pM, 460 pM, 465 pM, 470 pM, 475 pM, 480 pM, 485 pM, 490 pM, 495 pM, 500 pM, 505 pM, 510 pM, 515 pM, 520 pM, 525 pM, 530 pM, 535 pM, 540 pM, 545 pM, 550 pM, 555 pM, 560 pM, 565 pM, 570 pM, 575 pM, 580 pM, 585 pM, 590 pM, 595 pM, 600 pM, 605 pM, 610 pM, 615 pM, 620 pM, 625 pM, 630 pM, 635 pM, 640 pM, 645 pM, 650 pM, 655 pM, 660 pM, 665 pM, 670 pM, 675 pM, 680 pM, 685 pM, 690 pM, 695 pM, 700 pM, 705 pM, 710 pM, 715 pM, 720 pM, 725 pM, 730 pM, 735 pM, 740 pM, 745 pM, 750 pM, 755 pM, 760 pM, 765 pM, 770 pM, 775 pM, 780 pM, 785 pM, 790 pM, 795 pM, 800 pM, 805 pM, 810 pM, 815 pM, 820 pM, 825 pM, 830 pM, 835 pM, 840 pM, 845 pM, 850 pM, 855 pM, 860 pM, 865 pM, 870 pM, 875 pM, 880 pM, 885 pM, 890 pM, 895 pM, 900 pM, 905 pM, 910 pM, 915 pM, 920 pM, 925 pM, 930 pM, 935 pM, 940 pM, 945 pM, 950 pM, 955 pM, 960 pM, 965 pM, 970 pM, 975 pM, 980 pM, 985 pM, 990 pM, 995 pM, 1 nM, 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 96 nM, 97 nM, 98 nM, or 99 nM, among other values.

The polypeptide (e.g., a single-chain polypeptide, antibody, antigen-binding fragment thereof, or construct thereof) may specifically bind TNFR2 at an epitope within:

(a) amino acids 142-146 of SEQ ID NO: 7 (KCRPG, SEQ ID NO: 19);

(b) amino acids 142-149 of SEQ ID NO: 7 (KCRPGFGV, SEQ ID NO: 20);

(c) amino acids 137-144 of SEQ ID NO: 7 (CAPLRKCR, SEQ ID NO: 11);

(d) amino acids 150-190 of SEQ ID NO: 7 (RPGTETSDVVCKPCAPGTFSNTTSSTDI-CRPHQICNVVAI, SEQ ID NO: 307);

(e) amino acids 161-169 of SEQ ID NO: 7 (CKP-CAPGTF, SEQ ID NO: 21);

(f) amino acids 75-128 of SEQ ID NO: 7 (CDSCED-STYTQLWNWVPECLSCGSRCSSDQVETQAC-TREQNRICTCRPGWYCAL, SEQ ID NO: 308), optionally in which the epitope is within amino acids 80-86 (DSTYTQL, SEQ ID NO: 8), 91-98 (PE-CLSCGS, SEQ ID NO: 9), or 116-123 (RICTCRPG, SEQ ID NO: 10) of SEQ ID NO: 7;

(g) amino acids 174-184 (SSTDICRPHQI, SEQ ID NO: 288) of SEQ ID NO: 7;

(h) amino acids 126-140 (CALSKQEGCRLCAPL, SEQ ID NO: 289) of SEQ ID NO: 7; and/or (i) amino acids 156-165 (TSDVVCKPCA, SEQ ID NO: 290) of SEQ ID NO: 7.

In some embodiments, the polypeptide (e.g., a single-chain polypeptide, antibody, antigen-binding fragment thereof, or construct thereof) specifically binds TNFR2 at two or more of the foregoing epitopes (e.g., at two, three, four, five, six, seven, eight, nine, ten, or more epitopes within the amino acid ranges set forth above).

In some embodiments, the polypeptide (e.g., a single-chain polypeptide, antibody, antigen-binding fragment thereof, or construct thereof) specifically binds TNFR2 with a $K_D$ of no greater than about 10 nM, such as a $K_D$ of no greater than about 1 nM. For example, the polypeptide (e.g., a single-chain polypeptide, antibody, antigen-binding fragment thereof, or construct thereof) may specifically bind TNFR2 with a $K_D$ of from about 1 pM to about 10 nM, such as a $K_D$ of about 1 pM, 5 pM, 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM, 100 pM, 105 pM, 110 pM, 115 pM, 120 pM, 125 pM, 130 pM, 135 pM, 140 pM, 145 pM, 150 pM, 155 pM, 160 pM, 165 pM, 170 pM, 175 pM, 180 pM, 185 pM, 190 pM, 195 pM, 200 pM, 205 pM, 210 pM, 215 pM, 220 pM, 225 pM, 230 pM, 235 pM, 240 pM, 245 pM, 250 pM, 255 pM, 260 pM, 265 pM, 270 pM, 275 pM, 280 pM, 285 pM, 290 pM, 295 pM, 300 pM, 305 pM, 310 pM, 315 pM, 320 pM, 325 pM, 330 pM, 335 pM, 340 pM, 345 pM, 350 pM, 355 pM, 360 pM, 365 pM, 370 pM, 375 pM, 380 pM, 385 pM, 390 pM, 395 pM, 400 pM, 405 pM, 410 pM, 415 pM, 420 pM, 425 pM, 430 pM, 435 pM, 440 pM, 445 pM, 450 pM, 455 pM, 460 pM, 465 pM, 470 pM, 475 pM, 480 pM, 485 pM, 490 pM, 495 pM, 500 pM, 505 pM, 510 pM, 515 pM, 520 pM, 525 pM, 530 pM, 535 pM, 540 pM, 545 pM, 550 pM, 555 pM, 560 pM, 565 pM, 570 pM, 575 pM, 580 pM, 585 pM, 590 pM, 595 pM, 600 pM, 605 pM, 610 pM, 615 pM, 620 pM, 625 pM, 630 pM, 635 pM, 640 pM, 645 pM, 650 pM, 655 pM, 660 pM, 665 pM, 670 pM, 675 pM, 680 pM, 685 pM, 690 pM, 695 pM, 700 pM, 705 pM, 710 pM, 715 pM, 720 pM, 725 pM, 730 pM, 735 pM, 740 pM, 745 pM, 750 pM, 755 pM, 760 pM, 765 pM, 770 pM, 775 pM, 780 pM, 785 pM, 790 pM, 795 pM, 800 pM, 805 pM, 810 pM, 815 pM, 820 pM, 825 pM, 830 pM, 835 pM, 840 pM, 845 pM, 850 pM, 855 pM, 860 pM, 865 pM, 870 pM, 875 pM, 880 pM, 885 pM, 890 pM, 895 pM, 900 pM, 905 pM, 910 pM, 915 pM, 920 pM, 925 pM, 930 pM, 935 pM, 940 pM, 945 pM, 950 pM, 955 pM, 960 pM, 965 pM, 970 pM, 975 pM, 980 pM, 985 pM, 990 pM, 995 pM, 1 nM, 5 nM, or 10 nM, among other values. In some embodiments, the polypeptide (e.g., a single-chain polypeptide, antibody, antigen-binding fragment thereof, or construct thereof) specifically binds TNFR2 with a $K_D$ of about 621 pM. In some embodiments, the polypeptide (e.g., a single-chain polypeptide, antibody, antigen-binding fragment thereof, or construct thereof) specifically binds TNFR2 with a $K_D$ of about 44 pM.

The polypeptide (e.g., a single-chain polypeptide, antibody, antigen-binding fragment thereof, or construct thereof) may specifically bind TNFR2 to form an antibody-antigen complex with a $k_{on}$ of at least about $10^4$ $M^{-1}s^{-1}$, such as a $k_{on}$ of from about $1\times10^4$ $M^{-1}s^{-1}$ to about $1\times10^8$ $M^{-1}s^{-1}$. For example, the polypeptide (e.g., a single-chain polypeptide, antibody, antigen-binding fragment thereof, or construct thereof) may specifically bind TNFR2 to form an antibody-antigen complex with a $k_{on}$ of about $1\times10^4$ $M^{-1}s^{-1}$, $2\times10^4$ $M^{-1}s^{-1}$, $3\times10^4$ $M^{-1}s^{-1}$, $4\times10^4$ $M^{-1}s^{-1}$, $5\times10^4$ $M^{-1}s^{-1}$, $6\times10^4$ $M^{-1}s^{-1}$, $7\times10^4$ $M^{-1}s^-$, $8\times10^4$ $M^{-1}s^{-1}$, $9\times10^4$ $M^{-1}s^{-1}$, $1\times10^5$ $M^{-1}s^{-1}$, $2\times10^5$ $M^{-1}s^{-1}$, $3\times10^5$ $M^{-1}s^{-1}$, $4\times10^5$ $M^{-1}s^{-1}$, $5\times10^5$ $M^{-1}s^{-1}$, $6\times10^5$ $M^{-1}s^{-1}$, $7\times10^5$ $M^{-1}s^{-1}$, $8\times10^5$ $M^{-1}s^{-1}$, $9\times10^5$ $M^{-1}s^{-1}$, $1\times10^6$ $M^{-1}s^{-1}$, $2\times10^6$ $M^{-1}s^{-1}$, $3\times10^6$ $M^{-1}s^{-1}$, $4\times10^6$ $M^{-1}s^{-1}$, $5\times10^6$ $M^{-1}s^{-1}$, $6\times10^6$ $M^{-1}s^{-1}$, $7\times10^6$ $M^{-1}s^{-1}$, $8\times10^6$ $M^{-1}s^{-1}$, $9\times10^6$ $M^{-1}s^{-1}$, $1\times10^7$ $M^{-1}s^{-1}$, $2\times10^7$ $M^{-1}s^{-1}$, $3\times10^7$ $M^{-1}s^{-1}$, $4\times10^7 M^{-1}s^{-1}$, $5\times10^7 M^{-1}s^{-1}$, $6\times10^7 M^{-1}s^{-1}$, $7\times10^7$ $M^{-1}s^{-1}$, $8\times10^7$ $M^{-1}s^{-1}$, $9\times10^7$ $M^{-1}s^{-1}$, or $1\times10^8$ $M^{-1}s^{-1}$. In some embodiments, the polypeptide (e.g., a single-chain polypeptide, antibody, antigen-binding fragment thereof, or construct thereof) specifically binds TNFR2 to form an antibody-antigen complex with a $k_{on}$ of about $4.9\times10^6$ $M^{-1}s^{-1}$. In some embodiments, the polypeptide (e.g., a single-chain polypeptide, antibody, antigen-binding fragment thereof, or construct thereof) specifically binds TNFR2 to form an antibody-antigen complex with a $k_{on}$ of about $3.6\times10^5$ $M^{-1}s^{-1}$.

The polypeptide (e.g., a single-chain polypeptide, antibody, antigen-binding fragment thereof, or construct thereof) may specifically bind TNFR2 to form an antibody-antigen complex that dissociates with a $k_{off}$ of, for example, no greater than about $10^{-3}$ $s^{-1}$, such as a $k_{off}$ of from about $10^{-6}$ $s^{-1}$ to about $10^{-3}$ $s^{-1}$ (e.g., a $k_{off}$ of about $1\times10^{-6}$ $s^{-1}$, $2\times10^{-6}$ $s^{-1}$, $3\times10^{-6}$ $s^{-1}$, $4\times10^{-6}$ $s^{-1}$, $5\times10^{-6}$ $s^{-1}$, $6\times10^{-6}$ $s^{-1}$, $7\times10^{-6}$ $s^{-1}$, $8\times10^{-6}$ $s^{-1}$, $9\times10^{-6}$ $s^{-1}$, $1\times10^{-5}$ $s^{-1}$, $2\times10^{-5}$ $s^{-1}$, $3\times10^{-5}$ $s^{-1}$, $4\times10^{-5}$ $s^{-1}$, $5\times10^{-5}$ $s^{-1}$, $6\times10^{-5}$ $s^{-1}$, $7\times10^{-5}$ $s^{-1}$, $8\times10^{-5}$ $s^{-1}$, $9\times10^{-5}$ $s^{-1}$, $1\times10^{-4}$ $s^{-1}$, $2\times10^{-4}$ $s^{-1}$, $3\times10^{-4}$ $s^{-1}$, $4\times10^{-4}$ $s^{-1}$, $5\times10^{-4}$ $s^{-1}$, $6\times10^{-4}$ $s^{-1}$, $7\times10^{-4}$ $s^{-1}$, $8\times10^{-4}$ $s^{-1}$, $9\times10^{-4}$ $s^{-1}$, or $1\times10^{-3}$ $s^{-1}$. In some embodiments, the antibody-antigen complex dissociates with a $k_{off}$ of about $2.2\times10^{-4}$ $s^{-1}$.

Polypeptides, such as single-chain polypeptides, antibodies, antigen-binding fragments thereof, and constructs thereof, described herein may inhibit TNFR2 signaling, e.g., in a cell that expresses TNFR2, such as a T-reg cell (e.g., a T-reg cell that expresses CD25$^{Hi}$), myeloid-derived suppressor cell (MDSC), and/or a TNFR2+ cancer cell. In some embodiments, the single-chain polypeptide, antibody, or antigen-binding fragment thereof reduces or inhibits the expression of one or more genes selected from the group consisting of CHUK, NFKBIE, NFKBIA, MAP3K11, TRAF2, TRAF3, relB, and cIAP2/BIRC3, as assessed, for example, by observing a decrease in the expression of one or more of the above genes or by other methods known in the art for assessing gene activation. For instance, antagonistic TNFR2 single-chain polypeptides, antibodies, antigen-binding fragments thereof, and constructs thereof may inhibit the expression or post-translational modification (e.g., phosphorylation) of one or more of CHUK, NFKBIE, NFKBIA, MAP3K11, TRAF2, TRAF3, relB, or cIAP2/BIRC3, e.g., by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% relative to the expression or post-translational modification (e.g., phosphorylation) of one or more of these proteins isolated from a sample not treated with an antagonistic TNFR2 single-chain polypeptide, antibody, antigen-binding fragment thereof, or construct thereof described herein. Exemplary assays that can be used to determine expression level and phosphorylation state are known in the art and include, e.g., Western blot assays to determine protein content and quantitative reverse transcription polymerase chain reaction (RT-PCR) experiments to determine mRNA content. In preferred embodiments, anti-TNFR2 polypeptides (e.g., single-chain polypeptides, antibodies, antigen-binding fragments thereof, and constructs thereof) are dominant TNFR2 antagonists and are, thus, capable of inhibiting TNFR2 activation even in the presence of a TNFR2 agonist (such as, e.g., TNFα or *Bacillus* Calmette-Guérin (BCG)) or a growth-promoting agent, such as IL-2.

Antagonistic TNFR2 polypeptides (e.g., single-chain polypeptides, antibodies, antigen-binding fragments thereof, and constructs thereof) described herein may exhibit one or more, or all, of the following properties:

(a) Suppression of the proliferation of, and/or direct killing of, T-reg cells (e.g., thereby reducing the quantity of T-reg cells in a population of cells by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, or 100%, relative to a population of cells not exposed to the polypeptide), for instance, by binding and inactivating TNFR2 on the T-reg cell surface;

(b) Suppression of the proliferation of, and/or direct killing of, MDSCs (e.g., thereby reducing the quantity of MDSCs in a population of cells by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, or 100%, relative to a population of cells not exposed to the polypeptide), for instance, by binding and inactivating TNFR2 on the MDSC surface;

(c) Promotion of the expansion of T effector cells, such as CD8+ T cells (e.g., thereby increasing the quantity of CD8+ effector T cells in a population of cells by about 1.1-fold, 1.2-fold, 1.3-fold, 1.4-fold, 1.5-fold, 1.6-fold, 1.7-fold, 1.8-fold, 1.9-fold, 2-fold, 2.1-fold, 2.2-fold, 2.3-fold, 2.4-fold, 2.5-fold, 2.6-fold, 2.7-fold, 2.8-fold, 2.9-fold, 3-fold, 3.1-fold, 3.2-fold, 3.3-fold, 3.4-fold, 3.5-fold, 3.6-fold, 3.7-fold, 3.8-fold, 3.9-fold, 4-fold, 4.1-fold, 4.2-fold, 4.3-fold, 4.4-fold, 4.5-fold, 4.6-fold, 4.7-fold, 4.8-fold, 4.9-fold, 5-fold, 5.1-fold, 5.2-fold, 5.3-fold, 5.4-fold, 5.5-fold, 5.6-fold, 5.7-fold, 5.8-fold, 5.9-fold, 6-fold, 6.1-fold, 6.2-fold, 6.3-fold, 6.4-fold, 6.5-fold, 6.6-fold, 6.7-fold, 6.8-fold, 6.9-fold, 7-fold, 7.1-fold, 7.2-fold, 7.3-fold, 7.4-fold, 7.5-fold, 7.6-fold, 7.7-fold, 7.8-fold, 7.9-fold, 8-fold, 8.1-fold, 8.2-fold, 8.3-fold, 8.4-fold, 8.5-fold, 8.6-fold, 8.7-fold, 8.8-fold, 8.9-fold, 9-fold, 9.1-fold, 9.2-fold, 9.3-fold, 9.4-fold, 9.5-fold, 9.6-fold, 9.7-fold, 9.8-fold, 9.9-fold, 10-fold, 20-fold, 30-fold, 40-fold, 50-fold, 60-fold, 70-fold, 80-fold, 90-fold, 100-fold, or more, relative to a population of cells not exposed to the polypeptide); and/or (d) Suppression of the proliferation of, and/or direct killing of, TNFR2-expressing cancer cells, such as a Hodgkin's lymphoma cell, a cutaneous non-Hodgkin's lymphoma cell, a T cell lymphoma cell, an ovarian cancer cell, a colon cancer cell, a multiple myeloma cell, a renal cell carcinoma cell, a skin cancer cell, a lung cancer cell, a liver cancer cell, an endometrial cancer cell, a hematopoietic or lymphoid cancer cell, a central nervous system cancer cell, a breast cancer cell, a pancreatic cancer cell, a stomach cancer cell, an esophageal cancer cell, and an upper gastrointestinal cancer cell (e.g., thereby reducing the quantity of TNFR2-expressing cancer cells in a population of cells by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, or 100%, relative to a population of cells not exposed to the polypeptide).

For example, an antagonistic TNFR2 polypeptide, such as a single-chain polypeptide, antibody, antigen-binding fragment thereof, and construct thereof, described herein can be used to reduce the total quantity of T-reg or cancer cells in a patient (such as a human patient) or within a sample (e.g., a sample isolated from a patient, such as a human patient undergoing treatment for cancer or an infectious disease as described herein) relative to a patient or sample, respectively, not treated with the polypeptide.

In some embodiments, the antagonistic TNFR2 polypeptide (e.g., a single-chain polypeptide, antibody, or antigen-binding fragment thereof) reduces expression of TNFR2, e.g., by a T-reg cell or a cancer cell (such as a TNFR2+ cancer cell, e.g., a Hodgkin's lymphoma cell, a cutaneous non-Hodgkin's lymphoma cell, a T cell lymphoma cell, an ovarian cancer cell, a colon cancer cell, a multiple myeloma cell, a renal cell carcinoma cell, a skin cancer cell, a lung cancer cell, a liver cancer cell, an endometrial cancer cell, a hematopoietic or lymphoid cancer cell, a central nervous system cancer cell, a breast cancer cell, a pancreatic cancer cell, a stomach cancer cell, an esophageal cancer cell, or an upper gastrointestinal cancer cell), and/or the secretion of soluble TNFR2 by one or more of the foregoing cells.

An antagonistic TNFR2 polypeptide (e.g., a single-chain polypeptide, antibody, antigen-binding fragment thereof, and construct thereof) described herein can be used to inhibit or reduce the proliferation of, or reduce the total quantity of, T-reg cells in a patient (e.g., a human patient) or in a sample (e.g., a sample isolated from a human patient undergoing treatment for cancer or an infectious disease as described herein).

An antagonistic TNFR2 polypeptide (e.g., a single-chain polypeptide, antibody, antigen-binding fragment thereof, and construct thereof) described herein can be used to inhibit or reduce the proliferation of, and/or to directly kill, T-reg cells (e.g., activated T-reg cells that express CD25$^{Hi}$) and/or cancer cells that express TNFR2. For instance, the cancer cells may be selected from the group consisting of a Hodgkin's lymphoma cell, a cutaneous non-Hodgkin's lymphoma cell, a T cell lymphoma cell, an ovarian cancer cell, a colon cancer cell, a multiple myeloma cell, a renal cell carcinoma cell, a skin cancer cell, a lung cancer cell, a liver cancer cell, an endometrial cancer cell, a hematopoietic or lymphoid cancer cell, a central nervous system cancer cell, a breast cancer cell, a pancreatic cancer cell, a stomach cancer cell, an esophageal cancer cell, or an upper gastrointestinal cancer cell. Without being limited by mechanism, binding of TNFR2 on the cancer cell may inhibit or reduce proliferation of the cancer cell and/or may directly kill the cancer cell, such as by promoting apoptosis of the cancer cell.

Antagonistic TNFR2 polypeptides (e.g., single-chain polypeptides, antibodies, antigen-binding fragments thereof, and constructs thereof) described herein bind TNFR2 on the surface of a MDSC (e.g., a cell that expresses all or a subset of proteins and small molecules selected from the group consisting of B7-1 (CD80), B7-H1 (PD-L1), CCR2, CD1d, CD1d1, CD2, CD31 (PECAM-1), CD43, CD44, complement component C5a R1, F4/80 (EMR1), Fcγ RIII (CD16), Fcγ RII (CD32), Fcγ RIIA (CD32a), Fcγ RIIB (CD32b), Fcγ RIIB/C (CD32b/c), Fcγ RIIC (CD32c), Fcγ RIIIA (CD16A), Fcγ RIIIB (CD16b), galectin-3, GP130, Gr-1 (Ly-6G), ICAM-1 (CD54), IL-1RI, IL-4Ra, IL-6Rα, integrin α4 (CD49d), integrin αL (CD11a), integrin αM (CD11b), M-CSFR, MGL1 (CD301a), MGL1/2 (CD301a/b), MGL2 (CD301b), nitric oxide, PSGL-1 (CD162), L-selectin (CD62L), siglec-3 (CD33), transferrin receptor (TfR), VEGFR1 (Fit-1), and VEGFR2 (KDR or Flk-1)). Particularly, MDSCs do not express proteins selected from the group consisting of B7-2 (CD86), B7-H4, CD11c, CD14, CD21, CD23 (FcεRII), CD34, CD35, CD40 (TNFRSF5), CD117 (c-kit), HLA-DR, and Sca-1 (Ly6). Binding of TNFR2 on the MDSC may inhibit or reduce proliferation of the MDSC and/or may directly kill the MDSC, such as by promoting apoptosis of the MDSC. Polypeptides, such as single-chain polypeptides, antibodies, antigen-binding fragments thereof, and constructs thereof, described herein may not require TNFα to inhibit the proliferation of T-reg cells, cancer cells (e.g., TNFR2-expressing cancer cells), and/or MDSCs.

In some embodiments, the polypeptides described herein, such as single-chain polypeptides, antibodies, antigen-binding fragments thereof, and constructs thereof, inhibit the proliferation of, and/or directly kill, T-reg cells with a greater potency in a patient suffering from cancer relative to a subject that does not have cancer. In some embodiments, the polypeptides described herein, such as single-chain polypeptides, antibodies, antigen-binding fragments thereof, and constructs thereof, inhibit the proliferation of, and/or directly kill, T-reg cells with a greater potency in the microenvironment of a tumor relative to a site that is free of cancer cells, such as a site distal from a tumor in a patient suffering from cancer.

For example, in some embodiments, the polypeptides described herein, such as single-chain polypeptides, antibodies, antigen-binding fragments thereof, and constructs thereof, inhibit the proliferation of, and/or directly kill, T-reg cells with a potency that is greater in the microenvironment of a tumor than in a site that is free of cancer cells, such as a site distal from a tumor in a patient suffering from cancer, or relative to a subject without cancer. For instance, the polypeptides described herein, such as single-chain polypeptides, antibodies, antigen-binding fragments thereof, and constructs thereof, may exhibit an $IC_{50}$ for inhibiting the proliferation of T-reg cells in a tumor microenvironment that is less than the $IC_{50}$ of the polypeptides for inhibiting the proliferation of T-reg cells in a site that is free of cancer cells by, for example, 1.1-fold, 1.2-fold, 1.3-fold, 1.4-fold, 1.5- fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 1,000-fold, 10,000-fold, or more. The polypeptides described herein, such as single-chain polypeptides, antibodies, antigen-binding fragments thereof, and constructs thereof, may inhibit the proliferation of T-reg cells with a potency that is greater in the microenvironment of a tumor containing T cell lymphoma cells (e.g., Hodgkin's or cutaneous non-Hodgkin's lymphoma cells), ovarian cancer cells, colon cancer cells, multiple myeloma cells, or renal cell carcinoma cells than in a site that is free of such cancer cells, such as a site distal from a tumor in a patient suffering from one or more of the foregoing cancers, or relative to a subject without cancer.

In some embodiments, the polypeptides described herein, such as single-chain polypeptides, antibodies, antigen-binding fragments thereof, and constructs thereof, inhibit or reduce the proliferation of, and/or directly kill, MDSCs with a greater potency in a patient suffering from cancer relative to a subject that does not have cancer. In some embodiments, the polypeptides described herein, such as single-chain polypeptides, antibodies, antigen-binding fragments thereof, and constructs thereof, inhibit or reduce the proliferation of, and/or directly kill, MDSCs with a greater potency in the microenvironment of a tumor relative to a site that is free of cancer cells, such as a site distal from a tumor in a patient suffering from cancer, or relative to a subject without cancer.

For example, antagonistic TNFR2 polypeptides (e.g., single-chain polypeptides, antibodies, antigen-binding fragments thereof, and constructs thereof) described herein may bind TNFR2 on the surface of a MDSC present within the microenvironment of a tumor, and may inhibit or reduce proliferation of the MDSC or may promote the apoptosis of the MDSC with a potency that is greater in the microenvironment of a tumor than at a site that is free of cancer cells, such as a site distal from a tumor in a patient suffering from cancer, or relative to a subject without cancer. For instance, the polypeptides described herein, such as single-chain polypeptides, antibodies, antigen-binding fragments thereof, and constructs thereof, may exhibit an $IC_{50}$ for inhibiting the proliferation of MDSCs in a tumor microenvironment that is less than the $IC_{50}$ of the polypeptides for inhibiting the proliferation of MDSCs in a site that is free of cancer cells by, for example, 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 1,000-fold, 10,000-fold, or more. The polypeptides described herein, such as single-chain polypeptides, antibodies, antigen-binding fragments thereof, and constructs thereof, may inhibit the proliferation of MDSCs or may promote the apoptosis of MDSCs with a potency that is greater in the microenvironment of a tumor containing T cell lymphoma cells (e.g., Hodgkin's or cutaneous non-Hodgkin's lymphoma cells), ovarian cancer cells, colon cancer cells, multiple myeloma cells, or renal cell carcinoma cells than in a site that is free of such cancer cells, such as a site distal from a tumor in a patient suffering from one or more of the foregoing cancers, or relative to a subject without cancer.

In some embodiments, the polypeptides described herein, such as single-chain polypeptides, antibodies, antigen-binding fragments thereof, and constructs thereof, expand T effector cells, such as CD8+ cytotoxic T cells, with a greater potency in a patient suffering from cancer relative to a subject that does not have cancer. In some embodiments, the polypeptides described herein, such as single-chain polypeptides, antibodies, antigen-binding fragments thereof, and constructs thereof, expand T effector cells, such as CD8+ cytotoxic T cells, with a greater potency in the microenvironment of a tumor relative to a site that is free of cancer cells, such as a site distal from a tumor in a patient suffering from cancer, or relative to a subject without cancer.

For instance, in some embodiments, the polypeptides described herein, such as single-chain polypeptides, antibodies, antigen-binding fragments thereof, and constructs thereof, directly expand T effector cells, such as CD8+ cytotoxic T cells, with a potency that is greater in the microenvironment of a tumor than in a site that is free of cancer cells, such as a site distal from a tumor in a patient suffering from cancer, or relative to a subject without cancer. For instance, the polypeptides described herein may have an $EC_{50}$ for expanding T effector cells in a cancer patient that is less than the $EC_{50}$ of the polypeptides for expanding T effector cells in a subject without cancer by, for example, 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 1,000-fold, 10,000-fold, or more. The polypeptides described herein, such as single-chain polypeptides, antibodies, antigen-binding fragments thereof, and constructs thereof, may directly expand T effector cells, such as CD8+ cytotoxic T cells, with a potency that is greater in the microenvironment of a tumor containing T cell lymphoma cells (e.g., Hodgkin's or cutaneous non-Hodgkin's lymphoma cells), ovarian cancer cells, colon cancer cells, multiple myeloma cells, or renal cell carcinoma cells than in a site that is free of such cancer cells, such as a site distal from a tumor in a patient suffering from one or more of the foregoing cancers or in a subject without cancer. In some embodiments, the T effector cells (e.g., CD8+ cytotoxic T cells) specifically react with an antigen present on one or more cancer cells, such as Hodgkin's lymphoma cells, cutaneous non-Hodgkin's lymphoma cells, T cell lymphoma cells, ovarian cancer cells, colon cancer cells, multiple myeloma cells, or renal cell carcinoma cells.

In some embodiments, the polypeptide is a human IgG2 isotype antibody or antigen-binding fragment thereof. Additionally or alternatively, the polypeptide may be an antibody or antigen-binding fragment thereof selected from the group consisting of a monoclonal antibody or antigen-binding fragment thereof, a polyclonal antibody or antigen-binding fragment thereof, a human antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a F(ab')$_2$ molecule, and a tandem scFv (taFv). In some embodiments, the antibody or antigen-binding fragment thereof contains two or more CDRs covalently bound to one another, e.g., by an amide bond, a thioether bond, a carbon-carbon bond, or a disulfide bridge, or by a linker, such as a linker described herein. In some embodiments, the antibody or antigen-binding fragment thereof is a human, humanized, or chimeric antibody or antigen-binding fragment thereof.

In some embodiments, the polypeptide (e.g., a single-chain polypeptide, antibody, antigen-binding fragment thereof, or construct thereof) is conjugated to a therapeutic agent, such as a cytotoxic agent (e.g., a cytotoxic agent described herein).

The antagonistic TNFR2 antibody of any of the above aspects can be a bispecific antibody, such as a bispecific monoclonal antibody, in which one arm of the antibody specifically binds TNFR2 and the other specifically binds an immune checkpoint protein, such as PD-1, PD-L1, or CTLA-4, among others described herein. The arm of the bispecific antibody that specifically binds TNFR2 may specifically bind, for example, an epitope of human TNFR2 defined by one or more amino acids within CRD3 and/or an epitope defined by one or more amino acids within CRD4. In some embodiments, the arm of the bispecific antibody that specifically binds TNFR2 specifically binds an epitope of human TNFR2 selected from:

(a) amino acids 142-146 of SEQ ID NO: 7 (KCRPG, SEQ ID NO: 19);

(b) amino acids 142-149 of SEQ ID NO: 7 (KCRPGFGV, SEQ ID NO: 20);

(c) amino acids 137-144 of SEQ ID NO: 7 (CAPLRKCR, SEQ ID NO: 11);

(d) amino acids 150-190 of SEQ ID NO: 7 (RPGTETSDVVCKPCAPGTFSNTTSSTDI-CRPHQICNVVAI, SEQ ID NO: 307);

(e) amino acids 161-169 of SEQ ID NO: 7 (CKPCAPGTF, SEQ ID NO: 21);

(f) amino acids 75-128 of SEQ ID NO: 7 (CDSCED-STYTQLWNWVPECLSCGSRCSSDQVETQAC-TREQNRICTCRPGWYCAL, SEQ ID NO: 308), optionally in which the epitope is within amino acids 80-86 (DSTYTQL, SEQ ID NO: 8), 91-98 (PE-CLSCGS, SEQ ID NO: 9), or 116-123 (RICTCRPG, SEQ ID NO: 10) of SEQ ID NO: 7;

(g) amino acids 174-184 (SSTDICRPHQI, SEQ ID NO: 288) of SEQ ID NO: 7;

(h) amino acids 126-140 (CALSKQEGCRLCAPL, SEQ ID NO: 289) of SEQ ID NO: 7; and (i) amino acids 156-165 (TSDVVCKPCA, SEQ ID NO: 290) of SEQ ID NO: 7.

In some embodiments, the bispecific antibody contains one arm that specifically binds TNFR2, such as an epitope of human TNFR2 described above, and one arm that specifically binds an immune checkpoint protein specifically binds PD-1. In some embodiments, the arm of the bispecific antibody that specifically binds PD-1 may specifically bind the same epitope(s) on PD-1 as nivolumab, pembrolizumab, avelumab, durvalumab, or atezolizumab. For example, the arm of the bispecific antibody that specifically binds PD-1 may competitively inhibit the binding of PD-1 to nivolumab, pembrolizumab, avelumab, durvalumab, and/or atezolizumab, as assessed, for example, using a competitive binding assay described herein or know in the art, such as a competitive ELISA.

In some embodiments, the bispecific antibody contains one arm that specifically binds TNFR2, such as an epitope of human TNFR2 described above, and one arm that specifically binds PD-L1. In some embodiments, the arm of the bispecific antibody that specifically binds PD-L1 may specifically bind the same epitope(s) on PD-L1 as atezolizumab or avelumab. For example, the arm of the bispecific antibody that specifically binds PD-L1 may competitively inhibit the binding of PD-L1 to atezolizumab and/or avelumab, for example, using a competitive binding assay described herein or know in the art, such as a competitive ELISA.

In some embodiments, the bispecific antibody contains one arm that specifically binds TNFR2, such as an epitope of human TNFR2 described above, and one arm that specifically binds CTLA-4. In some embodiments, the arm of the bispecific antibody that specifically binds CTLA-4 may specifically bind the same epitope(s) on CTLA-4 as ipilimumab or tremelimumab. For example, the arm of the bispecific antibody that specifically binds CTLA-4 may competitively inhibit the binding of CTLA-4 to ipilimumab and/or tremelimumab, as assessed, for example, using a competitive binding assay described herein or know in the art, such as a competitive ELISA.

A second aspect features a construct containing a first polypeptide domain and a second polypeptide domain. The first polypeptide domain and the second polypeptide domain are each, independently, an antigen-binding fragment of the first aspect or any of the embodiments thereof. The first polypeptide domain and the second polypeptide domain may be bound to one another, for example, by a covalent linker, such as a linker that contains (e.g., is) an amide bond or a disulfide bond.

A third aspect features a polynucleotide encoding the polypeptide (e.g., a single-chain polypeptide, antibody, antigen-binding fragment thereof, or construct thereof) of the first aspect and/or the construct of the second aspect or any of the embodiments thereof.

A fourth aspect features a vector encoding the polynucleotide of the third aspect. The vector may be an expression vector, such as a eukaryotic expression vector. In some embodiments, the vector is a viral vector, such as an adenovirus (e.g., a serotype 1-57 adenovirus, such as a serotype 2, 5, 11, 12, 24, 26, 34, 35, 40, 48, 49, 50, 52, or Pan9 adenovirus), retrovirus (e.g., a γ-retrovirus or a lentivirus), poxvirus, adeno-associated virus, baculovirus, herpes simplex virus, or a vaccinia virus (e.g., a modified vaccinia Ankara virus).

A fifth aspect features an isolated host cell containing the polynucleotide of the third aspect and/or the vector of the fourth aspect. The host cell may be a prokaryotic cell or a eukaryotic cell, such as a mammalian cell (e.g., a Chinese hamster ovary (CHO) cell). The host cell may be one that is described, e.g., in Dinnis and James, Biotechnology and Bioengineering 91:180-189, 2005, the disclosure of which is incorporated herein by reference.

A sixth aspect features a pharmaceutical composition containing a polypeptide (e.g., a single-chain polypeptide, antibody, antigen-binding fragment thereof, or construct thereof) that specifically binds human TNFR2 and exhibits an antagonistic effect on TNFR2 activity upon the binding. The polypeptide may be, for example, an antibody or antigen-binding fragment of the first aspect or any of the embodiments thereof. Additionally or alternatively, the antibody or antigen-binding fragment thereof may be one that specifically binds human TNFR2 at an epitope within CRD3 and/or CRD4 and does not bind TNFR2 at an epitope defined by one or more amino acids within CRD1, in which at least 10% of the antibody or antigen-binding fragment thereof in the pharmaceutical composition is present in a single disulfide-bonded isoform, such as the IgG2-A or IgG2-B disulfide-bonded isoform. In some embodiments, about 10% to about 99.999% of the antibody or antigen-binding fragment thereof in the pharmaceutical composition is present in a single disulfide-bonded isoform, such as from about 11% to about 99.9%, about 12% to about 99.9%, 13% to about 99.9%, about 14% to about 99.9%, about 15% to about 99%, about 16% to about 99.9%, about 17% to about 99.9%, about 18% to about 99.9%, about 19% to about 99.9%, about 20% to about 99.9%, about 21% to about 99.9%, about 22% to about 99.9%, about 23% to about 99.9%, about 24% to about 99.9%, about 25% to about 99.9%, about 26% to about 99.9%, about 27% to about 99.9%, about 28% to about 99.9%, about 29% to about 99.9%, about 30% to about 99.9%, about 31% to about 99.9%, about 32% to about 99.9%, about 33% to about 99.9%, about 34% to about 99.9%, about 35% to about 99.9%, about 36% to about 99.9%, about 37% to about 99.9%, about 38% to about 99.9%, about 39% to about 99.9%, about 40% to about 99.9%, about 41% to about 99.9%, about 42% to about 99.9%, about 43% to about 99.9%, about 44% to about 99.9%, about 45% to about 99.9%, about 46% to about 99.9%, about 47% to about 99.9%, about 48% to about 99.9%, about 49% to about 99.9%, about 50% to about 99.9%, about 51% to about 99.9%, about 52% to about 99.9%, about 53% to about 99.9%, about 54% to about 99.9%, about 55% to about 99.9%, about 56% to about 99.9%, about 57% to about 99.9%, about 58% to about 99.9%, about 59% to about 99.9%, about 60% to about 99.9%, about 61% to about 99.9%, about 62% to about 99.9%, about 63% to about 99.9%, about 64% to about 99.9%, about 65% to about 99.9%, about 66% to about 99.9%, about 67% to about 99.9%, about 68% to about 99.9%, about 69% to about 99.9%, about 70% to about 99.9%, about 71% to about 99.9%, about 72% to about 99.9%, about 73% to about 99.9%, about 74% to about 99.9%, about 75% to about 99.9%, about 76% to about 99.9%, about 77% to about 99.9%, about 78% to about 99.9%, about 79% to about 99.9%, about 80% to about 99.9%, about 81% to about 99.9%, about 82% to about 99.9%, about 83% to about 99.9%, about 84% to about 99.9%, about 85% to about 99.9%, about 86% to about 99.9%, about 87% to about 99.9%, about 88% to about 99.9%, about 89% to about 99.9%, about 90% to about 99.9%, about 91% to about 99.9%, about 92% to about 99.9%, about 93% to about 99.9%, about 94% to about 99.9%, about 95% to about 99.9%, about 96% to about 99.9%, about 97% to about 99.9%, about 98% to about 99.9%, or about 99% to about 99.99% of the antibody or antigen-binding fragment thereof.

In some embodiments, at least about 10% of the antibody or antigen-binding fragment thereof in the pharmaceutical composition is present in a single disulfide-bonded isoform. In some embodiments, at least about 15% of the antibody or antigen-binding fragment thereof in the pharmaceutical composition is present in a single disulfide-bonded isoform. In some embodiments, at least about 20% of the antibody or antigen-binding fragment thereof in the pharmaceutical composition is present in a single disulfide-bonded isoform. In some embodiments, at least about 25% of the antibody or antigen-binding fragment thereof in the pharmaceutical composition is present in a single disulfide-bonded isoform. In some embodiments, at least about 30% of the antibody or antigen-binding fragment thereof in the pharmaceutical composition is present in a single disulfide-bonded isoform. In some embodiments, at least about 35% of the antibody or antigen-binding fragment thereof in the pharmaceutical composition is present in a single disulfide-bonded isoform. In some embodiments, at least about 40% of the antibody or antigen-binding fragment thereof in the pharmaceutical composition is present in a single disulfide-bonded isoform. In some embodiments, at least about 45% of the antibody or antigen-binding fragment thereof in the pharmaceutical composition is present in a single disulfide-bonded isoform. In some embodiments, at least about 50% of the antibody or antigen-binding fragment thereof in the pharmaceutical composition is present in a single disulfide-bonded isoform. In some embodiments, at least about 60% of the antibody or antigen-binding fragment thereof in the pharmaceutical composition is present in a single disulfide-bonded isoform. In some embodiments, at least about 65% of the antibody or antigen-binding fragment thereof in the pharmaceutical composition is present in a single disulfide-bonded isoform. In some embodiments, at least about 70% of the antibody or antigen-binding fragment thereof in the pharmaceutical composition is present in a single disulfide-bonded isoform. In some embodiments, at least about 75% of the antibody or antigen-binding fragment thereof in the pharmaceutical composition is present in a single disulfide-bonded isoform. In some embodiments, at least about 80% of the antibody or antigen-binding fragment thereof in the pharmaceutical composition is present in a single disulfide-bonded isoform. In some embodiments, at least about 85% of the antibody or antigen-binding fragment thereof in the pharmaceutical composition is present in a single disulfide-bonded isoform. In some embodiments, at least about 90% of the antibody or antigen-binding fragment thereof in the pharmaceutical composition is present in a single disulfide-bonded isoform. In some embodiments, at least about 95% of the antibody or antigen-binding fragment thereof in the pharmaceutical composition is present in a single disulfide-bonded isoform. In some embodiments, at least about 96% of the antibody or antigen-binding fragment thereof in the pharmaceutical composition is present in a single disulfide-bonded isoform. In some embodiments, at least about 97% of the antibody or antigen-binding fragment thereof in the pharmaceutical composition is present in a single disulfide-bonded isoform. In some embodiments, at least about 98% of the antibody or antigen-binding fragment thereof in the pharmaceutical composition is present in a single disulfide-bonded isoform. In some embodiments, at least about 99% of the antibody or antigen-binding fragment thereof in the pharmaceutical composition is present in a single disulfide-bonded isoform. In some embodiments, at least about 99.9% of the antibody or antigen-binding fragment thereof in the pharmaceutical composition is present in a single disulfide-bonded isoform.

In some embodiments, the antibody or antigen-binding fragment thereof yields only a single detectable band upon gel electrophoresis analysis performed under non-reducing conditions.

In some embodiments, the single disulfide-bonded isoform of the antibody or antigen-binding fragment is IgG2-A, as described herein. In some embodiments, the single disulfide-bonded isoform of the antibody or antigen-binding fragment is IgG2-B, as described herein.

Additionally or alternatively, the pharmaceutical composition may contain the construct of the second aspect or any embodiments thereof, the polynucleotide of the third aspect or any embodiments thereof, the vector of the fourth aspect or any embodiments thereof, and/or the host cell of the fifth aspect or any embodiments thereof. The pharmaceutical composition may further contain a pharmaceutically acceptable carrier or excipient.

In some embodiments, the polypeptide (e.g., a single-chain polypeptide, antibody, antigen-binding fragment thereof, or construct thereof) is present in the pharmaceutical composition in an amount of from about 0.001 mg/ml to about 100 mg/ml, such as an amount of from about 0.01 mg/ml to about 10 mg/ml.

The pharmaceutical composition may further contain an additional therapeutic agent, such as an immunotherapy agent. In some embodiments, the immunotherapy agent is selected from the group consisting of an anti-CTLA-4 agent, an anti-PD-1 agent, an anti-PD-L1 agent, an anti-PD-L2 agent, a TNF-α cross-linking agent, a TRAIL cross-linking agent, an anti-CD27 agent, an anti-CD30 agent, an anti-CD40 agent, an anti-4-1BB agent, an anti-GITR agent, an anti-OX40 agent, an anti-TRAILR1 agent, an anti-TRAILR2 agent, an anti-TWEAK agent, an anti-TWEAKR agent, an anti-cell surface lymphocyte protein agent, an anti-BRAF agent, an anti-MEK agent, an anti-CD33 agent, an anti-CD20 agent, an anti-HLA-DR agent, an anti-HLA class I agent, an anti-CD52 agent, an anti-A33 agent, an anti-GD3 agent, an anti-PSMA agent, an anti-Ceacan 1 agent, an anti-Galedin 9 agent, an anti-HVEM agent, an anti-VISTA agent, an anti-B7 H4 agent, an anti-HHLA2 agent, an anti-CD155 agent, an anti-CD80 agent, an anti-BTLA agent, an anti-CD160 agent, an anti-CD28 agent, an anti-CD226 agent, an anti-CEACAM1 agent, an anti-TIM3 agent, an anti-TIGIT agent, an anti-CD96 agent, an anti-CD70 agent, an anti-CD27 agent, an anti-LIGHT agent, an anti-CD137 agent, an anti-DR4 agent, an anti-CR5 agent, an anti-TNFRS agent, an anti-TNFR1 agent, an anti-FAS agent, an anti-CD95 agent, an anti-TRAIL agent, an anti-DR6 agent, an anti-EDAR agent, an anti-NGFR agent, an anti-OPG agent, an anti-RANKL agent, an anti-LTβ receptor agent, an anti-BCMA agent, an anti-TACI agent, an anti-BAFFR agent, an anti-EDAR2 agent, an anti-TROY agent, and an anti-RELT agent. For example, the immunotherapy agent may be an anti-CTLA-4 agent, an anti-PD-1 agent, or an anti-PD-L1 agent.

In some embodiments, the immunotherapy agent is selected from the group consisting of an anti-CTLA-4 antibody or antigen-binding fragment thereof, an anti-PD-1 antibody or antigen-binding fragment thereof, an anti-PD-L1 antibody or antigen-binding fragment thereof, an anti-PD-L2 antibody or antigen-binding fragment thereof, a TNF-α cross-linking antibody or antigen-binding fragment thereof, a TRAIL cross-linking antibody or antigen-binding fragment thereof, an anti-CD27 antibody or antigen-binding fragment thereof, an anti-CD30 antibody or antigen-binding fragment thereof, an anti-CD40 antibody or antigen-binding fragment thereof, an anti-4-1BB antibody or antigen-binding fragment thereof, an anti-GITR antibody or antigen-binding fragment thereof, an anti-OX40 antibody or antigen-binding fragment thereof, an anti-TRAILR1 antibody or antigen-binding fragment thereof, an anti-TRAILR2 antibody or antigen-binding fragment thereof, an anti-TWEAK antibody or antigen-binding fragment thereof, an anti-TWEAKR antibody or antigen-binding fragment thereof, an anti-cell surface lymphocyte protein antibody or antigen-binding fragment thereof, an anti-BRAF antibody or antigen-binding fragment thereof, an anti-MEK antibody or antigen-binding fragment thereof, an anti-CD33 antibody or antigen-binding fragment thereof, an anti-CD20 antibody or antigen-binding fragment thereof, an anti-HLA-DR antibody or antigen-binding fragment thereof, an anti-HLA class I antibody or antigen-binding fragment thereof, an anti-CD52 antibody or antigen-binding fragment thereof, an anti-A33 antibody or antigen-binding fragment thereof, an anti-GD3 antibody or antigen-binding fragment thereof, an anti-PSMA antibody or antigen-binding fragment thereof, an anti-Ceacan 1 antibody or antigen-binding fragment thereof, an anti-Galedin 9 antibody or antigen-binding fragment thereof, an anti-HVEM antibody or antigen-binding fragment thereof, an anti-VISTA antibody or antigen-binding fragment thereof, an anti-B7 H4 antibody or antigen-binding fragment thereof, an anti-HHLA2 antibody or antigen-binding fragment thereof, an anti-CD155 antibody or antigen-binding fragment thereof, an anti-CD80 antibody or antigen-binding fragment thereof, an anti-BTLA antibody or antigen-binding fragment thereof, an anti-CD160 antibody or antigen-binding fragment thereof, an anti-CD28 antibody or antigen-binding fragment thereof, an anti-CD226 antibody or antigen-binding fragment thereof, an anti-CEACAM1 antibody or antigen-binding fragment thereof, an anti-TIM3 antibody or antigen-binding fragment thereof, an anti-TIGIT antibody or antigen-binding fragment thereof, an anti-CD96 antibody or antigen-binding fragment thereof, an anti-CD70 antibody or antigen-binding fragment thereof, an anti-CD27 antibody or antigen-binding fragment thereof, an anti-LIGHT antibody or antigen-binding fragment thereof, an anti-CD137 antibody or antigen-binding fragment thereof, an anti-DR4 antibody or antigen-binding fragment thereof, an anti-CR5 antibody or antigen-binding fragment thereof, an anti-TN-FRS antibody or antigen-binding fragment thereof, an anti-TNFR1 antibody or antigen-binding fragment thereof, an anti-FAS antibody or antigen-binding fragment thereof, an anti-CD95 antibody or antigen-binding fragment thereof, an anti-TRAIL antibody or antigen-binding fragment thereof, an anti-DR6 antibody or antigen-binding fragment thereof, an anti-EDAR antibody or antigen-binding fragment thereof, an anti-NGFR antibody or antigen-binding fragment thereof, an anti-OPG antibody or antigen-binding fragment thereof, an anti-RANKL antibody or antigen-binding fragment thereof, an anti-LTβ receptor antibody or antigen-binding fragment thereof, an anti-BCMA antibody or antigen-binding fragment thereof, an anti-TACI antibody or antigen-binding fragment thereof, an anti-BAFFR antibody or antigen-binding fragment thereof, an anti-EDAR2 antibody or antigen-binding fragment thereof, an anti-TROY antibody or antigen-binding fragment thereof, and an anti-RELT antibody or antigen-binding fragment thereof. For example, the immunotherapy agent may be an anti-CTLA-4 antibody or antigen-binding fragment thereof, an anti-PD-1 antibody or antigen-binding fragment thereof, or an anti-PD-L1 antibody or antigen-binding fragment thereof.

In some embodiments, the pharmaceutical composition contains an anti-CTLA-4 antibody or antigen-binding fragment thereof, such as ipilimumab or tremelimumab. Additionally or alternatively, the pharmaceutical composition may contain an anti-PD-1 antibody or antigen-binding fragment thereof, such as nivolumab, pembrolizumab, avelumab, durvalumab, or atezolizumab.

In some embodiments, the immunotherapy agent is an anti-cell surface lymphocyte protein antibody or antigen-binding fragment thereof, such as an antibody or antigen-binding fragment thereof that binds one or more of CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49, CD50, CD51, CD52, CD53, CD54, CD55, CD56, CD57, CD58, CD59, CD60, CD61, CD62, CD63, CD64, CD65, CD66, CD67, CD68, CD69, CD70, CD71, CD72, CD73, CD74, CD75, CD76, CD77, CD78, CD79, CD80, CD81, CD82, CD83, CD84, CD85, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD120, CD121, CD122, CD123, CD124, CD125, CD126, CD127, CD128, CD129, CD130, CD131, CD132, CD133, CD134, CD135, CD136, CD137, CD138, CD139, CD140, CD141, CD142, CD143, CD144, CD145, CD146, CD147, CD148, CD149, CD150, CD151, CD152, CD153, CD154, CD155, CD156, CD157, CD158, CD159, CD160, CD161, CD162, CD163, CD164, CD165, CD166, CD167, CD168, CD169, CD170, CD171, CD172, CD173, CD174, CD175, CD176, CD177, CD178, CD179, CD180, CD181, CD182, CD183, CD184, CD185, CD186, CD187, CD188, CD189, CD190, CD191, CD192, CD193, CD194, CD195, CD196, CD197, CD198, CD199, CD200, CD201, CD202, CD203, CD204, CD205, CD206, CD207, CD208, CD209, CD210, CD211, CD212, CD213, CD214, CD215, CD216, CD217, CD218, CD219, CD220, CD221, CD222, CD223, CD224, CD225, CD226, CD227, CD228, CD229, CD230, CD231, CD232, CD233, CD234, CD235, CD236, CD237, CD238, CD239, CD240, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CD293, CD294, CD295, CD296, CD297, CD298, CD299, CD300, CD301, CD302, CD303, CD304, CD305, CD306, CD307, CD308, CD309, CD310, CD311, CD312, CD313, CD314, CD315, CD316, CD317, CD318, CD319, and/or CD320.

In some embodiments, the immunotherapy agent is an agent (e.g., a polypeptide, antibody, antigen-binding fragment thereof, a single-chain polypeptide, or construct thereof) that binds a chemokine or lymphokine, such as a chemokine or lymphokine involved in tumor growth. For instance, the immunotherapy agent may be an agent (e.g., polypeptide, antibody, antigen-binding fragment thereof, single-chain polypeptide, or construct thereof) that bind and inhibits the activity of one or more, or all, of CXCL1, CXCL2, CXCL3, CXCL8, CCL2 and CCL5. In some embodiments, the immunotherapy agent is an agent (e.g., a polypeptide, antibody, antigen-binding fragment thereof, a single-chain polypeptide, or construct thereof) that binds and inhibits the activity of one or more, or all, of CCL3, CCL4, CCL8, and CCL22.

The immunotherapy agent may be capable of specifically binding one or more of the immunological targets described in Table 1 of Mahoney et al., *Cancer Immunotherapy,* 14:561-584 (2015), the disclosure of which is incorporated herein by reference in its entirety. For example, the immunotherapy agent may be an agent, such as an antibody or antigen-binding fragment thereof, that specifically binds one or more of OX40L, TL1A, CD40L, LIGHT, BTLA, LAG3, TIM3, Singlecs, ICOS, B7-H3, B7-H4, VISTA, TMIGD2, BTNL2, CD48, KIR, LIR, LIR antibody, ILT, NKG2D, NKG2A, MICA, MICB, CD244, CSF1R, IDO, TGFβ, CD39, CD73, CXCR4, CXCL12, SIRPA, CD47, VEGF, or neuropilin.

In some embodiments, the immunotherapy agent is Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and/or small molecular therapies like Vorinostat.

In some embodiments, the pharmaceutical composition contains a bispecific antibody, such as a bispecific monoclonal antibody, in which one arm of the antibody specifically binds TNFR2 and the other specifically binds an immune checkpoint protein, such as PD-1, PD-L1, or CTLA-4, among others described herein. The arm of the bispecific antibody that specifically binds TNFR2 may specifically bind, for example, an epitope of human TNFR2 defined by one or more amino acids within CRD3 and/or an epitope defined by one or more amino acids within CRD4, such as an epitope on human TNFR2 described above and herein as giving rise to an antagonistic (e.g., a dominant antagonistic) phenotype.

In some embodiments, the bispecific antibody contains one arm that specifically binds TNFR2, such as an epitope of human TNFR2 described above, and one arm that specifically binds an immune checkpoint protein specifically binds PD-1. In some embodiments, the arm of the bispecific antibody that specifically binds PD-1 may specifically bind the same epitope(s) on PD-1 as nivolumab, pembrolizumab, avelumab, durvalumab, or atezolizumab. For example, the arm of the bispecific antibody that specifically binds PD-1 may competitively inhibit the binding of PD-1 to nivolumab, pembrolizumab, avelumab, durvalumab, and/or atezolizumab, as assessed, for example, using a competitive binding assay described herein or know in the art, such as a competitive ELISA.

In some embodiments, the bispecific antibody contains one arm that specifically binds TNFR2, such as an epitope of human TNFR2 described above, and one arm that specifically binds PD-L1. In some embodiments, the arm of the bispecific antibody that specifically binds PD-L1 may specifically bind the same epitope(s) on PD-L1 as atezolizumab or avelumab. For example, the arm of the bispecific antibody that specifically binds PD-L1 may competitively inhibit the binding of PD-L1 to atezolizumab and/or avelumab, for example, using a competitive binding assay described herein or know in the art, such as a competitive ELISA.

In some embodiments, the bispecific antibody contains one arm that specifically binds TNFR2, such as an epitope of human TNFR2 described above, and one arm that specifically binds CTLA-4. In some embodiments, the arm of the bispecific antibody that specifically binds CTLA-4 may specifically bind the same epitope(s) on CTLA-4 as ipilimumab or tremelimumab. For example, the arm of the bispecific antibody that specifically binds CTLA-4 may competitively inhibit the binding of CTLA-4 to ipilimumab and/or tremelimumab, as assessed, for example, using a competitive binding assay described herein or know in the art, such as a competitive ELISA.

In some embodiments, the additional therapeutic agent in the pharmaceutical composition is a chimeric antigen receptor (CAR-T) agent, a chemotherapeutic agent, a small molecule anti-cancer agent, or a cancer vaccine.

In some embodiments, the additional therapeutic agent in the pharmaceutical composition is a chimeric antigen receptor (CAR-T) agent, such as a T cell engineered to express a T cell receptor that specifically binds one or more antigens expressed on the surface of a cancer cell. The antibody or antigen-binding fragment thereof, single-chain polypeptide, construct, polynucleotide, vector, or host cell described herein (e.g., a TNFR2 antagonist antibody or antigen-binding fragment thereof) may be formulated for co-administration with a CAR-T agent for instance, by admixing the antibody or antigen-binding fragment thereof, single-chain polypeptide, construct, polynucleotide, vector, or host cell with the CAR-T agent. In some embodiments, the antibody or antigen-binding fragment thereof, single-chain polypeptide, construct, polynucleotide, vector, or host cell is formulated for administration separately from the chemotherapeutic agent, such as by way of serial administration.

In some embodiments, the additional therapeutic agent in the pharmaceutical composition is a chemotherapeutic agent, such as a chemotherapeutic agent described herein.

The antibody or antigen-binding fragment thereof, single-chain polypeptide, construct, polynucleotide, vector, or host cell described herein (e.g., a TNFR2 antagonist antibody or antigen-binding fragment thereof) may be formulated for co-administration with a chemotherapeutic agent, for instance, by admixing the antibody or antigen-binding fragment thereof, single-chain polypeptide, construct, polynucleotide, vector, or host cell with the chemotherapeutic agent. In some embodiments, the antibody or antigen-binding fragment thereof, single-chain polypeptide, construct, polynucleotide, vector, or host cell is formulated for administration separately from the chemotherapeutic agent. In some embodiments, the chemotherapeutic agent is conjugated directly to the antibody or antigen-binding fragment thereof, single-chain polypeptide, construct, polynucleotide, vector, or host cell, for instance, using bond-forming techniques described herein or known in the art.

In some embodiments, the additional therapeutic agent is a small molecule anti-cancer agent, such as a small molecule described in Imai et al., Nature Reviews Cancer 6:714-727 (2006), the disclosure of which is incorporated herein by reference.

In some embodiments, the additional therapeutic agent is a cancer vaccine, such as a vaccine described in Palucka et al., Journal of Immunology 186:1325-1331 (2011), the disclosure of which is incorporated herein by reference.

A seventh aspect features a method of producing the polypeptide (e.g., a single-chain polypeptide, antibody, antigen-binding fragment thereof, or construct thereof) of the first aspect and/or the construct of the second aspect or any embodiments thereof. The method may include expressing a polynucleotide encoding the polypeptide or construct in a host cell (e.g., a host cell described herein) and recovering the polypeptide from host cell medium.

An eighth aspect features a method of reducing or inhibiting an immune response mediated by a T-reg cell in a mammal (e.g., a human) by administering to the mammal the polypeptide (e.g., a single-chain polypeptide, antibody, antigen-binding fragment thereof, or construct thereof) of the first aspect or any embodiments thereof, the construct of the second aspect or any embodiments thereof, the polynucleotide of the third aspect or any embodiments thereof, the vector of the fourth aspect or any embodiments thereof, the host cell of the fifth aspect or any embodiments thereof, and/or the pharmaceutical composition of the sixth aspect or any embodiments thereof.

A ninth aspect features a method of treating a cell proliferation disorder in a mammal (e.g., a human) by administering to the mammal the polypeptide (e.g., a single-chain polypeptide, antibody, antigen-binding fragment thereof, or construct thereof) of the first aspect or any embodiments thereof, the construct of the second aspect or any embodiments thereof, the polynucleotide of the third aspect or any embodiments thereof, the vector of the fourth aspect or any embodiments thereof, the host cell of the fifth aspect or any embodiments thereof, and/or the pharmaceutical composition of the sixth aspect or any embodiments thereof.

The cell proliferation disorder may be, for example, a cancer, such as a cancer selected from the group consisting of leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, and throat cancer. In some embodiments, the cancer is selected from the group consisting of Hodgkin's lymphoma, cutaneous non-Hodgkin's lymphoma, T cell lymphoma, ovarian cancer, colon cancer, multiple myeloma, renal cell carcinoma, skin cancer, lung cancer, liver cancer, endometrial cancer, a cancer of the hematopoietic or lymphatic system, a cancer of the central nervous system, breast cancer, pancreatic cancer, stomach cancer, esophageal cancer, and a cancer of the upper gastrointestinal tract. In some embodiments, the cancer is selected from the group consisting of T cell lymphoma, ovarian cancer, and colon cancer.

In some embodiments, the cancer is selected from the group consisting of acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T-cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, renal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

A tenth aspect features a method of treating an infectious disease in a mammal (e.g., a human) by administering to the mammal the polypeptide (e.g., a single-chain polypeptide, antibody, antigen-binding fragment thereof, or construct thereof) of the first aspect or any embodiments thereof, the construct of the second aspect or any embodiments thereof, the polynucleotide of the third aspect or any embodiments thereof, the vector of the fourth aspect or any embodiments thereof, the host cell of the fifth aspect or any embodiments thereof, and/or the pharmaceutical composition of the sixth aspect or any embodiments thereof. The infectious disease may be, for example, caused by a virus, bacterium, fungus, and/or parasite.

In some embodiments, the infectious disease is caused by a virus selected from the group consisting of hepatitis C virus, Yellow fever virus, Kadam virus, Kyasanur Forest disease virus, Langat virus, Omsk hemorrhagic fever virus, Powassan virus, Royal Farm virus, Karshi virus, tick-borne encephalitis virus, Neudoerfi virus, Sofjin virus, Louping ill virus, Negishi virus, Meaban virus, Saumarez Reef virus, Tyuleniy virus, Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana *myotis* leukoencephalitis virus, Phnom Penh bat virus, Rio Bravo virus, Tamana bat virus, cell fusing agent virus, Ippy virus, Lassa virus, lymphocytic choriomeningitis virus (LCMV), Mobala virus, Mopeia virus, Amapari virus, Flexal virus, Guanarito virus, Junin virus, Latino virus, Machupo virus, Oliveros virus, Paraná virus, Pichinde virus, Pirital virus, Sabid virus, Tacaribe virus, Tamiami virus, Whitewater Arroyo virus, Chapare virus, Lujo virus, Hantaan virus, Sin Nombre virus, Dugbe virus, Bunyamwera virus, Rift Valley fever virus, La Crosse virus, California encephalitis virus, Crimean-Congo hemorrhagic fever (CCHF) virus, Ebola virus, Marburg virus, Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus, smallpox virus, monkeypox virus, vaccinia virus, herpes simplex virus, human herpes virus, cytomegalovirus (CMV), Epstein-Barr virus (EBV), Varicella-Zoster virus, Kaposi's sarcoma associated-herpesvirus (KSHV), influenza virus, severe acute respiratory syndrome (SARS) virus, rabies virus, vesicular stomatitis virus (VSV), human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, mumps virus, poliovirus, human enterovirus (A, B, C, and D), hepatitis A virus, coxsackievirus, hepatitis B virus, human papilloma virus, adeno-associated virus, astrovirus, JC virus, BK virus, SV40 virus, Norwalk virus, rotavirus, human immunodeficiency virus (HIV), human T-lymphotropic virus Types I and II.

In some embodiments, the infectious disease is caused by a bacterium belonging to a genus selected from the group consisting of *Salmonella, Streptococcus, Bacillus, Listeria, Corynebacterium, Nocardia, Neisseria, Actnobacter, Moraxella, Enterobacteriacece, Pseudomonas, Escherichia, Klebsiella, Serratia, Enterobacter, Proteus, Salmonella, Shigella, Yersinia, Haemophilus, Bordatella, Legionella, Pasteurella, Francisella, Brucella, Bartonella, Clostridium, Vibrio, Campylobacter*, and *Staphylococcus*.

In some embodiments, the infectious disease is caused by a fungus selected from the group consisting of *Aspergillus, Candida, Malassezia, Trichosporon, Fusarium, Acremonium, Rhizopus, Mucor, Pneumocystis*, and *Absidia*.

In some embodiments, the infectious disease is caused by a parasite selected from the group consisting of *Entamoeba hystolytica, Giardia lamblia, Cryptosporidium muris,* Trypanosomatida *gambiense,* Trypanosomatida *rhodesiense,* Trypanosomatida crusi, *Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis,* and *Histomonas meleagridis.* Exemplary helminthic parasites include richuris *trichiura, Ascaris lumbricoides, Enterobius vermicularis, Ancylostoma duodenale, Necator americanus, Strongyloides stercoralis, Wuchereria bancrofti,* and *Dracunculus medinensis, Schistosoma mansoni, Schistosoma haematobium, Schistosoma japonicum, Fasciola hepatica, Fasciola gigantica, Heterophyes, Paragonimus westermani, Taenia solium, Taenia saginata, Hymenolepis nana,* and *Echinococcus granulosus.*

In some embodiments of the eighth, ninth, and/or tenth aspect, the method further includes administering to the human an immunotherapy agent. The immunotherapy agent may be, e.g., selected from the group consisting of an anti-CTLA-4 agent, an anti-PD-1 agent, an anti-PD-L1 agent, an anti-PD-L2 agent, a TNF-α cross-linking agent, a TRAIL cross-linking agent, an anti-CD27 agent, an anti-CD30 agent, an anti-CD40 agent, an anti-4-1BB agent, an anti-GITR agent, an anti-OX40 agent, an anti-TRAILR1 agent, an anti-TRAILR2 agent, an anti-TWEAK agent, an anti-TWEAKR agent, an anti-cell surface lymphocyte protein agent, an anti-BRAF agent, an anti-MEK agent, an anti-CD33 agent, an anti-CD20 agent, an anti-HLA-DR agent, an anti-HLA class I agent, an anti-CD52 agent, an anti-A33 agent, an anti-GD3 agent, an anti-PSMA agent, an anti-Ceacan 1 agent, an anti-Galedin 9 agent, an anti-HVEM agent, an anti-VISTA agent, an anti-B7 H4 agent, an anti-HHLA2 agent, an anti-CD155 agent, an anti-CD80 agent, an anti-BTLA agent, an anti-CD160 agent, an anti-CD28 agent, an anti-CD226 agent, an anti-CEACAM1 agent, an anti-TIM3 agent, an anti-TIGIT agent, an anti-CD96 agent, an anti-CD70 agent, an anti-CD27 agent, an anti-LIGHT agent, an anti-CD137 agent, an anti-DR4 agent, an anti-CR5 agent, an anti-TNFRS agent, an anti-TNFR1 agent, an anti-FAS agent, an anti-CD95 agent, an anti-TRAIL agent, an anti-DR6 agent, an anti-EDAR agent, an anti-NGFR agent, an anti-OPG agent, an anti-RANKL agent, an anti-LTβ receptor agent, an anti-BCMA agent, an anti-TACI agent, an anti-BAFFR agent, an anti-EDAR2 agent, an anti-TROY agent, and an anti-RELT agent, such as an anti-CTLA-4 agent, an anti-PD-1 agent, and/or an anti-PD-L1 agent.

The immunotherapy agent administered to the human may be, for example, selected from the group consisting of an anti-CTLA-4 antibody or antigen-binding fragment thereof, an anti-PD-1 antibody or antigen-binding fragment thereof, an anti-PD-L1 antibody or antigen-binding fragment thereof, an anti-PD-L2 antibody or antigen-binding fragment thereof, a TNF-α cross-linking antibody or antigen-binding fragment thereof, a TRAIL cross-linking antibody or antigen-binding fragment thereof, an anti-CD27 antibody or antigen-binding fragment thereof, an anti-CD30 antibody or antigen-binding fragment thereof, an anti-CD40 antibody or antigen-binding fragment thereof, an anti-4-1BB antibody or antigen-binding fragment thereof, an anti-GITR antibody or antigen-binding fragment thereof, an anti-OX40 antibody or antigen-binding fragment thereof, an anti-TRAILR1 antibody or antigen-binding fragment thereof, an anti-TRAILR2 antibody or antigen-binding fragment thereof, an anti-TWEAK antibody or antigen-binding fragment thereof, an anti-TWEAKR antibody or antigen-binding fragment thereof, an anti-cell surface lymphocyte protein antibody or antigen-binding fragment thereof, an anti-BRAF antibody or antigen-binding fragment thereof, an anti-MEK antibody or antigen-binding fragment thereof, an anti-CD33 antibody or antigen-binding fragment thereof, an anti-CD20 antibody or antigen-binding fragment thereof, an anti-HLA-DR antibody or antigen-binding fragment thereof, an anti-HLA class I antibody or antigen-binding fragment thereof, an anti-CD52 antibody or antigen-binding fragment thereof, an anti-A33 antibody or antigen-binding fragment thereof, an anti-GD3 antibody or antigen-binding fragment thereof, an anti-PSMA antibody or antigen-binding fragment thereof, an anti-Ceacan 1 antibody or antigen-binding fragment thereof, an anti-Galedin 9 antibody or antigen-binding fragment thereof, an anti-HVEM antibody or antigen-binding fragment thereof, an anti-VISTA antibody or antigen-binding fragment thereof, an anti-B7 H4 antibody or antigen-binding fragment thereof, an anti-HHLA2 antibody or antigen-binding fragment thereof, an anti-CD155 antibody or antigen-binding fragment thereof, an anti-CD80 antibody or antigen-binding fragment thereof, an anti-BTLA antibody or antigen-binding fragment thereof, an anti-CD160 antibody or antigen-binding fragment thereof, an anti-CD28 antibody or antigen-binding fragment thereof, an anti-CD226 antibody or antigen-binding fragment thereof, an anti-CEACAM1 antibody or antigen-binding fragment thereof, an anti-TIM3 antibody or antigen-binding fragment thereof, an anti-TIGIT antibody or antigen-binding fragment thereof, an anti-CD96 antibody or antigen-binding fragment thereof, an anti-CD70 antibody or antigen-binding fragment thereof, an anti-CD27 antibody or antigen-binding fragment thereof, an anti-LIGHT antibody or antigen-binding fragment thereof, an anti-CD137 antibody or antigen-binding fragment thereof, an anti-DR4 antibody or antigen-binding fragment thereof, an anti-CR5 antibody or antigen-binding fragment thereof, an anti-TNFRS antibody or antigen-binding fragment thereof, an anti-TNFR1 antibody or antigen-binding fragment thereof, an anti-FAS antibody or antigen-binding fragment thereof, an anti-CD95 antibody or antigen-binding fragment thereof, an anti-TRAIL antibody or antigen-binding fragment thereof, an anti-DR6 antibody or antigen-binding fragment thereof, an anti-EDAR antibody or antigen-binding fragment thereof, an anti-NGFR antibody or antigen-binding fragment thereof, an anti-OPG antibody or antigen-binding fragment thereof, an anti-RANKL antibody or antigen-binding fragment thereof, an anti-LTβ receptor antibody or antigen-binding fragment thereof, an anti-BCMA antibody or antigen-binding fragment thereof, an anti-TACI antibody or antigen-binding fragment thereof, an anti-BAFFR antibody or antigen-binding fragment thereof, an anti-EDAR2 antibody or antigen-binding fragment thereof, an anti-TROY antibody or antigen-binding fragment thereof, and an anti-RELT antibody or antigen-binding fragment thereof. In some embodiments, the immunotherapy agent administered to the human is an anti-CTLA-4 antibody or antigen-binding fragment thereof, an anti-PD-1 antibody or antigen-binding fragment thereof, or an anti-PD-L1 antibody or antigen-binding fragment thereof.

In some embodiments of the eighth, ninth, and/or tenth aspect, the method includes administering to the mammal (e.g., a human) an anti-CTLA-4 antibody or antigen-binding fragment thereof, such as ipilimumab or tremelimumab. Additionally or alternatively, the method may include administering to the human an anti-PD-1 antibody or antigen-binding fragment thereof, such as nivolumab, pembrolizumab, avelumab, durvalumab, or atezolizumab.

In some embodiments of the eighth, ninth, and/or tenth aspect, the method includes administering to the mammal (e.g., a human) an anti-cell surface lymphocyte protein antibody or antigen-binding fragment thereof, such as an antibody or antigen-binding fragment thereof that binds one or more of CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49, CD50, CD51, CD52, CD53, CD54, CD55, CD56, CD57, CD58, CD59, CD60, CD61, CD62, CD63, CD64, CD65, CD66, CD67, CD68, CD69, CD70, CD71, CD72, CD73, CD74, CD75, CD76, CD77, CD78, CD79, CD80, CD81, CD82, CD83, CD84, CD85, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD120, CD121, CD122, CD123, CD124, CD125, CD126, CD127, CD128, CD129, CD130, CD131, CD132, CD133, CD134, CD135, CD136, CD137, CD138, CD139, CD140, CD141, CD142, CD143, CD144, CD145, CD146, CD147, CD148, CD149, CD150, CD151, CD152, CD153, CD154, CD155, CD156, CD157, CD158, CD159, CD160, CD161, CD162, CD163, CD164, CD165, CD166, CD167, CD168, CD169, CD170, CD171, CD172, CD173, CD174, CD175, CD176, CD177, CD178, CD179, CD180, CD181, CD182, CD183, CD184, CD185, CD186, CD187, CD188, CD189, CD190, CD191, CD192, CD193, CD194, CD195, CD196, CD197, CD198, CD199, CD200, CD201, CD202, CD203, CD204, CD205, CD206, CD207, CD208, CD209, CD210, CD211, CD212, CD213, CD214, CD215, CD216, CD217, CD218, CD219, CD220, CD221, CD222, CD223, CD224, CD225, CD226, CD227, CD228, CD229, CD230, CD231, CD232, CD233, CD234, CD235, CD236, CD237, CD238, CD239, CD240, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CD293, CD294, CD295, CD296, CD297, CD298, CD299, CD300, CD301, CD302, CD303, CD304, CD305, CD306, CD307, CD308, CD309, CD310, CD311, CD312, CD313, CD314, CD315, CD316, CD317, CD318, CD319, and/or CD320.

In some embodiments of the eighth, ninth, and/or tenth aspect, the method includes administering to the mammal (e.g., a human) an agent (e.g., a polypeptide, antibody, antigen-binding fragment thereof, a single-chain polypeptide, or construct thereof) that binds a chemokine or lymphokine, such as a chemokine or lymphokine involved in tumor growth. For instance, the immunotherapy agent may be an agent (e.g., polypeptide, antibody, antigen-binding fragment thereof, single-chain polypeptide, or construct thereof) that bind and inhibits the activity of one or more, or all, of CXCL1, CXCL2, CXCL3, CXCL8, CCL2 and CCL5. In some embodiments, the immunotherapy agent is an agent (e.g., a polypeptide, antibody, antigen-binding fragment thereof, a single-chain polypeptide, or construct thereof) that binds and inhibits the activity of one or more, or all, of CCL3, CCL4, CCL8, and CCL22.

In some embodiments of the eighth, ninth, and/or tenth aspect, the method includes administering to the mammal (e.g., a human) an immunotherapy agent capable of specifically binding one or more of the immunological targets described in Table 1 of Mahoney et al., *Cancer Immunotherapy*, 14:561-584 (2015), the disclosure of which is incorporated herein by reference in its entirety. For example, the immunotherapy agent may be an agent, such as an antibody or antigen-binding fragment thereof, that specifically binds one or more of OX40L, TL1A, CD40L, LIGHT, BTLA, LAG3, TIM3, Singlecs, ICOS, B7-H3, B7-H4, VISTA, TMIGD2, BTNL2, CD48, KIR, LIR, LIR antibody, ILT, NKG2D, NKG2A, MICA, MICB, CD244, CSF1R, IDO, TGFβ, CD39, CD73, CXCR4, CXCL12, SIRPA, CD47, VEGF, or neuropilin.

In some embodiments of the eighth, ninth, and/or tenth aspect, the method includes administering to the mammal (e.g., a human) an immunotherapy agent selected from the group consisting of Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and small molecular therapies like Vorinostat.

In some embodiments, the method includes administering to the mammal (e.g., a human) a CAR-T agent, a chemotherapeutic agent, a small molecule anti-cancer agent, or a cancer vaccine, such as a CAR-T agent, chemotherapeutic agent, small molecule anti-cancer agent, or cancer vaccine described above and herein.

In some embodiments, the polypeptide, such as the single-chain polypeptide, antibody, antigen-binding fragment thereof, or construct, which specifically binds TNFR2 is administered to the mammal (e.g., a human) in an amount of from about 0.001 mg/kg to about 100 mg/kg, such as in an amount of from about 0.01 mg/kg to about 10 mg/kg.

An eleventh aspect features a kit containing the polypeptide (e.g., a single-chain polypeptide, antibody, antigen-binding fragment thereof, or construct thereof) of the first aspect or any embodiments thereof, the construct of the second aspect or any embodiments thereof, the polynucleotide of the third aspect or any embodiments thereof, the vector of the fourth aspect or any embodiments thereof, the host cell of the fifth aspect or any embodiments thereof, and/or the pharmaceutical composition of the sixth aspect or any embodiments thereof.

In some embodiments, the kit contains instructions for transfecting the vector into a host cell. Additionally or alternatively, the kit may contain instructions for expressing the polypeptide (e.g., a single-chain polypeptide, antibody, antigen-binding fragment thereof, or construct thereof) in the host cell. The kit may include a reagent that can be used to express the polypeptide (e.g., a single-chain polypeptide, antibody, antigen-binding fragment thereof, or construct thereof) in the host cell. In some embodiments, the kit includes instructions for administering the agent to a mammal (e.g., a human), such as a human patient suffering from a cell proliferation disorder and/or an infectious disease described herein. In some embodiments, the kit contains instructions for making or using the agent.

Definitions

As used herein, the term "about" refers to a value that is no more than 10% above or below the value being described. For example, the term "about 5 nM" indicates a range of from 4.5 nM to 5.5 nM.

As used herein, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, primatized antibodies, heteroconjugate antibodies (e.g., bi- tri- and quad-specific antibodies, diabodies, triabodies, and tetrabodies), and antigen-binding fragments of antibodies, including e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')$_2$ fragments) that are capable of specifically binding to a target protein. Fab and F(ab')$_2$ fragments lack the Fc fragment of an intact antibody, clear more rapidly from the circulation of the animal, and may have less non-specific tissue binding than an intact antibody (see Wahl et al., J. Nucl. Med. 24:316, 1983; incorporated herein by reference).

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be a Fab, F(ab')$_2$, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the V$_L$, V$_H$, C$_L$, and C$_H$1 domains; (ii) a F(ab')$_2$ fragment, a bivalent fragment comprising two Fab fragments linked by a disulfide bridge at the hinge region; (iii) a Fd fragment consisting of the V$_H$ and C$_H$1 domains; (iv) a Fv fragment consisting of the V$_L$ and V$_H$ domains of a single arm of an antibody, (v) a dAb including V$_H$ and V$_L$ domains; (vi) a dAb fragment (Ward et al., Nature 341:544-546, 1989), which consists of a V$_H$ domain; (vii) a dAb which consists of a V$_H$ or a V$_L$ domain; (viii) an isolated complementarity determining region (CDR); and (ix) a combination of two or more isolated CDRs which may optionally be joined by a synthetic linker. Furthermore, although the two domains of the Fv fragment, V$_L$ and V$_H$, are coded for by separate genes, they can be joined, using recombinant methods, by a linker that enables them to be made as a single protein chain in which the V$_L$ and V$_H$ regions pair to form monovalent molecules (known as single-chain Fv (scFv); see, e.g., Bird et al., Science 242: 423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in some embodiments, by chemical peptide synthesis procedures known in the art.

As used herein, the terms "anti-tumor necrosis factor receptor 2 antibody," "TNFR2 antibody," "anti-TNFR2 antibody portion," and/or "anti-TNFR2 antibody fragment" and the like include any protein or peptide-containing molecule that includes at least a portion of an immunoglobulin molecule, such as, but not limited, to at least one complementarity determining region (CDR) of a heavy or light chain or a ligand-binding portion thereof, a heavy chain or light chain variable region, a heavy chain or light chain constant region, or any portion thereof, that is capable of specifically binding to TNFR2. For instance, two or more portions of an immunoglobulin molecule may be covalently bound to one another, e.g., via an amide bond, a thioether bond, a carbon-carbon bond, a disulfide bridge, or by a linker, such as a linker described herein or known in the art. TNFR2 antibodies also include antibody-like protein scaffolds, such as the tenth fibronectin type III domain ($^{10}$Fn3), which contains BC, DE, and FG structural loops similar in structure and solvent accessibility to antibody CDRs. The tertiary structure of the $^{10}$Fn3 domain resembles that of the variable region of the IgG heavy chain, and one of skill in the art can graft, e.g., the CDRs of a TNFR2 monoclonal antibody onto the fibronectin scaffold by replacing residues of the BC, DE, and FG loops of $^{10}$Fn3 with residues from the CDR-H1, CDR-H2, or CDR-H3 regions of a TNFR2 monoclonal antibody.

As used herein, the terms "antagonist TNFR2 antibody" and "antagonistic TNFR2 antibody" refer to TNFR2 antibodies that are capable of inhibiting or reducing activation of TNFR2, attenuating one or more signal transduction pathways mediated by TNFR2, and/or reducing or inhibiting at least one activity mediated by activation of TNFR2. For example, antagonistic TNFR2 antibodies may inhibit or reduce the growth and proliferation of regulatory T cells. Antagonistic TNFR2 antibodies may inhibit or reduce TNFR2 activation by blocking TNFR2 from binding TNFα. In this way, antagonistic TNFR2 antibodies may block the trimerization of TNFR2 that would otherwise be induced by interacting with TNFα, thus resulting in suppression of TNFR2 activity.

As used herein, the term "bispecific antibodies" refers to antibodies (e.g., monoclonal, often human or humanized antibodies) that have binding specificities for at least two different antigens. For example, one of the binding specificities can be directed towards TNFR2, the other can be for any other antigen, e.g., for a cell-surface protein, receptor, receptor subunit, tissue-specific antigen, virally derived protein, virally encoded envelope protein, bacterially derived protein, or bacterial surface protein, etc.

As used herein, the phrase "chemotherapeutic agent" refers to any chemical agent with therapeutic usefulness in the treatment of cancer, such as a cancer described herein. Chemotherapeutic agents encompass both chemical and biological agents. These agents can function to inhibit a cellular activity upon which a cancer cell depends for continued survival. Categories of chemotherapeutic agents include alkylating/alkaloid agents, antimetabolites, hormones, hormone analogs, and antineoplastic drugs. Exemplary chemotherapeutic agents suitable for use in conjunction with the compositions and methods described herein include, without limitation, those set forth in Slapak and Kufe, Principles of Cancer Therapy, Chapter 86 in Harrison's Principles of Internal medicine, 14$^{th}$ edition; Perry et al., Chemotherapeutic, Chapter 17 in Abeloff, Clinical Oncology 2$^{nd}$ ed., 2000; Baltzer L. and Berkery R. (eds): Oncology Pocket Guide to Chemotherapeutic, 2$^{nd}$ ed. St. Luois, mosby-Year Book, 1995; Fischer D. S., Knobf M. F., Durivage H. J. (eds): The Cancer Chemotherapeutic Handbook, 4$^{th}$ ed. St. Luois, Mosby-Year Handbook, the disclosures of each of which are incorporated herein by reference as they pertain to chemotherapeutic agents.

As used herein, the term "chimeric" antibody refers to an antibody having variable domain sequences (e.g., CDR sequences) derived from an immunoglobulin of one source organism, such as rat or mouse, and constant regions derived from an immunoglobulin of a different organism (e.g., a human, another primate, pig, goat, rabbit, hamster, cat, dog, guinea pig, member of the bovidae family (such as cattle, bison, buffalo, elk, and yaks, among others), cow, sheep, horse, or bison, among others). Methods for producing chimeric antibodies are known in the art. See, e.g., Morrison, 1985, Science 229(4719): 1202-7; Oi et al, 1986, BioTechniques 4214-221; Gillies et al, 1985, J. Immunol. Methods 125:191-202; U.S. Pat. Nos. 5,807,715; 4,816,567; and 4,816,397; incorporated herein by reference.

As used herein, the term "complementarity determining region" (CDR) refers to a hypervariable region found both in the light chain and the heavy chain variable domains. The more highly conserved portions of variable domains are called the framework regions (FRs). As is appreciated in the art, the amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may comprising modifications in these hybrid hypervariable positions. The variable domains of native heavy and light chains each comprise four framework regions that primarily adopt a β-sheet configuration, connected by three CDRs, which form loops that connect, and in some cases form part of, the β-sheet structure. The CDRs in each chain are held together in close proximity by the FR regions in the order FR1-CDR1-FR2-CDR2-FR3-CDR3-FR4 and, with the CDRs from the other antibody chains, contribute to the formation of the target binding site of antibodies (see Kabat et al, Sequences of Proteins of Immunological Interest (National Institute of Health, Bethesda, Md. 1987; incorporated herein by reference). As used herein, numbering of immunoglobulin amino acid residues is done according to the immunoglobulin amino acid residue numbering system of Kabat et al, unless otherwise indicated.

As used herein, the terms "conservative mutation," "conservative substitution," or "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 2 below.

TABLE 2

Representative physicochemical properties
of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |

TABLE 2-continued

Representative physicochemical properties
of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in $A^3$: 50-100 is small, 100-150 is intermediate, 150-200 is large, and >200 is bulky From this table it is appreciated that the conservative amino acid families include, e.g., (i) G, A, V, L, I, P, and M; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

Amino acid substitutions may be represented herein using the convention: (AA1)(N)(AA2), where "AA1" represents the amino acid normally present at particular site within an amino acid sequence, "N" represents the residue number within the amino acid sequence at which the substitution occurs, and "AA2" represents the amino acid present in the amino acid sequence after the substitution is effectuated. For example, the notation "C232S" in the context of an antibody hinge region, such as an IgG2 antibody hinge region, refers to a substitution of the naturally-occurring cysteine residue for a serine residue at amino acid residue 232 of the indicated hinge amino acid sequence. Likewise, the notation "C233S" in the context of an antibody hinge region, such as an IgG2 antibody hinge region, refers to a substitution of the naturally-occurring cysteine residue for a serine residue at amino acid residue 233 of the indicated hinge amino acid sequence.

As used herein, the term "conjugate" refers to a compound formed by the chemical bonding of a reactive functional group of one molecule with an appropriately reactive functional group of another molecule.

As used herein in the context of a TNFR2 antagonist, the term "construct" refers to a fusion protein containing a first polypeptide domain bound to a second polypeptide domain. The polypeptide domains may each independently be antagonistic TNFR2 single chain polypeptides, for instance, as described herein. The first polypeptide domain may be covalently bound to the second polypeptide domain, for instance, by way of a linker, such as a peptide linker or a disulfide bridge, among others. Exemplary linkers that may be used to join the polypeptide domains of an antagonistic TNFR2 construct include, without limitation, those that are described in Leriche et al., Bioorg. Med. Chem., 20:571-582 (2012), the disclosure of which is incorporated herein by reference in its entirety.

As used herein, the term "derivatized antibodies" refers to antibodies that are modified by a chemical reaction so as to cleave residues or add chemical moieties not native to an isolated antibody. Derivatized antibodies can be obtained by glycosylation, acetylation, pegylation, phosphorylation, amidation, derivatization by addition of known chemical protecting/blocking groups, proteolytic cleavage, linkage to a cellular ligand or other protein. Any of a variety of chemical modifications can be carried out by known techniques, including, without limitation, specific chemical cleavage, acetylation, formylation, metabolic synthesis of tunicamycin, etc. using established procedures. Additionally, the derivative can contain one or more non-natural amino acids, e.g., using amber suppression technology (see, e.g., U.S. Pat. No. 6,964,859; incorporated herein by reference).

As used herein, the term "diabodies" refers to bivalent antibodies comprising two polypeptide chains, in which each polypeptide chain includes $V_H$ and $V_L$ domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain. In order to fold into their native structure, peptides configured in this way typically trimerize so as to position the VH and VL domains of neighboring peptide chains spatially proximal to one another to permit proper folding (see Holliger et al., Proc. Natl. Acad. Sci. USA 90:6444-48, 1993; incorporated herein by reference).

As used herein, a "disulfide-bonded isoform" of an antibody or antigen-binding fragment thereof is a form of the antibody or antigen-binding fragment thereof having a particular internal disulfide bonding pattern. Disulfide-bonded isoforms are structural isomers of a given antibody or antigen-binding fragment thereof that do not differ from one another in amino acid sequence but exhibit different disulfide bond connectivities. For example, in the context of a human IgG2 antibody or variant thereof, the antibody may exist in one of four possible disulfide-bonded isoforms, represented herein as isoforms IgG2-A, IgG2-B, IgG2-A/B₁, and IgG2-A/B₂. The disulfide bonding connectivities within each of these isoforms are shown graphically in FIGS. 13A-13D.

As used herein, a "dominant antagonist" of TNFR2 is an antagonist (e.g., an antagonistic polypeptide, such as a single-chain polypeptide, antibody, or antigen-binding fragment thereof) that is capable of inhibiting TNFR2 activation even in the presence of a TNFR2 agonist, such as TNFα, or IL-2. For example, a TNFR2 antagonist is a dominant antagonist if the $IC_{50}$ of the antagonist increases by less than 200% (e.g., less than 200%, 100%, 50%, 45%, 40%, 35%, 30%, 25%, 20%, 15%, 10%, 5%, 1%, or less) in the presence of a TNFR2 agonist (e.g., TNFα) or IL-2 relative to the $IC_{50}$ of the antagonist as measured in the same assay in the absence of a TNFR2 agonist, such as TNFα, or IL-2. Inhibition of TNFR2 activation can be assessed, for instance, by measuring the inhibition of proliferation of TNFR2+ cells, such as T-reg cells, cancer cells that express TNFR2, or myeloid-derived suppressor cells, as well as by measuring the inhibition of NFκB signaling (e.g., by monitoring the reduction in expression of one or more genes selected from the group consisting of CHUK, NFκBIE, NFκBIA, MAP3K11, TRAF2, TRAF3, relB, and cIAP2/BIRC3 in a conventional gene expression assay).

As used herein, a "dual variable domain immunoglobulin" ("DVD-Ig") refers to an antibody that combines the target-binding variable domains of two monoclonal antibodies via linkers to create a tetravalent, dual-targeting single agent. (Gu et al., Meth. Enzymol., 502:25-41, 2012; incorporated by reference herein). Suitable linkers for use in the light chains of the DVDs described herein include those identified on Table 2.1 on page 30 of Gu et al.: the short K chain linkers ADAAP (SEQ ID NO: 118) (murine) and TVAAP (SEQ ID NO: 119) (human); the long κ chain linkers ADAAPTVSIFP (SEQ ID NO: 120) (murine) and TVAAPSVFIFPP (SEQ ID NO: 121) (human); the short λ chain linker QPKAAP (SEQ ID NO: 122) (human); the long λ chain linker QPKAAPSVTLFPP (SEQ ID NO: 123) (human); the GS-short linker GGSGG (SEQ ID NO: 124), the GS-medium linker GGSGGGGSG (SEQ ID NO: 125), and the GS-long linker GGSGGGGSGGGGS (SEQ ID NO: 126) (all GS linkers are murine and human). Suitable linkers for use in the heavy chains of the DVDs include those identified on Table 2.1 on page 30 of Gu & Ghayur, 2012, Methods in Enzymology 502:25-41, incorporated by reference herein: the short linkers AKTTAP (SEQ ID NO: 127) (murine) and ASTKGP (SEQ ID NO: 128) (human); the long linkers AKTTAPSVYPLAP (SEQ ID NO: 129) (murine) and ASTKGPSVFPLAP (SEQ ID NO: 130) (human); the GS-short linker GGGGSG (SEQ ID NO: 131), the GS-medium linker GGGGSGGGGS (SEQ ID NO: 26), and the GS-long linker GGGGSGGGGSGGGG (SEQ ID NO: 133) (all GS linkers are murine and human).

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "epitope" refers to a portion of an antigen that is recognized and bound by a polypeptide, such as an antibody, antigen-binding fragment thereof, single-chain polypeptide, or construct as described herein. In the context of a protein antigen (such as TNFR2, e.g., human TNFR2 designated by SEQ ID NO: 7 or TNFR2 of a non-human mammal, such as a non-human mammal described herein), an epitope may be a continuous epitope, which is a single, uninterrupted segment of one or more amino acids covalently linked to one another by peptide bonds in which all of the component amino acids bind the polypeptide (e.g., antibody, antigen-binding fragment thereof, single-chain polypeptide, or construct thereof). Exemplary assays for determining the binding of an antagonistic TNFR2 polypeptide to specific amino acids within an antigen are described in Example 1, below. Continuous epitopes may be composed, for instance, of 1, 5, 10, 15, 20, or more amino acids within an antigen, such as a TNFR2 protein described herein (for instance, human TNFR2 designated by SEQ ID NO: 7). For example, a continuous epitope may be composed of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more amino acids within an antigen). Examples of continuous epitopes on TNFR2 that are bound by antagonistic polypeptides (e.g., single-chain polypeptides, antibodies, antigen-binding fragments thereof, and constructs thereof) described herein include one or more continuous residues of, or all residues of, the SSTDICRPHQI motif (SEQ ID NO: 288), one or more continuous residues of, or all residues of, the CALSKQEGCRLCAPL motif (SEQ ID NO: 289), and one or more continuous residues of, or all residues of, the TSDVVCKPCA motif (SEQ ID NO: 290), as well as corresponding regions on TNFR2 proteins of non-human mammals (e.g., bison, cattle, and others described herein). In some embodiments, an epitope may be a discontinuous epitope, which contains two or more segments of amino acids each separated from one another in an antigen's amino acid sequence by one or more intervening amino acid residues. Discontinuous epitopes may be composed, for instance, of 1, 2, 3, 4, 5, 6, 7, 8, 9, 10, or more such segments of amino acid residues, such as one or more (e.g., 1, 2, 3, 4, 5, 6, 7, 8, 9, 10, or more) segments containing amino acids from within one or more of the SSTDICRPHQI motif (SEQ ID NO: 288), the CALSKQEGCRLCAPL motif (SEQ ID NO: 289), and the TSDVVCKPCA motif (SEQ ID NO: 290) within human TNFR2, as well as corresponding regions on TNFR2 proteins of non-human mammals (e.g., bison, cattle, and others described herein). Despite this separation by intervening amino acids, the segments that compose a discontinuous epitope may be, for instance, spatially proximal to one another in the three-dimensional conformation of the antigen. Exemplary discontinuous epitopes on TNFR2 that are bound by antagonistic polypeptides (e.g., single-chain polypeptides, antibodies, antigen-binding fragments thereof, and constructs thereof) described herein include epitopes containing the following elements: (i) one or more residues, or all residues, of the SSTDICRPHQI motif (SEQ ID NO: 288); (ii) one or more residues, or all residues, of the CALSKQEGCRLCAPL motif (SEQ ID NO: 289), and (iii) one or more residues, r all residues, of the TSDVVCKPCA motif (SEQ ID 290). Additional examples of discontinuous epitopes on TNFR2 that are bound by antagonistic polypeptides (e.g., single-chain polypeptides, antibodies, antigen-binding fragments thereof, and constructs thereof) described herein include epitopes containing elements (i) and (ii) above, epitopes containing elements (i) and (iii) above, and epitopes containing elements (ii) and (iii) above.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "framework region" or "FW region" includes amino acid residues that are adjacent to the CDRs. FW region residues may be present in, for example, human antibodies, rodent-derived antibodies (e.g., murine antibodies), humanized antibodies, primatized antibodies, chimeric antibodies, antibody fragments (e.g., Fab fragments), single-chain antibody fragments (e.g., scFv fragments), antibody domains, and bispecific antibodies, among others.

As used herein, the term "fusion protein" refers to a protein that is joined via a covalent bond to another molecule. A fusion protein can be chemically synthesized by, e.g., an amide-bond forming reaction between the N-terminus of one protein to the C-terminus of another protein. Alternatively, a fusion protein containing one protein covalently bound to another protein can be expressed recombinantly in a cell (e.g., a eukaryotic cell or prokaryotic cell) by expression of a polynucleotide encoding the fusion protein, for example, from a vector or the genome of the cell. A fusion protein may contain one protein that is covalently bound to a linker, which in turn is covalently bound to another molecule. Examples of linkers that can be used for the formation of a fusion protein include peptide-containing linkers, such as those that contain naturally occurring or non-naturally occurring amino acids. In some embodiments, it may be desirable to include D-amino acids in the linker, as these residues are not present in naturally-occurring proteins and are thus more resistant to degradation by endogenous proteases. Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

As used herein, the term "heterospecific antibodies" refers to monoclonal, preferably human or humanized, antibodies that have binding specificities for at least two different antigens. Traditionally, the recombinant production of heterospecific antibodies is based on the co-expression of two immunoglobulin heavy chain-light chain pairs, where the two heavy chains have different specificities (Milstein et al., Nature 305:537, 1983). Similar procedures are disclosed, e.g., in WO 93/08829, U.S. Pat. Nos. 6,210,668; 6,193,967; 6,132,992; 6,106,833; 6,060,285; 6,037,453; 6,010,902; 5,989,530; 5,959,084; 5,959,083; 5,932,448; 5,833,985; 5,821,333; 5,807,706; 5,643,759, 5,601,819; 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986); incorporated herein by reference. Heterospecific antibodies can include Fc mutations that enforce correct chain association in multi-specific antibodies, as described by Klein et al, mAbs 4(6):653-663, 2012; incorporated herein by reference.

As used herein, the term "hinge region" refers to the domain of an antibody or antigen-binding fragment thereof (e.g., an IgG2 antibody or antigen-binding fragment thereof) located between the antigen-binding portion(s) of the antibody or antigen-binding fragment thereof, such as the Fab region of the antibody or antigen-binding fragment thereof, and the portion of the antibody or antigen-binding fragment thereof that dictates the isotype of the antibody or antigen-binding fragment thereof, such as the Fc region of the antibody or antigen-binding fragment thereof. For example, in the context of a monoclonal antibody, the hinge region is the polypeptide situated approximately in the center of each heavy chain, connecting the $C_H1$ domain to the CH2 and CH3 domains. The hinge region of an antibody or antigen-binding fragment thereof may provide a chemical linkage between chains of the antibody or antigen-binding fragment thereof. For instance, in a monoclonal antibody, the cysteine residues within the hinge region form inter-chain disulfide bonds, thereby providing explicit covalent bonds between heavy chains. The amino acid sequence of wild-type human IgG2 is ERKCCVECPPCP (SEQ ID NO: 292). As used herein, antibody hinge regions are numbered according to the numbering system of Kabat et al, Sequences of Proteins of Immunological Interest (National Institute of Health, Bethesda, Md. 1987), the disclosure of which is incorporated herein by reference. For example, using the numbering scheme of Kabat et al, the wild-type human IgG2 hinge region set forth in SEQ ID NO: 292 is numbered from residues 226 to 243, such that the N-terminal glutamate residue of SEQ ID NO: 292 is residue 226 and the C-terminal proline residue of SEQ ID NO: 292 is residue 243. Throughout the present disclosure, variant IgG2 hinge regions, such as the variant set forth in SEQ ID NO: 291 (ERKCCVECPPCP), are numbered according to the convention of Kabat et al unless explicitly stated to the contrary.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A human antibody can be produced in a human cell (e.g., by recombinant expression), or by a non-human animal or a prokaryotic or eukaryotic cell that is capable of expressing functionally rearranged human immunoglobulin (e.g., heavy chain and/or light chain) genes. Further, when a human antibody is a single-chain antibody, it can include a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. See U.S. Pat. Nos. 4,444,887 and 4,716,111; and PCT publications WO 1998/46645; WO 1998/50433; WO 1998/24893; WO 1998/16654; WO 1996/34096; WO 1996/33735; and WO 1991/10741; incorporated herein by reference. Human antibodies can also be produced using transgenic mice that are incapable of expressing functional endogenous immunoglobulins, but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598; incorporated by reference herein.

As used herein, the term "humanized" antibodies refers to forms of non-human (e.g., murine) antibodies that are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin. All or substantially all of the FR regions may also be those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., Nature 332:323-7, 1988; U.S. Pat. Nos. 5,530,101; 5,585,089; 5,693,761; 5,693,762; and U.S. Pat. No. 6,180,370 to Queen et al; EP239400; PCT publication WO 91/09967; U.S. Pat. No. 5,225,539; EP592106; and EP519596; incorporated herein by reference.

As used herein, the term "hydrophobic side-chain" refers to an amino acid side-chain that exhibits low solubility in water relative due to, e.g., the steric or electronic properties of the chemical moieties present within the side-chain. Examples of amino acids containing hydrophobic side-chains include those containing unsaturated aliphatic hydrocarbons, such as alanine, valine, leucine, isoleucine, proline, and methionine, as well as amino acids containing aromatic ring systems that are electrostatically neutral at physiological pH, such as tryptophan, phenylalanine, and tyrosine.

As used herein, the term "immunotherapy agent" refers to a compound, such as an antibody, antigen-binding fragment thereof, single-chain polypeptide, or construct as described herein, that specifically binds an immune checkpoint protein (e.g., immune checkpoint receptor or ligand) and exerts an antagonistic effect on the receptor or ligand, thereby reducing or inhibiting the signal transduction of the receptor or ligand that would otherwise lead to a downregulation of the immune response. Immunotherapy agents include compounds, such as antibodies, antigen-binding fragments, single-chain polypeptides, and constructs, capable of specifically binding receptors expressed on the surfaces of hematopoietic cells, such as lymphocytes (e.g., T cells), and suppressing the signaling induced by the receptor or ligand that would otherwise lead to tolerance towards an endogenous ("self") antigen, such as a tumor-associated antigen. Immunotherapy agents may reduce the signaling induced by the receptor or ligand by, for example, 1%, 2%, 3%, 4%, 5%, 10%, 20%, 30%, 40%, 50%, 60%, 70%, 80%, 90%, 95%, 96%, 97%, 98%, 99%, 99.9%, or 100% relative to the signaling induced by the receptor or ligand exhibited in the absence of the immunotherapy agent. Exemplary assays that can be used to measure the extent of receptor or ligand signaling include, for example, enzyme-linked immunosorbant assay (ELISA) techniques to measure protein expression alterations that are associated with a particular signal transduction pathway, as well as polymerase chain reaction (PCR)-based techniques, such as quantitative PCR, reverse-transcription PCR, and real-time PCR experiments useful for determining changes in gene expression associated with a particular signal transduction pathway, among others.

Exemplary methods that can be used to determine whether an agent is an "immunotherapy agent" include the assays described in Mahoney et al., Cancer Immunotherapy, 14:561-584 (2015), the disclosure of which is incorporated herein by reference in its entirety. Examples of immunotherapy agents include, e.g., antibodies or antigen-binding fragments thereof that specifically bind one or more of OX40L, TL1A, CD40L, LIGHT, BTLA, LAG3, TIM3, Singlecs, ICOS, B7-H3, B7-H4, VISTA, TMIGD2, BTNL2, CD48, KIR, LIR, LIR antibody, ILT, NKG2D, NKG2A, MICA, MICB, CD244, CSF1R, IDO, TGFβ, CD39, CD73, CXCR4, CXCL12, SIRPA, CD47, VEGF, and neuropilin. Additional example of immunotherapy agents include Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and/or small molecular therapies like Vorinostat. Particular examples of immunotherapy agents that may be used in conjunction with the compositions and methods described herein include anti-PD-1 antibodies and antigen-binding fragments thereof, such as nivolumab, pembrolizumab, avelumab, durvalumab, and atezolizumab, as well as anti-PD-L1 antibodies and antigen-binding fragments thereof, such as atezolizumab and avelumab, and anti-CTLA-4 antibodies and antigen-binding fragments thereof, such as ipilimumab or tremelimumab.

As used herein, the term "monoclonal antibody" refers to an antibody that is derived from a single clone, including any eukaryotic, prokaryotic, or phage clone, and not the method by which it is produced.

As used herein, the term "multi-specific antibodies" refers to antibodies that exhibit affinity for more than one target antigen. Multi-specific antibodies can have structures similar to full immunoglobulin molecules and include Fc regions, for example IgG Fc regions. Such structures can include, but not limited to, IgG-Fv, IgG-(scFv)$_2$, DVD-lg, (scFv)$_2$-(scFv)$_2$-Fc and (scFv)$_2$-Fc-(scFv)$_2$. In case of IgG-(scFv)$_2$, the scFv can be attached to either the N-terminal or the C-terminal end of either the heavy chain or the light chain. Exemplary multi-specific molecules that include Fc regions and into which anti-TNFR2 antibodies or antigen-binding fragments thereof can be incorporated have been reviewed by Kontermann, 2012, mAbs 4(2):182-197, Yazaki et al, 2013, Protein Engineering, Design & Selection 26(3): 187-193, and Grote et al, 2012, in Proetzel & Ebersbach (eds.), Antibody Methods and Protocols, Methods in Molecular Biology vol. 901, chapter 16:247-263; incorporated herein by reference. In some embodiments, antibody fragments can be components of multi-specific molecules without Fc regions, based on fragments of IgG or DVD or scFv. Exemplary multi-specific molecules that lack Fc regions and into which antibodies or antibody fragments can be incorporated include scFv dimers (diabodies), trimers (tiabodies) and tetramers (tetrabodies), Fab dimers (conjugates by adhesive polypeptide or protein domains) and Fab trimers (chemically conjugated), are described by Hudson and Souriau, 2003, Nature Medicine 9:129-134; incorporated herein by reference.

As used herein, the term "myeloid-derived suppressor cell" or "MDSC" refers to a cell of the immune system that modulates the activity of a variety of effector cells and antigen-presenting cells, such as T cells, NK cells, dendritic cells, and macrophages, among others. Myeloid derived suppressor cells are distinguished by their gene expression profile, and express all or a subset of proteins and small molecules selected from the group consisting of B7-1 (CD80), B7-H1 (PD-L1), CCR2, CD1d, CD1d1, CD2, CD31 (PECAM-1), CD43, CD44, complement component C5a R1, F4/80 (EMR1), Fcγ RIII (CD16), Fcγ RII (CD32), Fcγ RIIA (CD32a), Fcγ RIIB (CD32b), Fcγ RIIB/C (CD32b/c), Fcγ RIIC (CD32c), Fcγ RIIIA (CD16A), Fcγ RIIIB (CD16b), galectin-3, GP130, Gr-1 (Ly-6G), ICAM-1 (CD54), IL-1 RI, IL-4Ra, IL-6Rα, integrin α4 (CD49d), integrin αL (CD11a), integrin αM (CD11b), M-CSFR, MGL1 (CD301a), MGL1/2 (CD301a/b), MGL2 (CD301b), nitric oxide, PSGL-1 (CD162), L-selectin (CD62L), siglec-3 (CD33), transferrin receptor (TfR), VEGFR1 (Fit-1), and VEGFR2 (KDR or Flk-1). Particularly, MDSCs do not express proteins selected from the group consisting of B7-2 (CD86), B7-H4, CD11c, CD14, CD21, CD23 (FcɛRII), CD34, CD35, CD40 (TNFRSF5), CD117 (c-kit), HLA-DR, and Sca-1 (Ly6).

As used herein, the terms "neutral TNFR2 polypeptide" and "phenotype-neutral TNFR2 polypeptide" refer to a polypeptide (such as a single-chain polypeptide, an antibody, or an antibody fragment) that binds TNFR2 and does not exert an antagonistic or an agonistic effect on TNFR2 activation. For instance, a TNFR2 polypeptide is a neutral TNFR2 polypeptide if the polypeptide binds TNFR2 and neither potentiates nor suppresses TNFR2 activation, for instance, as assessed by measuring the proliferation of TNFR2-expressing cells (e.g., T-reg cells, TNFR2+ cancer cells, and/or MDSCs) and/or by measuring the expression of one or more NFκB target genes, such as CHUK, NFKBIE, NFKBIA, MAP3K11, TRAF2, TRAF3, relB, and/or cIAP2/BIRC3.

As used herein, the term "non-native constant region" refers to an antibody constant region that is derived from a source that is different from the antibody variable region or that is a human-generated synthetic polypeptide having an amino sequence that is different from the native antibody constant region sequence. For instance, an antibody containing a non-native constant region may have a variable region derived from a non-human source (e.g., a mouse, rat, or rabbit) and a constant region derived from a human source (e.g., a human antibody constant region), or a constant region derived from another primate, pig, goat, rabbit, hamster, cat, dog, guinea pig, member of the bovidae family (such as cattle, bison, buffalo, elk, and yaks, among others), cow, sheep, horse, or bison, among others).

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, the term "primatized antibody" refers to an antibody comprising framework regions from primate-derived antibodies and other regions, such as CDRs and/or constant regions, from antibodies of a non-primate source. Methods for producing primatized antibodies are known in the art. See e.g., U.S. Pat. Nos. 5,658,570; 5,681,722; and 5,693,780; incorporated herein by reference. For instance, a primatized antibody or antigen-binding fragment thereof described herein can be produced by inserting the CDRs of a non-primate antibody or antigen-binding fragment thereof into an antibody or antigen-binding fragment thereof that contains one or more framework regions of a primate.

As used herein, the term "proliferation" in the context of a population of cells, such as a population of TNFR2+ cells (e.g., T-reg cells, MDSCs, or TNFR2+ cancer cells) refers to mitotic and cytokinetic division of a cell so as to produce a plurality of cells. Cell proliferation may be evidenced, for example, by a finding that the quantity of cells (e.g., TNFR2+ cells) in a sample of cells has increased over a given time period, such as over the course of one or more hours, days, or weeks. One of skill in the art may monitor cell proliferation using a variety of known techniques, such as by way of visual microscopy, hemocytometry, flow cytometry, fluorescence activated cell sorting, and other assays known in the art. In the present disclosure, cell proliferation is considered to be "inhibited" when the rate of proliferation of a population of cells, such as a population of TNFR2+ cells contacted with an antagonistic TNFR2 polypeptide described herein, is decreased relative to the rate of proliferation of a population of control cells, such as a population of TNFR2+ cells not contacted with the antagonistic TNFR2 polypeptide. A decrease in the rate of proliferation may manifest, for example, as a reduction in the quantity of cells of interest in a sample over a given time period, such as a reduction in the quantity of cells of interest in a sample of 1%, 2%, 3%, 4%, 5%, 6%, 7%, 8%, 9%, 10%, 11%, 12%, 13%, 14%, 15%, 20%, 25%, 30%, 35%, 40%, 45%, 50%, 60%, 70%, 80%, 90%, or more, over a given time period. Additionally or alternatively, inhibition of cell proliferation may be evidenced by a finding that the rate at which cells of interest (e.g., TNFR2+ cells contacted with an antagonistic TNFR2 polypeptide described herein) are dividing is reduced, e.g., by %, 2%, 3%, 4%, 5%, 6%, 7%, 8%, 9%, 10%, 11%, 12%, 13%, 14%, 15%, 20%, 25%, 30%, 35%, 40%, 45%, 50%, 60%, 70%, 80%, 90%, or more, relative to the rate at which control cells (e.g., TNFR2+ cells not contacted with the antagonistic TNFR2 polypeptide) are dividing.

As used herein, the term "operatively linked" in the context of a polynucleotide fragment is intended to mean that the two polynucleotide fragments are joined such that the amino acid sequences encoded by the two polynucleotide fragments remain in-frame.

As used herein, the term "pharmacokinetic profile" refers to the absorption, distribution, metabolism, and clearance of a drug over time following administration of the drug to a patient.

As used herein, a "recessive antagonist" of TNFR2 is an antagonist (e.g., an antagonistic polypeptide, such as a single-chain polypeptide, antibody, or antigen-binding fragment thereof) that inhibits TNFR2 activation to a significantly lesser extent in the presence of a TNFR2 agonist, such as TNFα, or IL-2 relative to the extent of inhibition of the same antagonist as measured in the absence of a TNFR2 agonist, such as TNFα, or IL-2. For example, a TNFR2 antagonist is a recessive antagonist if the $IC_{50}$ of the antagonist increases by, e.g., 10-fold, 20-fold, 30-fold, 40-fold, 50-fold, 60-fold, 70-fold, 80-fold, 90-fold, 100-fold, or more in the presence of a TNFR2 agonist (e.g., TNFα or *Bacillus* Calmette-Guérin (BCG)) or IL-2 relative to the $IC_{50}$ of the antagonist as measured in the same assay the absence of a TNFR2 agonist, such as TNFα, or IL-2. Inhibition of TNFR2 activation can be assessed, for instance, by measuring the inhibition of proliferation of TNFR2+ cells, such as T-reg cells, cancer cells that express TNFR2, or myeloid-derived suppressor cells, as well as by measuring the inhibition of NFκB signaling (e.g., by monitoring the reduction in expression of one or more genes selected from the group consisting of CHUK, NFKBIE, NFKBIA, MAP3K11, TRAF2, TRAF3, relB, and cIAP2/BIRC3 in a conventional gene expression assay).

As used herein, the term "regulatory sequence" includes promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, CA, 1990); incorporated herein by reference.

As used herein, the term "scFv" refers to a single-chain Fv antibody in which the variable domains of the heavy chain and the light chain from an antibody have been joined to form one chain. scFv fragments contain a single polypeptide chain that includes the variable region of an antibody light chain (VL) (e.g., CDR-L1, CDR-L2, and/or CDR-L3) and the variable region of an antibody heavy chain (VH) (e.g., CDR-H1, CDR-H2, and/or CDR-H3) separated by a linker. The linker that joins the VL and VH regions of a scFv fragment can be a peptide linker composed of proteinogenic amino acids. Alternative linkers can be used to so as to increase the resistance of the scFv fragment to proteolytic degradation (e.g., linkers containing D-amino acids), in order to enhance the solubility of the scFv fragment (e.g., hydrophilic linkers such as polyethylene glycol-containing linkers or polypeptides containing repeating glycine and serine residues), to improve the biophysical stability of the molecule (e.g., a linker containing cysteine residues that form intramolecular or intermolecular disulfide bonds), or to attenuate the immunogenicity of the scFv fragment (e.g., linkers containing glycosylation sites). scFv molecules are known in the art and are described, e.g., in U.S. Pat. No. 5,892,019, Flo et al., (Gene 77:51, 1989); Bird et al., (Science 242:423, 1988); Pantoliano et al., (Biochemistry 30:10117, 1991); Milenic et al., (Cancer Research 51:6363, 1991); and Takkinen et al., (Protein Engineering 4:837, 1991). The VL and VH domains of a scFv molecule can be derived from one or more antibody molecules. It will also be understood by one of ordinary skill in the art that the variable regions of the scFv molecules described herein can be modified such that they vary in amino acid sequence from the antibody molecule from which they were derived. For example, in one embodiment, nucleotide or amino acid substitutions leading to conservative substitutions or changes at amino acid residues can be made (e.g., in CDR and/or framework residues). Alternatively or in addition, mutations are made to CDR amino acid residues to optimize antigen binding using art recognized techniques. scFv fragments are described, for example, in WO 2011/084714; incorporated herein by reference.

As used herein, the phrase "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a $K_D$ of less than 100 nM. For example, an antibody or antigen-binding fragment thereof that specifically binds to an antigen will bind to the antigen with a $K_D$ of up to 100 nM (e.g., between 1 pM and 100 nM). An antibody or antigen-binding fragment thereof that does not exhibit specific binding to a particular antigen or epitope thereof will exhibit a $K_D$ of greater than 100 nM (e.g., greater than 500 nm, 1 μM, 100 μM, 500 μM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

As used herein, the terms "subject" and "patient" refer to an organism that receives treatment for a particular disease or condition as described herein (such as cancer or an infectious disease). Examples of subjects and patients include mammals, such as humans, primates, pigs, goats, rabbits, hamsters, cats, dogs, guinea pigs, members of the bovidae family (such as cattle, bison, buffalo, elk, and yaks, among others), cows, sheep, horses, and bison, among others, receiving treatment for diseases or conditions, for example, cell proliferation disorders, such as cancer or infectious diseases.

As used herein, the term "transfection" refers to any of a wide variety of techniques commonly used for the introduction of exogenous DNA into a prokaryotic or eukaryotic host cell, e.g., electroporation, lipofection, calcium-phosphate precipitation, DEAE-dextran transfection and the like.

As used herein, the terms "treat" or "treatment" refer to therapeutic treatment, in which the object is to prevent or slow down (lessen) an undesired physiological change or disorder, such as the progression of a cell proliferation disorder, such as cancer, or an infectious disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in which the condition or disorder is to be prevented.

As used herein, the term "tumor microenvironment" refers to cancer cells that form a tumor and the population of non-cancer cells, molecules, and/or blood vessels within the tumor or that border or surround the cancer cells.

As used herein, the terms "tumor necrosis factor receptor superfamily," "TNFR superfamily," or "TNFRS" refer to a group of type I transmembrane proteins with a carboxy-terminal intracellular domain and an amino-terminal extracellular domain characterized by a common cysteine-rich domain (CRD). The TNFR superfamily includes receptors that mediate cellular signaling as a consequence of binding to one or more ligands in the TNF superfamily. The TNFR superfamily can be divided into two subgroups: receptors containing the intracellular death domain and those lacking this domain. The death domain is an 80 amino acid motif that propagates apoptotic signal transduction cascades following receptor activation. Exemplary TNFR super family members that contain the intracellular death domain include TNFR1, while TNFR2 represents a TNFR super family protein that does not contain this domain. Members of the TNFR superfamily include TNFR1, TNFR2, RANK, CD30, CD40, Lymphotoxin beta receptor (LT-βR), OX40, Fas receptor, Decoy receptor 3 (DCR3), CD27, 4-1BB, Death receptor 4 (DR4), Death receptor 5 (DR5), Decoy receptor 1 (DCR1), Decoy receptor 2 (DCR2), Osteoprotegrin, TWEAK receptor, TACI, BAFF receptor, Herpesvirus entry mediator, Nerve growth factor receptor, B cell maturation antigen, Glucocorticoid-induced TNFR-related, TROY, Death receptor 6 (DR6), Death receptor 3 (DR3), and Ectodysplasin A2 receptor.

As used herein, the terms "tumor necrosis factor receptor 2 signaling," "TNFR2 signaling," "TNFR2 signal transduction," and the like, are used interchangeably and refer to the cellular events that normally occur upon activation of TNFR2 on the surface of a TNFR2+ cell, such as T-reg cell, MDSC, or TNFR2+ cancer cell, by an endogenous TNFR2 ligand, such as TNFα. TNFR2 signaling may be evidenced by a finding that expression is increased for one or more genes selected from the group consisting of CHUK, NFK-BIE, NFKBIA, MAP3K11, TRAF2, TRAF3, relB, and cIAP2/BIRC3. TNFR2 signaling is considered to be "inhibited" as used herein when the expression (and/or post-translational modification in the event that such a modification is required for activity of the encoded protein) of one or more, or all, of the foregoing genes is decreased in a TNFR2+ cell upon contacting the cell with an agent, such as a TNFR2 antagonist polypeptide described herein, relative to a TNFR2+ cell that is not contacted with the agent (e.g., TNFR2 antagonist polypeptide). TNFR2 signaling is considered to be "inhibited," for example, when the expression or post-translational modification (e.g., phosphorylation) of one or more of CHUK, NFKBIE, NFKBIA, MAP3K11, TRAF2, TRAF3, relB, or cIAP2/BIRC3, in a TNFR2+ cell contacted with an antagonistic TNFR2 polypeptide is decreased by about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% relative to the expression or post-translational modification (e.g., phosphorylation) of one or more of these genes in a TNFR2+ cell not contacted with the antagonistic TNFR2 polypeptide. Exemplary assays that can be used to determine expression level and phosphorylation state are known in the art and include, e.g., Western blot assays to determine protein content and quantitative reverse transcription polymerase chain reaction (RT-PCR) experiments to determine mRNA content.

As used herein the term "variable region CDR" includes amino acids in a CDR or complementarity determining region as identified using sequence or structure based methods. As used herein, the term "CDR" or "complementarity determining region" refers to the noncontiguous antigen-binding sites found within the variable regions of both heavy and light chain polypeptides. These particular regions have been described by Kabat et al., J. Biol. Chem. 252:6609-6616, 1977 and Kabat, et al., Sequences of Proteins of Immunological Interest, Fifth Edition, U.S. Department of Health and Human Services, NIH Publication No. 91-3242, 1991; by Chothia et al., (J. Mol. Biol. 196-901-917, 1987), and by MacCallum et al., (J. Mol. Biol. 262:732-745, 1996) where the definitions include overlapping or subsets of amino acid residues when compared against each other. The term "CDR" may be, for example, a CDR as defined by Kabat based on sequence comparisons.

As used herein, the term "vector" includes a nucleic acid vector, e.g., a DNA vector, such as a plasmid, a RNA vector, virus or other suitable replicon (e.g., viral vector). A variety of vectors have been developed for the delivery of poly-nucleotides encoding exogenous proteins into a prokaryotic or eukaryotic cell. Examples of such expression vectors are disclosed in, e.g., WO 1994/11026; incorporated herein by reference. Expression vectors described herein contain a polynucleotide sequence as well as, e.g., additional sequence elements used for the expression of proteins and/or the integration of these polynucleotide sequences into the genome of a mammalian cell. Certain vectors that can be used for the expression of antibodies and antibody fragments described herein include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "VH" refers to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain of a native antibody has at the amino terminus a variable domain (VH) followed by a number of constant domains. Each light chain of a native antibody has a variable domain at the amino terminus (VL) and a constant domain at the carboxy terminus.

BRIEF DESCRIPTION OF THE FIGURES

FIG. 1 shows the amino acid sequence of human TNFR2 (SEQ ID NO: 7). Human TNFR2 is numbered herein starting with an N-terminal methionine at position 1 and concluding with a C-terminal serine at position 461 (SEQ ID NO: 7). All references to amino acid positions within TNFR2 are made in the context of the TNFR2 numbering scheme shown in FIG. 1. The binding of residues shown in bold and underlined font (KCRPG, SEQ ID NO: 19), along with other epitopes present in cysteine-rich domain 3 (CRD3) and CRD4 of human TNFR2 (residues 121-162 and 162-202 of SEQ ID NO: 7, respectively) and equivalent regions within TNFR2 of non-humans, such as non-human mammals, promotes antagonism of TNFR2 signaling. The binding of italicized residues (KCSPG, SEQ ID NO: 12), along with other epitopes present in CRD1 of human TNFR2 (residues 48-76 of SEQ ID NO: 7) and equivalent regions within TNFR2 of non-humans, such as non-human mammals, disfavors TNFR2 antagonism.

FIGS. 13A-13D are a series of schematics comparing the disulfide bonding arrangement present in each of the IgG2-A (FIG. 13A), IgG2-B (FIG. 13B), IgG2-A/B$_1$ (FIG. 13C), and IgG2-A/B$_2$ (FIG. 13D) isoforms of a human IgG2 isotype antibody. Thin lines represent disulfide bonds connecting various portions of each antibody heavy chain or light chain, which are represented by shaded rectangles. Heavy chains are represented by the longer, outermost rectangles of each antibody. Within each heavy chain, black shading denotes the constant region, and light shading denotes the variable region. Light chains are represented by the shorter, innermost rectangles of each antibody. Within each light chain, darker shading denotes the constant region, and lighter shading denotes the variable region.

DETAILED DESCRIPTION

Figure 2:
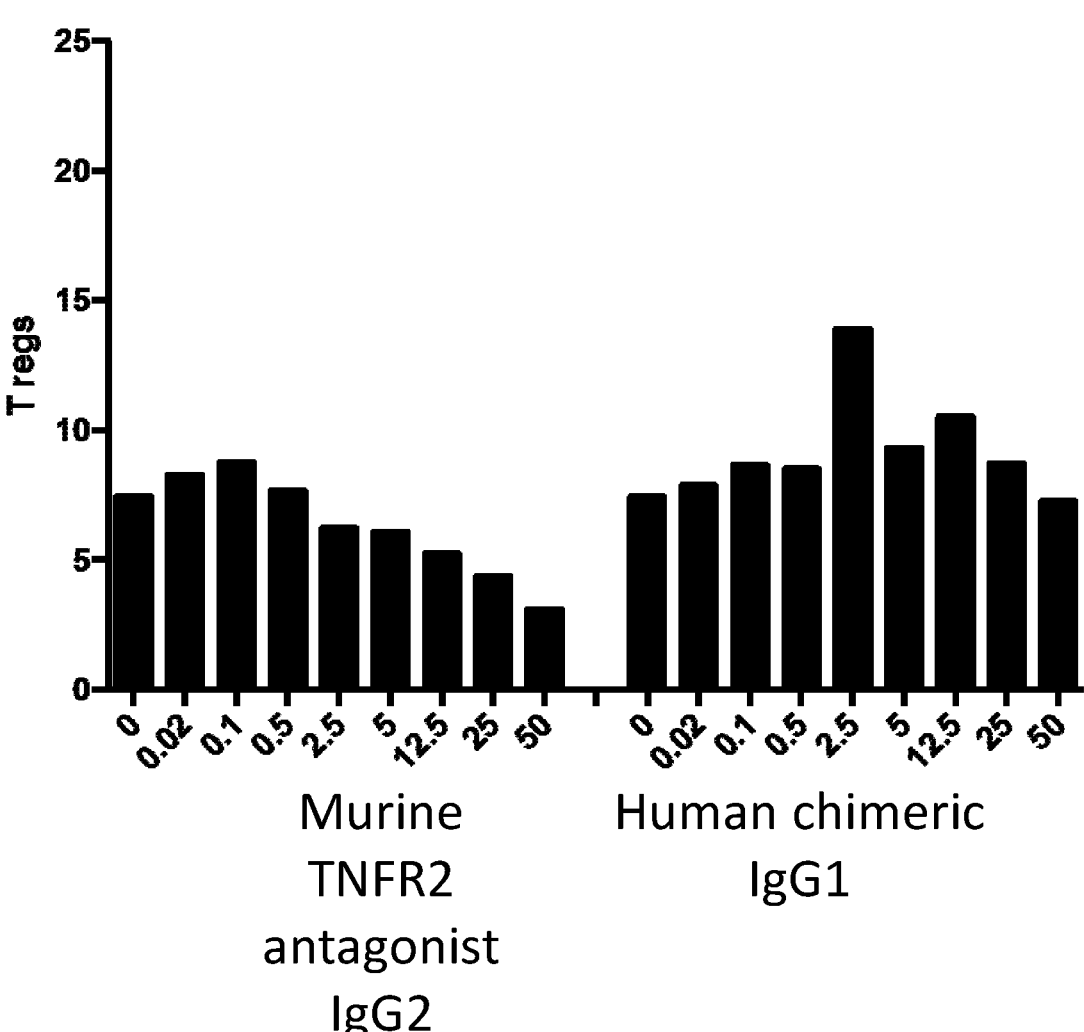
FIG. 2 is a graph contrasting the effects of murine monoclonal TNFR2 antagonist antibody TNFRAB2 on the viability of regulatory T (T-reg) cells in vitro (left) with the effects of a human chimeric version of TNFRAB2 on the viability of T-reg cells under the same assay conditions (right). TNFRAB2 is a murine IgG2 antibody, and the human chimeric TNFR2 antagonist antibody tested in this example has a human IgG1 isotype. Values along the x-axis represent antibody concentration in units of pg/ml. Values along the y-axis represent the percentage of T-reg cells present in an in vitro cell sample after the sample is incubated with the indicated concentration of TNFR2 antibody.

Antagonistic TNFR2 polypeptides described herein, such as single-chain polypeptides, antibodies, antigen-binding fragments thereof, and constructs thereof, inhibit the activation of TNFR2 on TNFR2-expressing cells. This may be effectuated, for instance, by binding TNFR2 (e.g., on the exterior surface of a T-reg cell, a cancer cell that expresses TNFR2, or a myeloid-derived suppressor cell (MDSC)) and preventing the receptor from adopting a three-dimensional conformation that is suitable for binding its cognate ligand, TNFα. TNFα potentiates TNFR2 signaling by nucleating a trimer of TNFR2 proteins. It is this trimerization event that brings individual TNFR2 proteins into close proximity and initiates TNFR2 signaling via the MAPK/NFκB/TRAF2/3 pathway, which ultimately leads to cell growth and escape from apoptosis. Antagonistic TNFR2 polypeptides described herein can antagonize this interaction, for instance, by binding the receptor and preventing receptor trimerization. For instance, one mechanism by which this may occur is through the formation of an anti-parallel TNFR2 dimer, which is an inactive structural form of the receptor.

The TNFR2 polypeptides described herein specifically bind to epitopes within TNFR2 that promote receptor antagonism and various advantageous downstream biological activities. Human TNFR2 contains four cysteine-rich domains (CRDs): CRD1 (amino acid residues 48-76 of SEQ ID NO: 7), CRD2 (amino acid residues 78-120 of SEQ ID NO: 7), CRD3 (amino acid residues 121-162 of SEQ ID NO: 7), and CRD4 (amino acid residues 162-202 of SEQ ID NO: 7). Antagonistic TNFR2 polypeptides described herein specifically bind TNFR2 at one or more epitopes within CRD3 and/or CRD4. In some embodiments, the antagonistic TNFR2 polypeptides do not bind epitopes within CRD1 and/or CRD2. For example, the polypeptides (e.g., single-chain polypeptides, antibodies, antigen-binding fragments thereof, or constructs thereof) of the disclosure may bind human TNFR2 at an epitope within one or more of the following residues:

(a) amino acids 142-146 of SEQ ID NO: 7 (KCRPG, SEQ ID NO: 19);

(b) amino acids 142-149 of SEQ ID NO: 7 (KCRPGFGV, SEQ ID NO: 20);

(c) amino acids 137-144 of SEQ ID NO: 7 (CAPLRKCR, SEQ ID NO: 11);

(d) amino acids 150-190 of SEQ ID NO: 7 (RPGTETSDVVCKPCAPGTFSNTTSSTDI-CRPHQICNVVAI, SEQ ID NO: 307);

(e) amino acids 161-169 of SEQ ID NO: 7 (CKP-CAPGTF, SEQ ID NO: 21);

(f) amino acids 75-128 of SEQ ID NO: 7 (CDSCED-STYTQLWNWVPECLSCGSRCSSDQVETQAC-TREQNRICTCRPGWYCAL, SEQ ID NO: 308), optionally in which the epitope is within amino acids 80-86 (DSTYTQL, SEQ ID NO: 8), 91-98 (PE-CLSCGS, SEQ ID NO: 9), or 116-123 (RICTCRPG, SEQ ID NO: 10) of SEQ ID NO: 7;

(g) amino acids 174-184 (SSTDICRPHQI, SEQ ID NO: 288) of SEQ ID NO: 7;

(h) amino acids 126-140 (CALSKQEGCRLCAPL, SEQ ID NO: 289) of SEQ ID NO: 7; and/or (i) amino acids 156-165 (TSDVVCKPCA, SEQ ID NO: 290) of SEQ ID NO: 7;

or an equivalent epitope within TNFR2 of a non-human mammal, such as a non-human mammal described herein.

The present disclosure is based, in part, on the discovery that anti-TNFR2 polypeptides demonstrate substantially improved TNFR2 antagonist effects when these molecules are in the form of an IgG2 isotype. As described in the examples below, it has presently been discovered that this class of TNFR2 polypeptides exhibits a surprisingly superior ability to disrupt TNFR2 signaling, attenuate T-reg cell and cancer cell growth, and augment the proliferation of effector T cells relative to TNFR2-binding polypeptides of other isotypes.

Another discovery underlying the present disclosure is the finding that antagonistic TNFR2 polypeptides that contain antigen-binding sites spatially separated from one another by about 133 Å or more exhibit unexpectedly superior TNFR2 antagonist effects relative to polypeptides that specifically bind TNFR2 at one or more of the epitopes described above but that contain antigen-binding sites separated from one another by fewer than about 133 Å. Examples of such polypeptides include IgG1 antibodies and antigen-binding fragments thereof that contain antigen-binding sites separated from one another by about 117 Å and IgG3 antibodies and antigen-binding fragments thereof that contain antigen-binding sites separated from one another by 125 Å.

Antagonistic TNFR2 polypeptides of the disclosure can be formulated into pharmaceutical compositions. Preferably, the polypeptides present in the pharmaceutical composition adopt a single disulfide-bonded isoform. For example, pharmaceutical compositions of the disclosure include those containing an antagonist TNFR2 polypeptide in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform. Antagonistic TNFR2 polypeptides of the disclosure may advantageously adopt an IgG2-A disulfide-bonded isoform, which has surprisingly been found to promote a substantially more robust level of TNFR2 antagonism relative to other IgG2 disulfide-bonded isoforms, such as the IgG2-B, IgG2-A/B$_1$, and IgG2-A/B$_2$ isoforms. These isoforms are shown graphically in FIGS. 13A-13D. Polypeptides of the disclosure may be engineered to predominantly adopt an IgG2-A isoform, for example, by introducing mutations into the IgG2 hinge region that prohibit the formation of other disulfide-bonded isoforms. Exemplary mutations in the amino acid sequence of a human IgG2 hinge region that promote the formation of the IgG2-A isoform at the exclusion of the remaining isoforms described above include the deletions and/or substitutions of the cysteine residues at positions 232 and 233 of the wild-type human IgG2 hinge amino acid sequence, which is set forth in SEQ ID NO: 291. For example, to engineer an IgG2 antibody or antigen-binding fragment thereof so as to predominantly adopt the IgG2-A isoform, one may introduce conservative amino acid substitutions at cysteine residues 232 and/or 233 of SEQ ID NO: 291. An exemplary IgG2 hinge region that exists predominantly in the IgG2-A isoform has the amino acid sequence of SEQ ID NO: 292, which contains C232S and C233S substitutions relative to SEQ ID NO: 291.

The following biological activities are examples of antagonistic TNFR2 phenotypes that are exhibited by polypeptides of the disclosure to a superior extent relative to TNFR2-binding polypeptides that (i) have an isotype other than IgG2, (ii) contain antigen-binding sites separated from one another by fewer than 133 Å, and/or (iii) do not exist predominantly in a single disulfide-bonded isoform (e.g., the IgG2-A isoform):

(a) Suppression of the proliferation of, and/or the direct killing of, T-reg cells, for instance, by binding and inactivating TNFR2 on the T-reg cell surface;

(b) Suppression of the proliferation of, and/or the direct killing of, MDSCs, for instance, by binding and inactivating TNFR2 on the MDSC surface;

(c) Promotion of the expansion of T effector cells, such as CD8+ T cells; and/or (d) Suppression of the proliferation of, and/or the direct killing of, TNFR2-expressing cancer cells, such as Hodgkin's lymphoma cells, cutaneous non-Hodgkin's lymphoma cells, T cell lymphoma cells, ovarian cancer cells, colon cancer cells, multiple myeloma cells, renal cell carcinoma cells, skin cancer cells, lung cancer cells, liver cancer cells, endometrial cancer cells, hematopoietic or lymphoid cancer cells, central nervous system cancer cells, breast cancer cells, pancreatic cancer cells, stomach cancer cells, esophageal cancer cells, and upper gastrointestinal cancer cells.

The sections that follow provide a description of exemplary characteristics of antagonistic TNFR2 polypeptides described herein, such as single-chain polypeptides, antibodies, antigen-binding fragments thereof, and constructs thereof, as well as their use in therapeutic methods.

Antagonistic TNFR2 Polypeptides

IgG2 Isotype Antibodies Promotes Optimal TNFR2 Antagonism

Figures 13A, 13B, 13C, 13D:
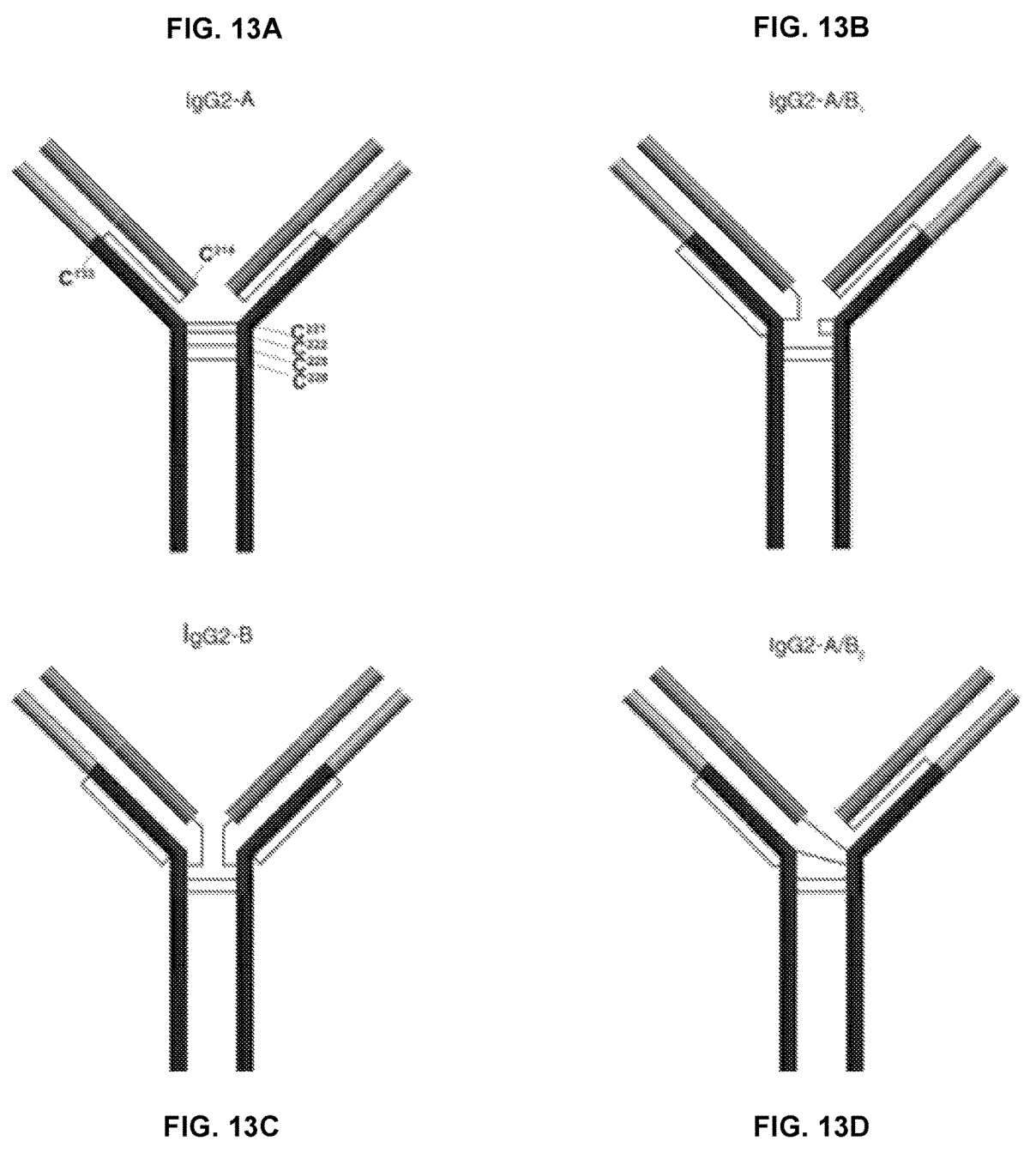

As described above and herein, optimal TNFR2 antagonism among human, humanized, and chimeric TNFR2 antagonist antibodies and antigen-binding fragment thereof is achieved when the antibody or antibody fragment has a human IgG2 isotype, particularly when the antibody or antibody fragment has an IgG2-A disulfide-bonded isoform. The disulfide bonding pattern of the various isoforms of human IgG2 antibodies are shown in FIGS. 13A-13D. As shown in FIG. 13A, the IgG2-A isoform exhibits disulfide bonding between cysteine residues C133 of the heavy chain and C214 of the light chain, as well as disulfide bonds between corresponding cysteine residues C221, C222, C225, and C228 present on each heavy chain.

To stabilize the IgG2-A disulfide-bonded isoform, mutations can be introduced into the IgG2 hinge region so as to prevent, or reduce the occurrence of, disulfide bonding between cysteine residues that are present as nonbonded thiols in the IgG2-A isoform. Examples of such mutations are amino acid substitutions or deletions at residues C232 and C233 of the human IgG2 hinge region. By removing one or both of these residues and optionally replacing these residues with amino acids that are incapable of forming disulfide bonds, one can bias the disulfide bonding pattern in a population of IgG2 isoforms towards the IgG2-A isoform. Examples of amino acid substitutions that can be used to obtain a population of IgG2-A isoform antibodies include conservative amino acid substitutions, such as the C232S and C233S amino acid substitutions. Due to the similar molecular volume and polarity of cysteine and serine, the C232S and C233S substitutions feature the beneficial effect of preserving the steric and electronegativity properties of the naturally-occurring cysteine residue while prohibiting the formation of a disulfide bond at position 232 and/or 233 of the IgG2 hinge region. By incorporating C232S and/or C233S substitutions into a TNFR2 antibody or fragment thereof, a population of TNFR2 antagonist antibodies or fragments having an IgG2-A isoform can be obtained. Methods of effectuating amino acid substitutions and deletions into an antibody or antigen-binding fragment thereof include mutagenesis techniques described herein and known in the art.

Spacing Between Antigen-Binding Sites

Antagonist TNFR2 polypeptide (e.g., single-chain polypeptides, antibody, antigen-binding fragment thereof, or construct thereof) described herein may contain antigen-binding sites (i.e., antigen-binding arms) that are separated from one another by a distance of at least about 133 Å, which is the spacing observed between antigen-binding arms in human IgG2 isotype antibodies. As described in the examples below, it has been discovered that this spacing gives rise to antibodies having optimal TNFR2 antagonistic properties. TNFR2 antagonist polypeptides of the disclosure include those containing antigen-binding arms separated by, e.g., a distance of from about 133 Å to about 160 Å, such as a distance of about 133 Å, 134 Å, 135 Å, 136 Å, 137 Å, 138 Å, 139 Å, 140 Å, 141 Å, 142 Å, 143 Å, 144 Å, 145 Å, 146 Å, 147 Å, 148 Å, 149 Å, 150 Å, 151 Å, 152 Å, 153 Å, 154 Å, 155 Å, 156 Å, 157 Å, 158 Å, 159 Å, or 160 Å). For example, the polypeptide (e.g., a single-chain polypeptide, antibody, antigen-binding fragment thereof, or construct thereof) may contain antigen-binding sites that are separated from one another by a distance of from about 133 Å to about 150 Å, such as by a distance of about 133 Å, 134 Å, 135 Å, 136 Å, 137 Å, 138 Å, 139 Å, 140 Å, 141 Å, 142 Å, 143 Å, 144 Å, 145 Å, 146 Å, 147 Å, 148 Å, 149 Å, or 150 Å. In some embodiments, the antigen-binding are separated from one another by a distance of from about 133 Å to about 145 Å, such as by a distance of about 133 Å, 134 Å, 135 Å, 136 Å, 137 Å, 138 Å, 139 Å, 140 Å, 141 Å, 142 Å, 143 Å, 144 Å, or 145 Å. In some embodiments, the antigen-binding are separated from one another by a distance of from about 133 Å to about 139 Å, such as by a distance of about 133 Å, 134 Å, 135 Å, 136 Å, 137 Å, 138 Å, or 139 Å. In some embodiments, the antigen-binding are separated from one another by a distance of from about 134 Å to about 139 Å, such as by a distance of about 134 Å, 135 Å, 136 Å, 137 Å, 138 Å, or 139 Å.

The TNFR2 antagonist polypeptides described herein may have, e.g., two, three, four, five, or more, antigen-binding arms separated by a distance specified above. Examples of antibody fragments that have two or more antigen-binding arms include, without limitation, diabodies, triabodies, F(ab')₂ molecules, and tandem scFv (taFv) molecules, among others. Methods of generating these antibody fragments include peptide synthesis and recombinant protein expression techniques described herein and known in the art.

There exist a variety of methods for measuring the distance between antigen-binding arms of an antibody or antibody fragment. For example, distances between antigen-binding arms of an antibody can be made by analyzing the three-dimensional structure of an antibody or antibody fragment using computer software, such as through the use of PYMOL® and other molecular imaging software. Three-dimensional structures of polypeptides, such as antibodies and antibody fragments, can be calculated using the data obtained from X-ray crystallography experiments and nuclear magnetic resonance (NMR) techniques known in the art. Examples of X-ray crystallography and NMR methods that can be used to obtain three-dimensional polypeptide structures are described, e.g., in Eigenbrot et al., Journal of Molecular Biology, 229:969-995, 1993; and Huang et al., Science, 317:1930-1934, 2007, the disclosures of each of which are incorporated herein by reference in their entirety.

Uniformity of Populations of TNFR2 Antagonist Polypeptides

Pharmaceutical compositions can be generated in which the TNFR2 antagonist polypeptide (e.g., antibody, antigen-binding fragment thereof, single-chain polypeptide, or construct thereof) described herein is present as a single disulfide-bonded isoform. For example, at least 10%, or more, of the polypeptide in the pharmaceutical composition may be present as a single disulfide-bonded isoform (e.g., the IgG2-A isoform). This may be achieved, for example, by way of amino acid substitutions or deletions at one or both of cysteine residues 232 and 233 of the wild-type human IgG2 hinge region, thereby preventing or reducing the occurrence of disulfide bonding that could give rise to an IgG2 isoform other than IgG2-A (see, e.g., FIGS. 13A-13D). The pharmaceutical compositions of the disclosure include those in which, for example, about 10% to about 99.999% of the antagonist TNFR2 polypeptide in the pharmaceutical composition is present in a single disulfide-bonded isoform, such as the IgG2-A isoform. For example, pharmaceutical compositions of the disclosure include those containing an antagonist TNFR2 polypeptide in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform.

Techniques for measuring the relative quantities of various disulfide-bonded isoforms present in a sample of an antagonist TNFR2 polypeptide include liquid chromatography techniques known in the art and described herein, such as those exemplified in Wypych et al., The Journal of Biological Chemistry, 283:16194-16205, 2008, the disclosure of which is incorporated herein by reference in its entirety.

Effects on TNFR2/MAPK/TRAF2/3 Signal Transduction Cascades

Anti-TFNR2 polypeptides (e.g., single-chain polypeptides, antibodies, and antigen-binding fragments thereof) described herein are capable of interacting with and inhibiting the activity of TNFR2. Thus, the anti-TNFR2 polypeptides described herein can selectively antagonize the TNFα-TNFR2 interaction rather than promote TNFR2 signaling. This is particularly important for therapeutic applications, such as cancer immunotherapy, as TNFR2 activation upon association with TNFα leads to propagation of the MAPK and TRAF2/3 signal cascade and activation of NFκB-mediated transcription of genes involved in T-reg cell growth and escape from apoptosis (Faustman, et al., Nat. Rev. Drug Disc., 9:482-493, 2010). The TNFR2 polypeptides (e.g., single-chain polypeptides, antibodies, and antigen-binding fragments thereof) described herein bind TNFR2 at one or more specific epitopes that prevent the receptor from forming a trimer with neighboring TNFR2 proteins. This trimerization activates intracellular signaling by TNFR2, which, e.g., promotes proliferation of TNFR2+ cells, such as T-reg cells, MDSCs, and/or TNFR2+ cancer cells. Advantageously, the TNFR2 antagonist polypeptides described herein bind TNFR2 at particular epitopes so as to stabilize TNFR2 in an anti-parallel dimer conformation, in which TNFα binding sites are sterically inaccessible. This prevents TNFα from nucleating TNFR2 trimer formation, which would otherwise trigger TNFR2 signal transduction. The polypeptides described herein can therefore be used to suppress the growth and proliferation of TNFR2+ cells, such as T-reg cells, MDSCs, and TNFR2+ cancer cells. The suppression of T-reg and MDSC proliferation, for instance, enables the proliferation of T effector cells that can mount an immune response against, e.g., a cancer cell or foreign pathogen. Thus, antagonistic TNFR2 polypeptides described herein can be administered to a mammalian subject, such as a human, with a cell proliferation disorder or an infectious disease, in order to enhance the effectiveness of an immune response (e.g., an immune response against cancer cells or pathogenic organisms) in the subject.

Effects on T-Reg Cell Proliferation

Antagonistic TNFR2 polypeptides, such as single-chain polypeptides, antibodies, or antigen-binding fragments thereof described herein, can be used to attenuate the activity of T-reg cells that typically accompanies T cell-mediated cytotoxicity against self cells, such as the attack of a tumor cell by a T lymphocyte. This can be achieved, for instance, due to the ability of antagonistic TNFR2 polypeptides described herein to inhibit the proliferation of, and/or to directly kill, T-reg cells. Antagonistic TNFR2 polypeptides can, thus, be administered (e.g., by any of a variety of routes of administration described herein) to a mammalian subject, such as a human, in order to prolong the duration of an adaptive immune response, such as a response against a cancer cell or a pathogenic organism. In this way, for example, antagonistic TNFR2 polypeptides, such as single-chain polypeptides, antibodies, or antigen-binding fragments thereof described herein, may synergize with existing techniques to enhance T lymphocyte-based therapy for cancer and for infectious diseases. For instance, TNFR2 antagonists described herein may be administered to suppress T-reg cell activity, thereby enhancing the cytotoxic effect of tumor reactive T cells. TNFR2 antagonists may also synergize with existing strategies to promote tumor-reactive T cell survival, such as lymphodepletion and growth factor therapy, and in turn prolong the duration of anti-tumor reactivity in vivo.

Antagonistic TNFR2 polypeptides, such as single-chain polypeptides, antibodies, and antigen-binding fragments thereof can also be used to treat a broad array of infectious diseases in a mammalian subject (e.g., a human), as inhibition of T-reg proliferation promotes the activity of CD8+ T lymphocytes capable of mounting an attack on pathogenic organisms. Additionally, antagonistic TNFR2 antibodies and antigen-binding fragments thereof described herein can be used to treat a wide variety of infectious diseases, such as *Mycobacterium tuberculosis*, in a human or an agricultural farm animal (e.g., a bovine mammal, pig, cow, horse, sheep, goat, cat, dog, rabbit, hamster, guinea pig, or other non-human mammal).

Direct Effects on TNFR2+ Cancer Cells

Antagonistic TNFR2 polypeptides, such as single-chain polypeptides, antibodies, or antigen-binding fragments thereof described herein may bind and inactivate TNFR2 on the surface of a cancer cell, such as a TNFR2+ tumor cell. For instance, antagonistic TNFR2 antibodies and antigen-binding fragments thereof described herein may bind TNFR2 on the surface a T cell lymphoma cell (e.g., a Hodgkin's or cutaneous non-Hodgkin's lymphoma cell), ovarian cancer cell, colon cancer cell, multiple myeloma cell, or renal cell carcinoma cell, among others. The ability of antagonistic TNFR2 antibodies and antigen-binding fragments thereof described herein to bind TNFR2 directly on a cancer cell provides another pathway by which these molecules may attenuate cancer cell survival and proliferation. For instance, an antagonistic TNFR2 polypeptide described herein, such as an antagonistic TNFR2 single-chain polypeptide, antibody, antigen-binding fragment thereof, or construct, may bind TNFR2 directly on the surface of a cancer cell (e.g., a cutaneous T cell lymphoma cell, ovarian cancer cell, colon cancer cell, or multiple myeloma cell, such as an ovarian cancer cell) in order to suppress the ability of the cell to proliferate and/or to promote apoptosis of the cell.

TNFR2 Antagonist Polypeptides are not Reliant on Additional TNFR2-Binding Agents for Activity Significantly, antagonistic TNFR2 polypeptides, such as single-chain polypeptides, antibodies, or antigen-binding fragments thereof described herein, are capable of binding TNFR2 and suppressing TNFR2-mediated signaling without the need for an endogenous TNFR2-binding agent, such as TNFα. Antagonistic TNFR2 polypeptides, such as single-chain polypeptides, antibodies, and antigen-binding fragments thereof described herein do not require TNFα to attenuate T-reg and/or cancer cell proliferation. Without being limited by mechanism, antagonistic TNFR2 antibodies or antigen-binding fragments thereof described herein may exhibit this property due to the ability of these antibodies or antigen-binding fragments thereof to bind TNFR2 at particular epitopes that, when bound, stabilize the antiparallel dimer conformation of this receptor. This structural configuration is not capable of potentiating NFκB signaling. By maintaining TNFR2 in an inactive structural state, antagonistic TNFR2 polypeptides described herein may prevent TNFR2 agonists from restoring cell growth and/or may result in the direct killing (e.g., by apoptosis) of a TNFR2+ cell, such as a T-reg cell, MDSC, or TNFR2+ cancer cell).

For instance, antagonistic TNFR2 polypeptides, such as single-chain polypeptides, antibodies, antigen-binding fragments thereof, and constructs thereof described herein, may bind TNFR2 on the surface of a TNFR2+ cell, such as a T-reg cell, cancer cell, or myeloid-derived suppressor cell (MDSC) and inhibit the proliferation of such cells in the presence or absence of TNFα. For example, antagonistic TNFR2 polypeptides, such as single-chain polypeptides, antibodies, and antigen-binding fragments thereof described herein, may inhibit the proliferation of such cells by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more, relative to such cells that are not treated with the TNFR2 antagonist polypeptide. The antagonistic TNFR2 polypeptide (e.g., single-chain polypeptide, antibody, or antigen-biding fragment thereof) may exhibit an ICs value in such a cell proliferation assay that is largely unchanged by the presence or absence of TNFα (e.g., an ICs value in the presence of TNFα that is changed by less than 50%, 45%, 40%, 35%, 25%, 20%, 15%, 10%, 9%, 8%, 7%, 6%, 5%, 4%, 3%, 2%, or less than 1% relative to the $IC_{50}$ value of the antagonistic TNFR2 polypeptide (e.g., single-chain polypeptide, antibody, or antigen-binding fragment thereof) in the same cell proliferation assay in the absence of TNFα). Examples of cell death assays that can be used to measure the antagonistic effects of TNFR2 antibodies are described herein, e.g., in Example 2 below. Similarly, antagonistic TNFR2 polypeptides, such as single-chain polypeptides, antibodies, antigen-binding fragments thereof, and constructs thereof described herein, may inhibit TNFR2 signaling as assessed by measuring the expression of one or more genes selected from the group consisting of CHUK, NFκBIE, NFκBIA, MAP3K11, TRAF2, TRAF3, relB, and cIAP2/BIRC3 by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more, relative to such cells that are not treated with the TNFR2 antagonist polypeptide. The antagonistic TNFR2 polypeptide (e.g., single-chain polypeptide, antibody, or antigen-biding fragment thereof) may exhibit an ICs value in such a gene expression assay that is largely unchanged by the presence or absence of TNFα (e.g., an ICs value in the presence of TNFα that is changed by less than 50%, 45%, 40%, 35%, 25%, 20%, 15%, 10%, 9%, 8%, 7%, 6%, 5%, 4%, 3%, 2%, or less than 1% relative to the $IC_{50}$ value of the antagonistic TNFR2 polypeptide (e.g., single-chain polypeptide, antibody, or antigen-binding fragment thereof) in the same gene expression assay in the absence of TNFα).

Direct Killing of T-Reg Cells, MDSCs, and TNFR2+ Cancer Cells

Antagonistic TNFR2 polypeptides disclosed herein, such as single-chain polypeptides, antibodies, antigen-binding fragments thereof, and constructs thereof, may, for instance, not only reduce the proliferation of T-reg cells, TNFR2+ cancer cells, and/or MDSCs, but may also induce the death of T-reg cells, TNFR2+ cancer cells, and/or MDSCs within a sample (e.g., within a patient, such as a human patient). Antagonistic TNFR2 polypeptides described herein may be capable, for instance, of reducing the total quantity of T-reg cells, cancer cells (such as cutaneous T cell lymphoma cells, ovarian cancer cells, colon cancer cells, renal cell carcinoma cells or multiple myeloma cells, among others), and/or MDSCs in a sample treated with an antagonist TNFR2 antibody or antigen-binding fragment thereof (such as a sample isolated from a human patient undergoing treatment for cancer or an infectious disease as described herein) by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more, relative to a sample not treated with an antagonist TNFR2 antibody or antigen-binding fragment thereof.

The ability of antagonistic TNFR2 polypeptides (e.g., single-chain polypeptides, antibodies, and antigen-binding fragments) described herein to attenuate T-reg, MDSC, and/or cancer cell growth may be due, in part, to the ability of these polypeptides to diminish the quantity of soluble TNFR2 within a sample (e.g., a sample isolated from a human patient undergoing treatment for cancer or an infectious disease as described herein). In the absence of this beneficial activity, soluble TNFR2 can be secreted by, e.g., T-reg cells, and could otherwise interfere with the ability of TNFR2 antagonists to localize to TNFR2 at the surface of a T-reg cell, TNFR2+ cancer cell, or MDSC by binding and sequestering such antagonists in the extracellular environment. By reducing TNFR2 secretion, antagonistic TNFR2 antibodies or antigen-binding fragments thereof described herein may render T-reg cells, TNFR2+ cancer cells, and/or MDSCs increasingly susceptible to therapeutic molecules, such as an antagonistic TNFR2 antibody or antigen-binding fragment thereof, and/or additional anti-cancer agents, such as those described herein or known in the art, that may be used in conjunction with the compositions and methods described herein.

Selective Modulation of Active (CD25$^{Hi}$ and CD45RA$^{Low}$) T-Reg Cells

Antagonistic TNFR2 polypeptides (e.g., single-chain polypeptides, antibodies, antigen-binding fragments, and constructs thereof) described herein may be capable of inhibiting the proliferation or reducing the total quantity of T-reg cells in a sample (e.g., a sample isolated from a human patient undergoing treatment for cancer or an infectious disease as described herein) and may act selectively on T-reg cells in an actively-dividing state. Antagonistic TNFR2 antibodies or antigen-binding fragments thereof described herein may selectively target active T-reg cells that express CD25$^{Hi}$ and CD45RA$^{Low}$, e.g., over resting T-reg cells that express CD25$^{Med}$ and CD45RA$^{Hi}$. For instance, antagonistic TNFR2 antibodies or antigen-binding fragments thereof described herein may be capable of reducing the proliferation of T-reg cells expressing CD25$^{Hi}$ and CD45RA$^{Low}$ by, e.g., 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or more relative to T-reg cells that do not express the CD25$^{Hi}$ and CD45RA$^{Low}$ proteins, such as T-reg cells that express CD25$^{Med}$ and CD45RA$^{Hi}$ proteins.

Modulation of T-Reg Cells, MDSCs, and T Effector Cells in the Tumor Microenvironment Antagonist TNFR2 polypeptides described herein, such as single-chain polypeptides, antibodies, and antigen-binding fragments thereof, may inhibit the proliferation of T-reg cells with a greater potency in a patient suffering from cancer relative to a subject that does not have cancer. The antagonist TNFR2 polypeptides described herein, such as single-chain polypeptides, antibodies, and antigen-binding fragments thereof, may inhibit the proliferation of T-reg cells with a greater potency in the microenvironment of a tumor relative to a site that is free of cancer cells, such as a site distal from a tumor in a patient suffering from cancer or in a subject without cancer. This effect may be determined using, for example, a cell death assay as described herein. For instance, the polypeptides described herein, such as single-chain polypeptides, antibodies, antigen-binding fragments thereof, and constructs thereof, may exhibit an IC$_{50}$ for reducing or inhibiting the proliferation of T-reg cells in the microenvironment of a tumor that is less than the IC$_{50}$ of the polypeptides for reducing or inhibiting the proliferation of T-reg cells in a site that is free of cancer cells by, for example, 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 1,000-fold, 10,000-fold, or more. Examples of cell death assays that can be used to measure the antagonistic effects of anti-TNFR2 polypeptides are described herein, e.g., in Example 2, below. The polypeptides described herein, such as single-chain polypeptides, antibodies, antigen-binding fragments thereof, and constructs thereof, may inhibit the proliferation of T-reg cells or may promote the apoptosis of T-reg cells with a potency that is greater in the microenvironment of a tumor containing TNFR2+ cancer cells, such as Hodgkin's lymphoma cells, cutaneous non-Hodgkin's lymphoma cells, T cell lymphoma cells, ovarian cancer cells, colon cancer cells, multiple myeloma cells, renal cell carcinoma cells, skin cancer cells, lung cancer cells, liver cancer cells, endometrial cancer cells, hematopoietic or lymphoid cancer cells, central nervous system cancer cells, breast cancer cells, pancreatic cancer cells, stomach cancer cells, esophageal cancer cells, and upper gastrointestinal cancer cells, than in a site that is free of such cancer cells, such as a site distal from a tumor in a patient suffering from one or more of the foregoing cancers or a in a subject without cancer.

Additionally, or alternatively, the polypeptides described herein, such as single-chain polypeptides, antibodies, antigen-binding fragments thereof, and constructs thereof, may inhibit the proliferation of MDSCs with a greater potency in a patient suffering from cancer relative to a subject that does not have cancer. The polypeptides described herein, such as single-chain polypeptides, antibodies, antigen-binding fragments thereof, and constructs thereof, may inhibit the proliferation of MDSCs with a greater potency in the microenvironment of a tumor relative to a site that is free of cancer cells, such as a site distal from a tumor in a patient suffering from cancer or in a subject without cancer. This effect may be determined using, for example, a cell death assay described herein. For instance, the polypeptides described herein, such as single-chain polypeptides, antibodies, antigen-binding fragments thereof, and constructs thereof, may have an $IC_{50}$ for reducing or inhibiting the proliferation of MDSCs in the microenvironment of a tumor that is less than the $IC_{50}$ of the polypeptides for reducing or inhibiting the proliferation of MDSCs in a site that is free of cancer cells by, for example, 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 1,000-fold, 10,000-fold, or more. Examples of cell death assays that can be used to measure the antagonistic effects of anti-TNFR2 polypeptides are described herein, e.g., in Example 2, below. The polypeptides described herein, such as single-chain polypeptides, antibodies, antigen-binding fragments thereof, and constructs thereof, may inhibit the proliferation of MDSCs or may promote the apoptosis of MDSCs with a potency that is greater in the microenvironment of a tumor containing TNFR2+ cancer cells, such as Hodgkin's lymphoma cells, cutaneous non-Hodgkin's lymphoma cells, T cell lymphoma cells, ovarian cancer cells, colon cancer cells, multiple myeloma cells, renal cell carcinoma cells, skin cancer cells, lung cancer cells, liver cancer cells, endometrial cancer cells, hematopoietic or lymphoid cancer cells, central nervous system cancer cells, breast cancer cells, pancreatic cancer cells, stomach cancer cells, esophageal cancer cells, and upper gastrointestinal cancer cells, than in a site that is free of such cancer cells, such as a site distal from a tumor in a patient suffering from one or more of the foregoing cancers or a in a subject without cancer.

Additionally, or alternatively, the polypeptides described herein, such as single-chain polypeptides, antibodies, antigen-binding fragments thereof, and constructs thereof, may expand T effector cells, such as CD8+ cytotoxic T cells, with a greater potency in a patient suffering from cancer relative to a subject that does not have cancer. In some embodiments, the polypeptides described herein, such as single-chain polypeptides, antibodies, and antigen-binding fragments thereof, expand T effector cells, such as CD8+ cytotoxic T cells, with a greater potency in the microenvironment of a tumor relative to a site that is free of cancer cells, such as a site distal from a tumor in a patient suffering from cancer or a in a subject without cancer. This effect may be determined using, for example, a cell proliferation assay described herein. For instance, the polypeptides described herein, such as single-chain polypeptides, antibodies, antigen-binding fragments thereof, and constructs thereof, may have an $EC_{50}$ for the expansion of T effector cells in the microenvironment of a tumor that is less than the $EC_{50}$ of the polypeptides for expanding T effector cells in a site that is free of cancer cells by, for example, 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 1,000-fold, 10,000-fold, or more. Examples of cell proliferation assays that can be used to measure the effects of anti-TNFR2 polypeptides on T effector cells are described herein, e.g., in Example 2, below.

The polypeptides described herein, such as single-chain polypeptides, antibodies, antigen-binding fragments thereof, and constructs thereof, may directly expand T effector cells, such as CD8+ cytotoxic T cells, with a potency that is greater in the microenvironment of a tumor containing TNFR2+ cancer cells, such as Hodgkin's lymphoma cells, cutaneous non-Hodgkin's lymphoma cells, T cell lymphoma cells, ovarian cancer cells, colon cancer cells, multiple myeloma cells, renal cell carcinoma cells, skin cancer cells, lung cancer cells, liver cancer cells, endometrial cancer cells, hematopoietic or lymphoid cancer cells, central nervous system cancer cells, breast cancer cells, pancreatic cancer cells, stomach cancer cells, esophageal cancer cells, and upper gastrointestinal cancer cells, than in a site that is free of such cancer cells, such as a site distal from a tumor in a patient suffering from one or more of the foregoing cancers or a in a subject without cancer. The T effector cells (e.g., CD8+ cytotoxic T cells) may, for example, specifically react with an antigen present on one or more cancer cells, such as Hodgkin's lymphoma cells, cutaneous non-Hodgkin's lymphoma cells, T cell lymphoma cells, ovarian cancer cells, colon cancer cells, multiple myeloma cells, renal cell carcinoma cells, skin cancer cells, lung cancer cells, liver cancer cells, endometrial cancer cells, hematopoietic or lymphoid cancer cells, central nervous system cancer cells, breast cancer cells, pancreatic cancer cells, stomach cancer cells, esophageal cancer cells, and upper gastrointestinal cancer cells, among cells of other cancers described herein.

Activity of Antigen-Binding Fragments of Full-Length TNFR2 Antagonist Antibodies Antagonistic TNFR2 antibodies described herein may inhibit, e.g., T-reg, cancer cell, and/or MDSC growth, or promote T effector cell growth, with a similar potency as that exhibited by antigen-binding fragments of such antibodies. For instance, removal of the Fc region of an antagonistic TNFR2 antibody described herein may not alter the ability of the molecule to attenuate the proliferation or reduce the total quantity of T-reg cells, MDSCs, and/or cancer cells in a sample (e.g., a sample isolated from a human patient undergoing treatment for cancer or an infectious disease as described herein). Antagonistic TNFR2 antibodies and antigen-binding fragments thereof described herein may function, for instance, by a pathway distinct from antibody-dependent cellular cytotoxicity (ADCC), in which a Fc region is required to recruit effector proteins in order to induce cell death. Additionally, antagonistic TNFR2 antibodies or antigen-binding fragments thereof may exhibit therapeutic activity in a variety of forms, such as a single-chain polypeptide (e.g., a single-chain polypeptide containing one or more CDRs covalently bound to one another, for instance, by an amide bond, a thioether bond, a carbon-carbon bond, or a disulfide bridge), a monoclonal antibody or antigen-binding fragment thereof, a polyclonal antibody or antigen-binding fragment thereof, a humanized antibody or antigen-binding fragment thereof, a primatized antibody or antigen-binding fragment thereof, a bispecific antibody or antigen-binding fragment thereof, a multi-specific antibody or antigen-binding fragment thereof, a dual-variable immunoglobulin domain, a monovalent antibody or antigen-binding fragment thereof, a chimeric antibody or antigen-binding fragment thereof, a single-chain Fv molecule (scFv), a diabody, a triabody, a nanobody, an antibody-like protein scaffold, a domain antibody, a Fv fragment, a Fab fragment, a $F(ab')_2$ molecule, and a tandem scFv (taFv).

Specific Binding Properties of Antagonistic TNFR2 Polypeptides

The specific binding of a polypeptide, such as a single-chain polypeptide, antibody, or antibody fragment described herein, to human TNFR2 can be determined by any of a variety of established methods. The affinity can be represented quantitatively by various measurements, including the concentration of antibody needed to achieve half-maximal inhibition of the TNFα-TNFR2 interaction in vitro ($IC_{50}$) and the equilibrium constant ($K_D$) of the antibody-TNFR2 complex dissociation. The equilibrium constant, $K_D$, that describes the interaction of TNFR2 with an antibody described herein is the chemical equilibrium constant for the dissociation reaction of a TNFR2-antibody complex into solvent-separated TNFR2 and antibody molecules that do not interact with one another.

Polypeptides (e.g., single-chain polypeptides, antibodies, and antigen-binding fragments) described herein include those that specifically bind to TNFR2 with a $K_D$ value of less than 100 nM (e.g., 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, or 1 nM). In some embodiments, polypeptides (e.g., single-chain polypeptides, antibodies, antigen-binding fragments, and constructs thereof) described herein specifically bind to TNFR2 with a $K_D$ value of less than 1 nM (e.g., (e.g., 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM, 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM, 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, 10 pM, 5 pM, or 1 pM).

Polypeptides described herein can also be characterized by a variety of in vitro binding assays. Examples of experiments that can be used to determine the $K_D$ or $IC_{50}$ of an anti-TNFR2 polypeptide include, e.g., surface plasmon resonance, isothermal titration calorimetry, fluorescence anisotropy, and ELISA-based assays, among others. ELISA represents a particularly useful method for analyzing antibody activity, as such assays typically require minimal concentrations of antibodies. A common signal that is analyzed in a typical ELISA assay is luminescence, which is typically the result of the activity of a peroxidase conjugated to a secondary antibody that specifically binds a primary antibody (e.g., a TNFR2 antibody described herein). Polypeptides (e.g., single-chain polypeptides, antibodies, and antigen-binding fragments) described herein are capable of binding TNFR2 and epitopes therein, such as epitopes containing one or more continuous or discontinuous residues within CRD3 and/or CRD4 of human TNFR2. Antagonistic polypeptides described herein may additionally bind isolated peptides derived from TNFR2 that structurally preorganize various residues in a manner that simulates the conformation of the above epitopes in the native protein. For instance, polypeptides (e.g., single-chain polypeptides, antibodies, antigen-binding fragments, and constructs thereof) described herein may bind peptides containing the amino acid sequence of any one of SEQ ID NOs: 11, 19, 20, and 34-117, or a peptide having up to five amino acid substitutions with respect to the amino acid sequence of any one of SEQ ID NOs: 11, 19, 20, and 34-117 (such as a peptide having up to five conservative amino acid substitutions with respect to the amino acid sequence of any one of SEQ ID NOs: 11, 19, 20, and 34-117), and/or a peptide having an amino acid sequence that is at least 85% identical (e.g., 85%, 90%, 95%, 96%, 97%, 98%, 99%, or 100% identical) to the amino acid sequence of any one of SEQ ID NOs: 11, 19, 20, and 34-117. In a direct ELISA experiment, this binding can be quantified, e.g., by analyzing the luminescence that occurs upon incubation of an HRP substrate (e.g., 2,2'-azinodi-3-ethylbenzthiazoline sulfonate) with an antigen-antibody complex bound to a HRP-conjugated secondary antibody.

Kinetic Properties of Antagonistic TNFR2 Polypeptides

In addition to the thermodynamic parameters of a TNFR2-polypeptide interaction, it is also possible to quantitatively characterize the kinetic association and dissociation of a polypeptide described herein with TNFR2. This can be done, e.g., by monitoring the rate of polypeptide-antigen (e.g., antibody-antigen) complex formation according to established procedures. For example, one can use surface plasmon resonance (SPR) to determine the rate constants for the formation ($k_{on}$) and dissociation ($k_{off}$) of an antibody-TNFR2 complex. These data also enable calculation of the equilibrium constant of ($K_D$) of antibody-TNFR2 complex dissociation, since the equilibrium constant of this unimolecular dissociation can be expressed as the ratio of the $k_{off}$ to $k_{on}$ values. SPR is a technique that is particularly advantageous for determining kinetic and thermodynamic parameters of receptor-antibody interactions since the experiment does not require that one component be modified by attachment of a chemical label. Rather, the receptor is typically immobilized on a solid metallic surface which is treated in pulses with solutions of increasing concentrations of antibody. Antibody-receptor binding induces distortion in the angle of reflection of incident light at the metallic surface, and this change in refractive index over time as antibody is introduced to the system can be fit to established regression models in order to calculate the association and dissociation rate constants of an antibody-receptor interaction.

Polypeptides (e.g., single-chain polypeptides, antibodies, antigen-binding fragments, and constructs thereof) described herein may exhibit high $k_{on}$ and low $k_{off}$ values upon interaction with TNFR2, consistent with high-affinity receptor binding. For example, polypeptides described herein may exhibit $k_{on}$ values in the presence of TNFR2 of greater than $10^4$ $M^{-1}s^{-1}$ (e.g., $1.0\times10^4$ $M^{-1}s^{-1}$, $1.5\times10^4$ $M^{-1}s^{-1}$, $2.0\times10^4$ $M^{-1}s^{-1}$, $2.5\times10^4$ $M^{-1}s^{-1}$, $3.0\times10^4$ $M^{-1}s^{-1}$, $3.5\times10^4$ $M^{-1}s^{-1}$, $4.0\times10^4$ $M^{-1}s^{-1}$, $4.5\times10^4$ $M^{-1}s^{-1}$, $5.0\times10^4$ $M^{-1}s^{-1}$, $5.5\times10^4$ $M^{-1}s^{-1}$, $6.0\times10^4$ $M^{-1}s^{-1}$, $6.5\times10^4$ $M^{-1}s^{-1}$, $7.0\times10^4$ $M^{-1}s^{-1}$, $7.5\times10^4$ $M^{-1}s^{-1}$, $8.0\times10^4$ $M^{-1}s^{-1}$, $8.5\times10^4$ $M^{-1}s^{-1}$, $9.0\times10^4$ $M^{-1}s^{-1}$, $9.5\times10^4$ $M^{-1}s^{-1}$, $1.0\times10^5$ $M^{-1}s^{-1}$, $1.5\times10^5$ $M^{-1}s^{-1}$, $2.0\times10^5$ $M^{-1}s^{-1}$, $2.5\times10^5$ $M^{-1}s^{-1}$, $3.0\times10^5$ $M^{-1}s^{-1}$, $3.5\times10^5$ $M^{-1}s^{-1}$, $4.0\times10^5$ $M^{-1}s^{-1}$, $4.5\times10^5$ $M^{-1}s^{-1}$, $5.0\times10^5$ $M^{-1}s^{-1}$, $5.5\times10^5$ $M^{-1}s^{-1}$, $6.0\times10^5$ $M^{-1}s^{-1}$, $6.5\times10^5$ $M^{-1}s^{-1}$, $7.0\times10^5$ $M^{-1}s^{-1}$, $7.5\times10^5$ $M^{-1}s^{-1}$, $8.0\times10^5$ $M^{-1}s^{-1}$, $8.5\times10^5$ $M^{-1}s^{-1}$, $9.0\times10^5$ $M^{-1}s^{-1}$, $9.5\times10^5$ $M^{-1}s^{-1}$, or $1.0\times10^6$ $M^{-1}s^{-1}$). Polypeptides (e.g., single-chain polypeptides, antibodies, antigen-binding fragments, and constructs thereof) described herein may exhibit low kw values when bound to TNFR2, as these polypeptides are capable of interacting with distinct TNFR2 epitopes with a high affinity. Residues within these epitopes may form strong intermolecular contacts with TFNR2, which can slow the dissociation of the antibody-TNFR2 complex. This high receptor affinity can manifest in low $k_{off}$ values. For instance, polypeptides described herein may exhibit kW values of less than $10^{-3}$ $s^{-1}$ when complexed to TNFR2 (e.g., $1.0\times10^{-3}$ $s^{-1}$, $9.5\times10^{-4}$ $s^{-1}$, $9.0\times10^{-4}$ $s^{-1}$, $8.5\times10^{-4}$ $s^{-1}$, $8.0\times10^{-4}$ $s^{-1}$, $7.5\times10^{-4}$ $s^{-1}$, $7.0\times10^{-4}$ $s^{-1}$, $6.5\times10^{-4}$ $s^{-1}$, $6.0\times10^{-4}$ $s^{-1}$, $5.5\times10^{-4}$ $s^{-1}$, $5.0\times10^{-4}$ $s^{-1}$, $4.5\times10^{-4}$ $s^{-1}$, $4.0\times10^{-4}$ $s^{-1}$, $3.5\times10^{-4}$ $s^{-1}$, $3.0\times10^{-4}$ $s^{-1}$, $2.5\times10^{-4}$ $s^{-1}$, $2.0\times10^{-4}$ $s^{-1}$, $1.5\times10^{-4}$ $s^{-1}$, $1.0\times10^{-4}$ $s^{-1}$, $9.5\times10^{-5}$ $s^{-1}$, $9.0\times10^{-5}$ $s^{-1}$, $8.5\times10^{-5}$ $s^{-1}$, $8.0\times10^{-5}$ $s^{-1}$, $7.5\times10^{-5}$ $s^{-1}$, $7.0\times10^{-5}$ $s^{-1}$, $6.5\times10^{-5}$ $s^{-1}$, $6.0\times10^{-5}$ $s^{-1}$, $5.5\times10^{-5}$ $s^{-1}$, $5.0\times10^{-5}$ $s^{-1}$, $4.5\times10^{-5}$ $s^{-1}$, $4.0\times10^{-5}$ $s^{-1}$, $3.5\times10^{-5}$ $s^{-1}$, $3.0\times10^{-5}$ $s^{-1}$, $2.5\times10^{-5}$ $s^{-1}$, $2.0\times10^{-5}$ $s^{-1}$, $1.5\times10^{-5}$ $s^{-1}$, or $1.0\times10^{-5}$ $s^{-1}$).

Epitopes within TNFR2 Bound by Antagonistic TNFR2 Polypeptides

Among the difficulties in developing anti-TNFR2 polypeptides (e.g., single-chain polypeptides, antibodies, and antigen-binding fragments) that are capable of antagonizing TNFR2 has been the elucidation of epitopes within TNFR2 that participate in antagonistic complex formation rather than epitopes that promote signal transduction. The present disclosure is based, in part, on the discovery of epitopes within TNFR2 that, when bound, promote receptor antagonism and the ability to promote one or more, or all, of the following advantageous biological activities:

(a) Suppression of the proliferation of, and/or the direct killing of, T-reg cells, for instance, by binding and inactivating TNFR2 on the T-reg cell surface;

(b) Suppression of the proliferation of, and/or the direct killing of, MDSCs, for instance, by binding and inactivating TNFR2 on the MDSC surface;

(c) Promotion of the expansion of T effector cells, such as CD8+ T cells; and/or (d) Suppression of the proliferation of, and/or the direct killing of, TNFR2-expressing cancer cells, such as Hodgkin's lymphoma cells, cutaneous non-Hodgkin's lymphoma cells, T cell lymphoma cells, ovarian cancer cells, colon cancer cells, multiple myeloma cells, renal cell carcinoma cells, skin cancer cells, lung cancer cells, liver cancer cells, endometrial cancer cells, hematopoietic or lymphoid cancer cells, central nervous system cancer cells, breast cancer cells, pancreatic cancer cells, stomach cancer cells, esophageal cancer cells, and upper gastrointestinal cancer cells.

Antagonistic TNFR2 polypeptides, such dominant antagonistic TNFR2 polypeptides (e.g., single-chain polypeptides, antibodies, antigen-binding fragments, and constructs thereof) described herein may specifically bind one or more of the following epitopes on human TNFR2:

(a) amino acids 142-146 of SEQ ID NO: 7 (KCRPG, SEQ ID NO: 19);

(b) amino acids 142-149 of SEQ ID NO: 7 (KCRPGFGV, SEQ ID NO: 20);

(c) amino acids 137-144 of SEQ ID NO: 7 (CAPLRKCR, SEQ ID NO: 11);

(d) amino acids 150-190 of SEQ ID NO: 7 (RPGTETSDVVCKPCAPGTFSNTTSSTDICRPHQICNVVAI, SEQ ID NO: 307);

(e) amino acids 161-169 of SEQ ID NO: 7 (CKPCAPGTF, SEQ ID NO: 21);

(f) amino acids 75-128 of SEQ ID NO: 7 (CDSCEDSTYTQLWNWVPECLSCGSRCSSDQVETQACTREQNRICTCRPGWYCAL, SEQ ID NO: 308), optionally in which the epitope is within amino acids 80-86 (DSTYTQL, SEQ ID NO: 8), 91-98 (PECLSCGS, SEQ ID NO: 9), or 116-123 (RICTCRPG, SEQ ID NO: 10) of SEQ ID NO: 7;

(g) amino acids 174-184 (SSTDICRPHQI, SEQ ID NO: 288) of SEQ ID NO: 7;

(h) amino acids 126-140 (CALSKQEGCRLCAPL, SEQ ID NO: 289) of SEQ ID NO: 7;

(i) amino acids 156-165 (TSDVVCKPCA, SEQ ID NO: 290) of SEQ ID NO: 7;

(j) an equivalent epitope within TNFR2 of a non-human mammal, such as a non-human mammal described herein, an epitope that exhibits at least 85% sequence identity (e.g., 85%, 90%, 95%, 97%, 99%, or 100% sequence identity) to any of the foregoing epitopes, and/or an epitope that contains one or more conservative amino acid substitutions relative to these epitopes.

In some embodiments, antagonistic TNFR2 polypeptides, such as dominant antagonistic TNFR2 polypeptides (e.g., single-chain polypeptides, antibodies, antigen-binding fragments, and constructs thereof) described herein do not bind one or more, or all, residues of 142-146 of SEQ ID NO: 7 within human TNFR2 (KCRPG, SEQ ID NO: 19). Additionally, antagonistic TNFR2 polypeptides described herein distinctly do not exhibit specific binding to an epitope containing residues 56-60 of SEQ ID NO: 7 within human TNFR2 (KCSPG, SEQ ID NO: 12). Polypeptides that exhibit the ability to bind one or more of the above epitopes within human TNFR2 and an epitope containing residues 56-60 of SEQ ID NO: 7 within human TNFR2 lack inhibitory (antagonistic) activity. As such, the ability of a TNFR2 polypeptide to discriminate among these epitopes and specifically interact with one or more of the epitopes described above and to not engage in specific binding with an epitope composed of residues 56-60 of SEQ ID NO: 7 within human TNFR2 characterizes polypeptides described herein that antagonize TNFR2 signaling.

One exemplary procedure that can be used to predict the inhibitory activity of a TNFR2 polypeptide described herein is to determine the affinity of the antibody or antibody fragment for a peptide containing the KCRPG motif (SEQ ID NO: 19), such as a linear or cyclic peptide that contains this motif. The peptide may be, for example, structurally pre-organized by virtue of one or more conformational constraints (e.g., backbone or side-chain-to-side-chain cyclization) in a manner that simulates the three-dimensional orientation of the KCRPG motif (SEQ ID NO: 19). For instance, antagonistic TNFR2 polypeptides described herein may specifically bind such a peptide with an affinity that is greater than that of the antagonistic TNFR2 polypeptide for a peptide fragment defined by residues 48-67 of SEQ ID NO: 7 within human TNFR2 (QTAQMCCSKCSPGQHAKVFC, SEQ ID NO: 18). For example, antagonistic TNFR2 polypeptides described herein may bind a peptide containing the KCRPG motif (SEQ ID NO: 19) with an affinity that is, e.g., 10-fold, 15-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, or more than 1000-fold greater than the affinity of the antagonistic polypeptide for a peptide having the amino acid sequence of SEQ ID NO: 18.

Antagonistic TNFR2 Polypeptides that Bind TNFR2 from Non-Human Animals

In addition to binding the epitopes detailed above within human TFNR2, antagonistic TNFR2 polypeptides described herein, such as dominant antagonistic TNFR2 polypeptides, also include those that specifically bind epitopes containing one or more equivalent motifs within TNFR2 from a non-human animal. The locations of epitopes equivalent those within human TNFR2 that give rise to an antagonistic phenotype upon binding are described, e.g., in WO 2016/187068 and WO 2017/197331, the disclosures of which are incorporated herein by reference in their entirety. Exemplary TNFR2 proteins of non-human animals that may be bound by antagonistic polypeptides of the present disclosure include, without limitation, TNFR2 proteins from cattle, bison, and other agricultural animals described herein.

The Antagonistic TNFR2 Antibody TNFRAB1

Exemplary antagonistic TNFR2 polypeptides described herein, such as single-chain polypeptides, antibodies, antigen-binding fragments thereof, and constructs thereof, may include one or more, or all, of the CDRs of TNFRAB1, a murine antibody that antagonizes the TNFRα-TNFR2 interaction. For instance, the CDR-H1, CDR-H2, CDR-H3, CDR-L1, CDR-L2, and/or CDR-L3 of TNFRAB1, and variants of these CDRs (e.g., variants that exhibit conservative amino acid substitutions relative to these CDR sequences) can be used to generate an antagonistic TNFR2 antibody or antigen-binding fragment thereof, for instance, using antibody humanization methods described herein or known in the art.

Antagonistic TNFR2 polypeptides (e.g., single-chain polypeptides, antibodies, and antigen-binding fragments) of the disclosure may exhibit binding properties that are the same as or similar to those of TNFRAB1. These properties are as follows: In the presence of TNFR2, TNFRAB1 exhibits a high $k_{on}$ value of $4.98 \times 10^6$ $M^{-1}s^{-1}$, as well as a low $k_{off}$ of $2.21 \times 10^{-4}$ $s^{-1}$ and a $K_D$ of about 44.4 pM in complex with TNFR2. The KCRPGFGV motif (SEQ ID NO: 20), and specifically, the KCRPG sequence (SEQ ID NO: 19), has been identified as a particularly important component of the functional epitope that establishes intermolecular contacts with TNFRAB1 as determined by epitope mapping analysis. The interaction of these residues with anti-TNFR2 antibodies of the disclosure selectively promotes antagonistic activity. Significantly, a TNFR2 epitope including amino acid residues 56-60 of SEQ ID NO: 7 within human TNFR2 (KCSPG, SEQ ID NO: 12) is distinctly not a part of the conformational epitope that is specifically bound by TNFRAB1 or antagonistic TNFR2 antibodies or antibody fragments of the disclosure, as specific binding to both of these epitopes has been shown to lead to a loss of, or significant reduction in, antagonistic activity.

In addition to binding an epitope contained within the sequence KCRPGFGV (SEQ ID NO: 20), TNFRAB1 also binds to a downstream epitope contained within a sequence defined by positions 161-169 of SEQ ID NO: 7 within human TNFR2 (CKPCAPGTF, SEQ ID NO: 21). TNFR2 antibodies and antibody fragments of the disclosure may also bind this epitope or a larger region within TNFR2 containing this epitope (e.g., a sequence that includes at least five continuous or discontinuous residues from positions 150-190 of SEQ ID NO: 7 within human TNFR2 (ARPGTETSDVVCKPCAPGTFSNTTSSTDI-CRPHQICNVVAI, SEQ ID NO: 22). TNFRAB1 contains two heavy chains, as well as two light chains. The heavy chains of TNFRAB1 contain the following amino acid sequence (CDRs are indicated in bold):

```
                                       (SEQ ID NO: 2)
EVQLQESGGGLVKPGGSLKLSCAASGFTFSSYVMSWVRQTPEKRLEWVA

TISSGGSYTYYPDSVKGRFTISRDNAKNTLYLQMSSLRSEDTAMYYCAR

QRVDGYSSYWYFDVWGAGTAVTVSS
```

The sequence of the TNFRAB1 light chain is as follows (CDRs are indicated in bold):

```
                                       (SEQ ID NO: 4)
DIVLTQSPAIMSASPGEKVTITCSASSSVYYMYWFQQKPGTSPKLWIYS

TSNLASGVPVRFSGSGSGTSYSLTISRMEAEDAATYYCQQRRNYPYTFG

GGTKLEIKRA
```

The heavy chain and light chain CDRs of TNFRAB2 are shown below:

```
TNFRAB1 CDR-H1:
                              (SEQ ID NO: 23)
GFTFSSY

TNFRAB1 CDR-H2:
                              (SEQ ID NO: 24)
SSGGSY

TNFRAB1 CDR-H3:
                              (SEQ ID NO: 25)
QRVDGYSSYWYFDV

TNFRAB1 CDR-L1:
                              (SEQ ID NO: 26)
SASSSVYYMY

TNFRAB1 CDR-L2:
                              (SEQ ID NO: 26)
STSNLAS

TNFRAB1 CDR-L3:
                              (SEQ ID NO: 28)
QQRRNYPYT
```

The Antagonistic TNFR2 Antibody TNFRAB2

Antagonistic TNFR2 polypeptides described herein, such as single-chain polypeptides, antibodies, antigen-binding fragments thereof, and constructs thereof, may include one or more, or all, of the CDRs of TNFRAB2, another antibody that antagonizes the TNFRα-TNFR2 interaction. For instance, the CDR-H1, CDR-H2, CDR-H3, CDR-L1, CDR-L2, and/or CDR-L3 of TNFRAB2, and variants of these CDRs (e.g., variants that exhibit conservative amino acid substitutions relative to these CDR sequences) can be used to generate an antagonistic TNFR2 antibody or antigen-binding fragment thereof, for instance, using antibody humanization methods described herein or known in the art.

For instance, antagonistic TNFR2 polypeptides (e.g., single-chain polypeptides, antibodies, and antigen-binding fragments) of the disclosure may exhibit binding properties that are the same as or similar to those of TNFRAB2. These properties are as follows: In the presence of TNFR2, TNFRAB2 exhibits a high $k_{on}$ value of $3.6099 \times 10^5$ $M^{-1}s^{-1}$, as well as a low $k_{off}$ of $2.24 \times 10^{-4}$ $s^{-1}$ and a $K_D$ of about 621 pM in complex with TNFR2. An epitope containing residues 137-144 of SEQ ID NO: 7 within human TNFR2 (CAPLRKCR, SEQ ID NO: 11) has been identified as a particularly important component of the functional epitope that establishes intermolecular contacts with TNFRAB2 as determined by epitope mapping analysis. Included in the present disclosure are TNFR2 antibodies and antibody fragments that specifically bind this epitope.

In addition to binding an epitope containing residues CAPLRKCR (SEQ ID NO: 11), TNFRAB2 also binds to epitopes that include one or more residues within positions 80-86 of SEQ ID NO: 7 within human TNFR2 (DSTYTQL, SEQ ID NO: 8), positions 91-98 of SEQ ID NO: 7 within human TNFR2 (PECLSCGS, SEQ ID NO: 9), as well as positions 116-123 of SEQ ID NO: 7 within human TNFR2 (RICTCRPG, SEQ ID NO: 10). TNFR2 antibodies and antibody fragments of the disclosure may also bind one or more of these epitopes. Antibodies and antibody fragments of the disclosure can be designed and identified using the knowledge of the epitopes specifically bound by TNFRAB2. For instance, one can use any of a variety of in vitro peptide display techniques or combinatorial antibody library screens as described herein or known in the art in order to screen for antibodies capable of binding these epitopes with high affinity and selectivity.

The heavy chain and light chain CDRs of TNFRAB2 are shown below:

```
TNFRAB2 CDR-H1:
                        (SEQ ID NO: 274)
GYTFTDYL

TNFRAB2 CDR-H2:
                        (SEQ ID NO: 258)
VDPEYGST

TNFRAB2 CDR-H3:
                        (SEQ ID NO: 259)
ARDDGSYSPFDYWG

TNFRAB2 CDR-L1:
                        (SEQ ID NO: 260)
QNINKY

TNFRAB2 CDR-L2:
TYS

TNFRAB2 CDR-L3:
                        (SEQ ID NO: 272)
CLQYVNLLT
```

Additionally, the CDR-L2 of TNFRAB2 is flanked by the N-terminal framework residues LLIR (SEQ ID NO: 262) and the C-terminal framework residues TLE. Accordingly, antagonistic TNFR2 polypeptides (e.g., single-chain polypeptides, antibodies, and antigen-binding fragments) of the disclosure include those that contain one or more of the above CDRs of TNFRAB2, as well as N-terminal LLIR (SEQ ID NO: 262) and C-terminal TLE residues that flank the CDR-L2 sequence of the antagonistic TNFR2 antibody or antigen-binding fragment thereof.

The Antagonistic TNFR2 Antibody TNFRAB3

Antagonistic TNFR2 polypeptides described herein, such as single-chain polypeptides, antibodies, antigen-binding fragments thereof, and constructs thereof, may exhibit binding properties that are the same as or similar to those of TNFRAB3. TNFRAB3 is a monoclonal antibody and a dominant TNFR2 antagonist. Monoclonal antibody TNFRAB3 has a CDR-H1 amino acid sequence of GYTFTDVI (SEQ ID NO: 293). TNFRAB3 binds epitopes within CDR3 and/or CRD4 of human TNFR2 at the exclusion of epitopes within CRD1 of human TNFR2.

As described in detail below, antagonistic TNFR2 polypeptides described herein (e.g., single-chain polypeptides, antibodies, antigen-binding fragments thereof, and constructs thereof) can be generated by producing and identifying antibodies that exhibit epitope-binding properties similar to those of TNFRAB3. Exemplary techniques for the production of polypeptides (e.g., single-chain polypeptides, antibodies, antigen-binding fragments thereof, and constructs thereof) that have epitope-binding properties similar to those of TNFRAB3 include, without limitation, the production of fully human, humanized, primatized, and chimeric antibodies that incorporate one or more, or all, of the complementarity-determining regions (CDRs) of TNFRAB3, as well as screening for polypeptides that specifically bind one or more, or all, epitopes on TNFR2 that are specifically bound by TNFRAB3.

The Antagonistic TNFR2 Antibody TNFRAB4

Antagonistic TNFR2 polypeptides described herein, such as single-chain polypeptides, antibodies, antigen-binding fragments thereof, and constructs thereof, may exhibit binding properties that are the same as or similar to those of TNFRAB4. TNFRAB4 is a monoclonal murine antibody described herein. This antibody is a dominant TNFR2 antagonist. Monoclonal antibody TNFRAB4 binds epitopes within human TNFR2 containing the following amino acid residues:

(a) residues 174-184 of SEQ ID NO: 7 within human TNFR2 (SSTDICRPHQI, SEQ ID NO: 288);

(b) residues 126-140 of SEQ ID NO: 7 within human TNFR2 (CALSKQEGCRLCAPL), SEQ ID NO: 289); and (c) residues 156-165 of SEQ ID NO: 7 within human TNFR2 (TSDWCKPCA), SEQ ID NO: 290).

As described in detail below, antagonistic TNFR2 polypeptides described herein (e.g., single-chain polypeptides, antibodies, antigen-binding fragments thereof, and constructs thereof) can be generated by producing and identifying antibodies that exhibit epitope-binding properties similar to those of TNFRAB4. Exemplary techniques for the production of polypeptides (e.g., single-chain polypeptides, antibodies, antigen-binding fragments thereof, and constructs thereof) that have epitope-binding properties similar to those of TNFRAB4 include, without limitation, the production of fully human, humanized, primatized, and chimeric antibodies that incorporate one or more, or all, of the complementarity-determining regions (CDRs) of TNFRAB4, as well as screening for polypeptides that specifically bind one or more, or all, epitopes on TNFR2 that are specifically bound by TNFRAB4.

The Antagonistic TNFR2 Antibody TNFRAB5

Antagonistic TNFR2 polypeptides described herein, such as single-chain polypeptides, antibodies, antigen-binding fragments thereof, and constructs thereof, may exhibit binding properties that are the same as or similar to those of TNFRAB5. TNFRAB5 is a monoclonal antibody and a dominant TNFR2 antagonist. Monoclonal antibody TNFRAB5 has a CDR-H1 amino acid sequence of GYTFTDYS (SEQ ID NO: 294). TNFRAB5 binds epitopes within CDR3 and/or CRD4 of human TNFR2 at the exclusion of epitopes within CRD1 of human TNFR2.

As described in detail below, antagonistic TNFR2 polypeptides described herein (e.g., single-chain polypeptides, antibodies, antigen-binding fragments thereof, and constructs thereof) can be generated by producing and identifying antibodies that exhibit epitope-binding properties similar to those of TNFRAB5. Exemplary techniques for the production of polypeptides (e.g., single-chain polypeptides, antibodies, antigen-binding fragments thereof, and constructs thereof) that have epitope-binding properties similar to those of TNFRAB5 include, without limitation, the production of fully human, humanized, primatized, and chimeric antibodies that incorporate one or more, or all, of the complementarity-determining regions (CDRs) of TNFRAB5, as well as screening for polypeptides that specifically bind one or more, or all, epitopes on TNFR2 that are specifically bound by TNFRAB5.

Fully Human, Humanized, Primatized, and Chimeric and Bodies

Antibodies described herein include fully human, humanized, primatized, and chimeric antibodies that contain one or more, or all, of the CDR sequences of TNFRAB1, TNFRAB2, TNFRAB3, TNFRAB4, or TNFRAB5 (e.g., the CDR-H1, CDR-H2, CDR-H3, CDR-L1, CDR-L2, and/or CDR-L3 sequences of TNFRAB1, TNFRAB2, TNFRAB3, TNFRAB4, or TNFRAB5). Additionally, antibodies described herein include fully human, humanized, primatized, and chimeric antibodies that contain one or more, or all, of the CDR-H1, CDR-H2, CDR-H3, CDR-L1, CDR-L2, and CDR-L3 sequences in which one or more, or all, of the CDR sequences exhibits at least 85% sequence identity (e.g., 90%, 95%, 96%, 97%, 98%, 99%, or 100% sequence identity) to the corresponding CDR sequence of TNFRAB1, TNFRAB2, TNFRAB3, TNFRAB4, or TNFRAB5). Antagonistic TNFR2 antibodies described herein further include fully human, humanized, primatized, and chimeric antibodies that contain one or more, or all, of the CDR-H1, CDR-H2, CDR-H3, CDR-L1, CDR-L2, and CDR-L3 sequences in which one or more, or all, of the CDR sequences contains one or more (for instance, up to 3) amino acid substitutions (e.g., one or more conservative amino acid substitutions) relative to the corresponding CDR sequence of TNFRAB1, TNFRAB2, TNFRAB3, TNFRAB4, or TNFRAB5. For example, antagonistic TNFR2 antibodies described herein can be generated by incorporating any one or more of the CDR sequences of TNFRAB1, TNFRAB2, TNFRAB3, TNFRAB4, or TNFRAB5 into the framework regions (e.g., FW1, FW2, FW3, and FW4) of a human antibody. Exemplary framework regions that can be used for the development of a humanized anti-TNFR2 antibody containing one or more of the CDRs of TNFRAB1, TNFRAB2, TNFRAB3, TNFRAB4, or TNFRAB5 include, without limitation, those described in U.S. Pat. Nos. 7,732,578, 8,093,068, and WO 2003/105782; the disclosures of each of which are incorporated herein by reference.

As an example, one strategy that can be used to design humanized antibodies described herein is to align the sequences of the heavy chain variable region and light chain variable region of TNFRAB1, TNFRAB2, TNFRAB3, TNFRAB4, or TNFRAB5 with the heavy chain variable region and light chain variable region of a consensus human antibody. Consensus human antibody heavy chain and light chain sequences are known in the art (see e.g., the "VBASE" human germline sequence database; see also Kabat, et al., Sequences of Proteins of Immunological Interest, Fifth Edition, U.S. Department of Health and Human Services, NIH Publication No. 91-3242, 1991; Tomlinson et al., J. Mol. Biol. 227:776-98, 1992; and Cox et al, Eur. J. Immunol. 24:827-836, 1994; the disclosure of which is incorporated herein by reference). In this way, the variable domain framework residues and CDRs can be identified by sequence alignment (see Kabat, supra). One can substitute, for example, one or more of the CDRs of the consensus human antibody with the corresponding CDR(s) of TNFRAB1, TNFRAB2, TNFRAB3, TNFRAB4, or TNFRAB5, in order to produce a humanized TNFR2 antagonist antibody. Exemplary variable domains of a consensus human antibody include the heavy chain variable domain:

```
                                  (SEQ ID NO: 32)
EVQLVESGGGLVQPGGSLRLSCAASGFTFSDYAMSWVRQAPGKGLEWVA

VISENGSDTYYADSVKGRFTISRDDSKNTLYLQMNSLRAEDTAVYYCAR

DRGGAVSYFDVWGQGTLVTVSS
``` and the light chain variable domain:

```
                                  (SEQ ID NO: 33)
DIQMTQSPSSLSASVGDRVTITCRASQDVSSYLAWYQQKPGKAPKLLIY

AASSLESGVPSRFSGSGSGTDFTLTISSLQPEDFATYYCQQYNSLPYTF

GQGTKVEIKRT
``` identified in U.S. Pat. No. 6,054,297; the disclosure of which is incorporated herein by reference (CDRs are shown in bold were determined according to the method of Chothia, et al., J. Mol. Biol, 196:901-917, 1987). These amino acid substitutions can be made, for example, by recombinant expression of polynucleotides encoding the heavy and light chains of a humanized antibody in a host cell using methods known in the art or described herein.

Similarly, this strategy can also be used to produce primatized antagonistic TNFR2 antibodies, as one can substitute, for example, one or more, or all, of the CDRs of a primate antibody consensus sequence with, for example, one or more, or all, of the CDRs of TNFRAB1, TNFRAB2, TNFRAB3, TNFRAB4, or TNFRAB5. Consensus primate antibody sequences known in the art (see e.g., U.S. Pat. Nos. 5,658,570; 5,681,722; and 5,693,780; the disclosures of each of which are incorporated herein by reference).

In some embodiments, it may be desirable to import particular framework residues in addition to CDR sequences from an antagonistic TNFR2 antibody, such as TNFRAB1, TNFRAB2, TNFRAB3, TNFRAB4, or TNFRAB5, into the heavy and/or light chain variable domains of a human antibody. For instance, U.S. Pat. No. 6,054,297 identifies several instances when it may be advantageous to retain certain framework residues from a particular antibody heavy chain or light chain variable region in the resulting humanized antibody. In some embodiments, framework residues may engage in non-covalent interactions with the antigen and thus contribute to the affinity of the antibody for the target antigen. In some embodiments, individual framework residues may modulate the conformation of a CDR, and thus indirectly influence the interaction of the antibody with the antigen. Certain framework residues may form the interface between VH and VL domains, and may therefore contribute to the global antibody structure. In some cases, framework residues may constitute functional glycosylation sites (e.g., Asn-X-Ser/Thr) which may dictate antibody structure and antigen affinity upon attachment to carbohydrate moieties. In cases such as those described above, it may be beneficial to retain certain framework residues of a TNFR2 antagonist antibody (e.g., TNFRAB1, TNFRAB2, TNFRAB3, TNFRAB4, or TNFRAB5 in, e.g., a humanized or primatized antagonistic antibody or antigen-binding fragment thereof, as various framework residues may promote high epitope affinity and improved biochemical activity of the antibody or antigen-binding fragment thereof.

Antibodies described herein also include antibody fragments, Fab domains, F(ab') molecules, F(ab')$_2$ molecules, single-chain variable fragments (scFvs), tandem scFv fragments, diabodies, triabodies, dual variable domain immunoglobulins, multi-specific antibodies, bispecific antibodies, and heterospecific antibodies that contain one or more, or all, of the CDRs of TNFRAB1, TNFRAB2, TNFRAB3, TNFRAB4, or TNFRAB5, or one or more, or all, of the CDR-H1, CDR-H2, CDR-H3, CDR-L1, CDR-L2, and CDR-L3 sequences in which one or more, or all, of the CDR sequences exhibits at least 85% sequence identity (e.g., 90%, 95%, 96%, 97%, 98%, 99%, or 100% sequence identity) to the corresponding CDR sequence of TNFRAB1, TNFRAB2, TNFRAB3, TNFRAB4, or TNFRAB5). Antagonistic TNFR2 antibodies described herein further include fully human, humanized, primatized, and chimeric antibodies that contain one or more, or all, of the CDR-H1, CDR-H2, CDR-H3, CDR-L1, CDR-L2, and CDR-L3 sequences in which one or more, or all, of the CDR sequences contains one or more (for instance, up to 3) amino acid substitutions (e.g., one or more conservative amino acid substitutions) relative to the corresponding CDR sequence of TNFRAB1, TNFRAB2, TNFRAB3, TNFRAB4, or TNFRAB5. These molecules can be expressed recombinantly, e.g., by incorporating polynucleotides encoding these proteins into expression vectors for transfection in a eukaryotic or prokaryotic cell using techniques described herein or known in the art, or synthesized chemically, e.g., by solid phase peptide synthesis methods described herein or known in the art.

Polypeptides described herein additionally include antibody-like scaffolds that contain, for example, one or more, or all, of the CDRs of TNFRAB1, TNFRAB2, TNFRAB3, TNFRAB4, or TNFRAB5, or one or more, or all, of the CDR-H1, CDR-H2, CDR-H3, CDR-L1, CDR-L2, and CDR-L3 sequences in which one or more, or all, of the CDR sequences exhibits at least 85% sequence identity (e.g., 90%, 95%, 96%, 97%, 98%, 99%, or 100% sequence identity) to the corresponding CDR sequence of TNFRAB1, TNFRAB2, TNFRAB3, TNFRAB4, or TNFRAB5) or contains one or more (for instance, up to 3) amino acid substitutions (e.g., one or more conservative amino acid substitutions) relative to the corresponding CDR sequence of TNFRAB1, TNFRAB2, TNFRAB3, TNFRAB4, or TNFRAB5. Examples of antibody-like scaffolds include proteins that contain a tenth fibronectin type III domain ($^{10}$Fn3), which contains BC, DE, and FG structural loops analogous to canonical antibodies. The tertiary structure of the $^{10}$Fn3 domain resembles that of the variable region of the IgG heavy chain, and one of skill in the art can graft, e.g., one or more, or all, of the CDR sequences of TNFRAB1, TNFRAB2, TNFRAB3, TNFRAB4, or TNFRAB5 or sequences having at least 85% sequence identity (e.g., 90%, 95%, 97%, 99%, or 100% sequence identity) to any one or more of these CDR sequences or sequences containing amino acid substitutions, such as conservative or nonconservative amino acid substitutions (e.g., up to 3 amino acid substitutions) relative to one or more of these CDR sequences onto the fibronectin scaffold by replacing residues of the BC, DE, and FG loops of $^{10}$Fn3 with residues of the corresponding CDR sequence of TNFRAB1, TNFRAB2, TNFRAB3, TNFRAB4, or TNFRAB5. This can be achieved by recombinant expression of a modified $^{10}$Fn3 domain in a prokaryotic or eukaryotic cell (e.g., using the vectors and techniques described herein). Examples of using the $^{10}$Fn3 domain as an antibody-like scaffold for the grafting of CDRs from antibodies onto the BC, DE, and FG structural loops are reported in WO 2000/034784, WO 2009/142773, WO 2012/088006, and U.S. Pat. No. 8,278,419; the disclosures of each of which are incorporated herein by reference.

Molecular Determinants of TNFR2 Affinity and Antagonism

The polypeptides of the disclosure may exhibit a series of shared structural features that give rise to a TNFR2 antagonist phenotype (e.g., a dominant TNFR2 antagonist phenotype). For example, alignment of the amino acid sequences of the CDR-H1 of each of TNRAB1, TNFRAB2, TNFRAB3, and TNFRAB5 demonstrate that these antibodies feature a conserved consensus sequence, as shown below:

```
                    (TNFRAB1 CDR-H1, SEQ ID NO: 23)
        G F T F S S Y (TNFRAB2 CDR-H1, SEQ ID NO: 274)
        G Y T F T D Y L
```

-continued

```
                    (TNFRAB3 CDR-H1, SEQ ID NO: 293)
        G Y T F T D V I (TNFRAB5 CDR-H1, SEQ ID NO: 294)
        G Y T F T D Y S (Consensus sequence, SEQ ID NO: 295)
        G (Y/F) T F (S/T) — Y —
```

Alignment of the sequences reveals a shared GXTFXXYX motif, in which "X" independently designates any amino acid, such as an aromatic residue (e.g., a tyrosine or phenylalanine residue) at position two, a polar, uncharged residue (e.g., a serine or threonine residue) at position five, a polar, optionally negatively charged residue (e.g., a serine, aspartic acid, or glutamic acid residue) at position six, and a leucine, isoleucine, or serine residue at position seven. It has been discovered that, despite originating from a variety of different animal types by way of immunization, surprisingly, antagonistic TNFR2 polypeptides that exhibit the phenotypes described herein exhibit a shared CDR-H1 core sequence.

Additionally, sequence analysis of the CDR-H2 regions of TNFRAB1 and TNFRAB2 similarly reveals a set of conserved amino acids at various positions throughout these regions:

```
                    (TNFRAB1 CDR-H2, SEQ ID NO: 24)
        SSG--GSY (TNFRAB2 CDR-H2, SEQ ID NO: 258)
        VDPEYGST (Consensus sequence)
        -----GS-
```

Analysis of this sequence alignment demonstrates that the CDR-H2 sequences exhibit a conserved GS motif at the C-terminal end of the CDR-H2 region, with side-chains of variable molecular size, polarity, and electrostatic charge tolerated at the remaining positions.

The CDR-H3 regions of antagonistic TNFR2 antibodies show a similar convergence towards a consensus amino acid sequence. Shown below are the CDR-H3 sequences of TNFRAB1, TNFRAB2, and TNFR2A3, another monoclonal antagonistic TNFR2 antibody. TNFR2A3 is described in WO 2017/197331, the disclosure of which is incorporated herein by reference in its entirety. An analysis of the residues common to the CDR-H3 sequences of these antibodies provides insight into the molecular features of antibodies that bind TNFR2 and exhibit an antagonistic effect, such as a dominant antagonistic effect. Epitope mapping analysis has shown that both TNFRAB1, TNFRAB2, and TNFR2A3 bind epitopes within TNFR2 that contain residues 142-146 of SEQ ID NO: 7 and do not bind epitopes containing residues 56-60 of SEQ ID NO: 7. The structural similarities between corresponding CDR-H3 regions provide a basis for predicting residue substitutions that may preserve or enhance TNFR2 affinity and antagonism (e.g., dominant antagonism). The CDR-H3 sequences of TNFRAB1, TNFRAB2, and TNFR2A3 are shown below:

```
                    (TNFRAB1 CDR-H3, SEQ ID NO: 25)
        QRVDGYSSYWYFDV (TNFRAB2 CDR-H3, SEQ ID NO: 259)
        ARDDG-S-YSPFDYWG
```

-continued

```
          (TNFR2A3 CDR-H3, SEQ ID NO: 284)
ARDDG-S-YSPFDYFG (Consensus sequence, SEQ ID NO: 309)
-R-DG-S-Y--FD---
```

Inspection of the CDR-H3 sequences of TNFRAB1, TNFRAB2, and TNFR2A3 reveals conserved arginine, aspartic acid, glycine, serine, tyrosine, and phenylalanine residues throughout this CDR. Notably, residues of varying steric and electrostatic properties are tolerated in the remaining positions. For instance, the first position of the CDR-H3 sequence tolerates amino acid residues of contrasting size and hydrogen bond-forming tendencies, as the first position of CDR-H3 in TNFRAB1 features a polar glutamine residue containing a carboxamide side-chain with hydrogen bond donor and acceptor moieties, while an alanine residue bearing an unfunctionalized methyl side-chain is found at the corresponding position in TNFRAB2 and TNFR2A3. Additionally, the third position in the above CDR-H3 sequences features a hydrophobic valine in TNFRAB1 and an anionic aspartic acid moiety in the corresponding position of TNFRAB2. Similarly, positions ten and eleven of the CDR-H3 of TNFRAB1 contain aromatic systems, while the corresponding residues in TNFRAB2 and TNFR2A3 contain polar and cyclic aliphatic substituents.

A similar analysis reveals molecular features common to the CDR-L sequences of TNFRAB1 and TNFRAB2. For instance, the CDR-L1 sequences of TNFRAB1 and TNFRAB2 are shown below:

```
          (TNFRAB1 CDR-L1, SEQ ID NO: 26)
SASSSVYYMY (TNFRAB2 CDR-L1, SEQ ID NO: 260)
Q-N--INK-Y (Consensus residue)
         Y
```

Inspection of these sequences reveals that a hydroxyl-containing tyrosine residue is featured at the final position of CDR-L1, while residues of varying physicochemical properties are tolerated at the remaining positions. Similarly, analysis of the CDR-L2 regions of TNFRAB1 and TNFRAB2 reveals a conserved amino acid at the final position in both regions:

```
          (TNFRAB1 CDR-L2, SEQ ID NO: 27)
STSNLAS (TNFRAB2 CDR-L2)
YT----S (Consensus sequence)
T----S
```

Analysis of the above sequence alignment demonstrates that serine residues are featured at the third position of these CDR-L2 sequences, while substitutions are widely tolerated at the remaining residues. Similarly, the CDR-L3 sequences of TNRAB1 and TNFRAB2 are as follows:

```
          (TNFRAB1 CDR-L3, SEQ ID NO: 28)
Q-QRRNYPY------T
```

-continued

```
          (TNFRAB2 CDR-L3, SEQ ID NO: 261)
CLQ---YVNL(L/I)T (Consensus sequence)
--Q---Y--------T
```

Analysis of the CDR-L3 sequences of TNFRAB1 and TNFRAB2 reveals a preference for tyrosine and threonine residues at distinct positions within these regions, while amino acids of a wide range of physicochemical characteristics are tolerated at other positions, including residues with cationic side-chains (Arg), conformationally restricted side-chains (Pro), and side-chains of varying polarity (e.g., Gln, Asn, Leu, and Val). Collectively, the shared structural features of the above CDR-H and CDR-L sequences provide insight into those residues that are important for selectively binding one or more residues of the KCRPG epitope of TNFR2 (positions 142-146 of SEQ ID NO: 7, shown in SEQ ID NO: 19) in an anti-parallel dimer configuration and demonstrate that certain amino acids can be varied while retaining affinity and dominant antagonistic activity.

Antagonistic TNFR2 polypeptides of the disclosure, such as dominant antagonistic TNFR2 polypeptides (e.g., single-chain polypeptides, antibodies, or antigen-binding fragments thereof) may therefore have heavy chain and light chain CDRs that contain the above consensus sequences. For instance, TNFR2 antagonists of the disclosure may have a CDR-H1 having the amino acid sequence $Z^4JZ^3Z^5(J)_2Z^5J$; a CDR-H2 having the amino acid sequence $(J)_5Z^4Z^3J$; a CDR-L1 having the amino acid sequence $(J)_5Z^5$; a CDR-L2 having the amino acid sequence $(J)_2Z^3$; and/or a CDR-L3 having the amino acid sequence $(J)_3Z^5(J)_4Z^3$; in which each J is independently a naturally occurring amino acid; each $Z^1$ is independently a naturally occurring amino acid containing a cationic side-chain at physiological pH; each $Z^2$ is independently a naturally occurring amino acid containing an anionic side-chain at physiological pH; each $Z^3$ is independently a naturally occurring amino acid containing a polar, uncharged side-chain at physiological pH; each $Z^4$ is independently a glycine or alanine; and each $Z^5$ is independently a naturally occurring amino acid containing a hydrophobic side-chain.

In some embodiments, antagonistic TNFR2 polypeptides of the disclosure, such as dominant antagonistic TNFR2 polypeptides (e.g., single-chain polypeptides, antibodies, or antigen-binding fragments thereof) may have a CDR-H1 having the amino acid sequence $GJTF(J)_2YJ$ (SEQ ID NO: 277); a CDR-H2 having the amino acid sequence $(J)_5GSJ$; a CDR-L1 having the amino acid sequence $(J)_5Y$; a CDR-L2 having the amino acid sequence $(J)_2S$; and/or a CDR-L3 having the amino acid sequence $(J)_3Y(J)_4T$; in which each J is independently a naturally occurring amino acid.

Antagonistic TNFR2 polypeptides of the disclosure, such as dominant antagonistic TNFR2 polypeptides (e.g., single-chain polypeptides, antibodies, or antigen-binding fragments thereof) may have a CDR-H1 having the amino acid sequence $Z^4YZ^3Z^5TDZ^5X$; a CDR-H2 having the amino acid sequence $VDPEYZ^4Z^3T$ (SEQ ID NO: 264); a CDR-L1 having the amino acid sequence $QNINKZ^5$ (SEQ ID NO: 268); a CDR-L2 having the amino acid sequence $TYZ^3$ or $YTZ^3$; and/or a CDR-L3 having the amino acid sequence $CLQZ^5VNLXZ^3$ (SEQ ID NO: 271); in which each $Z^1$ is independently an amino acid containing a cationic side-chain at physiological pH; each $Z^2$ is independently an amino acid containing an anionic side-chain at physiological pH; each $Z^3$ is independently an amino acid containing a polar, uncharged side-chain at physiological pH; each $Z^4$ is independently a glycine or alanine; each $Z^5$ is independently an amino acid containing a hydrophobic side-chain; and each X is independently leucine or isoleucine.

In some embodiments, antagonistic TNFR2 polypeptides of the disclosure, such as dominant antagonistic TNFR2 polypeptides (e.g., single-chain polypeptides, antibodies, or antigen-binding fragments thereof) may have a CDR-H1 having the amino acid sequence GYTFTDYX (SEQ ID NO: 257), or an amino acid sequence having up to two amino acid substitutions relative to this sequence; a CDR-H2 having the amino acid sequence VDPEYGST (SEQ ID NO: 258), or an amino acid sequence having up to two amino acid substitutions relative to this sequence; a CDR-L1 having the amino acid sequence QNINKY (SEQ ID NO: 260), or an amino acid sequence having up to two amino acid substitutions relative to this sequence; a CDR-L2 having the amino acid sequence TYS or YTS; and/or a CDR-L3 having the amino acid sequence CLQYVNLXT (SEQ ID NO: 261), or an amino acid sequence having up to two amino acid substitutions relative to this sequence.

For example, in some embodiments, antagonistic TNFR2 polypeptides of the disclosure, such as dominant antagonistic TNFR2 polypeptides (e.g., single-chain polypeptides, antibodies, or antigen-binding fragments thereof) may have a CDR-H1 having the amino acid sequence GYTFTDYL (SEQ ID NO: 274), or an amino acid sequence having up to two amino acid substitutions relative to this sequence; and a CDR-L3 having the amino acid sequence CLQYVNLIT (SEQ ID NO: 273), or an amino acid sequence having up to two amino acid substitutions relative to this sequence. The present disclosure is based in part on the discovery that this particular combination of CDR-H1 and CDR-L3 regions promote the selective killing of activated T-reg cells and potentiate augmented T effector cell proliferation. As described herein, these phenotypes are beneficial for the treatment of cancers and infectious diseases, as the ability to deplete activated T-reg cell populations in a patient suffering from such pathologies can lessen the attenuation of cytotoxic CD8+ T cells, thereby enabling effector cells to mount an immune response against cancerous and infectious cells. Exemplary Humanized TNFR2 Antibodies and Antigen-Binding Fragments Thereof Examples of humanized antagonistic TNFR2 antibodies and antigen-binding fragments thereof of the disclosure include those having a heavy chain and/or light chain shown in Table 1, which is reproduced below. As described in further detail in the Examples, the antagonistic TNFR2 antibodies described in Table 1, above, were developed by humanization of murine monoclonal antibodies using humanization techniques described herein. In addition to humanization, the antibodies shown in Table 1 incorporate C232S and C233S substitutions within the immunoglobulin hinge region. As described above, these substitutions confer a variety of beneficial properties to antagonistic TNFR2 antibodies, including an elevated inhibitory effect on TNFR2 signalling (and, thus, heightened Treg depletion and effector T cell proliferation). Exemplary antagonistic TNFR2 antibodies and antigen-binding fragments of the disclosure include those shown in Table 1, above, as well as those that contain a heavy chain and/or light chain having at least 85% sequence identity (e.g., at least 85%, 86%, 87%, 88%, 89%, 90%, 91%, 92%, 93%, 94%, 95%, 96%, 97%, 98%, 99%, or 100% sequence identity) to a heavy chain and/or light chain shown in Table 1.

Examples of humanized antagonistic TNFR2 antibodies and antigen-binding fragments thereof also include antibodies and antigen-binding fragments containing one or more, or all, of the CDRs shown in Table 1, above, or another CDR described herein. For example, humanized TNFR2 antibodies or antigen-binding fragments of the disclosure may contain a CDR-H1 having the amino acid sequence GJTF $(J)_2Y$ (SEQ ID NO: 276) or GJTF$(J)_2$YJ (SEQ ID NO: 277), in which each J is independently a naturally occurring amino acid. In some embodiments, the polypeptide (e.g., a single-chain polypeptide, antibody, antigen-binding fragment thereof, or construct thereof) further contains:

(a) a CDR-H2 having the amino acid sequence $(J)_3$GSJ or $(J)_5$GSJ;

(b) a CDR-H3 having the amino acid sequence JRJDGJSJY$(J)_2$FDJ (SEQ ID NO: 278) or JRJDGSY $(J)_2$FD$(J)_3$ (SEQ ID NO: 279);

(c) a CDR-L1 having the amino acid sequence $(J)_9Y$ or $(J)_5Y$;

(d) a CDR-L2 having the amino acid sequence $(J)_6S$ or $(J)_2S$; and/or (e) a CDR-L3 having the amino acid sequence $(J)_5Y(J)_2T$ or $(J)_3Y(J)_4T$, in which each J is independently a naturally occurring amino acid.

The humanized antibody or antigen-binding fragment thereof may contain a CDR-H1 having the amino acid sequence $Z^4FZ^3Z^5SSZ^5$ or $Z^4YZ^3Z^5TDZ^5X$;

In which each $Z^3$ is independently an amino acid including a polar, uncharged side-chain at physiological pH;

each $Z^4$ is independently a glycine or alanine;

each $Z^5$ is independently an amino acid including a hydrophobic side-chain; and each X is independently leucine or isoleucine.

In some embodiments, the humanized antibody or antigen-binding fragment thereof further contains:

(a) a CDR-H2 having the amino acid sequence SSGZ$^4$Z$^3$Y (SEQ ID NO: 263) or VDPEYZ$^4$Z$^3$T (SEQ ID NO: 264);

(b) a CDR-H3 having the amino acid sequence QZ$^1$VZ$^2$Z$^4$YZ$^3$SZ$^5$WYZ$^5$Z$^2$Z$^5$ (SEQ ID NO: 265) or AZ$^1$DZ$^2$Z$^4$Z$^3$Z$^5$SPZ$^5$Z$^2$Z$^5$WG (SEQ ID NO: 266);

(c) a CDR-L1 having the amino acid sequence SASSSVYYMZ$^5$ (SEQ ID NO: 267) or QNINKZ$^5$ (SEQ ID NO: 268);

(d) a CDR-L2 having the amino acid sequence STSN-LAZ$^3$ (SEQ ID NO: 269), TYZ$^3$, or YTZ$^3$; and/or (e) a CDR-L3 having the amino acid sequence QQRRNZ$^5$PYZ$^3$ (SEQ ID NO: 270) or CLQZ$^5$VNLXZ$^3$ (SEQ ID NO: 271);

in which each $Z^1$ is independently an amino acid including a cationic side-chain at physiological pH;

each $Z^2$ is independently an amino acid including an anionic side-chain at physiological pH;

each $Z^3$ is independently an amino acid including a polar, uncharged side-chain at physiological pH;

each $Z^4$ is independently a glycine or alanine;

each $Z^5$ is independently an amino acid including a hydrophobic side-chain; and each X is independently leucine or isoleucine.

The humanized antibody or antigen-binding fragment thereof may contain a CDR-H1 having the amino acid sequence GFTFSSY (SEQ ID NO: 23), GYTFTDYX (SEQ ID NO: 257), or an amino acid sequence having up to two amino acid substitutions (e.g., conservative amino acid substitutions) relative to these sequences, in which each X is independently leucine or isoleucine, optionally in which the amino acid substitutions are conservative amino acid substitutions. In some embodiments, the humanized antibody or antigen-binding fragment thereof further contains:

(a) a CDR-H2 having the amino acid sequence SSGGSY (SEQ ID NO: 24), VDPEYGST (SEQ ID NO: 258), or an amino acid sequence having up to two amino acid substitutions (e.g., conservative amino acid substitutions) relative to these sequences;

(b) a CDR-H3 having the amino acid sequence QRVDGYSSYWYFDV (SEQ ID NO: 25), ARDDG-SYSPFDYWG (SEQ ID NO: 259), ARDDGSYS-PFDY (SEQ ID NO: 296), or an amino acid sequence having up to two amino acid substitutions (e.g., conservative amino acid substitutions) relative to these sequences;

(c) a CDR-L1 having the amino acid sequence SASSSVYYMY (SEQ ID NO: 26), QNINKY (SEQ ID NO: 260), or an amino acid sequence having up to two amino acid substitutions (e.g., conservative amino acid substitutions) relative to these sequences;

(d) a CDR-L2 having the amino acid sequence STSNLAS (SEQ ID NO: 27), TYS, YTS, or an amino acid sequence having up to two amino acid substitutions (e.g., conservative amino acid substitutions) relative to SEQ ID NO: 27; and/or (e) a CDR-L3 having the amino acid sequence QQRRNY-PYT (SEQ ID NO: 28), CLQYVNLXT (SEQ ID NO: 261), or an amino acid sequence having up to two amino acid substitutions (e.g., conservative amino acid substitutions) relative to these sequences.

In some embodiments, the humanized antibody or antigen-binding fragment thereof contains a heavy chain including one or more of the following CDRs:

(a) a CDR-H1 having the amino acid sequence GFTFSSY (SEQ ID NO: 23);

(b) a CDR-H2 having the amino acid sequence SSGGSY (SEQ ID NO: 24); and (c) a CDR-H3 having the amino acid sequence QRVDGYSSYWYFDV (SEQ ID NO: 25).

The humanized antibody or antigen-binding fragment thereof may contain, for example, a heavy chain having one or more of the following CDRs:

(a) a CDR-H1 having the amino acid sequence GYTFTDYX (SEQ ID NO: 257);

(b) a CDR-H2 having the amino acid sequence VDPEYGST (SEQ ID NO: 258); and (c) a CDR-H3 having the amino acid sequence ARDDG-SYSPFDYWG (SEQ ID NO: 259);

in which each X is independently leucine or isoleucine.

In some embodiments, the CDR-H1 has the amino acid sequence GYTFTDYL (SEQ ID NO: 274). In some embodiments, the CDR-H1 has the amino acid sequence GYTFTDYI (SEQ ID NO: 275). In some embodiments, the CDR-H1 has the amino acid sequence GYTFTDVI (SEQ ID NO: 293). In some embodiments, the CDR-H1 has the amino acid sequence GYTFTDYS (SEQ ID NO: 294).

Additionally or alternatively, the humanized antibody or antigen-binding fragment thereof may contain, for example, a light chain having one or more of the following CDRs:

(a) a CDR-L1 having the amino acid sequence SASSSVYYMY (SEQ ID NO: 26);

(b) a CDR-L2 having the amino acid sequence STSNLAS (SEQ ID NO: 27); and (c) a CDR-L3 having the amino acid sequence QQRRNY-PYT (SEQ ID NO: 28).

In some embodiments, the humanized antibody or antigen-binding fragment thereof contains a light chain having one or more of the following CDRs:

(a) a CDR-L1 having the amino acid sequence QNINKY (SEQ ID NO: 260);

(b) a CDR-L2 having the amino acid sequence TYS or YTS; and (c) a CDR-L3 having the amino acid sequence CLQYVNLXT (SEQ ID NO: 261);

in which each X is independently leucine or isoleucine.

In some embodiments, the CDR-L2 has the amino acid sequence TYS. In some embodiments, the CDR-L2 has the amino acid sequence YTS. The CDR-L3 may have the amino acid sequence CLQYVNLLT (SEQ ID NO: 272). In some embodiments, the CDR-L3 has the amino acid sequence CLQYVNLIT (SEQ ID NO: 273).

The humanized antibody or antigen-binding fragment thereof may contain three heavy chain CDRs, including:

(a) a CDR-H1 having the amino acid sequence GFTFSSY (SEQ ID NO: 23);

(b) a CDR-H2 having the amino acid sequence SSGGSY (SEQ ID NO: 24); and (c) a CDR-H3 having the amino acid sequence QRVDGYSSYWYFDV (SEQ ID NO: 25);

and may further contain three light chain CDRs, including:

(a) a CDR-L1 having the amino acid sequence SASSSVYYMY (SEQ ID NO: 26);

(b) a CDR-L2 having the amino acid sequence STSNLAS (SEQ ID NO: 27); and (c) a CDR-L3 having the amino acid sequence QQRRNY-PYT (SEQ ID NO: 28).

In some embodiments, the humanized antibody or antigen-binding fragment thereof contains three heavy chain CDRs, including:

(a) a CDR-H1 having the amino acid sequence GYTFTDYX (SEQ ID NO: 257), such as GYTFTDYL (SEQ ID NO: 274) or GYTFTDYI (SEQ ID NO: 275), preferably GYTFTDYL (SEQ ID NO: 274);

(b) a CDR-H2 having the amino acid sequence VDPEYGST (SEQ ID NO: 258); and (c) a CDR-H3 having the amino acid sequence ARDDG-SYSPFDYWG (SEQ ID NO: 259);

and further contains three light chain CDRs, including:

(d) a CDR-L1 having the amino acid sequence QNINKY (SEQ ID NO: 260);

(e) a CDR-L2 having the amino acid sequence TYS or YTS; and (f) a CDR-L3 having the amino acid sequence CLQYVNLXT (SEQ ID NO: 261), such as CLQYVNLLT (SEQ ID NO: 272) or CLQYVNLIT (SEQ ID NO: 273), preferably CLQYVNLIT (SEQ ID NO: 273), in which each X is independently leucine or isoleucine.

In some embodiments, the humanized antibody or antigen-binding fragment thereof includes a framework region having the amino acid sequence LLIR (SEQ ID NO: 262) bound to the N-terminus of the CDR-L2 and/or a framework region having the amino acid sequence TLE bound to the C-terminus of the CDR-L2.

Nucleic Acids and Expression Systems

Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be prepared by any of a variety of established techniques. For instance, an antagonistic TNFR2 antibody or antigen-binding fragment thereof described herein can be prepared by recombinant expression of immunoglobulin light and heavy chain genes in a host cell. To express an antibody recombinantly, a host cell can be transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel et al., eds., Greene Publishing Associates, 1989), and in U.S. Pat. No. 4,816,397; the disclosures of each of which are incorporated herein by reference.

Vectors for Expression of Antagonistic TNFR2 Polypeptides

Viral genomes provide a rich source of vectors that can be used for the efficient delivery of exogenous genes into the genome of a cell (e.g., a eukaryotic or prokaryotic cell) and may be used to express a TNFR2 antagonist polypeptide described herein (e.g., any one or more of antibodies 1-25 described in Table 1 and variants thereof, such as an antibody or antigen-binding fragment containing one or more, or all, of the CDRs set forth in Table 1). Viral genomes are particularly useful vectors for gene delivery because the polynucleotides contained within such genomes are typically incorporated into the genome of a target cell by generalized or specialized transduction. These processes occur as part of the natural viral replication cycle, and do not require added proteins or reagents in order to induce gene integration. Examples of viral vectors include a retrovirus, adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses useful for delivering polynucleotides encoding antibody light and heavy chains or antibody fragments described herein include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., (U.S. Pat. No. 5,801,030; the disclosures of each of which are incorporated herein by reference.

Genome Editing Techniques

In addition to viral vectors, a variety of additional methods have been developed for the incorporation of genes, e.g., those encoding antibody light and heavy chains, single-chain polypeptides, single-chain variable fragments (scFvs), tandem scFvs, Fab domains, F(ab')$_2$ domains, diabodies, and triabodies, among others, into the genomes of target cells for polypeptide expression. One such method that can be used for incorporating polynucleotides encoding anti-TNFR2 polypeptides (e.g., single-chain polypeptides, antibodies, antigen-binding fragments thereof, or constructs thereof) described herein (e.g., any one or more of antibodies 1-25 described in Table 1 and variants thereof, such as an antibody or antigen-binding fragment containing one or more, or all, of the CDRs set forth in Table 1) into prokaryotic or eukaryotic cells includes transposons. Transposons are polynucleotides that encode transposase enzymes and contain a polynucleotide sequence or gene of interest flanked by excision sites at the 5' and 3' positions. Once a transposon has been delivered into a cell, expression of the transposase gene commences and results in active enzymes that cleave the gene of interest from the transposon. This activity is mediated by the site-specific recognition of transposon excision sites by the transposase. In some embodiments, these excision sites may be terminal repeats or inverted terminal repeats. Once excised from the transposon, the gene of interest can be integrated into the genome of a prokaryotic or eukaryotic cell by transposase-catalyzed cleavage of similar excision sites that exist within nuclear genome of the cell. This allows the gene encoding an anti-TNFR2 antibody or fragment or domain thereof to be inserted into the cleaved nuclear DNA at the excision sites, and subsequent ligation of the phosphodiester bonds that join the gene of interest to the DNA of the prokaryotic or eukaryotic cell genome completes the incorporation process. In some embodiments, the transposon may be a retrotransposon, such that the gene encoding the antibody is first transcribed to an RNA product and then reverse-transcribed to DNA before incorporation in the prokaryotic or eukaryotic cell genome. Exemplary transposon systems include the piggybac transposon (described in detail in WO 2010/085699) and the sleeping beauty transposon (described in detail in US20050112764); the disclosures of each of which are incorporated herein by reference.

Another useful method for the integration of nucleic acid molecules encoding anti-TNFR2 polypeptides (e.g., single-chain polypeptides, antibodies, or antigen-binding fragments thereof) described herein (e.g., any one or more of antibodies 1-25 described in Table 1 and variants thereof, such as an antibody or antigen-binding fragment containing one or more, or all, of the CDRs set forth in Table 1) into the genome of a prokaryotic or eukaryotic cell is the clustered regularly interspaced short palindromic repeats (CRISPR)/Cas system, which is a system that originally evolved as an adaptive defense mechanism in bacteria and archaea against infection by viruses. The CRISPR/Cas system consists of palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can theoretically design a CRISPR/Cas system to cleave any target DNA molecule of interest. This technique has been exploited in order to edit eukaryotic genomes (Hwang et al., Nat. Biotech., 31:227-229, 2013) and can be used as an efficient means of site-specifically editing eukaryotic or prokaryotic genomes in order to cleave DNA prior to the incorporation of a polynucleotide encoding an anti-TNFR2 polypeptides (e.g., single-chain polypeptides, antibodies, or antigen-binding fragments thereof) described herein. The use of CRISPR/Cas to modulate gene expression has been described in U.S. Pat. No. 8,697,359, the disclosure of which is incorporated herein by reference.

Alternative methods for site-specifically cleaving genomic DNA prior to the incorporation of a polynucleotide encoding a TNFR2 antibody or antibody fragment described herein (e.g., any one or more of antibodies 1-25 described in Table 1 and variants thereof, such as an antibody or antigen-binding fragment containing one or more, or all, of the CDRs set forth in Table 1) include the use of zinc finger nucleases and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. Zinc finger nucleases and TALENs for use in genome editing applications are described in Urnov et al. (Nat. Rev. Genet., 11:636-646, 2010); and in Joung et al., (Nat. Rev. Mol. Cell. Bio. 14:49-55, 2013); incorporated herein by reference. Additional genome editing techniques that can be used to incorporate polynucleotides encoding antibodies described herein into the genome of a prokaryotic or eukaryotic cell include the use of ARCUS™ meganucleases that can be rationally designed so as to site-specifically cleave genomic DNA. The use of these enzymes for the incorporation of polynucleotides encoding antagonistic TNFR2 polypeptides (e.g., single-chain polypeptides, antibodies, antigen-binding fragments thereof, or constructs thereof) described herein into the genome of a prokaryotic or eukaryotic cell is particularly advantageous in view of the structure-activity relationships that have been established for such enzymes. Single-chain meganucleases can thus be modified at certain amino acid positions in order to create nucleases that selectively cleave DNA at desired locations. These single-chain nucleases have been described extensively, e.g., in U.S. Pat. Nos. 8,021,867 and 8,445,251; the disclosures of each of which are incorporated herein by reference.

Polynucleotide Sequence Elements

To express antagonistic TNFR2 polypeptides (e.g., single-chain polypeptides, antibodies, antigen-binding fragments thereof, or constructs thereof) described herein (e.g., any one or more of antibodies 1-25 described in Table 1 and variants thereof, such as an antibody or antigen-binding fragment containing one or more, or all, of the CDRs set forth in Table 1), polynucleotides encoding partial or full-length light and heavy chains, e.g., polynucleotides that encode a one or more, or all, of the CDR sequences of an antibody or antigen-binding fragment thereof described herein, can be inserted into expression vectors such that the genes are operatively linked to transcriptional and translational control sequences. The expression vector and expression control sequences are chosen to be compatible with the expression host cell used. Polynucleotides encoding the light chain gene and the heavy chain of a TNFR2 antibody can be inserted into separate vectors, or, optionally, both polynucleotides can be incorporated into the same expression vector using established techniques described herein or known in the art.

In addition to polynucleotides encoding the heavy and light chains of an antibody (or a polynucleotide encoding a single-chain polypeptide, an antibody fragment, such as a scFv molecule, or a construct described herein), the recombinant expression vectors described herein may carry regulatory sequences that control the expression of the antibody chain genes in a host cell. The design of the expression vector, including the selection of regulatory sequences, may depend on such factors as the choice of the host cell to be transformed or the level of expression of protein desired. For instance, suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Viral regulatory elements, and sequences thereof, are described in detail, for instance, in U.S. Pat. Nos. 5,168,062, 4,510,245, and 4,968,615, the disclosures of each of which are incorporated herein by reference.

In addition to the antibody chain genes and regulatory sequences, the recombinant expression vectors described herein can carry additional sequences, such as sequences that regulate replication of the vector in host cells (e.g., origins of replication) and selectable marker genes. A selectable marker gene facilitates selection of host cells into which the vector has been introduced (see e.g., U.S. Pat. Nos. 4,399,216, 4,634,665 and 5,179,017). For example, typically the selectable marker gene confers resistance to cytotoxic drugs, such as G418, puromycin, blasticidin, hygromycin or methotrexate, to a host cell into which the vector has been introduced. Suitable selectable marker genes include the dihydrofolate reductase (DHFR) gene (for use in DHFR" host cells with methotrexate selection/amplification) and the neo gene (for G418 selection). In order to express the light and heavy chains of a TNFR2 antibody or a TNFR2 antibody fragment, the expression vector(s) containing polynucleotides encoding the heavy and light chains can be transfected into a host cell by standard techniques.

Polynucleotides Encoding Modified Antagonistic TNFR2 Polypeptides

Antagonistic TNFR2 polypeptides of the disclosure include any one or more of antibodies 1-25 described in Table 1 and variants thereof, such as an antibody or antigen-binding fragment containing one or more, or all, of the CDRs set forth in Table 1. Additionally or alternatively, antagonistic TNFR2 polypeptides (e.g., single-chain polypeptides, antibodies, antigen-binding fragments thereof, or constructs thereof) described herein may contain one or more, or all, of the CDRs of TNFRAB1, TNFRAB2, TNFRAB3, TNFRAB4, or TNFRAB5, or one or more, or all, of the CDR-H1, CDR-H2, CDR-H3, CDR-L1, CDR-L2, and CDR-L3 sequences in which one or more, or all, of the CDR sequences exhibits at least 85% sequence identity (e.g., 90%, 95%, 96%, 97%, 98%, 99%, or 100% sequence identity) to the corresponding CDR sequence of TNFRAB1, TNFRAB2, TNFRAB3, TNFRAB4, or TNFRAB5) or contains one or more (for instance, up to 3) amino acid substitutions (e.g., one or more conservative amino acid substitutions) relative to the corresponding CDR sequence of TNFRAB1, TNFRAB2, TNFRAB3, TNFRAB4, or TNFRAB5, but may feature differences in one or more framework regions of TNFRAB1, TNFRAB2, TNFRAB3, TNFRAB4, or TNFRAB5. For instance, one or more framework regions of TNFRAB1, TNFRAB2, TNFRAB3, TNFRAB4, or TNFRAB5 may be substituted with the framework region of a human antibody. Exemplary framework regions include, for example, human framework regions described in U.S. Pat. No. 7,829,086, and primate framework regions as described in EP 1945668; the disclosures of each of which are incorporated herein by reference. To generate nucleic acids encoding such TNFR2 antibodies, DNA fragments encoding, e.g., at least one, or both, of the light chain variable regions and the heavy chain variable regions can be produced by chemical synthesis (e.g., by solid phase polynucleotide synthesis techniques), in vitro gene amplification (e.g., by polymerase chain reaction techniques), or by replication of the polynucleotide in a host organism. For instance, nucleic acids encoding antagonistic TNFR2 antibodies described herein may be obtained by amplification and modification of germline DNA or cDNA encoding light and heavy chain variable sequences so as to incorporate one or more, or all, of the CDRs of TNFRAB1, TNFRAB2, TNFRAB3, TNFRAB4, or TNFRAB5 into the framework residues of a consensus antibody.

In some embodiments, a humanized antagonistic TNFR2 antibody (such as a humanized antibody described in Table 1) may include one or more, or all, of the CDR-H1, CDR-H2, CDR-H3, CDR-L1, CDR-L2, and CDR-L3 sequences in which one or more, or all, of the CDR sequences exhibits at least 85% sequence identity (e.g., 90%, 95%, 96%, 97%, 98%, 99%, or 100% sequence identity) to the corresponding CDR sequence of TNFRAB1, TNFRAB2, TNFRAB3, TNFRAB4, or TNFRAB5) or contains one or more (for instance, up to 3) amino acid substitutions (e.g., one or more conservative amino acid substitutions) relative to the corresponding CDR sequence of TNFRAB1, TNFRAB2, TNFRAB3, TNFRAB4, or TNFRAB5. This can be achieved, for example, by performing site-directed mutagenesis of germline DNA or cDNA and amplifying the resulting polynucleotides using the polymerase chain reaction (PCR) according to established procedures. Germline DNA sequences for human heavy and light chain variable region genes are known in the art (see, e.g., the "VBASE" human germline sequence database; see also Kabat et al., Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al., Eur. J. Immunol. 24:827-836, 1994; incorporated herein by reference). Chimeric nucleic acid constructs encoding human heavy and light chain variable regions containing one or more, or all, of the CDRs of TNFRAB1, TNFRAB2, TNFRAB3, TNFRAB4, or TNFRAB5, or a similar sequence as described above, can be produced, e.g., using established cloning techniques known in the art. Additionally, a polynucleotide encoding a heavy chain variable region containing the one or more of the CDRs of TNFRAB1, TNFRAB2, TNFRAB3, TNFRAB4, or TNFRAB5, or a similar sequence as described above, can be synthesized and used as a template for mutagenesis to generate a variant as described herein using routine mutagenesis techniques. Alternatively, a DNA fragment encoding the variant can be directly synthesized (e.g., by established solid phase nucleic acid chemical synthesis procedures).

Once DNA fragments encoding VH segments containing one or more, or all, of the CDR-H1, CDR-H2, and CDR-H3 sequences of TNFRAB1, TNFRAB2, TNFRAB3, TNFRAB4, or TNFRAB5 are obtained, these DNA fragments can be further manipulated by standard recombinant DNA techniques, e.g., to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker.

The isolated DNA encoding the VH region of an antagonistic TNFR2 antibody described herein can be converted to a full-length heavy chain gene (as well as a Fab heavy chain gene), e.g., by operatively linking the $V_H$-encoding DNA to another DNA molecule encoding heavy chain constant region domains (CH1, CH2, CH3, and, optionally, CH4). The sequences of human heavy chain constant region genes are known in the art (see e.g., Kabat et al., Sequences of Proteins of Immunological Interest, Fifth Edition, U.S. Department of Health and Human Services, NIH Publication No. 91-3242, 1991) and DNA fragments encompassing these regions can be obtained by standard PCR amplification. The heavy chain constant region can be an IgG1, IgG2, IgG3, IgG4, IgA, IgE, IgM or IgD constant region, and in certain embodiments is an IgG1 constant region. For a Fab fragment heavy chain gene, the VH-encoding DNA can be operatively linked to another DNA molecule encoding only the heavy chain CH1 domain.

Isolated DNA encoding the VL region of an antagonistic TNFR2 antibody can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., Sequences of Proteins of Immunological Interest, Fifth Edition (U.S. Department of Health and Human Services, NIH Publication No. 91-3242, 1991)) and DNA fragments encompassing these regions can be obtained, e.g., by amplification in a prokaryotic or eukaryotic cell of a polynucleotide encoding these regions, by PCR amplification, or by chemical polynucleotide synthesis. The light chain constant region can be a kappa (κ) or lambda (λ) constant region, but in certain embodiments is a kappa constant region. To create a scFv gene, the VH and VL-encoding DNA fragments are operatively linked to another fragment encoding a flexible linker, e.g., a polynucleotide encoding a flexible, hydrophilic amino acid sequence, such as the amino acid sequence $(Gly_4Ser)_3$, such that the $V_H$ and $V_L$ sequences can be expressed as a contiguous single-chain protein, with the $V_L$ and $V_H$ regions joined by the linker (see e.g., Bird et al., Science 242:423-426, 1988; Huston et al., Proc. Natl. Acad. Sci. USA 85:5879-5883, 1988; McCafferty et al., Nature 348:552-554, 1990).

Recombinant DNA technology can also be used to remove some or all of the DNA encoding either or both of the light and heavy chains that is not necessary for binding to TNFR2. The molecules expressed from such truncated DNA molecules are also encompassed by the antibodies described herein. In addition, bifunctional antibodies can be produced in which one heavy contains one or more, or all, of the CDRs of TNFRAB1, TNFRAB2, TNFRAB3, TNFRAB4, or TNFRAB5, or a similar CDR sequence as described above, and the other heavy chain and/or the light chains are specific for an antigen other than TNFR2. Such antibodies can be generated, e.g., by crosslinking a heavy chain and light chain containing one or more, or all, of the CDRs of TNFRAB1, TNFRAB2, TNFRAB3, TNFRAB4, or TNFRAB5, or a similar CDR sequence as described above, to a heavy chain and light chain of a second antibody specific for a different antigen, for instance, using standard chemical crosslinking methods (e.g., by disulfide bond formation). Bifunctional antibodies can also be made by expressing a nucleic acid molecule engineered to encode a bifunctional antibody in a prokaryotic or eukaryotic cell.

Dual specific antibodies, i.e., antibodies that bind TNFR2 and a different antigen using the same binding site, can be produced by mutating amino acid residues in the light chain and/or heavy chain CDRs. In some embodiments, dual specific antibodies that bind two antigens, such as TNFR2 and a second cell-surface receptor, can be produced by mutating amino acid residues in the periphery of the antigen binding site (Bostrom et al., Science 323:1610-1614, 2009). Dual functional antibodies can be made by expressing a polynucleotide engineered to encode a dual specific antibody.

Modified antagonistic TNFR2 antibodies and antibody fragments described herein can also be produced by chemical synthesis (e.g., by the methods described in Solid Phase Peptide Synthesis, 2nd ed., 1984 The Pierce Chemical Co., Rockford, 111; incorporated herein by reference). Variant antibodies can also be generated using a cell-free synthetic platform (see, e.g., Chu et al., Biochemia No. 2, 2001 (Roche Molecular Biologicals); incorporated herein by reference).

Host Cells for Expression of Antagonistic TNFR2 Polypeptides

It is possible to express the polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) in either prokaryotic or eukaryotic host cells. In certain embodiments, expression of polypeptides (e.g., single-chain polypeptides, antibodies, or antigen-binding fragments thereof) is performed in eukaryotic cells, e.g., mammalian host cells, for optimal secretion of a properly folded and immunologically active antibody. Exemplary mammalian host cells for expressing the recombinant antibodies or antigen-binding fragments thereof described herein include Chinese Hamster Ovary (CHO cells) (including DHFR CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), NSO myeloma cells, COS cells, 293 cells, and SP2/0 cells. Additional cell types that may be useful for the expression of antibodies and fragments thereof include bacterial cells, such as BL-21 (DE3) E. coli cells, which can be transformed with vectors containing foreign DNA according to established protocols. Additional eukaryotic cells that may be useful for expression of antibodies include yeast cells, such as auxotrophic strains of S. cerevisiae, which can be transformed and selectively grown in incomplete media according to established procedures known in the art. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown.

Polypeptides (e.g., single-chain polypeptides, antibodies, antigen-binding fragments thereof, and constructs thereof) can be recovered from the culture medium using standard protein purification methods. Host cells can also be used to produce portions of intact antibodies, such as Fab fragments or scFv molecules. Also included herein are methods in which the above procedure is varied according to established protocols known in the art. For example, it can be desirable to transfect a host cell with DNA encoding either the light chain or the heavy chain (but not both) of an antagonistic TNFR2 antibody described herein in order to produce an antigen-binding fragment of the antibody.

Once an antagonistic TNFR2 polypeptide (e.g., single-chain polypeptide, antibody, antigen-binding fragment thereof, or construct thereof) described herein (e.g., any one or more of antibodies 1-25 described in Table 1 and variants thereof, such as an antibody or antigen-binding fragment containing one or more, or all, of the CDRs set forth in Table 1) has been produced by recombinant expression, it can be purified by any method known in the art, such as a method useful for purification of an immunoglobulin molecule, for example, by chromatography (e.g., ion exchange, affinity, particularly by affinity for TNFR2 after Protein A or Protein G selection, and sizing column chromatography), centrifugation, differential solubility, or by any other standard technique for the purification of proteins. Further, the antagonistic TNFR2 polypeptides described herein or fragments thereof can be fused to heterologous polypeptide sequences described herein or otherwise known in the art to facilitate purification or to produce therapeutic conjugates (see "Antagonistic TNFR2 polypeptide conjugates," below).

Once isolated, an anti-TNFR2 single-chain polypeptide, antibody, or antigen-binding fragments thereof can, if desired, be further purified, e.g., by high performance liquid chromatography (see, e.g., Fisher, Laboratory Techniques in Biochemistry and Molecular Biology (Work and Burdon, eds., Elsevier, 1980); incorporated herein by reference), or by gel filtration chromatography, such as on a Superdex™ 75 column (Pharmacia Biotech AB, Uppsala, Sweden).

Platforms for Generating and Affinity-Maturing Antagonistic Anti-TNFR2 Polypeptides Mapping Epitopes of TNFR2 that Promote Receptor Antagonism Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be produced by screening libraries of polypeptides (e.g., single-chain polypeptides, antibodies, antigen-binding fragments thereof, and constructs thereof) for functional molecules that are capable of binding epitopes within TNFR2 that selectively promote receptor antagonism rather than receptor activation. Such epitopes can be modeled by screening antibodies or antigen-binding fragments thereof against a series of linear or cyclic peptides containing residues that correspond to a desired epitope within TNFR2.

As an example, peptides containing individual fragments isolated from TNFR2 that promote receptor antagonism can be synthesized by peptide synthesis techniques described herein or known in the art. These peptides can be immobilized on a solid surface and screened for molecules that bind antagonistic TNFR2 polypeptides (e.g., single-chain polypeptides, antibodies, antigen-binding fragments thereof, and constructs thereof), e.g., using an ELISA-based screening platform using established procedures. Using this assay, peptides that specifically bind TNFRAB1, TNFRAB2, TNFRAB3, TNFRAB4, or TNFRAB5, or any one or more of antibodies 1-25 described in Table 1 or a variant thereof, such as an antibody or antigen-binding fragment containing one or more, or all, of the CDRs set forth in Table 1, with high affinity therefore contain residues within epitopes of TNFR2 that preferentially bind these antibodies. Peptides identified in this manner (e.g., peptides having the sequence of any one of SEQ ID NOs: 11, 19, 20, and 34-117) can be used to screen libraries of polypeptides (e.g., single-chain polypeptides, antibodies, antigen-binding fragments thereof, and constructs thereof) in order to identify antagonistic TNFR2 polypeptides. Moreover, since these peptides act as surrogates for epitopes within TNFR2 that promote receptor antagonism, polypeptides generated using this screening technique may bind the corresponding epitopes in TNFR2 and are expected to be antagonistic of receptor activity.

Screening of Libraries for Antagonistic TNFR2 Polypeptides

Methods for high throughput screening of polypeptide (e.g., single-chain polypeptide, antibody, antibody fragment, or construct thereof) libraries for molecules capable of binding epitopes within TNFR2 (e.g., peptides having the sequence of any one of SEQ ID NOs: 11, 19, 20, and 34-117) include, without limitation, display techniques including phage display, bacterial display, yeast display, mammalian display, ribosome display, mRNA display, and cDNA display. The use of phage display to isolate ligands that bind biologically relevant molecules has been reviewed, e.g., in Felici et al. (Biotechnol. Annual Rev. 1:149-183, 1995), Katz (Annual Rev. Biophys. Biomol. Struct. 26:27-45, 1997), and Hoogenboom et al. (Immunotechnology 4:1-20, 1998). Several randomized combinatorial peptide libraries have been constructed to select for polypeptides that bind different targets, e.g., cell surface receptors or DNA (reviewed by Kay (Perspect. Drug Discovery Des. 2, 251-268, 1995), Kay et al., (Mol. Divers. 1:139-140, 1996)). Proteins and multimeric proteins have been successfully phage-displayed as functional molecules (see EP 0349578A, EP 4527839A, EP 0589877A; Chiswell and McCafferty (Trends Biotechnol. 10, 80-84 1992)). In addition, functional antibody fragments (e.g. Fab, single-chain Fv [scFv]) have been expressed (McCafferty et al. (Nature 348: 552-554, 1990), Barbas et al. (Proc. Natl. Acad Sci. USA 88:7978-7982, 1991), Clackson et al. (Nature 352:624-628, 1991)). These references are hereby incorporated by reference in their entirety.

(i) Phage Display Techniques

As an example, phage display techniques can be used in order to screen libraries of polypeptides (e.g., single-chain polypeptides, antibodies, antigen-binding fragments thereof, and constructs thereof) for functional molecules capable of binding cyclic or polycyclic peptides containing epitopes within TNFR2 that promote receptor antagonism (e.g., peptides having the sequence of any one of SEQ ID NOs: 11, 19, 20, and 34-117). For instance, libraries of polynucleotides encoding single-chain antibody fragments, such as scFv fragments, that contain randomized hypervariable regions can be obtained using established procedures (e.g., solid phase polynucleotide synthesis or error-prone PCR techniques, see McCullum et al. (Meth. Mol. Biol., 634:103-109, 2010); incorporated herein by reference). These randomized polynucleotides can subsequently be incorporated into a viral genome such that the randomized antibody chains encoded by these genes are expressed on the surface of filamentous phage, e.g., by a covalent bond between the antibody chain and a coat protein (e.g., pill coat protein on the surface of M13 phage). This provides a physical connection between the genotype and phenotype of the antibody chain. In this way, libraries of phage that display diverse antibody chains containing random mutations in hypervariable regions can be screened for the ability of the exterior antibody chains to bind TNFR2 epitopes (e.g., peptides having the sequence of any one of SEQ ID NOs: 11, 19, 20, and 34-117) that are immobilized to a surface using established procedures. For instance, such peptides can be physically bound to the surface of a microtiter plate by forming a covalent bond between the peptide and an epitope tag (e.g., biotin) and incubating the peptide in wells of a microtiter plate that have been previously coated with a complementary tag (e.g., avidin) that binds the tag attached to the peptide with high affinity. Suitable epitope tags include, without limitation, maltose-binding protein, glutathione-S-transferase, a poly-histidine tag, a FLAG-tag, a myc-tag, human influenza hemagglutinin (HA) tag, biotin, streptavidin. Peptides containing the epitopes presented by these molecules are capable of being immobilized on surfaces containing such complementary molecules as maltose, glutathione, a nickel-containing complex, an anti-FLAG antibody, an anti-myc antibody, an anti-HA antibody, streptavidin, or biotin, respectively. In this way, phage can be incubated with a surface containing an immobilized TNFR2-derived peptide for a time suitable to allow binding of the antibody to the constrained peptide and in the presence of an appropriate buffer system (e.g., one that contains physiological salt concentration, ionic strength, and is maintained at physiological pH by a buffering agent). The surface can then be washed (e.g., with phosphate buffer containing 0.1% Tween-20) so as to remove phage that do not present antibody chains that interact with the TNFR2-derived peptides with an affinity greater than a particular threshold value.

The affinity of the polypeptides that remain after this initial panning (i.e., screening) step can be modulated by adjusting the conditions of the washing step (e.g., by including mildly acidic or basic components, or by including other TNFR2-derived peptides at a low concentration in order to compete with immobilized peptides for antigen-binding sites). In this way, the population of phage that remains bound to the surfaces of the microtiter plate following the washing step is enriched for phage that bind TNFR2-derived peptide epitopes that promote receptor antagonism. The remaining phage can then be amplified by eluting the phage from the surface containing these peptides (e.g., by altering the ambient pH, ionic strength, or temperature) so as to diminish protein-protein interaction strength. The isolated phage can then be amplified, e.g., by infecting bacterial cells, and the resulting phage can optionally be subjected to panning by additional iterations of screening so as to further enrich the population of phage for those harboring higher-affinity anti-TNFR2 polypeptides. Following these panning stages, phage that display high-affinity antibodies or antigen-binding fragments thereof can subsequently be isolated and the genomes of these phage can be sequenced in order to identify the polynucleotide and polypeptide sequences of the encoded antibodies. Phage display techniques such as this can be used to generate, e.g., antibody chains, such as scFv fragments, tandem scFv fragments, and other antigen-binding fragments described herein that can be used as antagonists of TNFR2. Exemplary phage display protocols for the identification of antibody chains and antigen-binding fragments thereof that bind a particular antigen with high affinity are well-established and are described, e.g., in U.S. Pat. No. 7,846,892, WO 1997/002342, U.S. Pat. No. 8,846, 867, and WO 2007/132917; the disclosures of each of which are incorporated herein by reference. Similar phage display techniques can be used to generate antibody-like scaffolds (e.g., $^{10}$Fn3 domains) described herein that bind epitopes within TNFR2 that promote receptor antagonism (e.g., epitopes presented by peptides with the sequence of any one of SEQ ID NOs: 11, 19, 20, and 34-117). Exemplary phage display protocols for the identification of antibody-like scaffold proteins are described, e.g., in WO 2009/086116; the disclosure of which is incorporated herein by reference).

(ii) Cell-Based Display Techniques

Other in vitro display techniques that exploit the linkage between genotype and phenotype of a solvent-exposed polypeptide include yeast and bacterial display. Yeast display techniques are established in the art and are often advantageous in that high quantities of antibodies (often up to 30,000) can be presented on the surface of an individual yeast cell (see, e.g., Boder et al. (Nat Biotechno. 15:553, 1997); incorporated herein by reference). The larger size of yeast cells over filamentous phage enables an additional screening strategy, as one can use flow cytometry to both analyze and sort libraries of yeast. For instance, established procedures can be used to generate libraries of bacterial cells or yeast cells that express polypeptides (e.g., single-chain polypeptides, antibodies, and antigen-binding fragments thereof) containing randomized hypervariable regions (see, e.g., see U.S. Pat. No. 7,749,501 and US 2013/0085072; the teachings of each which are incorporated herein by reference). For instance, large libraries of yeast cells that express polynucleotides encoding naïve scFv fragments can be made using established procedures (de Bruin et al., Nat Biotechnol 17:397, 1999; incorporated herein by reference). Yeast cells expressing these polynucleotides can then be incubated with two different fluorescent molecules during the panning steps: one dye that binds conserved residues within the antibody and thus reflects the amount of antibody displayed, and another dye that fluoresces at a different wavelength and binds the antigen and thus indicates the amount of antigen bound. For instance, one of skill in the art can use a TNFR2-derived peptide containing the sequence of any one of SEQ ID NOs: 11, 19, 20, and 34-117 that has been conjugated to an epitope tag (e.g., biotin), optionally at the N- or C-terminus of the peptide or at a residue that is not expected to interfere with antibody-antigen binding. This enables a fluorescent dye labeled with a complementary tag (e.g., avidin) to localize to the antibody-antigen complex. This results in great flexibility and immediate feedback on the progress of a selection. In contrast to phage display, by normalizing to antibody display levels, antibodies with higher affinities, rather than greater expression levels can easily be selected. In fact, it is possible to distinguish and sort antibodies whose affinities differ by only two-fold (VanAntwerp and Wittrup (*Biotechnol Prog* 16:31, 2000)).

(iii) Nucleotide Display Techniques

Display techniques that utilize in vitro translation of randomized polynucleotide libraries also provide a powerful approach to generating antagonistic TNFR2 polypeptides described herein. For instance, randomized DNA libraries encoding polypeptides (e.g., single-chain polypeptides, antibodies, and antigen-binding fragments thereof) that contain mutations within designated hypervariable regions can be obtained, e.g., using established PCR-based mutagenesis techniques as described herein. The polynucleotides of these libraries may contain transcription regulating sequences, such as promoters and transcription terminating sequences, and may additionally encode sequences that increase the rate of translation of the resulting mRNA construct (e.g., IRES sequences, 5' and 3' UTRs, a poly-adenylation tract, etc). These polynucleotide libraries can be incubated in an appropriately buffered solution containing RNA polymerase and RNA nucleoside triphosphates (NTPs) in order to enable transcription of the DNA sequences to competent mRNA molecules, which can subsequently be translated by large and small ribosomal subunits, aminoacyl tRNA molecules, and translation initiation and elongation factors present in solution (e.g., using the PURExpress® In Vitro Protein Synthesis Kit, New England Biolabs®). Designed mRNA modifications can enable the antibody product to remain covalently bound to the mRNA template by a chemical bond to puromycin (e.g., see Keefe (Curr. Protoc. Mol. Biol., Chapter 24, Unit 24.5, 2001); incorporated herein by reference). This genotype-phenotype linkage can thus be used to select for antibodies that bind a TNFR2-derived peptide (e.g., a peptide that has the sequence of any one of SEQ ID NOs: 11, 19, 20, and 34-117) by incubating mRNA:antibody fusion constructs with a peptide immobilized to a surface and panning in a fashion similar to phage display techniques (see, e.g., WO 2006/072773; incorporated herein by reference).

Optionally, polypeptides (e.g., single-chain polypeptides, antibodies, and antigen-binding fragments thereof) described herein can be generated using a similar technique, except the antibody product may be bound non-covalently to the ribosome-mRNA complex rather than covalently via a puromycin linker. This platform, known as ribosome display, has been described, e.g., in U.S. Pat. No. 7,074,557; incorporated herein by reference. Alternatively, antibodies can be generated using cDNA display, a technique analogous to mRNA display with the exception that cDNA, rather than mRNA, is covalently bound to an antibody product via a puromycin linker. cDNA display techniques offer the advantage of being able to perform panning steps under increasingly stringent conditions, e.g., under conditions in which the salt concentration, ionic strength, pH, and/or temperature of the environment is adjusted in order to screen for antibodies with particularly high affinity for TNFR2-derived peptides. This is due to the higher natural stability of double-stranded cDNA over single-stranded mRNA. cDNA display screening techniques are described, e.g., in Ueno et al. (Methods Mol. Biol., 805:113-135, 2012); incorporated herein by reference.

In addition to generating antagonistic TNFR2 polypeptides (e.g., single-chain polypeptides, antibodies, antigen-binding fragments thereof, and constructs thereof) described herein, in vitro display techniques (e.g., those described herein and those known in the art) also provide methods for improving the affinity of an antagonistic TNFR2 polypeptide described herein. For instance, rather than screening libraries of antibodies and fragments thereof containing completely randomized hypervariable regions, one can screen narrower libraries of antibodies and antigen-binding fragments thereof that feature targeted mutations at specific sites within hypervariable regions. This can be accomplished, e.g., by assembling libraries of polynucleotides encoding antibodies or antigen-binding fragments thereof that encode random mutations only at particular sites within hypervariable regions. These polynucleotides can then be expressed in, e.g., filamentous phage, bacterial cells, yeast cells, mammalian cells, or in vitro using, e.g., ribosome display, mRNA display, or cDNA display techniques in order to screen for antibodies or antigen-binding fragments thereof that specifically bind TNFR2 epitopes (e.g., peptides containing the sequence of any one of SEQ ID NOs: 11, 19, 20, and 34-117) with improved binding affinity. Yeast display, for instance, is well-suited for affinity maturation, and has been used previously to improve the affinity of a single-chain antibody to a $K_D$ of 48 fM (Boder et al. (Proc Natl Acad Sci USA 97:10701, 2000)).

Additional in vitro techniques that can be used for the generation and affinity maturation of antagonistic TNFR2 polypeptides (e.g., single-chain polypeptides, antibodies, and antigen-binding fragments thereof) described herein include the screening of combinatorial libraries of antibodies or antigen-binding fragments thereof for functional molecules capable of specifically binding TNFR2-derived peptides (e.g., a peptide having the amino acid sequence of any one of SEQ ID NOs: 11, 19, 20, and 34-117). Combinatorial antibody libraries can be obtained, e.g., by expression of polynucleotides encoding randomized hypervariable regions of an antibody or antigen-binding fragment thereof in a eukaryotic or prokaryotic cell. This can be achieved, e.g., using gene expression techniques described herein or known in the art. Heterogeneous mixtures of antibodies can be purified, e.g., by Protein A or Protein G selection, sizing column chromatography), centrifugation, differential solubility, and/or by any other standard technique for the purification of proteins. Libraries of combinatorial libraries thus obtained can be screened, e.g., by incubating a heterogeneous mixture of these antibodies with a peptide derived from TNFR2 that has been immobilized to a surface (e.g., a peptide having the amino acid sequence of any one of SEQ ID NOs: 11, 19, 20, and 34-117 immobilized to the surface of a solid-phase resin or a well of a microtiter plate) for a period of time sufficient to allow antibody-antigen binding. Non-binding antibodies or fragments thereof can be removed by washing the surface with an appropriate buffer (e.g., a solution buffered at physiological pH (approximately 7.4) and containing physiological salt concentrations and ionic strength, and optionally containing a detergent, such as TWEEN-20). Antibodies that remain bound can subsequently be detected, e.g., using an ELISA-based detection protocol (see, e.g., U.S. Pat. No. 4,661,445; the disclosure of which is incorporated herein by reference).

Additional techniques for screening combinatorial libraries of polypeptides (e.g., single-chain polypeptides, antibodies, antigen-binding fragments thereof, and constructs thereof) for those that specifically bind TNFR2-derived peptides (e.g., a peptide containing the amino acid sequence of any one of SEQ ID NOs: 11, 19, 20, and 34-117) include the screening of one-bead-one-compound libraries of antibody fragments. Antibody fragments can be chemically synthesized on a solid bead (e.g., using established split-and-pool solid phase peptide synthesis protocols) composed of a hydrophilic, water-swellable material such that each bead displays a single antibody fragment. Heterogeneous bead mixtures can then be incubated with a TNFR2-derived peptide that is optionally labeled with a detectable moiety (e.g., a fluorescent dye) or that is conjugated to an epitope tag (e.g., biotin, avidin, FLAG tag, HA tag) that can later be detected by treatment with a complementary tag (e.g., avidin, biotin, anti-FLAG antibody, anti-HA antibody, respectively). Beads containing antibody fragments that specifically bind a TNFR2-derived peptide (e.g., a peptide containing the amino acid sequence of any one of SEQ ID NOs: 11, 19, 20, and 34-117) can be identified by analyzing the fluorescent properties of the beads following incubation with a fluorescently-labeled antigen or complementary tag (e.g., by confocal fluorescence microscopy or by fluorescence-activated bead sorting; see, e.g., Muller et al. (J. Biol. Chem., 16500-16505, 1996); incorporated herein by reference). Beads containing antibody fragments that specifically bind TNFR2-derived peptides can thus be separated from those that do not contain high-affinity antibody fragments. The sequence of an antibody fragment that specifically binds a TNFR2-derived peptide can be determined by techniques known in the art, including, e.g., Edman degradation, tandem mass spectrometry, matrix-assisted laser-desorption time-of-flight mass spectrometry (MALDI-TOF MS), nuclear magnetic resonance (NMR), and 2D gel electrophoresis, among others (see, e.g., WO 2004/062553; the disclosures of each of which are incorporated herein by reference).

Negative Screens of Polypeptides

In addition to the above-described methods for screening for a single-chain polypeptide, antibody, or antibody fragment that specifically binds to an epitope derived from human TNFR2 that promotes receptor antagonism, one can additionally perform negative screens in order to eliminate antibodies or antibody fragments that may also bind an epitope that contains the KCSPG (SEQ ID NO: 12) sequence. For instance, mixtures of antibodies or antibody fragments isolated as a result of any of the above-described screening techniques can be screened for antibodies or antibody fragments that also specifically bind to a peptide derived from human TNFR2 that contains the KCSPG (SEQ ID NO: 12) motif, such as a peptide containing residues 48-67 of SEQ ID NO: 7 (QTAQMCCSKCSPGQHAKVFC, SEQ ID NO: 18). This can be accomplished using any of the above-described methods or variations thereof, e.g., such that the antibodies or antibody fragments being screened are those that were previously identified as being capable of specifically binding a peptide containing one or more residues of SEQ ID NOs: 11, 19, 20, and 34-117. Exemplary techniques useful for a negative screen include those described above or known in the art, such as phage display, yeast display, bacterial display, ribosome display, mRNA display, cDNA display, or surface-based combinatorial library screens (e.g., in an ELISA format). This screening technique represents a useful strategy for identifying an antagonistic TNFR2 antibody or antibody fragment, as antibodies or antibody fragments capable of binding TNFR2 epitopes containing the KCSPG (SEQ ID NO: 12) sequence lack, or have significantly reduced, antagonistic activity.

Immunization of a Non-Human Mammal

Another strategy that can be used to produce antagonistic TNFR2 antibodies and antigen-binding fragments thereof described herein includes immunizing a non-human mammal. Examples of non-human mammals that can be immunized in order to produce antagonistic TNFR2 antibodies and fragments thereof described herein include rabbits, mice, rats, goats, guinea pigs, hamsters, horses, and sheep, as well as non-human primates. For instance, established procedures for immunizing primates are known in the art (see, e.g., WO 1986/6004782; incorporated herein by reference). Immunization represents a robust method of producing monoclonal antibodies by exploiting the antigen specificity of B lymphocytes. For example, monoclonal antibodies can be prepared by the Kohler-Millstein procedure (described, e.g., in EP 0110716; incorporated herein by reference), wherein spleen cells from a non-human animal (e.g., a primate) immunized with a peptide that presents a TNFR2-derived antigen that promotes receptor antagonism (e.g., a peptide containing the amino acid sequence of any one of SEQ ID NOs: 11, 19, 20, and 34-117). A clonally-expanded B lymphocyte produced by immunization can be isolated from the serum of the animal and subsequently fused with a myeloma cell in order to form a hybridoma. Hybridomas are particularly useful agents for antibody production, as these immortalized cells can provide a lasting supply of an antigen-specific antibody. Antibodies from such hybridomas can subsequently be isolated using techniques known in the art, e.g., by purifying the antibodies from the cell culture medium by affinity chromatography, using reagents such as Protein A or Protein G.

Antagonistic TNFR2 Polypeptide Conjugates

Prior to administration of antagonistic TNFR2 polypeptides (e.g., single-chain polypeptides, antibodies, and antigen-binding fragments thereof) described herein (e.g., any one or more of antibodies 1-25 described in Table 1 and variants thereof, such as an antibody or antigen-binding fragment containing one or more, or all, of the CDRs set forth in Table 1) to a mammalian subject (e.g., a human), it may be desirable to conjugate the antibody or fragment thereof to a second molecule, e g., to modulate the activity of the antibody in vivo. Antagonistic TNFR2 antibodies and fragments thereof can be conjugated to other molecules at either the N-terminus or C-terminus of a light or heavy chain of the antibody using any one of a variety of established conjugation strategies that are well-known in the art. Examples of pairs of reactive functional groups that can be used to covalently tether an antagonistic TNFR2 antibody or fragment thereof to another molecule include, without limitation, thiol pairs, carboxylic acids and amino groups, ketones and amino groups, aldehydes and amino groups, thiols and alpha,beta-unsaturated moieties (such as maleimides or dehydroalanine), thiols and alpha-halo amides, carboxylic acids and hydrazides, aldehydes and hydrazides, and ketones and hydrazides.

Antagonistic TNFR2 polypeptides (e.g., single-chain polypeptides, antibodies, antigen-binding fragments thereof, and constructs thereof) can be covalently appended directly to another molecule by chemical conjugation as described. Alternatively, fusion proteins containing antagonistic TNFR2 antibodies and fragments thereof can be expressed recombinantly from a cell (e.g., a eukaryotic cell or prokaryotic cell). This can be accomplished, for example, by incorporating a polynucleotide encoding the fusion protein into the nuclear genome of a cell (e.g., using techniques described herein or known in the art). Optionally, antibodies and fragments thereof described herein can be joined to a second molecule by forming a covalent bond between the antibody and a linker. This linker can then be subsequently conjugated to another molecule, or the linker can be conjugated to another molecule prior to ligation to the anti-TNFR2 antibody or fragment thereof. Examples of linkers that can be used for the formation of a conjugate include polypeptide linkers, such as those that contain naturally occurring or non-naturally occurring amino acids. In some embodiments, it may be desirable to include D-amino acids in the linker, as these residues are not present in naturally-occurring proteins and are thus more resistant to degradation by endogenous proteases. Fusion proteins containing polypeptide linkers can be made using chemical synthesis techniques, such as those described herein, or through recombinant expression of a polynucleotide encoding the fusion protein in a cell (e.g., a prokaryotic or eukaryotic cell). Linkers can be prepared using a variety of strategies that are well known in the art, and depending on the reactive components of the linker, can be cleaved by enzymatic hydrolysis, photolysis, hydrolysis under acidic conditions, hydrolysis under basic conditions, oxidation, disulfide reduction, nucleophilic cleavage, or organometallic cleavage (Leriche et al., Bioorg. Med. Chem., 20:571-582, 2012).

Drug-Polypeptide Conjugates

An antagonistic TNFR2 polypeptide (e.g., single-chain polypeptide, antibody, and antigen-binding fragment thereof) described herein (e.g., any one or more of antibodies 1-25 described in Table 1 and variants thereof, such as an antibody or antigen-binding fragment containing one or more, or all, of the CDRs set forth in Table 1) can additionally be conjugated to, admixed with, or administered separately from a therapeutic agent, such as a cytotoxic molecule. Conjugates described herein may be applicable to the treatment or prevention of a disease associated with aberrant cell proliferation, such as a cancer described herein. Exemplary cytotoxic agents that can be conjugated to, admixed with, or administered separately from an antagonistic TNFR2 polypeptide include, without limitation, antineoplastic agents such as: acivicin; aclarubicin; acodazole hydrochloride; acronine; adozelesin; adriamycin; aldesleukin; altretamine; ambomycin; a. metantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; camptothecin; caracemide; carbetimer; carboplatin; carmustine; carubicin hydrochloride; carzelesin; cedefingol; chlorambucil; cirolemycin; cisplatin; cladribine; combretestatin a-4; crisnatol mesylate; cyclophosphamide; cytarabine; dacarbazine; daca (n-[2-(dimethyl-amino) ethyl] acridine-4-carboxamide); dactinomycin; daunorubicin hydrochloride; daunomycin; decitabine; dexormaplatin; dezaguanine; dezaguanine mesylate; diaziquone; docetaxel; dolasatins; doxorubicin; doxorubicin hydrochloride; droloxifene; droloxifene citrate; dromostanolone propionate; duazomycin; edatrexate; eflornithine hydrochloride; ellipticine; elsamitrucin; enloplatin; enpromate; epipropidine; epirubicin hydrochloride; erbulozole; esorubicin hydrochloride; estramustine; estramustine phosphate sodium; etanidazole; ethiodized oil i 131; etoposide; etoposide phosphate; etoprine; fadrozole hydrochloride; fazarabine; fenretinide; floxuridine; fludarabine phosphate; fluorouracil; 5-fdump; flurocitabine; fosquidone; fostriecin sodium; gemcitabine; gemcitabine hydrochloride; gold au 198; homocamptothecin; hydroxyurea; idarubicin hydrochloride; ifosfamide; ilmofosine; interferon alfa-2a; interferon alfa-2b; interferon alfa-nl; interferon alfa-n3; interferon beta-i a; interferon gamma-i b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peploycinsulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; rhizoxin; rhizoxin d; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; strontium chloride sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; thymitaq; tiazofurin; tirapazamine; tomudex; top53; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine; vinblastine sulfate; vincristine; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 2-chlorodeoxyadenosine; 2' deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N, N'-Bis (2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; cisplatin; carboplatin; ormaplatin; oxaliplatin; C1-973; DWA 2114R; JM216; JM335; Bis (platinum); tomudex; azacitidine; cytarabine; gemcitabine; 6-mercaptopurine; 6-thioguanine; hypoxanthine; teniposide 9-amino camptothecin; topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-hydroxyphenyl) retinamide; 13-cis retinoic acid; 3-methyl TTNEB; 9-cis retinoic acid; fludarabine (2-F-ara-AMP); or 2-chlorodeoxyadenosine (2-Cda).

Other therapeutic compounds that can be conjugated to, admixed with, or administered separately from an antagonistic TNFR2 single-chain polypeptide, antibody, or antigen-binding fragment thereof described herein in order to treat, prevent, or study the progression of a disease associated with aberrant cell proliferation include, but are not limited to, cytotoxic agents such as 20-pi-1,25 dihydroxyvitamin D3; 5-ethynyluracil; abiraterone; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin Ill derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox;

diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; episteride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; rnerbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single-chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Labeled Anti-TNFR2 Polypeptides

In some embodiments, antagonistic TNFR2 single-chain polypeptides, antibodies, antigen-binding fragments thereof, or constructs described herein (e.g., any one or more of antibodies 1-25 described in Table 1 and variants thereof, such as an antibody or antigen-binding fragment containing one or more, or all, of the CDRs set forth in Table 1) are conjugated to another molecule (e.g., an epitope tag) for the purpose of purification or detection. Examples of such molecules that are useful in protein purification include those that present structural epitopes capable of being recognized by a second molecule. This is a common strategy that is employed in protein purification by affinity chromatography, in which a molecule is immobilized on a solid support and exposed to a heterogeneous mixture containing a target protein conjugated to a molecule capable of binding the immobilized compound. Examples of epitope tag molecules that can be conjugated to antagonistic TNFR2 polypeptides for the purposes of molecular recognition include, without limitation, maltose-binding protein, glutathione-S-transferase, a poly-histidine tag, a FLAG-tag, a myc-tag, human influenza hemagglutinin (HA) tag, biotin, streptavidin. Conjugates containing the epitopes presented by these molecules are capable of being recognized by such complementary molecules as maltose, glutathione, a nickel-containing complex, an anti-FLAG antibody, an anti-myc antibody, an anti-HA antibody, streptavidin, or biotin, respectively. For example, one can purify an antagonistic TNFR2 antibody or fragment thereof described herein that has been conjugated to an epitope tag from a complex mixture of other proteins and biomolecules (e.g., DNA, RNA, carbohydrates, phospholipids, etc) by treating the mixture with a solid phase resin containing an complementary molecule that can selectively recognize and bind the epitope tag of the antagonistic anti-TNFR2 antibody or fragment thereof. Examples of solid phase resins include agarose beads, which are compatible with purifications in aqueous solution.

An antagonistic TNFR2 polypeptide described herein can also be covalently appended to a fluorescent molecule, e.g., to detect the antibody or antigen-binding fragment thereof by fluorimetry and/or by direct visualization using fluorescence microscopy. Exemplary fluorescent molecules that can be conjugated to antibodies described herein include green fluorescent protein, cyan fluorescent protein, yellow fluorescent protein, red fluorescent protein, phycoerythrin, allophycocyanin, hoescht, 4',6-diamidino-2-phenylindole (DAPI), propidium iodide, fluorescein, coumarin, rhodamine, tetramethylrhoadmine, and cyanine. Additional examples of fluorescent molecules suitable for conjugation to antibodies described herein are well-known in the art and have been described in detail in, e.g., U.S. Pat. Nos. 7,417, 131 and 7,413,874, each of which is incorporated by reference herein.

Antagonistic TNFR2 polypeptides containing a fluorescent molecule are particularly useful for monitoring the cell-surface localization properties of antibodies and fragments thereof described herein. For instance, one can expose cultured mammalian cells (e.g., T-reg cells) to antagonistic TNFR2 polypeptides described herein that have been covalently conjugated to a fluorescent molecule and subsequently analyze these cells using conventional fluorescent microscopy techniques known in the art. Confocal fluorescent microscopy is a particularly powerful method for determining cell-surface localization of antagonistic TNFR2 polypeptides, as individual planes of a cell can be analyzed in order to distinguish antibodies or fragments thereof that have been internalized into a cell's interior, e.g., by receptor-mediated endocytosis, from those that are bound to the external face of the cell membrane. Additionally, cells can be treated with antagonistic TNFR2 antibodies conjugated to a fluorescent molecule that emits visible light of a particular wavelength (e.g., fluorescein, which fluoresces at about 535 nm) and an additional fluorescent molecule that is known to localize to a particular site on the T-reg cell surface and that fluoresces at a different wavelength (e.g., a molecule that localizes to CD25 and that fluoresces at about 599 nm). The resulting emission patterns can be visualized by confocal fluorescence microscopy and the images from these two wavelengths can be merged in order to reveal information regarding the location of the antagonistic TNFR2 antibody or antigen-binding fragment thereof on the T-reg cell surface with respect to other receptors.

Bioluminescent proteins can also be incorporated into a fusion protein for the purposes of detection and visualization of an antagonistic TNFR2 polypeptide, such as a single-chain polypeptide, antibody, or fragment thereof. Bioluminescent proteins, such as Luciferase and aequorin, emit light as part of a chemical reaction with a substrate (e.g., luciferin and coelenterazine). Exemplary bioluminescent proteins suitable for use as a diagnostic sequence and methods for their use are described in, e.g., U.S. Pat. Nos. 5,292,658, 5,670,356, 6,171,809, and 7,183,092, each of which is herein incorporated by reference. Antagonistic TNFR2 antibodies or fragments thereof labeled with bioluminescent proteins are a useful tool for the detection of antibodies described herein following an in vitro assay. For instance, the presence of an antagonistic TNFR2 antibody that has been conjugated to a bioluminescent protein can be detected among a complex mixture of additional proteins by separating the components of the mixture using gel electrophoresis methods known in the art (e.g., native gel analysis) and subsequently transferring the separated proteins to a membrane in order to perform a Western blot. Detection of the antagonistic TNFR2 polypeptide among the mixture of other proteins can be achieved by treating the membrane with an appropriate Luciferase substrate and subsequently visualizing the mixture of proteins on film using established protocols.

The polypeptides (e.g., single-chain polypeptides, antibodies, antigen-binding fragments thereof, and constructs thereof) described herein can also be conjugated to a molecule comprising a radioactive nucleus, such that an antibody or fragment thereof described herein can be detected by analyzing the radioactive emission pattern of the nucleus. Alternatively, an antagonistic TNFR2 antibody or fragment thereof can be modified directly by incorporating a radioactive nucleus within the antibody during the preparation of the protein. Radioactive isotopes of methionine ($^{35}$S), nitrogen ($^{15}$N), or carbon ($^{13}$C) can be incorporated into antibodies or fragments thereof described herein by, e.g., culturing bacteria in media that has been supplemented with nutrients containing these isotopes. Optionally, tyrosine derivatives containing a radioactive halogen can be incorporated into an antagonistic TNFR2 polypeptide by, e.g., culturing bacterial cells in media supplemented with radiolabeled tyrosine. It has been shown that tyrosine functionalized with a radioactive halogen at the C2 position of the phenol system are rapidly incorporated into elongating polypeptide chains using the endogenous translation enzymes in vivo (U.S. Pat. No. 4,925,651; incorporated herein by reference). The halogens include fluorine, chlorine, bromine, iodine, and astatine. Additionally, antagonistic TNFR2 polypeptides can be modified following isolation and purification from cell culture by functionalizing polypeptides described herein with a radioactive isotope. The halogens represent a class of isotopes that can be readily incorporated into a purified protein by aromatic substitution at tyrosine or tryptophan, e.g., via reaction of one or more of these residues with an electrophilic halogen species. Examples of radioactive halogen isotopes include $^{18}$F, $^{75}$Br, $^{77}$Br, $^{122}$I, $^{123}$I, $^{124}$I, $^{125}$I, $^{129}$I, $^{131}$I, or $^{211}$At.

Another alternative strategy for the incorporation of a radioactive isotope is the covalent attachment of a chelating group to the antagonistic TNFR2 polypeptide, such as a single-chain polypeptide, antibody, fragment thereof, or construct. Chelating groups can be covalently appended to an antagonistic TNFR2 antibody or fragment thereof by attachment to a reactive functional group, such as a thiol, amino group, alcohol, or carboxylic acid. The chelating groups can then be modified to contain any of a variety of metallic radioisotopes, including, without limitation, such radioactive nuclides as $^{125}$I, $^{67}$Ga, $^{111}$In, $^{99}$Tc, $^{169}$Yb, $^{185}$Re, $^{123}$I, $^{124}$I, $^{125}$I, $^{131}$I, $^{99m}$Tc, $^{111}$In, $^{64}$Cu, $^{67}$Cu, $^{186}$Re, $^{188}$Re, $^{177}$Lu, $^{90}$Y, $^{77}$As, $^{72}$As, $^{86}$Y, $^{89}$Zr, $^{211}$At, $^{212}$Bi, $^{213}$Bi, or $^{255}$Ac.

In some embodiments, it may be desirable to covalently conjugate the polypeptides (e.g., single-chain polypeptides, antibodies, fragments thereof, or construct thereof) described herein with a chelating group capable of binding a metal ion from heavy elements or rare earth ions, such as $Gd^{3+}$, $Fe^{3+}$, $Mn^{3+}$, or $Cr^{2+}$. Conjugates containing chelating groups that are coordinated to such paramagnetic metals are useful as in MRI imaging applications. Paramagnetic metals include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). In this way, antagonistic TNFR2 polypeptides can be detected by MRI spectroscopy. For instance, one can administer antagonistic TNFR2 antibodies or fragments thereof conjugated to chelating groups bound to paramagnetic ions to a mammalian subject (e.g., a human patient) in order to monitor the distribution of the antibody following administration. This can be achieved by administration of the antibody to a patient by any of the administration routes described herein, such as intravenously, and subsequently analyzing the location of the administered antibody by recording an MRI of the patient according to established protocols.

Antagonistic TNFR2 polypeptides (e.g., single-chain polypeptides, antibodies, antigen-binding fragments thereof, and constructs thereof) can additionally be conjugated to other molecules for the purpose of improving the solubility and stability of the protein in aqueous solution. Examples of such molecules include PEG, PSA, bovine serum albumin (BSA), and human serum albumin (HSA), among others. For instance, one can conjugate an antagonistic TNFR2 polypeptide to carbohydrate moieties in order to evade detection of the antibody or fragment thereof by the immune system of the patient receiving treatment. This process of hyperglycosylation reduces the immunogenicity of therapeutic proteins by sterically inhibiting the interaction of the protein with B cell receptors in circulation. Alternatively, antagonistic TNFR2 antibodies or fragments thereof can be conjugated to molecules that prevent clearance from human serum and improve the pharmacokinetic profile of antibodies described herein. Exemplary molecules that can be conjugated to or inserted within anti-TNFR2 antibodies or fragments thereof described herein so as to attenuate clearance and improve the pharmacokinetic profile of these antibodies and fragments include salvage receptor binding epitopes. These epitopes are found within the Fc region of an IgG immunoglobulin and have been shown to bind Fc receptors and prolong antibody half-life in human serum. The insertion of salvage receptor binding epitopes into anti-TNFR2 antibodies or fragments thereof can be achieved, e.g., as described in U.S. Pat. No. 5,739,277; incorporated herein by reference.

Modified Antagonistic TNFR2 Polypeptides

In addition to conjugation to other therapeutic agents and labels for identification or visualization, antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can also be modified so as to improve their pharmacokinetic profile, biophysical stability, or inhibitory capacity. For instance, any cysteine residue not involved in maintaining the proper conformation of the antagonistic TNFR2 polypeptide may be substituted with an isosteric or isoelectronic amino acid (e.g., serine) in order to improve the oxidative stability of the molecule and prevent aberrant crosslinking. Conversely, cystine bond(s) may be added to the antibody or fragment thereof to improve its stability (particularly where the antibody is an antibody fragment, such as an Fv fragment). This can be accomplished, e.g., by altering a polynucleotide encoding the antibody heavy and light chains or a polynucleotide encoding an antibody fragment so as to encode one or more additional pairs of cysteine residues that can form disulfide bonds under oxidative conditions in order to reinforce antibody tertiary structure (see, e.g., U.S. Pat. No. 7,422,899; incorporated herein by reference).

Another useful modification that may be made to antagonistic TNFR2 polypeptides (e.g., single-chain polypeptides, antibodies, antigen-binding fragments thereof, and constructs thereof) described herein includes altering the glycosylation profile of these antibodies and fragments thereof. This can be achieved, e.g., by substituting, inserting, or deleting amino acids in an antagonistic TNFR2 antibody so as to insert or remove a glycosylation site. Glycosylation of antibodies typically occurs in N-linked or O-linked fashion. N-linked glycosylation is a process whereby the attachment of a carbohydrate moiety to an antibody occurs at the side-chain of an asparagine residue. Consensus amino acid sequences for N-linked glycosylation include the tripeptide sequences asparagine-X-serine (NXS) and asparagine-X-threonine (NXT), where X is any amino acid except proline. The insertion of either of these tripeptide sequences in a polypeptide (e.g., an antagonistic TNFR2 antibody) creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine are also competent substrates for glycoside formation. Addition of glycosylation sites to an anti-TNFR2 antibody can thus be accomplished by altering the amino acid sequence of the antibody (e.g., using recombinant expression techniques as described herein) such that it contains one or more of the above-described tripeptide sequences to promote N-linked glycosylation, or one or more serine or threonine residues to the sequence of the original antibody engender O-linked glycosylation (see, e.g., U.S. Pat. No. 7,422,899; incorporated herein by reference).

In alternative cases, it may be desirable to modify the antibody or fragment thereof described herein with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. For instance, cysteine residues may be introduced in the Fc region of an anti-TNFR2 antibody or fragment thereof (e.g., by recombinant expression techniques as described herein), so as to facilitate additional inter-chain disulfide bond formation in this region. The homodimeric antibody thus generated may have increased conformational constraint, which may foster improved internalization capability and/or increased complement-mediated cell killing and antibody-dependent cellular cytotoxicity (ADCC). Homodimeric antibodies with enhanced anti-tumor activity may also be prepared using heterobifunctional cross-linkers as described, for example, in Wolff et al. (Canc. Res., 53:2560-2565, 1993); incorporated herein by reference. Alternatively, an antibody can be engineered which has dual Fc regions and may thereby have enhanced complement lysis and ADCC capabilities (see Stevenson et al. (Anti-Canc. Drug Des., 3:219-230, 1989); incorporated herein by reference).

The serum half-life of antagonistic TNFR2 polypeptides (e.g., single-chain polypeptides, antibodies, and antigen-binding fragments thereof) described herein can be improved in some embodiments by incorporating one more amino acid modifications, such as by altering the CH1 or CL region of the Fab domain to introduce a salvage receptor motif, e.g., that found in the two loops of a CH2 domain of an Fc region of an IgG. Such alterations are described, for instance, in U.S. Pat. Nos. 5,869,046 and 6,121,022; incorporated herein by reference. Additional framework modifications can also be made to reduce immunogenicity of the antibody or fragment thereof or to reduce or remove T cell epitopes that reside therein, as described for instance in US2003/0153043; incorporated herein by reference.

Methods of Treatment

Antagonistic TNFR2 polypeptides, such a dominant antagonistic TNFR2 polypeptide described herein (e.g., any one or more of antibodies 1-25 described in Table 1 and variants thereof, such as an antibody or antigen-binding fragment containing one or more, or all, of the CDRs set forth in Table 1), can be used to treat a patient suffering from a cell proliferation disorder (such as a cancer described herein), an infectious disease (such as a viral, bacterial, fungal, or parasitic infection described herein), or another disease mediated by TNFR2 signaling. These indications are explained in detail in the sections that follow.

Methods of Treating Cell Proliferation Disorders

Antagonistic TNFR2 polypeptides (e.g., single-chain polypeptides, antibodies, antigen-binding fragments thereof, and constructs thereof) described herein, such as dominant antagonistic TNFR2 polypeptides, are useful therapeutics for the treatment of a wide array of cancers and cell proliferation disorders. Antagonistic TNFR2 polypeptides (e.g., single-chain polypeptides, antibodies, antigen-binding fragments thereof, and constructs thereof), such as dominant antagonistic TNFR2 polypeptides, can be administered to a mammalian subject, such as a human, suffering from a cell proliferation disorder, such as cancer, e.g., to enhance the effectiveness of the adaptive immune response against the target cancer cells.

Exemplary compositions of the disclosure that can be used for these purposes include antagonistic TNFR2 polypeptides (e.g., any one or more of antibodies 1-25 described in Table 1 and variants thereof, such as an antibody or antigen-binding fragment containing one or more, or all, of the CDRs set forth in Table 1), such as those with at least two TNFR2 binding sites in which the binding sites are spatially separated from one another by about 133 Å or more, as well as those having a human IgG2 isotype, for example, a human IgG2-A isotype (e.g., antagonistic TNFR2 antibodies, antigen-binding fragments thereof, and constructs thereof having a human IgG2 hinge region having a C232S and/or C233S amino acid substitution). Compositions of the disclosure that can be used for these purposes also include pharmaceutical compositions containing antagonistic TNFR2 polypeptides that adopt a single disulfide-bonded isoform, such as those in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform.

In particular, antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be administered to a mammalian subject, such as a human, to inhibit T-reg cell growth and activation, which allows tumor-infiltrating T lymphocytes to localize to cells presenting tumor-associated antigens and to promote cytotoxicity. In addition, polypeptides described herein may synergize with existing adoptive T cell therapy platforms, as one of the limitations on the effectiveness of this strategy has been the difficulty of prolonging cytotoxicity of tumor-reactive T cells following infusion into a mammalian subject (e.g., a human). Polypeptides described herein may also promote the activity of allogeneic T lymphocytes, which may express foreign MHC proteins and may be increasingly susceptible to inactivation by the host immune system. For example, antagonistic TNFR2 polypeptides described herein can mitigate the T-reg-mediated depletion of tumor-reactive T cells by suppressing the growth and proliferation of T-reg cells that typically accompanies T cell infusion. For instance, polypeptides (e.g., single-chain polypeptides, antibodies, antigen-binding fragments thereof, and constructs thereof) described herein may be capable of reducing the growth of T-reg cells by about 50% to about 200% relative to untreated cells (e.g., 50%, 75%, 100%, 125%, 150%, 175%, or 200%). The reduction in cellular growth does not require the presence of TNFα. In some embodiments, polypeptides (e.g., single-chain polypeptides, antibodies, antigen-binding fragments thereof, and constructs thereof) described herein may be capable of restricting the growth of T-reg cells in the presence of TNFα to between 90% and 150% relative to untreated cells (e.g., 90%, 100%, 110%, 120%, 130%, 140%, or 150%). Antagonistic TNFR2 polypeptides (e.g., single-chain polypeptides, antibodies, antigen-binding fragments thereof, and constructs thereof) described herein are also capable of restricting the proliferation of T-reg cells to less than 70% (e.g., 60%, 50%, 40%, 30%, 20%, 10%, 5%, or 1%) of that of an untreated population of T-reg cells. Antagonistic TNFR2 polypeptides (e.g., single-chain polypeptides, antibodies, antigen-binding fragments thereof, and constructs thereof) described herein are also capable of decreasing the survival of T-reg cells by about 10% (e.g., by about 20%, 30%, 40%, or 50%, or more) relative to an untreated population of T-reg cells.

Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be administered to a mammalian subject (e.g., a human) suffering from cancer in order to improve the condition of the patient by promoting the immune response against cancer cells and tumorogenic material. Polypeptides described herein can be administered to a subject, e.g., via any of the routes of administration described herein. Polypeptides described herein can also be formulated with excipients, biologically acceptable carriers, and may be optionally conjugated to, admixed with, or co-administered separately (e.g., sequentially) with additional therapeutic agents, such as anti-cancer agents. Cancers that can be treated by administration of antibodies or antigen-binding fragments thereof described herein include such cancers as leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, and throat cancer. Particular cancers that can be treated by administration of antibodies or antigen-binding fragments thereof described herein include, without limitation, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/ rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, nonhodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

For example, antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be administered to a patient (e.g., a mammalian patient, such as a human patient) in order to treat a cancer characterized by TNFR2+ cancer cells, such as Hodgkin's lymphoma, cutaneous non-Hodgkin's lymphoma, T cell lymphoma, ovarian cancer, colon cancer, multiple myeloma, renal cell carcinoma, skin cancer, lung cancer, liver cancer, endometrial cancer, a hematopoietic or lymphoid cancer, a central nervous system cancer (e.g., glioma, blastoma, or another cancer of the central nervous system described herein or known in the art), breast cancer, pancreatic cancer, stomach cancer, esophageal cancer, and upper gastrointestinal cancer.

An antagonistic TNFR2 polypeptide described herein (e.g., any one or more of antibodies 1-25 described in Table 1 and variants thereof, such as an antibody or antigen-binding fragment containing one or more, or all, of the CDRs set forth in Table 1) can also be co-administered with a therapeutic antibody that exhibits reactivity towards a cancer cell. In this way, antagonistic TNFR2 polypeptides (e.g., single-chain polypeptides, antibodies, antigen-binding fragments thereof, and constructs thereof) described herein may synergize not only with the adaptive immune response, e.g., by prolonging T lymphocyte tumor reactivity, but also with other inhibitors of tumor cell growth. Examples of additional therapeutic antibodies that can be used to treat cancer and other cell proliferation disorders include those that exhibit reactivity with a tumor antigen or a cell-surface protein that is overexpressed on the surface of a cancer cell. Exemplary antibodies that can be admixed, co-administered, or sequentially administered with antagonistic TNFR2 polypeptides described herein include, without limitation, Trastuzamb (HERCEPTIN®), Bevacizumab (AVASTIN®), Cetuximab (ERBITUX®), Panitumumab (VECTIBIX®), Ipilimumab (YERVOY®), Rituximab (RITUXAN® and MABTHERA®), Alemtuzumab (CAMPATH®), Ofatumumab (ARZERRA®), Gemtuzumab ozogamicin (MYLOTARG®), Brentuximab vedotin (ADCETRIS®), $^{90}$Y-Ibritumomab Tiuxetan (ZEVALIN®), and$^{131}$I-Tositumomab (BEXXAR®), which are described in detail in Scott et al. (Cancer Immun., 12:14-21, 2012); incorporated herein by reference.

A physician having ordinary skill in the art can readily determine an effective amount of an antagonistic TNFR2 polypeptide, such as single-chain polypeptide, antibody, antibody fragment, or construct described herein (e.g., any one or more of antibodies 1-25 described in Table 1 and variants thereof, such as an antibody or antigen-binding fragment containing one or more, or all, of the CDRs set forth in Table 1), for administration to a mammalian subject (e.g., a human) in need thereof. For example, a physician could start prescribing doses of a polypeptide described herein at levels lower than that required in order to achieve the desired therapeutic effect and gradually increase the dosage until the desired effect is achieved. Alternatively, a physician may begin a treatment regimen by administering an antagonistic TFNR2 polypeptide, such as a single-chain polypeptide, antibody, antibody fragment, or construct at a high dose and subsequently administer progressively lower doses until a therapeutic effect is achieved (e.g., a reduction in the volume of one or more tumors, a decrease in the population of T-reg cells, or remission of a cell proliferation disorder). In general, a suitable daily dose of a single-chain polypeptide, antibody, antigen-binding fragment thereof, or construct described herein will be an amount of the compound which is the lowest dose effective to produce a therapeutic effect. An antagonistic TNFR2 polypeptide described herein may be administered, e.g., by injection, such as by intravenous, intramuscular, intraperitoneal, or subcutaneous injection, optionally proximal to the site of the target tissue (e.g., a tumor). A daily dose of a therapeutic composition of an antagonistic TNFR2 polypeptide described herein may be administered as a single dose or as two, three, four, five, six or more doses administered separately at appropriate intervals throughout the day, week, month, or year, optionally, in unit dosage forms. While it is possible for an antagonistic TNFR2 polypeptide described herein to be administered alone, it may also be administered as a pharmaceutical formulation in combination with excipients, carriers, and optionally, additional therapeutic agents.

Polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be monitored for their ability to attenuate the progression of a cell proliferation disease, such as cancer, by any of a variety of methods known in the art. For instance, a physician may monitor the response of a mammalian subject (e.g., a human) to treatment with a polypeptide, such as a single-chain polypeptide, antibody, antibody fragment, or construct described herein by analyzing the volume of one or more tumors in the patient. For example, polypeptides (e.g., single-chain polypeptides, antibodies, antigen-binding fragments thereof, and constructs thereof) described herein may be capable of reducing tumor volume by between 1% and 100% (e.g., 1%, 5%, 10%, 20%, 30%, 40%, 50%, 60%, 70%, 80%, 90%, 95%, 99%, or 100%). Alternatively, a physician may monitor the responsiveness of a subject (e.g., a human) to treatment with antagonistic TNFR2 polypeptides, such as single-chain polypeptides, antibodies, antigen-binding fragments thereof, or constructs described herein by analyzing the T-reg cell population in the lymph of a particular subject. For instance, a physician may withdraw a sample of blood from a mammalian subject (e.g., a human) and determine the quantity or density of T-reg cells (e.g., CD4+ CD25+ FOXP3+ T-reg cells or CD17+ T-reg cells) using established procedures, such as fluorescence activated cell sorting.

Methods of Treating Infectious Diseases

Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can also be used for treating infectious diseases, such as those caused by any one or more of a virus, a bacterium, a fungus, or a parasite (e.g., a eukaryotic parasite). For instance, antagonistic TNFR2 polypeptides (e.g., single-chain polypeptides, antibodies, antigen-binding fragments thereof, and constructs thereof) can be administered to a mammalian subject (e.g., a human) suffering from an infectious disease in order to treat the disease, as well as to alleviate one or more symptoms of the disease.

Exemplary compositions of the disclosure that can be used for these purposes include antagonistic TNFR2 polypeptides (e.g., any one or more of antibodies 1-25 described in Table 1 and variants thereof, such as an antibody or antigen-binding fragment containing one or more, or all, of the CDRs set forth in Table 1), such as those with at least two TNFR2 binding sites in which the binding sites are spatially separated from one another by about 133 Å or more, as well as those having a human IgG2 isotype, for example, a human IgG2-A isotype (e.g., antagonistic TNFR2 antibodies, antigen-binding fragments thereof, and constructs thereof having a human IgG2 hinge region having a C232S and/or C233S amino acid substitution). Compositions of the disclosure that can be used for these purposes also include pharmaceutical compositions containing antagonistic TNFR2 polypeptides that adopt a single disulfide-bonded isoform, such as those in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform.

For example, antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be used for treating, or alleviating one or more symptoms of, viral infections in a mammalian subject, such as a human, that are caused by, e.g., a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana *myotis* leukoencephalitis virus, Phnom Penh bat virus, Rio Bravo virus, Tamana bat virus, and the Cell fusing agent virus; a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Paraná virus, Pichinde virus, Pirital virus, Sabid virus, Tacaribe virus, Tamiami virus, Whitewater Arroyo virus, Chapare virus, and Lujo virus; a member of the Bunyaviridae family (e.g., a member of the Hantavirus, Nairovirus, Orthobunya-virus, and Phlebovirus genera), which includes the Hantaan virus, Sin Nombre virus, Dugbe virus, Bunyamwera virus, Rift Valley fever virus, La Crosse virus, California encephalitis virus, and Crimean-Congo hemorrhagic fever (CCHF) virus; a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikun-gunya virus; a member of the Poxviridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sar-coma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picomaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T lymphotropic virus Types I and II (HTLV-1 and HTLV-2, respectively); Friend Leukemia Virus; and transmissible spongiform encepha-lopathy, such as chronic wasting disease. Particularly, meth-ods described herein include administering an antagonistic TNFR2 polypeptide described herein to a human in order to treat an HIV infection (such as a human suffering from AIDS).

Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can also be used for treating, or alleviating one or more symptoms of, bacterial infections in a mammalian subject (e.g., a human). Examples of bacterial infections that may be treated by administration of an antagonistic TNFR2 poly-peptide, such as a single-chain polypeptide, antibody, or antibody fragment described herein include, without limita-tion, those caused by bacteria within the genera *Streptococ-cus, Bacillus, Listeria, Corynebacterium, Nocardia, Neis-seria, Actinobacter, Moraxella*, Enterobacteriacece (e.g., *E. coli*, such as O157:H7), *Pseudomonas* (such as *Pseudomo-nas aeruginosa*), *Escherichia, Klebsiella, Serratia, Entero-bacter, Proteus, Salmonella, Shigella, Yersinia, Haemophi-lus, Bordetella* (such as *Bordetella pertussis*), *Legionella, Pasteurella, Francisella, Brucella, Bartonella, Clostridium, Vbrio, Campylobacter, Staphylococcus, Mycobacterium* (such as *Mycobacterium tuberculosis* and *Mycobacterium avium* paratuberculosis, and *Helicobacter* (such as *Helico-bacter pylori* and *Helicobacter hepaticus*). Particularly, methods described herein include administering an antago-nistic TNFR2 polypeptide, such as a single-chain polypep-tide, antibody, antigen-binding fragment thereof, or con-struct that contains one or more, or all, of the CDR sequences of TNFRAB1, TNFRAB2, TNFRAB3, TNFRAB4, or TNFRAB5, such as a human, humanized, or chimeric variant of TNFRAB1, TNFRAB2, TNFRAB3, TNFRAB4, or TNFRAB5, to a human or a non-human mammal in order to treat a *Mycobacterium tuberculosis* infection. Particular methods described herein include administering an antagonistic TNFR2 polypeptide described herein to bovine mammals or bison in order to treat a *Mycobacterium tuberculosis* infection. Additionally, meth-ods described herein include administering an antagonistic TNFR2 polypeptide described herein to a human or a non-human mammal in order to treat a *Mycobacterium avium* paratuberculosis infection. Particular methods described herein include administering an antagonistic TNFR2 polypeptide described herein to bovine mammals or bison in order to treat a *Mycobacterium avium* paratuber-culosis infection.

Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can also be administered to a mammalian subject (e.g., a human) for treating, or alleviating one or more symptoms of, parasitic infections caused by a protozoan parasite (e.g., an intestinal protozoa, a tissue protozoa, or a blood protozoa) or a helminthic parasite (e.g., a nematode, a helminth, an adenophorea, a secementea, a trematode, a fluke (blood flukes, liver flukes, intestinal flukes, and lung flukes), or a cestode). Exemplary protozoan parasites that can be treated according to the methods described herein include, without limitation, *Entamoeba* hystolytica, *Giardia lamblia*, *Cryptosporidium muris*, Trypanosomatida *gambiense*, Trypanosomatida *rhodesiense*, Trypanosomatida crusi, *Leishmania mexicana*, *Leishmania braziliensis*, *Leishmania tropica*, *Leishmania donovani*, *Leishmania major*, *Toxoplasma gondii*, *Plasmodium vivax*, *Plasmodium ovale*, *Plasmodium malariae*, *Plasmodium falciparum*, *Plasmodium yoelli*, *Trichomonas vaginalis*, and *Histomonas meleagridis*. Exemplary helminthic parasites include richuris *trichiura*, *Ascaris lumbricoides*, *Enterobius vermicularis*, *Ancylostoma duodenale*, *Necator americanus*, *Strongyloides stercoralis*, *Wuchereria bancrofti*, and *Dracunculus medinensis*, *Schistosoma mansoni*, *Schistosoma haematobium*, *Schistosoma japonicum*, *Fasciola hepatica*, *Fasciola gigantica*, *Heterophyes*, *Paragonimus westermani*, *Taenia solium*, *Taenia saginata*, *Hymenolepis nana*, and *Echinococcus granulosus*. Additional parasitic infections that can be treated according to the methods described herein include Onchocercas *volvulus*.

Antagonistic TNFR2 polypeptides (e.g., single-chain polypeptides, antibodies, and antigen-binding fragments thereof, such as any one or more of antibodies 1-25 described in Table 1 and variants thereof, such as an antibody or antigen-binding fragment containing one or more, or all, of the CDRs set forth in Table 1) can also be administered to a mammalian subject (e.g., a human) in order to treat, or to alleviate one or more symptoms of, fungal infections. Examples of fungal infections that may be treated according to the methods described herein include, without limitation, those caused by, e.g., *Aspergillus*, *Candida*, *Malassezia*, *Trichosporon*, *Fusarium*, *Acremonium*, *Rhizopus*, *Mucor*, *Pneumocystis*, and *Absidia*. Exemplary fungal infections that can be treated according to the methods described herein also include *Pneumocystis carinii*, *Paracoccidioides brasiliensis* and *Histoplasma capsulatum*.

Pharmaceutical Compositions

Pharmaceutical compositions containing an antagonistic TNFR2 polypeptide, such as a single-chain polypeptide, antibody, antigen-binding fragment thereof, or construct described herein can (e.g., any one or more of antibodies 1-25 described in Table 1 and variants thereof, such as an antibody or antigen-binding fragment containing one or more, or all, of the CDRs set forth in Table 1) be prepared using methods known in the art. Exemplary antagonistic TNFR2 polypeptides that can be incorporated into pharmaceutical compositions of the disclosure include those with at least two TNFR2 binding sites in which the binding sites are spatially separated from one another by about 133 Å or more, as well as those having a human IgG2 isotype, for example, a human IgG2-A isotype (e.g., antagonistic TNFR2 antibodies, antigen-binding fragments thereof, and constructs thereof having a human IgG2 hinge region having a C232S and/or C233S amino acid substitution).

Pharmaceutical compositions described herein may contain an antagonistic TNFR2 polypeptide described herein (e.g., any one or more of antibodies 1-25 described in Table 1 and variants thereof, such as an antibody or antigen-binding fragment containing one or more, or all, of the CDRs set forth in Table 1) in combination with one or more pharmaceutically acceptable excipients. For instance, pharmaceutical compositions described herein can be prepared using, e.g., physiologically acceptable carriers, excipients or stabilizers (*Remington's Pharmaceutical Sciences* 16th edition, Osol, A. Ed. (1980); incorporated herein by reference), and in a desired form, e.g., in the form of lyophilized formulations or aqueous solutions. The compositions can also be prepared so as to contain the active agent (e.g., an antagonistic anti-TNFR2 antibody or fragment thereof) at a desired concentration. For example, a pharmaceutical composition described herein may contain at least 10% (e.g., 10%, 20%, 30%, 40%, 50%, 60%, 70%, 80%, 90%, 95%, 97%, 98%, 99%, 99.5%, 99.9%, or 100%) active agent by weight (w/w).

Additionally, an active agent (e.g., an antagonistic TNFR2 polypeptide described herein, such as a dominant antagonistic TNFR2 polypeptide described herein) that can be incorporated into a pharmaceutical formulation can itself have a desired level of purity. For example, a polypeptide, such as a single-chain polypeptide, antibody, or antigen-binding fragment thereof described herein may be characterized by a certain degree of purity after isolating the antibody from cell culture media or after chemical synthesis, e.g., of a single-chain antibody fragment (e.g., scFv) by established solid phase peptide synthesis methods or native chemical ligation as described herein. An antagonistic TNFR2 polypeptide described herein may be at least 10% pure prior to incorporating the antibody into a pharmaceutical composition (e.g., 10%, 20%, 30%, 40%, 50%, 60%, 70%, 80%, 90%, 95%, 97%, 98%, 99%, 99.5%, 99.9%, 99.99%, or 100% pure).

Additionally, antagonistic TNFR2 polypeptides of the disclosure (e.g., any one or more of antibodies 1-25 described in Table 1 and variants thereof, such as an antibody or antigen-binding fragment containing one or more, or all, of the CDRs set forth in Table 1) may be incorporated into a pharmaceutical composition such that many of the polypeptides present in the pharmaceutical composition adopt a single disulfide-bonded isoform. For example, pharmaceutical compositions of the disclosure include those containing an antagonist TNFR2 polypeptide in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform, such as the IgG2-A isoform described herein.

Pharmaceutical compositions of antagonistic TNFR2 polypeptides described herein (e.g., any one or more of antibodies 1-25 described in Table 1 and variants thereof, such as an antibody or antigen-binding fragment containing one or more, or all, of the CDRs set forth in Table 1) can be prepared for storage as lyophilized formulations or aqueous solutions by mixing the antibody having the desired degree of purity with optional pharmaceutically acceptable carriers, excipients or stabilizers typically employed in the art, e.g., buffering agents, stabilizing agents, preservatives, isotonifiers, non-ionic detergents, antioxidants, and other miscellaneous additives. See, e.g., Remington's Pharmaceutical Sciences, 16th edition (Osol, ed. 1980; incorporated herein by reference). Such additives must be nontoxic to the recipients at the dosages and concentrations employed.

Buffering Agents

Buffering agents help to maintain the pH in the range which approximates physiological conditions. They can be present at concentration ranging from about 2 mM to about 50 mM. Suitable buffering agents for use with antagonistic TNFR2 polypeptides (e.g., single-chain polypeptides, antibodies, and antigen-binding fragments thereof) described herein include both organic and inorganic acids and salts thereof such as citrate buffers {e.g., monosodium citrate-disodium citrate mixture, citric acid-trisodium citrate mixture, citric acid-monosodium citrate mixture, etc.), succinate buffers {e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers {e.g., fumaric acid-monosodium fumarate mixture, fumaric acid-disodium fumarate mixture, monosodium fumarate-disodium fumarate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers {e.g., acetic acid-sodium acetate mixture, acetic acid-sodium hydroxide mixture, etc.). Additionally, phosphate buffers, histidine buffers and trimethylamine salts such as Tris can be used.

Preservatives

Preservatives can be added to a composition described herein to retard microbial growth, and can be added in amounts ranging from 0.2%-1% (w/v). Suitable preservatives for use with antagonistic TNFR2 polypeptides (e.g., single-chain polypeptides, antibodies, antigen-binding fragments thereof, and constructs thereof) described herein include phenol, benzyl alcohol, meta-cresol, methyl paraben, propyl paraben, octadecyldimethylbenzyl ammonium chloride, benzalconium halides {e.g., chloride, bromide, and iodide), hexamethonium chloride, and alkyl parabens such as methyl or propyl paraben, catechol, resorcinol, cyclohexanol, and 3-pentanol. Isotonifiers sometimes known as "stabilizers" can be added to ensure isotonicity of liquid compositions described herein and include polhydric sugar alcohols, for example trihydric or higher sugar alcohols, such as glycerin, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from 0.1 to 10,000 weights per part of weight active protein.

Detergents

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

Other Pharmaceutical Carriers

Alternative pharmaceutically acceptable carriers that can be incorporated into a pharmaceutical composition described herein may include dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. A composition containing an antagonistic TNFR2 antibody described herein may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

Compositions and Methods for Combination Therapy

Pharmaceutical compositions described herein may optionally include more than one active agent. For instance, compositions described herein may contain an antagonistic TNFR2 polypeptide (e.g., a single-chain polypeptide, antibody, antigen-binding fragment thereof, or construct described herein, such as any one or more of antibodies 1-25 described in Table 1 and variants thereof, such as an antibody or antigen-binding fragment containing one or more, or all, of the CDRs set forth in Table 1) conjugated to, admixed with, or administered separately from another pharmaceutically active molecule, e.g., a cytotoxic agent, an antibiotic, or a T lymphocyte (e.g., a gene-edited T lymphocyte for use in CAR-T therapy). For instance, an antagonistic TNFR2 polypeptide or therapeutic conjugate thereof (e.g., a drug-antibody conjugate described herein), may be admixed with one or more additional active agents that can be used to treat cancer or another cell proliferation disorder (e.g., neoplasm). Alternatively, pharmaceutical compositions described herein may be formulated for co-administration or sequential administration with one or more additional active agents that can be used to treat cancer or other cell proliferation disorders. Examples of additional active agents that can be used to treat cancer and other cell proliferation disorders and that can be conjugated to, admixed with, or administered separately from an antagonistic TNFR2 polypeptide described herein include cytotoxic agents (e.g., those described herein), as well as antibodies that exhibit reactivity with a tumor antigen or a cell-surface protein that is overexpressed on the surface of a cancer cell. Exemplary antibodies that can be conjugated to, admixed with, or administered separately from antagonistic TNFR2 antibodies described herein include, without limitation, Trastuzamb (HERCEPTIN®), Bevacizumab (AVASTIN®), Cetuximab (ERBITUX®), Panitumumab (VECTIBIX®), Ipilimumab (YERVOY®), Rituximab (RITUXAN® and MABTHERA®), Alemtuzumab (CAMPATH®), Ofatumumab (ARZERRA®), Gemtuzumab ozogamicin (MYLOTARG®), Brentuximab vedotin (ADCETRIS®), $^{90}$Y-Ibritumomab Tiuxetan (ZEVALIN®), and $^{131}$I-Tositumomab (BEXXAR®), which are described in detail in Scott et al. (Cancer Immun., 12:14-21, 2012); incorporated herein by reference.

Additional agents that can be conjugated to, admixed with, or administered separately from antagonistic TNFR2 polypeptides described herein (e.g., any one or more of antibodies 1-25 described in Table 1 and variants thereof, such as an antibody or antigen-binding fragment containing one or more, or all, of the CDRs set forth in Table 1) include T lymphocytes that exhibit reactivity with a specific antigen associated with a particular pathology. For instance, antagonistic TNFR2 polypeptides described herein can be formulated for administration with a T cell that expresses a chimeric antigen receptor (CAR-T) in order to treat a cell proliferation disorder, such as a cancer described herein. Antagonistic TNFR2 polypeptides (e.g., single-chain polypeptides, antibodies, and antigen-binding fragments thereof) can synergize with CAR-T therapy by preventing T-reg cells from deactivating T lymphocytes that have been genetically modified so as to express tumor-reactive antigen receptors. In this way, CAR-T cells can be administered to a patient prior to, concurrently with, or after administration of an antagonistic TNFR2 polypeptide in order to treat a mammalian subject (e.g., a human) suffering from a cell proliferation disorder, such as cancer.

CAR-T therapy is a particularly robust platform for targeting cancer cells in view of the ability to genetically engineer T lymphocytes to express an antigen receptor specific to a tumor-associated antigen. For instance, identification of antigens overexpressed on the surfaces of tumors and other cancer cells can inform the design and discovery of chimeric T cell receptors, which are often composed of cytoplasmic and transmembrane domains derived from a naturally-occurring T cell receptor operatively linked to an extracellular scFv fragment that specifically binds to a particular antigenic peptide. T cells can be genetically modified in order to express an antigen receptor that specifically binds to a particular tumor antigen by any of a variety of genome editing techniques described herein or known in the art. Exemplary techniques for modifying a T cell genome so as to incorporate a gene encoding a chimeric antigen receptor include the CRISPER/Cas, zinc finger nuclease, TALEN, ARCUS™ platforms described herein. Methods for the genetic engineering of CAR-T lymphocytes have been described, e.g., in WO 2014/127261, WO 2014/039523, WO 2014/099671, and WO 20120790000; the disclosures of each of which are incorporated by reference herein.

CAR-T cells useful in the compositions and methods described herein include those that have been genetically modified such that the cell does not express the endogenous T cell receptor. For instance, a CAR-T cell may be modified by genome-editing techniques, such as those described herein, so as to suppress expression of the endogenous T cell receptor in order to prevent graft-versus-host reactions in a patient receiving a CAR-T infusion. Additionally, or alternatively, CAR-T cells can be genetically modified so as to reduce the expression of one or more endogenous MHC proteins. This is a particularly useful technique for the infusion of allogeneic T lymphocytes, as recognition of foreign MHC proteins represents one mechanism that promotes allograft rejection. One of skill in the art can also modify a T lymphocyte so as to suppress the expression of immune suppressor proteins, such as programmed cell death protein 1 (PD-1) and cytotoxic T lymphocyte-associated protein 4 (CTLA-4). These proteins are cell surface receptors that, when activated, attenuate T cell activation. Infusion of CAR-T cells that have been genetically modified so as to diminish the expression of one or more immunosuppressor proteins represents one strategy that can be used to prolong the T lymphocyte-mediated cytotoxicity in vivo.

In addition to deleting specific genes, one can also modify CAR-T cells in order to express a T cell receptor with a desired antigen specificity. For instance, one can genetically modify a T lymphocyte in order to express a T cell receptor that specifically binds to a tumor-associated antigen in order to target infused T cells to cancer cells. An exemplary T cell receptor that may be expressed by a CAR-T cell is one that binds PD-1, a cell surface protein that is often overexpressed on various tumor cells. As PD-L1 activates PD-1 on the surface of T lymphocytes, targeting this tumor antigen with CAR-T therapy can synergize with antagonistic TNFR2 antibodies or antibody fragments described herein in order to increase the duration of an immune response mediated by a T lymphocyte in vivo. CAR-T cells can also be modified so as to express a T cell receptor that specifically binds an antigen associated with one or more infectious disease, such as an antigen derived from a viral protein, a bacterial cell, a fungus, or other parasitic organism.

Other pharmaceutical compositions described herein include those that contain an antagonistic TNFR2 antibody or antibody fragment (e.g., any one or more of antibodies 1-25 described in Table 1 and variants thereof, such as an antibody or antigen-binding fragment containing one or more, or all, of the CDRs set forth in Table 1), interferon alpha, and/or one or more antibiotics that can be administered to a patient (e.g., a human patient) suffering from an infectious disease. For instance, an antagonistic TNFR2 antibody or antibody fragment can be conjugated to, admixed with, or administered separately from an antibiotic useful for treating one or more infectious diseases, such as amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, meropenem, cefadroxil, cefazolin, cefazlexin, cefaclor, cefoxitin, cefprozil, cefuroxime, cefdinir, cefditoren, cefoperazone, clindamycin, lincomycin, daptomycin, erythromycin, linezolid, torezolid, amoxicillin, ampicillin, bacitracin, ciprofloxacin, doxycycline, and tetracycline, among others.

Immunotherapy Agents

An antagonistic TNFR2 polypeptide (e.g., a single-chain polypeptide, antibody, antigen-binding fragment thereof, or construct thereof) described herein (e.g., any one or more of antibodies 1-25 described in Table 1 and variants thereof, such as an antibody or antigen-binding fragment containing one or more, or all, of the CDRs set forth in Table 1) may be admixed, conjugated, administered with, or administered separately from, an immunotherapy agent, for instance, for the treatment of a cancer or infectious disease, such as a cancer or infectious disease described herein. Exemplary immunotherapy agents useful in conjunction with the compositions and methods described herein include, without limitation, an anti-CTLA-4 agent, an anti-PD-1 agent, an anti-PD-L1 agent, an anti-PD-L2 agent, an anti-TNF-α cross-linking agent, an anti-TRAIL cross-linking agent, an anti-CD27 agent, an anti-CD30 agent, an anti-CD40 agent, an anti-4-1BB agent, an anti-GITR agent, an anti-OX40 agent, an anti-TRAILR1 agent, an anti-TRAILR2 agent, and an anti-TWEAKR agent, as well as, for example, agents directed toward the immunological targets described in Table 1 of Mahoney et al., Cancer Immunotherapy, 14:561-584 (2015), the disclosure of which is incorporated herein by reference in its entirety. For example, the immunotherapy agent may be an anti-CTLA-4 antibody or antigen-binding fragment thereof, such as ipilimumab and tremelimumab. The immunotherapy agent may be an anti-PD-1 antibody or antigen-binding fragment thereof, such as nivolumab, pembrolizumab, avelumab, durvalumab, and atezolizumab. The immunotherapy agent may be an anti-PD-L1 antibody or antigen-binding fragment thereof, such as atezolizumab or avelumab. As other examples, immunological target 4-1BB ligand may be targeted with an anti-4-1BB ligand antibody; immunological target OX40L may be targeted with an anti-OX40L antibody; immunological target GITR may be targeted with an anti-GITR antibody; immunological target CD27 may be targeted with an anti-CD27 antibody; immunological target TL1A may be targeted with an anti-TL1A antibody; immunological target CD40L or CD40 may be targeted with an anti-CD40L antibody; immunological target LIGHT may be targeted with an anti-LIGHT antibody; immunological target BTLA may be targeted with an anti-BTLA antibody; immunological target LAG3 may be targeted with an anti-LAG3 antibody; immunological target TIM3 may be targeted with an anti-TIM3 antibody; immunological target Singlecs may be targeted with an anti-Singlecs antibody; immunological target ICOS ligand may be targeted with an anti-ICOS ligand antibody; immunological target B7-H3 may be targeted with an anti-B7-H3 antibody; immunological target B7-H4 may be targeted with an anti-B7-H4 antibody; immunological target VISTA may be targeted with an anti-VISTA antibody; immunological target TMIGD2 may be targeted with an anti-TMIGD2 antibody; immunological target BTNL2 may be targeted with an anti-BTNL2 antibody; immunological target CD48 may be targeted with an anti-CD48 antibody; immunological target KIR may be targeted with an anti-KIR antibody; immunological target LIR may be targeted with an anti-LIR antibody; immunological target ILT may be targeted with an anti-ILT antibody; immunological target NKG2D may be targeted with an anti-NKG2D antibody; immunological target NKG2A may be targeted with an anti-NKG2A antibody; immunological target MICA may be targeted with an anti-MICA antibody; immunological target MICB may be targeted with an anti-MICB antibody; immunological target CD244 may be targeted with an anti-CD244 antibody; immunological target CSF1R may be targeted with an anti-CSF1R antibody; immunological target IDO may be targeted with an anti-IDO antibody; immunological target TGFβ may be targeted with an anti-TGFβ antibody; immunological target CD39 may be targeted with an anti-CD39 antibody; immunological target CD73 may be targeted with an anti-CD73 antibody; immunological target CXCR4 may be targeted with an anti-CXCR4 antibody; immunological target CXCL12 may be targeted with an anti-CXCL12 antibody; immunological target SIRPA may be targeted with an anti-SIRPA antibody; immunological target CD47 may be targeted with an anti-CD47 antibody; immunological target VEGF may be targeted with an anti-VEGF antibody; and immunological target neuropilin may be targeted with an anti-neuropilin antibody (see, e.g., Table 1 of Mahoney et al.).

Immunotherapy agents that may be used in conjunction with the compositions and methods described herein include, for instance, an anti-TWEAK agent, an anti-cell surface lymphocyte protein agent, an anti-BRAF agent, an anti-MEK agent, an anti-CD33 agent, an anti-CD20 agent, an anti-HLA-DR agent, an anti-HLA class I agent, an anti-CD52 agent, an anti-A33 agent, an anti-GD3 agent, an anti-PSMA agent, an anti-Ceacan 1 agent, an anti-Galedin 9 agent, an anti-HVEM agent, an anti-VISTA agent, an anti-B7 H4 agent, an anti-HHLA2 agent, an anti-CD155 agent, an anti-CD80 agent, an anti-BTLA agent, an anti-CD160 agent, an anti-CD28 agent, an anti-CD226 agent, an anti-CEACAM1 agent, an anti-TIM3 agent, an anti-TIGIT agent, an anti-CD96 agent, an anti-CD70 agent, an anti-CD27 agent, an anti-LIGHT agent, an anti-CD137 agent, an anti-DR4 agent, an anti-CR5 agent, an anti-TNFRS agent, an anti-TNFR1 agent, an anti-FAS agent, an anti-CD95 agent, an anti-TRAIL agent, an anti-DR6 agent, an anti-EDAR agent, an anti-NGFR agent, an anti-OPG agent, an anti-RANKL agent, an anti-LTβ receptor agent, an anti-BCMA agent, an anti-TACI agent, an anti-BAFFR agent, an anti-EDAR2 agent, an anti-TROY agent, and an anti-RELT agent. For instance, the immunotherapy agent may be an anti-TWEAK antibody or antigen-binding fragment thereof, an anti-cell surface lymphocyte protein antibody or antigen-binding fragment thereof, an anti-BRAF antibody or antigen-binding fragment thereof, an anti-MEK antibody or antigen-binding fragment thereof, an anti-CD33 antibody or antigen-binding fragment thereof, an anti-CD20 antibody or antigen-binding fragment thereof, an anti-HLA-DR antibody or antigen-binding fragment thereof, an anti-HLA class I antibody or antigen-binding fragment thereof, an anti-CD52 antibody or antigen-binding fragment thereof, an anti-A33 antibody or antigen-binding fragment thereof, an anti-GD3 antibody or antigen-binding fragment thereof, an anti-PSMA antibody or antigen-binding fragment thereof, an anti-Ceacan 1 antibody or antigen-binding fragment thereof, an anti-Galedin 9 antibody or antigen-binding fragment thereof, an anti-HVEM antibody or antigen-binding fragment thereof, an anti-VISTA antibody or antigen-binding fragment thereof, an anti-B7 H4 antibody or antigen-binding fragment thereof, an anti-HHLA2 antibody or antigen-binding fragment thereof, an anti-CD155 antibody or antigen-binding fragment thereof, an anti-CD80 antibody or antigen-binding fragment thereof, an anti-BTLA antibody or antigen-binding fragment thereof, an anti-CD160 antibody or antigen-binding fragment thereof, an anti-CD28 antibody or antigen-binding fragment thereof, an anti-CD226 antibody or antigen-binding fragment thereof, an anti-CEACAM1 antibody or antigen-binding fragment thereof, an anti-TIM3 antibody or antigen-binding fragment thereof, an anti-TIGIT antibody or antigen-binding fragment thereof, an anti-CD96 antibody or antigen-binding fragment thereof, an anti-CD70 antibody or antigen-binding fragment thereof, an anti-CD27 antibody or antigen-binding fragment thereof, an anti-LIGHT antibody or antigen-binding fragment thereof, an anti-CD137 antibody or antigen-binding fragment thereof, an anti-DR4 antibody or antigen-binding fragment thereof, an anti-CR5 antibody or antigen-binding fragment thereof, an anti-TNFRS antibody or antigen-binding fragment thereof, an anti-TNFR1 antibody or antigen-binding fragment thereof, an anti-FAS antibody or antigen-binding fragment thereof, an anti-CD95 antibody or antigen-binding fragment thereof, an anti-TRAIL antibody or antigen-binding fragment thereof, an anti-DR6 antibody or antigen-binding fragment thereof, an anti-EDAR antibody or antigen-binding fragment thereof, an anti-NGFR antibody or antigen-binding fragment thereof, an anti-OPG antibody or antigen-binding fragment thereof, an anti-RANKL antibody or antigen-binding fragment thereof, an anti-LTβ receptor antibody or antigen-binding fragment thereof, an anti-BCMA antibody or antigen-binding fragment thereof, an anti-TACI antibody or antigen-binding fragment thereof, an anti-BAFFR antibody or antigen-binding fragment thereof, an anti-EDAR2 antibody or antigen-binding fragment thereof, an anti-TROY antibody or antigen-binding fragment thereof, or an anti-RELT antibody or antigen-binding fragment thereof.

In some embodiments, the immunotherapy agent is an anti-cell surface lymphocyte protein antibody or antigen-binding fragment thereof, such as an antibody or antigen-binding fragment thereof that binds one or more of CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49, CD50, CD51, CD52, CD53, CD54, CD55, CD56, CD57, CD58, CD59, CD60, CD61, CD62, CD63, CD64, CD65, CD66, CD67, CD68, CD69, CD70, CD71, CD72, CD73, CD74, CD75, CD76, CD77, CD78, CD79, CD80, CD81, CD82, CD83, CD84, CD85, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD120, CD121, CD122, CD123, CD124, CD125, CD126, CD127, CD128, CD129, CD130, CD131, CD132, CD133, CD134, CD135, CD136, CD137, CD138, CD139, CD140, CD141, CD142, CD143, CD144, CD145, CD146, CD147, CD148, CD149, CD150, CD151, CD152, CD153, CD154, CD155, CD156, CD157, CD158, CD159, CD160, CD161, CD162, CD163, CD164, CD165, CD166, CD167, CD168, CD169, CD170, CD171, CD172, CD173, CD174, CD175, CD176, CD177, CD178, CD179, CD180, CD181, CD182, CD183, CD184, CD185, CD186, CD187, CD188, CD189, CD190, CD191, CD192, CD193, CD194, CD195, CD196, CD197, CD198, CD199, CD200, CD201, CD202, CD203, CD204, CD205, CD206, CD207, CD208, CD209, CD210, CD211, CD212, CD213, CD214, CD215, CD216, CD217, CD218, CD219, CD220, CD221, CD222, CD223, CD224, CD225, CD226, CD227, CD228, CD229, CD230, CD231, CD232, CD233, CD234, CD235, CD236, CD237, CD238, CD239, CD240, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CD293, CD294, CD295, CD296, CD297, CD298, CD299, CD300, CD301, CD302, CD303, CD304, CD305, CD306, CD307, CD308, CD309, CD310, CD311, CD312, CD313, CD314, CD315, CD316, CD317, CD318, CD319, and/or CD320.

In some embodiments, the immunotherapy agent is an agent (e.g., a polypeptide, antibody, antigen-binding fragment thereof, a single-chain polypeptide, or construct thereof) that binds a chemokine or lymphokine, such as a chemokine or lymphokine involved in tumor growth. For instance, exemplary immunotherapy agents that may be used in conjunction with the compositions and methods described herein include agents (e.g., polypeptides, antibodies, antigen-binding fragments thereof, single-chain polypeptides, and constructs thereof) that bind and inhibit the activity of one or more, or all, of CXCL1, CXCL2, CXCL3, CXCL8, CCL2 and CCL5. Exemplary chemokines involved in tumor growth and that may be targeted using an immunotherapy agent as described herein include those described, for instance, in Chow et al., Cancer Immunol. Res., 2:1125-1131, 2014, the disclosure of which is incorporated herein by reference. Exemplary immunotherapy agents that may be used in conjunction with the compositions and methods described herein additionally include agents (e.g., polypeptides, antibodies, antigen-binding fragments thereof, single-chain polypeptides, and constructs thereof) that bind and inhibit the activity of one or more, or all, of CCL3, CCL4, CCL8, and CCL22, which are described, for instance, in Balkwill, Nat. Rev. Cancer, 4:540-550, 2004, the disclosure of which is incorporated herein by reference.

Additional examples of immunotherapy agents that can be used in conjunction with the compositions and methods described herein include Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and/or small molecular therapies like Vorinostat.

Using the methods described herein, an antagonistic TNFR2 polypeptide (e.g., a single-chain polypeptide, antibody, antigen-binding fragment thereof, or construct thereof) described herein (e.g., any one or more of antibodies 1-25 described in Table 1 and variants thereof, such as an antibody or antigen-binding fragment containing one or more, or all, of the CDRs set forth in Table 1) may be co-administered with (e.g., admixed with) or administered separately from an immunotherapy agent. For example, an antagonistic TNFR2 polypeptide described herein (such as a single-chain polypeptide, antibody, antigen-binding fragment thereof, or construct described herein) may be administered to a patient, such as a human patient suffering from a cancer or infectious disease, simultaneously or at different times. In some embodiments, the antagonistic TNFR2 polypeptide (e.g., a single-chain polypeptide, antibody, antigen-binding fragment thereof, or construct described herein) is administered to the patient prior to administration of an immunotherapy agent to the patient. Alternatively, the antagonistic TNFR2 polypeptide (e.g., a single-chain polypeptide, antibody, antigen-binding fragment thereof, or construct described herein) may be administered to the patient after an immunotherapy agent. For example, the antagonistic TNFR2 polypeptide (e.g., a single-chain polypeptide, antibody, antigen-binding fragment thereof, or construct described herein) may be administered to the patient after a failed immunotherapy treatment. A physician of skill in the art can monitor the efficacy of immunotherapy treatment to determine whether the therapy has successfully ameliorated the pathology being treated (such as a cancer or infectious disease, e.g., a cancer or infectious disease described herein) using methods described herein and known in the art.

For instance, a physician of skill in the art may monitor the quantity of cancer cells in a sample isolated from a patient (e.g., a blood sample or biopsy sample), such as a human patient, for instance, using flow cytometry or FACS analysis. Additionally, or alternatively, a physician of skill in the art can monitor the progression of a cancerous disease in a patient, for instance, by monitoring the size of one or more tumors in the patient, for example, by CT scan, MRI, or X-ray analysis. A physician of skill in the art may monitor the progression of a cancer, such as a cancer described herein, by evaluating the quantity and/or concentration of tumor biomarkers in the patient, such as the quantity and/or concentration of cell surface-bound tumor associated antigens or secreted tumor antigens present in the blood of the patient as an indicator of tumor presence. A finding that the quantity of cancer cells, the size of a tumor, and/or the quantity or concentration of one or more tumor antigens present in the patient or in a sample isolated from the patient has not decreased, for instance, by a statistically significant amount following administration of the immunotherapy agent within a specified time period (e.g., from 1 day to 6 months, such as 1 day, 2 days, 3 days, 4 days, 5 days, 6 days, 7 days, 2 weeks, 3 weeks, 4 weeks, 2 months, 3 months, 4 months, 5 months, or 6 months) can indicate that the immunotherapy treatment has failed to ameliorate the cancer. Based on this indication, a physician of skill in the art may administer an antagonistic TNFR2 polypeptide described herein, such as a single-chain polypeptide, antibody, antigen-binding fragment thereof, or construct described herein. Similarly, a physician a physician of skill in the art may monitor the quantity of bacterial, fungal, or parasitic cells, or the quantity of viral particles in a sample isolated from a patient suffering from an infectious disease, such as an infectious disease described herein. Additionally, or alternatively, a physician of skill in the art may monitor the progression of an infectious disease by evaluating the symptoms of a patient suffering from such a pathology. For instance, a physician may monitor the patient by determining whether the frequency and/or severity of one or more symptoms of the infectious disease have stabilized (e.g., remained the same) or decreased following treatment with an immunotherapy agent. A finding that the quantity of bacterial, fungal, or parasitic cells or viral particles in a sample isolated from the patient and/or a finding that the frequency or severity of one or more symptoms of the infectious disease have not decreased, for instance, by a statistically significant amount following administration of the immunotherapy agent within a specified time period (e.g., from 1 day to 6 months, such as 1 day, 2 days, 3 days, 4 days, 5 days, 6 days, 7 days, 2 weeks, 3 weeks, 4 weeks, 2 months, 3 months, 4 months, 5 months, or 6 months) can indicate that the immunotherapy treatment has failed to ameliorate the infectious disease. Based on this indication, a physician of skill in the art may administer an antagonistic TNFR2 polypeptide described herein, such as a single-chain polypeptide, antibody, antigen-binding fragment thereof, or construct described herein.

Chemotherapy Agents and Radiation Therapy

Additionally, or alternatively, an antagonistic TNFR2 polypeptide (e.g., a single-chain polypeptide, antibody, antigen-binding fragment thereof, or construct thereof) described herein (e.g., any one or more of antibodies 1-25 described in Table 1 and variants thereof, such as an antibody or antigen-binding fragment containing one or more, or all, of the CDRs set forth in Table 1) may be admixed, conjugated, administered with, or administered separately from, a chemotherapy agent, for example, for the treatment of cancer, such as a cancer described herein. Exemplary chemotherapy agents useful in conjunction with the compositions and methods described herein include, without limitation, Abiraterone Acetate, ABITREXATE® (Methotrexate), ABRAXANE® (Paclitaxel Albumin), ADRIAMYCIN®, bleomycin, vinblastine, and dacarbazine (ABVD), ADRIAMYCIN®, bleomycin, vincristine sulfate, and etoposide phosphate (ABVE), ADRIAMYCIN®, bleomycin, vincristine sulfate, etoposide phosphate, prednisone, and cyclophosphamide (ABVE-PC), doxorubicin and cyclophosphamide (AC), doxorubicin, cyclophosphamide, and paclitaxel or docetaxel (AC-T), ADCETRIS® (Brentuximab Vedotin), cytarabine, daunorubicin, and etoposide (ADE), ado-trastuzumab emtansine, ADRIAMYCIN® (doxorubicin hydrochloride), afatinib dimaleate, AFINITOR® (Everolimus), AKYNZEO® (netupitant and palonosetron hydrochloride), ALDARA® (imiquimod), aldesleukin, ALECENSA® (alectinib), alectinib, alemtuzumab, ALKERAN® for Injection (Melphalan Hydrochloride), ALKERAN® tablets (melphalan), ALIMTA® (pemetrexed disodium), ALOXI® (palonosetron hydrochloride), AMBOCHLORIN® (chlorambucil), AMBOCLORIN® (Chlorambucil), aminolevulinic acid, anastrozole, aprepitant, AREDIA® (pamidronate disodium), ARIMIDEX® (anastrozole), AROMASIN® (exemestane), ARRANON® (nelarabine), arsenic trioxide, ARZERRA® (ofatumumab), asparaginase *Erwinia chrysanthemi*, AVASTIN® (bevacizumab), axitinib, azacitidine, BEACOPP Becenum (carmustine), BELEODAQ® (Belinostat), belinostat, bendamustine hydrochloride, bleomycin, etoposide, and cisplatin (BEP), bevacizumab, bexarotene, BEXXAR® (tositumomab and iodine $^{131}$I tositumomab), bicalutamide, BiCNU (carmustine), bleomycin, blinatumomab, BLINCYTO® (blinatumomab), bortezomib, BOSULIF® (bosutinib), bosutinib, brentuximab vedotin, busulfan, BUSULFEX® (busulfan), cabazitaxel, cabozantinib-S-malate, CAF, CAMPATH® (alemtuzumab), CAMPTOSAR® (irinotecan hydrochloride), capecitabine, CAPOX, CARAC® (fluorouracil), carboplatin, CARBOPLATIN-TAXOL®, carfilzomib, CARMUBRIS® (carmustine), carmustine, carmustine implant, CASODEX® (bicalutamide), CEENU (lomustine), cisplatin, etoposide, and methotrexate (CEM), ceritinib, CERUBIDINE® (daunorubicin hydrochloride), CERVARIX® (recombinant HPV bivalent vaccine), cetuximab, chlorambucil, chlorambucil-prednisone, CHOP, cisplatin, CLAFEN® (cyclophosphamide), clofarabine, CLOFAREX® (clofarabine), CLOLAR® (Clofarabine), CMF, cobimetinib, cometriq (cabozantinib-S-malate), COPDAC, COPP, COPP-ABV, COSMEGEN® (dactinomycin), COTELLIC® (cobimetinib), crizotinib, CVP, cyclophosphamide, CYFOS® (ifosfamide), CYRAMZA® (ramucirumab), cytarabine, cytarabine liposome, CYTOSAR-U® (cytarabine), CYTOXAN® (cyclophosphamide), dabrafenib, dacarbazine, DACOGEN® (decitabine), dactinomycin, daratumumab, DARZALEX® (daratumumab), dasatinib, daunorubicin hydrochloride, decitabine, degarelix, denileukin diftitox, denosumab, DEPOCYT® (cytarabine liposome), dexamethasone, dexrazoxane hydrochloride, dinutuximab, docetaxel, DOXIL® (doxorubicin hydrochloride), doxorubicin hydrochloride, DOX-SL® (doxorubicin hydrochloride), DTIC-DOME® (dacarbazine), EFUDEX (fluorouracil), ELITEK® (rasburicase), ELLENCE® (epirubicin hydrochloride), elotuzumab, ELOXATIN® (oxaliplatin), eltrombopag olamine, EMEND® (aprepitant), EMPLICITI® (elotuzumab), enzalutamide, epirubicin hydrochloride, EPOCH, ERBITUX® (cetuximab), eribulin mesylate, ERIVEDGE® (vismodegib), erlotinib hydrochloride, ERWINAZE® (asparaginase *Erwinia chrysanthemi*), ETOPOPHOS® (etoposide phosphate), etoposide, etoposide phosphate, EVACET® (doxorubicin hydrochloride liposome), everolimus, EVISTA® (raloxifene hydrochloride), EVOMELA® (melphalan hydrochloride), exemestane, 5-FU (5-fluorouracil), FARESTON® (toremifene), FARYDAK® (panobinostat), FASLODEX® (fulvestrant), FEC, FEMARA® (letrozole), filgrastim, FLUDARA® (fludarabine phosphate), fludarabine phosphate, FLUOROPLEX® (fluorouracil), fluorouracil injection, flutamide, FOLEX® (methotrexate), FOLEXS PFS (methotrexate), FOLFIRI, FOLFIRI-bevacizumab, FOLFIRI-cetuximab, FOLFIRINOX, FOLFOX, FOLOTYN® (pralatrexate), FU-LV, fulvestrant, GARDA-SIL® (recombinant HPV quadrivalent vaccine), GARDA-SIL 9® (recombinant HPV nonavalent vaccine), GAZYVA® (obinutuzumab), gefitinib, gemcitabine hydrochloride, gemcitabine-cisplatin, gemcitabine-oxaliplatin, gemtuzumab ozogamicin, GEMZAR® (gemcitabine hydrochloride), GILOTRIF® (afatinib dimaleate), GLEEVEC® (imatinib mesylate), GLIADEL® (carmustine implant), GLIADEL® wafer (carmustine implant), glucarpidase, goserelin acetate, HALAVEN® (eribulin mesylate), HERCEP-TIN® (trastuzumab), HPV bivalent vaccine, HYCAMTIN® (topotecan hydrochloride), Hyper-CVAD, IBRANCE (palbociclib), IBRITUMOMAB® tiuxetan, ibrutinib, ICE, ICLUSIG® (ponatinib hydrochloride), IDAMYCIN® (idarubicin hydrochloride), idarubicin hydrochloride, idelalisib, IFEX® (ifosfamide), ifosfamide, ifosfamidum, IL-2 (aldesleukin), imatinib mesylate, IMBRUVICA® (ibrutinib), ilmiquimod, IMLYGIC® (talimogene laherparepvec), INLYTA (axitinib), recombinant interferon alpha-2b, intron A, tositumomab, such as $^{131}$I tositumomab, ipilimumab, IRESSA® (gefitinib), irinotecan hydrochloride, ISTODAX® (romidepsin), ixabepilone, ixazomib citrate, IXEMPRA® (ixabepilone), JAKAFI® (ruxolitinib phosphate), JEVTANA® (cabazitaxel), KADCYLA® (ado-trastuzumab emtansine), KEOXIFENE® (raloxifene hydrochloride, KEPIVANCE® (palifermin), KEYTRUDA® (pembrolizumab), KYPROLIS® (carfilzomib), lanreotide acetate, lapatinib ditosylate, lenalidomide, lenvatinib mesylate, LENVIMA® (lenvatinib mesylate), letrozole, leucovorin calcium, leukeran (chlorambucil), leuprolide acetate, levulan (aminolevulinic acid), LINFOLIZIN® (chlorambucil), LIPODOX® (doxorubicin hydrochloride liposome), lomustine, LONSURF® (trifluridine and tipiracil hydrochloride), LUPRON® (leuprolide acetate), LYNPARZA® (olaparib), MARQIBO® (vincristine sulfate liposome), MATULANE® (procarbazine hydrochloride), mechlorethamine hydrochloride, megestrol acetate, MEKINIST® (trametinib), melphalan, melphalan hydrochloride, mercaptopurine, MESNEX® (mesna), METHAZOLASTONE® (temozolomide), methotrexate, methotrexate LPF, MEX-ATE® (methotrexate), MEXATE-AQ® (methotrexate), mitomycin C, mitoxantrone hydrochloride, MITOZYTREX® (mitomycin C), MOPP, MOZOBIL® (plerixafor), MUSTARGEN® (mechlorethamine hydrochloride), MUTAMYCIN® (mitomycin C), MYLERAN® (busulfan), MYLOSAR® (azacitidine), MYLOTARG® (gemtuzumab ozogamicin), nanoparticle paclitaxel, NAVELBINE® (vinorelbine tartrate), NECITUMUMAB, nelarabine, NEOSAR® (cyclophosphamide), netupitant and palonosetron hydrochloride, NEUPOGEN® (filgrastim), NEXAVAR® (sorafenib tosylate), NILOTINIB, NIN-LARO® (ixazomib citrate), nivolumab, NOLVADEX® (tamoxifen citrate), NPLATE® (romiplostim), obinutuzumab, ODOMZO® (sonidegib), OEPA, ofatumumab, OFF, olaparib, omacetaxine mepesuccinate, ONCASPAR® (pegaspargase), ondansetron hydrochloride, ONIVYDE® (irinotecan hydrochloride liposome), ONTAK® (denileukin diftitox), OPDIVO® (nivolumab), OPPA, osimertinib, oxaliplatin, paclitaxel, paclitaxel albumin-stabilized nanoparticle formulation, PAD, palbociclib, palifermin, palonosetron hydrochloride, palonosetron hydrochloride and netupitant, pamidronate disodium, panitumumab, panobinostat, PARA-PLAT® (carboplatin), PARPLATIN® (carboplatin), pazopanib hydrochloride, PCV, pegaspargase, peginterferon alpha-2b, PEG-INTRON® (peginterferon alpha-2b), pembrolizumab, pemetrexed disodium, PERJETA® (pertuzumab), pertuzumab, PLATINOL® (cisplatin), PLATI- NOL-AQ® (cisplatin), plerixafor, pomalidomide, POMALYST® (pomalidomide), ponatinib hydrochloride, PORTRAZZA® (necitumumab), pralatrexate, prednisone, procarbazine hydrochloride, PROLEUKIN® (aldesleukin), PROLIA® (denosumab), PROMACTA (eltrombopag olamine), PROVENGE® (sipuleucel-T), PURINETHOL® (mercaptopurine), PURIXAN® (mercaptopurine), $^{223}$Ra dichloride, raloxifene hydrochloride, ramucirumab, rasburicase, R-CHOP, R-CVP, recombinant human papillomavirus (HPV), recombinant interferon alpha-2b, regorafenib, R-EP-OCH, REVLIMID® (lenalidomide), RHEUMATREX® (methotrexate), RITUXAN® (rituximab), rolapitant hydrochloride, romidepsin, romiplostim, rubidomycin (daunorubicin hydrochloride), ruxolitinib phosphate, SCLEROSOL® intrapleural aerosol (talc), siltuximab, sipuleucel-T, somatuline depot (lanreotide acetate), sonidegib, sorafenib tosylate, SPRYCEL® (dasatinib), STANFORD V, sterile talc powder (talc), STERITALC® (talc), STIVARGA® (regorafenib), sunitinib malate, SUTENT® (sunitinib malate), SYL-ATRON® (peginterferon alpha-2b), SYLVANT® (siltuximab), SYNOVIR® (thalidomide), SYNRIBO® (omacetaxine mepesuccinate), thioguanine, TAC, TAFINLAR® (dabrafenib), TAGRISSO® (osimertinib), talimogene laherparepvec, tamoxifen citrate, tarabine PFS (cytarabine), TARCEVA (erlotinib hydrochloride), TARGRETIN® (bexarotene), TASIGNA® (nilotinib), TAXOL® (paclitaxel), TAXOTERE® (docetaxel), TEMODAR® (temozolomide), temsirolimus, thalidomide, THALOMID® (thalidomide), thioguanine, thiotepa, TOLAK® (topical fluorouracil), topotecan hydrochloride, toremifene, TORI-SEL® (temsirolimus), TOTECT® (dexrazoxane hydrochloride), TPF, trabectedin, trametinib, TREANDA® (bendamustine hydrochloride), trifluridine and tipiracil hydrochloride, TRISENOX® (arsenic trioxide), TYKERB® (lapatinib ditosylate), UNITUXIN® (dinutuximab), uridine triacetate, VAC, vandetanib, VAMP, VARUBI® (rolapitant hydrochloride), vectibix (panitumumab), VeIP, VELBAN® (vinblastine sulfate), VELCADE® (bortezomib), VELSAR (vinblastine sulfate), VEMURAFENIB, VIADUR (leuprolide acetate), VIDAZA (azacitidine), vinblastine sulfate, VINCASAR® PFS (vincristine sulfate), vincristine sulfate, vinorelbine tartrate, VIP, vismodegib, VISTOGARD® (uridine triacetate), VORAXAZE® (glucarpidase), vorinostat, VOTRIENT® (pazopanib hydrochloride), WELLCO-VORIN® (leucovorin calcium), XALKORI® (crizotinib), XELODA® (capecitabine), XELIRI, XELOX, XGEVA® (denosumab), XOFIGO® (mRa dichloride), XTANDI® (enzalutamide), YERVOY® (ipilimumab), YONDELIS® (trabectedin), ZALTRAP® (ziv-aflibercept), ZARXIO® (filgrastim), ZELBORAF® (vemurafenib), ZEVALIN® (ibritumomab tiuxetan), ZINECARD® (dexrazoxane hydrochloride), ziv-aflibercept, ZOFRAN® (ondansetron hydrochloride), ZOLADEX® (gGoserelin acetate), zoledronic acid, ZOLINZA® (vorinostat), ZOMETA® (zoledronic acid), ZYDELIG® (idelalisib), ZYKADIA® (ceritinib), and ZYTIGA (abiraterone acetate).

Using the methods described herein, an antagonistic TNFR2 polypeptide (e.g., a single-chain polypeptide, antibody, antigen-binding fragment thereof, or construct thereof) described herein may be co-administered with (e.g., admixed with) or administered separately from a chemotherapy agent for the treatment of cancer. For example, an antagonistic TNFR2 polypeptide described herein (such as a single-chain polypeptide, antibody, antigen-binding fragment thereof, or construct described herein) may be administered to a patient, such as a human patient suffering from a cancer, simultaneously or at different times. In some embodiments, the antagonistic TNFR2 polypeptide (e.g., a single-chain polypeptide, antibody, antigen-binding fragment thereof, or construct described herein) is administered to the patient prior to administration of a chemotherapy agent to the patient. Alternatively, the antagonistic TNFR2 polypeptide (e.g., a single-chain polypeptide, antibody, antigen-binding fragment thereof, or construct described herein) may be administered to the patient after a chemotherapy agent. For example, the antagonistic TNFR2 polypeptide (e.g., a single-chain polypeptide, antibody, antigen-binding fragment thereof, or construct described herein) may be administered to the patient after a failed chemotherapy treatment. A physician of skill in the art can monitor the efficacy of chemotherapy treatment to determine whether the therapy has successfully ameliorated the pathology being treated (such as a cancer described herein) using methods described herein and known in the art.

For instance, a physician of skill in the art may monitor the quantity of cancer cells in a sample isolated from a patient (e.g., a blood sample or biopsy sample), such as a human patient, for instance, using flow cytometry or FACS analysis. Additionally, or alternatively, a physician of skill in the art can monitor the progression of a cancerous disease in a patient, for instance, by monitoring the size of one or more tumors in the patient, for example, by CT scan, MRI, or X-ray analysis. A physician of skill in the art may monitor the progression of a cancer, such as a cancer described herein, by evaluating the quantity and/or concentration of tumor biomarkers in the patient, such as the quantity and/or concentration of cell surface-bound tumor associated antigens or secreted tumor antigens present in the blood of the patient as an indicator of tumor presence. A finding that the quantity of cancer cells, the size of a tumor, and/or the quantity or concentration of one or more tumor antigens present in the patient or a sample isolated from the patient has not decreased, for instance, by a statistically significant amount following administration of the chemotherapy agent within a specified time period (e.g., from 1 day to 6 months, such as 1 day, 2 days, 3 days, 4 days, 5 days, 6 days, 7 days, 2 weeks, 3 weeks, 4 weeks, 2 months, 3 months, 4 months, 5 months, or 6 months) can indicate that the chemotherapy treatment has failed to ameliorate the cancer. Based on this indication, a physician of skill in the art may administer an antagonistic TNFR2 polypeptide described herein, such as a single-chain polypeptide, antibody, antigen-binding fragment thereof, or construct described herein.

Additionally, or alternatively, an antagonistic TNFR2 polypeptide (e.g., a single-chain polypeptide, antibody, antigen-binding fragment thereof, or construct thereof) described herein may be administered simultaneously with, or administered separately from, radiation therapy. For instance, a physician of skill in the art may administer radiation therapy to a patient, such as a human patient suffering from a cancer described herein, by treating the patient with external and/or internal electromagnetic radiation. The energy delivered by such radiation, which is typically in the form of X-rays, gamma rays, and similar forms of low-wavelength energy, can cause oxidative damage to the DNA of cancer cells, thereby leading to cell death, for instance, by apoptosis. External radiation therapy can be administered, for instance, using machinery such as a radiation beam to expose the patient to a controlled pulse of electromagnetic radiation. Additionally, or alternatively, the patient may be administered internal radiation, for instance, by administering to the patient a therapeutic agent that contains a radioactive substituent, such as agents that contain $^{223}$Ra or $^{131}$I, which emit high-energy alpha and beta particles, respectively. Exemplary therapeutic agents that may be conjugated to a radiolabel include, for example, small molecule chemotherapeutics, antibodies, and antigen-binding fragments thereof, among others. For instance, an antagonistic TNFR2 polypeptide (e.g., a single-chain polypeptide, antibody, antigen-binding fragment thereof, or construct thereof) described herein may be conjugated to a radioactive substituent or a moiety that ligate such a substituent, for example, using bond-forming techniques known in the art or described herein. Such conjugates can be administered to the subject in order to deliver a therapeutic dosage of radiation therapy and a TNFR2 antagonist described herein in a simultaneous administration (see, for example, "Antagonistic TNFR2 polypeptide conjugates," above).

In some embodiments, the antagonistic TNFR2 polypeptide (e.g., a single-chain polypeptide, antibody, antigen-binding fragment thereof, or construct described herein) is administered to the patient after failed radiation treatment. A physician of skill in the art can monitor the efficacy of radiation treatment to determine whether the therapy has successfully ameliorated the pathology being treated (such as a cancer described herein) using, e.g., methods described herein. For instance, a physician of skill in the art may monitor the quantity of cancer cells in a sample isolated from a patient (e.g., a blood sample or biopsy sample), such as a human patient, for instance, using flow cytometry or FACS analysis. Additionally, or alternatively, a physician of skill in the art can monitor the progression of a cancerous disease in a patient, for instance, by monitoring the size of one or more tumors in the patient, for example, by CT scan, MRI, or X-ray analysis. A physician of skill in the art may monitor the progression of a cancer, such as a cancer described herein, by evaluating the quantity and/or concentration of tumor biomarkers in the patient, such as the quantity and/or concentration of cell surface-bound tumor associated antigens or secreted tumor antigens present in the blood of the patient as an indicator of tumor presence. A finding that the quantity of cancer cells, the size of a tumor, and/or the quantity or concentration of one or more tumor antigens present in the patient or a sample isolated from the patient has not decreased, for instance, by a statistically significant amount following administration of the radiation therapy within a specified time period (e.g., from 1 day to 6 months, such as 1 day, 2 days, 3 days, 4 days, 5 days, 6 days, 7 days, 2 weeks, 3 weeks, 4 weeks, 2 months, 3 months, 4 months, 5 months, or 6 months) can indicate that the radiation treatment has failed to ameliorate the cancer. Based on this indication, a physician of skill in the art may administer an antagonistic TNFR2 polypeptide described herein, such as a single-chain polypeptide, antibody, antigen-binding fragment thereof, or construct described herein.

In some embodiments, a physician of skill in the art may administer to a patient suffering from cancer a chemotherapeutic agent, radiation therapy, and a TNFR2 antagonist described herein (such as a single-chain polypeptide, antibody, antigen-binding fragment thereof, or construct described herein). The TNFR2 antagonist described herein, chemotherapeutic agent, and radiation therapy may be administered to the patient simultaneously (for instance, in a single pharmaceutical composition or as multiple compositions administered to the patient at the same time) or at different times. In some embodiments, the TNFR2 antagonist (such as an antibody, antigen-binding fragment thereof, single-chain polypeptide, or construct described herein) is administered to the patient first, and the chemotherapeutic agent and radiation therapy follow. Alternatively, the TNFR2 antagonist (such as a single-chain polypeptide, antibody, antigen-binding fragment thereof, or construct described herein) may be administered to the patient following chemotherapy and radiation treatment. For example, the antagonistic TNFR2 polypeptide (e.g., a single-chain polypeptide, antibody, antigen-binding fragment thereof, or construct described herein) may be administered to the patient after failed chemotherapy and/or radiation treatment.

A physician of skill in the art can monitor the efficacy of chemotherapy and radiation treatment to determine whether the therapy has successfully ameliorated the pathology being treated (such as a cancer described herein) using methods described herein, such as the methods described above. For instance, a physician of skill in the art may monitor the quantity of cancer cells in a sample isolated from a patient (e.g., a blood sample or biopsy sample), such as a human patient, for instance, using flow cytometry or FACS analysis. Additionally, or alternatively, a physician of skill in the art can monitor the progression of a cancerous disease in a patient, for instance, by monitoring the size of one or more tumors in the patient, for example, by CT scan, MRI, or X-ray analysis. A physician of skill in the art may monitor the progression of a cancer, such as a cancer described herein, by evaluating the quantity and/or concentration of tumor biomarkers in the patient, such as the quantity and/or concentration of cell surface-bound tumor associated antigens or secreted tumor antigens present in the blood of the patient as an indicator of tumor presence and even measure serum soluble TNFR2. One skilled in the art would expect a decrease in the number of activated T-regs, and increase in the numbers of T effectors and a decrease in the total number of cancer cells. Because of the specificity of these TNFR2 antibodies for cancer, the clinical monitoring would be expected to be most dramatic in the tumor microenvironment. A finding that the quantity of cancer cells, the size of a tumor, and/or the quantity or concentration of one or more tumor antigens present in the patient or a sample isolated from the patient has not decreased, for instance, by a statistically significant amount following administration of the chemotherapy agent and radiation within a specified time period (e.g., from 1 day to 6 months, such as 1 day, 2 days, 3 days, 4 days, 5 days, 6 days, 7 days, 2 weeks, 3 weeks, 4 weeks, 2 months, 3 months, 4 months, 5 months, or 6 months) can indicate that the chemotherapy and radiation treatment has failed to ameliorate the cancer. Based on this indication, a physician of skill in the art may administer an antagonistic TNFR2 polypeptide described herein, such as a single-chain polypeptide, antibody, antigen-binding fragment thereof, or construct described herein.

Blood-Brain Barrier Penetration

In certain embodiments, antagonistic TNFR2 polypeptides (e.g., single-chain polypeptides, antibodies, antigen-binding fragments thereof, and constructs thereof) described herein can be formulated to ensure proper distribution in vivo. For example, the blood-brain barrier (BBB) excludes many highly hydrophilic compounds. To ensure that the therapeutic compositions described herein cross the BBB (if desired), they can be formulated, for example, in liposomes. Methods of manufacturing liposomes have been described, e.g., U.S. Pat. Nos. 4,522,811; 5,374,548; and 5,399,331. The liposomes may comprise one or more moieties that are selectively transported into specific cells or organs, thereby enhancing targeted drug delivery (see, e.g., V. V. Ranade (*J. Clin. Pharmacol.* 29:685, 1989)). Exemplary targeting moieties include, e.g., folate or biotin (see, e.g., U.S. Pat. No. 5,416,016); mannosides (Umezawa et al. (Biochem. Biophys. Res. Commun. 153:1038, 1988)); antibodies (P. G.

Bloeman et al. (FEBS Lett. 357:140, 1995); M. Owais et al. (Antimicrob. Agents Chemother. 39:180, 1995)); surfactant protein A receptor (Briscoe et al. (Am. J. Physiol. 1233:134, 1995)); the disclosures of each of which are incorporated herein by reference.

Routes of Administration and Dosing

Antagonistic TNFR2 polypeptides (e.g., single-chain polypeptides, antibodies, antigen-binding fragments thereof, and constructs thereof) described herein (e.g., any one or more of antibodies 1-25 described in Table 1 and variants thereof, such as an antibody or antigen-binding fragment containing one or more, or all, of the CDRs set forth in Table 1) can be administered to a mammalian subject (e.g., a human) by a variety of routes such as orally, transdermally, subcutaneously, intranasally, intravenously, intramuscularly, intraocularly, intratumorally, parenterally, topically, intrathecally and intracerebroventricularly. The most suitable route for administration in any given case will depend on the particular polypeptide administered, the patient, pharmaceutical formulation methods, administration methods (e.g., administration time and administration route), the patient's age, body weight, sex, severity of the diseases being treated, the patient's diet, and the patient's excretion rate.

The effective dose of an antagonistic TNFR2 polypeptide described herein can range, for instance, from about 0.0001 to about 100 mg/kg of body weight per single (e.g., bolus) administration, multiple administrations or continuous administration (e.g., a continuous infusion), or to achieve a serum concentration of 0.0001-5000 µg/mL serum concentration per single (e.g., bolus) administration, multiple administrations or continuous administration (e.g., continuous infusion), or any effective range or value therein depending on the condition being treated, the route of administration and the age, weight, and condition of the subject. In certain embodiments, e.g., for the treatment of cancer, each dose can range from about 0.0001 mg to about 500 mg/kg of body weight. For instance, a pharmaceutical composition described herein may be administered in a daily dose in the range of 0.001-100 mg/kg (body weight). The dose may be administered one or more times (e.g., 2-10 times) per day, week, month, or year to a mammalian subject (e.g., a human) in need thereof.

Antagonistic TNFR2 polypeptides described herein (e.g., single-chain polypeptides, antibodies, antigen-binding fragments thereof, and constructs thereof) can be administered to a patient by way of a continuous intravenous infusion or as a single bolus administration. The antagonistic TNFR2 polypeptides described herein (e.g., e.g., single-chain polypeptides, antibodies, antigen-binding fragments thereof, and constructs thereof) may be administered to a patient in an amount of, for example, from 0.01 µg to about 5 g in a volume of, for example, from 10 µL to 10 mL. The antagonistic TNFR2 polypeptides may be administered to a patient over the course of several minutes to several hours. For example, the antagonistic TNFR2 polypeptides described herein may be administered to a patient over the course of from 5 minutes to 5 hours, such as over the course of 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 80 minutes, 90 minutes, 95 minutes, 100 minutes, 105 minutes, 110 minutes, 115 minutes, 120 minutes, 125 minutes, 130 minutes, 135 minutes, 140 minutes, 145 minutes, 150 minutes, 155 minutes, 160 minutes, 165 minutes, 170 minutes, 175 minutes, 180 minutes, 185 minutes, 190 minutes, 195 minutes, 200 minutes, 205 minutes, 210 minutes, 215 minutes, 220 minutes, 225 minutes, 230 minutes, 235 minutes, 240 minutes, 245 minutes, 250 minutes, 255 minutes, 260 minutes, 265 minutes, 270 minutes, 275 minutes, 280 minutes, 285 minutes, 290 minutes, 295 minutes, or 300 minutes, or more.

Antagonistic TNFR2 polypeptides (e.g., single-chain polypeptides, antibodies, antigen-binding fragments thereof, and constructs thereof) described herein may be administered in combination with an immunotherapy agent, such as an anti-PD-1 antibody or antigen-binding fragment thereof, an anti-PD-L1 antibody or antigen-binding fragment thereof, and/or an anti-CTLA-4 antibody or antigen-binding fragment thereof. Exemplary anti-PD-1 antibodies include nivolumab, pembrolizumab, avelumab, durvalumab, and atezolizumab. Exemplary anti-CTLA4 antibodies include ipilimumab and tremelimumab. Exemplary anti-PD-L1 antibodies include atezolizumab and avelumab.

When an anti-PD-1 antibody or antigen-binding fragment thereof is administered to a patient (e.g., a patient having cancer or an infectious disease described herein) in combination with an antagonist TNFR2 polypeptide, the anti-PD-1 antibody may be administered to the patient by way of a single bolus administration or continuous intravenous infusion. For example, pembrolizumab may be administered to a human patient by way of a continuous intravenous infusion of 200 mg over the course of 30 minutes, for instance, every three weeks, as needed (KEYTRUDA® (pembrolizumab) [package insert]. Merck Sharp & Dohme Corp., Whitehouse Station, NJ, the disclosure of which is incorporated herein by reference in its entirety). In another example, nivolumab may be administered to a patient by way of a continuous intravenous infusion of 240 mg over the course of 30 minutes, for instance, every two weeks as needed. Alternatively, nivolumab may be administered to a patient by way of a continuous intravenous infusion of 480 mg over the course of 30 minutes, for instance, every four weeks as needed (OPDIVO® (nivolumab) [package insert]. Bristol-Myers Squibb Company, Princeton, NJ, the disclosure of which is incorporated herein by reference in its entirety).

When an anti-CTLA-4 antibody or antigen-binding fragment thereof is administered to a patient (e.g., a patient having cancer or an infectious disease described herein) in combination with an antagonist TNFR2 polypeptide, the anti-CTLA-4 antibody may be administered to the patient by way of a single bolus administration or continuous intravenous infusion. For example, ipilimumab may be administered to a human patient by way of a continuous intravenous infusion of 3 mg/kg over the course of 90 minutes, for instance, every three weeks, as needed, or by way of a continuous intravenous infusion of 10 mg/kg over the course of 90 minutes every three weeks for four doses, followed by 10 mg/kg over the course of 90 minutes every 12 weeks for up to 3 years (YERVOY® (ipilimumab) [package insert]. Bristol-Myers Squibb Company, Princeton, NJ, the disclosure of which is incorporated herein by reference in its entirety).

When TNFR2 antagonist polypeptides (e.g., single-chain polypeptides, antibodies, antigen-binding fragments thereof, and constructs thereof) are administered to a patient in combination with an immunotherapy agent, such as an anti-PD-1 antibody or anti-CTLA-4 antibody, the antagonist TNFR2 polypeptide and the immunotherapy agent may be co-administered to the patient, for example, by way of a continuous intravenous infusion or bolus administration of the first agent, followed by a continuous intravenous infusion or bolus administration of the second agent. The administration of the two agents may occur concurrently. Alternatively, the administration of the antagonist TNFR2 antibody or antigen-binding fragment thereof may precede or follow the administration of the immunotherapy agent. In some embodiments, administration of the second agent (e.g., the antagonist TNFR2 polypeptide) commences within from about 5 minutes to about 4 weeks, or more, of the end of the administration of the first agent (e.g., the immunotherapy agent). For example, administration of the second agent may commence within about 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, or more, of the end of the administration of the first agent.

Therapeutic compositions can be administered with medical devices known in the art. For example, in an embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in conjunction with the compositions and methods described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

Kits Containing Antagonistic Anti-TNFR2 Polypeptides

Also included herein are kits that contain antagonistic TNFR2 polypeptides (e.g., single-chain polypeptides, antibodies, antigen-binding fragments thereof, and constructs thereof, such as any one or more of antibodies 1-25 described in Table 1 and variants thereof, such as an antibody or antigen-binding fragment containing one or more, or all, of the CDRs set forth in Table 1). The kits provided herein may contain any of the antagonistic TNFR2 polypeptides described above, as well as any of the polynucleotides encoding these polypeptides, vectors containing these polynucleotides, or cells engineered to express and secrete antibodies described herein (e.g., prokaryotic or eukaryotic cells).

Exemplary compositions of the disclosure that can be incorporated into a kit described herein include antagonistic TNFR2 polypeptides, such as those with at least two TNFR2 binding sites in which the binding sites are spatially separated from one another by about 133 Å or more, as well as those having a human IgG2 isotype, for example, a human IgG2-A isotype (e.g., antagonistic TNFR2 antibodies, antigen-binding fragments thereof, and constructs thereof having a human IgG2 hinge region having a C232S and/or C233S amino acid substitution). Compositions of the disclosure that can be incorporated into kits described herein also include pharmaceutical compositions containing antagonistic TNFR2 polypeptides that adopt a single disulfide-bonded isoform, such as those in which, e.g., 10%, 20%, 30%, 40%, 50%, 60%, 70%, 80%, 90%, 95%, 96%, 97%, 98%, 99%, 99.9%, 99.99%, or more, of the polypeptide in the pharmaceutical composition is present in a single disulfide-bonded isoform.

A kit described herein may include reagents that can be used to produce the compositions described herein (e.g., antagonistic TNFR2 polypeptides, such as single-chain polypeptides, antibodies, constructs, conjugates containing antagonistic TNFR2 polypeptides, polynucleotides encoding antagonistic anti-TNFR2 polypeptides, vectors containing these polynucleotides). Optionally, kits described herein may include reagents that can induce the expression of antagonistic TNFR2 polypeptides within cells (e.g., mammalian cells), such as doxycycline or tetracycline. In other cases, a kit described herein may contain a compound capable of binding and detecting a fusion protein that contains an antagonistic TNFR2 antibody and an epitope tag. For instance, in such cases a kit described herein may contain maltose, glutathione, a nickel-containing complex, an anti-FLAG antibody, an anti-myc antibody, an anti-HA antibody, biotin, or streptavidin.

Kits described herein may also include reagents that are capable of detecting an antagonistic TNFR2 polypeptide (e.g., single-chain polypeptide, antibody, fragment thereof, or construct thereof) directly. Examples of such reagents include secondary antibodies that selectively recognize and bind particular structural features within the Fc region of an anti-TNFR2 antibody described herein. Kits described herein may contain secondary antibodies that recognize the Fc region of an antagonistic TNFR2 antibody and that are conjugated to a fluorescent molecule. These antibody-fluorophore conjugates provide a tool for analyzing the localization of antagonistic anti-TNFR2 antibodies, e.g., in a particular tissue or cultured mammalian cell using established immunofluorescence techniques. In some embodiments, kits described herein may include additional fluorescent compounds that exhibit known sub-cellular localization patterns. These reagents can be used in combination with another antibody-fluorophore conjugate, e.g., one that specifically recognizes a different receptor on the cell surface in order to analyze the localization of an anti-TNFR2 antibody relative to other cell-surface proteins.

Kits described herein may also contain a reagent that can be used for the analysis of a patient's response to treatment by administration of antagonistic TNFR2 polypeptides (e.g., single-chain polypeptides, antibodies, antigen-binding fragments thereof, and constructs thereof) described herein. For instance, kits described herein may include an antagonistic TNFR2 antibody and one or more reagents that can be used to determine the quantity of T-reg cells in a blood sample withdrawn from a subject (e.g., a human) that is undergoing treatment with an antibody described herein. Such a kit may contain, e.g., antibodies that selectively bind cell-surface antigens presented by T-reg cells, such as CD4 and CD25. Optionally, these antibodies may be labeled with a fluorescent dye, such as fluorescein or tetramethylrhodamine, in order to facilitate analysis of T-reg cells by fluorescence-activated cell sorting (FACS) methods known in the art. Kits described herein may optionally contain one or more reagents that can be used to quantify tumor-reactive T lymphocytes in order to determine the effectiveness of an antagonistic TNFR2 polypeptide described herein in restoring tumor-infiltrating lymphocyte proliferation. For instance, kits described herein may contain an antibody that selectively binds cell-surface markers on the surface of a cytotoxic T cell, such as CD8 or CD3. Optionally, these antibodies may be labeled with fluorescent molecules so as to enable quantitation by FACS analysis.

A kit described herein may also contain one or more reagents useful for determining the affinity and selectivity of an antagonistic TNFR2 polypeptide described herein for one or more peptides derived from TNFR2 (e.g., a peptide containing the sequence of any one of SEQ ID NOs: 11, 19, 20, and 34-117). For instance, a kit may contain an antagonistic TNFR2 polypeptide and one or more reagents that can be used in an ELISA assay to determine the $K_D$ of an antibody described herein for one or more peptides that present a TNFR2 epitope in a conformation similar to that of the epitope in the native protein. A kit may contain, e.g., a microtiter plate containing wells that have been previously conjugated to avidin, and may contain a library of TNFR2-derived peptides, each of which conjugated to a biotin moiety. Such a kit may optionally contain a secondary antibody that specifically binds to the Fc region of an antagonistic TNFR2 antibody described herein, and the secondary antibody may be conjugated to an enzyme (e.g., horseradish peroxidase) that catalyzes a chemical reaction that results in the emission of luminescent light.

Kits described herein may also contain antagonistic TNFR2 polypeptides described herein and reagents that can be conjugated to such an antibody, including those previously described (e.g., a cytotoxic agent, a fluorescent molecule, a bioluminescent molecule, a molecule containing a radioactive isotope, a molecule containing a chelating group bound to a paramagnetic ion, etc). These kits may additionally contain instructions for how the conjugation of an antagonistic TNFR2 antibody described herein to a second molecule, such as those described above, can be achieved.

A kit described herein may also contain a vector containing a polynucleotide that encodes an antagonistic TNFR2 polypeptide, such as any of the vectors described herein. Alternatively, a kit may include mammalian cells (e.g., CHO cells) that have been genetically altered to express and secrete antagonistic TNFR2 antibodies or fragments thereof from the nuclear genome of the cell. Such a kit may also contain instructions describing how expression of the antagonistic TNFR2 antibody or fragment thereof from a polynucleotide can be induced, and may additionally include reagents (such as, e.g., doxycycline or tetracycline) that can be used to promote the transcription of these polynucleotides. Such kits may be useful for the manufacture of antagonistic TNFR2 antibodies or antigen-binding fragments thereof described herein.

Other kits described herein may include tools for engineering a prokaryotic or eukaryotic cell (e.g., a CHO cell or a BL21(DE3) E. coli cell) so as to express and secrete an antagonistic TNFR2 polypeptide described herein from the nuclear genome of the cell. For example, a kit may contain CHO cells stored in an appropriate media and optionally frozen according to methods known in the art. The kit may also provide a vector containing a polynucleotide that encodes a nuclease (e.g., such as the CRISPER/Cas, zinc finger nuclease, TALEN, ARCUS™ nucleases described herein) as well as reagents for expressing the nuclease in the cell. The kit can additionally provide tools for modifying the polynucleotide that encodes the nuclease so as to enable one to alter the DNA sequence of the nuclease in order to direct the cleavage of a specific target DNA sequence of interest. Examples of such tools include primers for the amplification and site-directed mutagenesis of the polynucleotide encoding the nuclease of interest. The kit may also include restriction enzymes that can be used to selectively excise the nuclease-encoding polynucleotide from the vector and subsequently re-introduce the modified polynucleotide back into the vector once the user has modified the gene. Such a kit may also include a DNA ligase that can be used to catalyze the formation of covalent phosphodiester linkages between the modified nuclease-encoding polynucleotide and the target vector. A kit described herein may also provide a polynucleotide encoding an antagonistic TNFR2 polypeptide, as well as a package insert describing the methods one can use to selectively cleave a particular DNA sequence in the genome of the cell in order to incorporate the polynucleotide encoding an antagonistic TNFR2 antibody into the genome at this site. Optionally, the kit may provide a polynucleotide encoding a fusion protein that contains an antagonistic TNFR2 antibody or fragment thereof and an additional polypeptide, such as, e.g., those described herein.

EXAMPLES

The following examples are put forth so as to provide those of ordinary skill in the art with a description of how the compositions and methods claimed herein are performed, made, and evaluated, and are intended to be purely exemplary described herein and are not intended to limit the scope of what the inventor regards as her invention.

Example 1. Mapping the Discrete Epitopes within TNFR2 that are Bound by Antagonistic TNFR2 Polypeptides Libraries of linear, cyclic, and bicyclic peptides derived from human TNFR2 were screened for distinct sequences within the protein that exhibit high affinity for TNFR2 antibody TNFRAB4. In order to screen conformational epitopes within TFNR2, peptides from distinct regions of the primary protein sequence were conjugated to one another to form chimeric peptides. These peptides contained cysteine residues at strategic positions within their primary sequences. This facilitated an intramolecular cross-linking strategy that was used to constrain individual peptides to a one of a wide array of three-dimensional conformations. Unprotected thiols of cysteine residues were cross-linked via nucleophilic substitution reactions with divalent and trivalent electrophiles, such as 2,6-bis(bromomethyl)pyridine and 1,3,5-tris(bromomethyl)benzene, so as to form conformationally restricted cyclic and bicyclic peptides, respectively. In this way, peptides containing unique combinations of amino acids from disparate regions of the TNFR2 primary sequence were constrained so as to structurally pre-organize epitopes that may resemble those presented in the native TNFR2 tertiary structure. Libraries containing these peptides were screened by immobilizing peptides to distinct regions of a solid surface and treating the surface in turn with an antagonistic TNFR2 antibody, such as TNFRAB1, TNFRAB2, TNFRAB3, TNFRAB4, or TNFRAB5, followed by a secondary antibody conjugated to horseradish peroxidase (HRP), and HRP substrate (2,2'-azino-di-3-ethylbenzthiazoline sulfonate) in the presence of hydrogen peroxide. The solid surface was washed in between treatment with successive reagents so as to remove excess or non-specifically bound materials. The luminescence of each region of each surface was subsequently analyzed using a charge coupled device (CCD)—camera and an image processing system.

The "Constrained Libraries of Peptides on Surfaces" (CLIPS) platform starts with the conversion of the target protein, e.g., TNFR2, into a library of up to 10,000 overlapping peptide constructs, using a combinatorial matrix design (Timmerman et al., J. Mol. Recognit., 20: 283-29, 2007). On a solid carrier, a matrix of linear peptides is synthesized, which are subsequently shaped into spatially defined CLIPS constructs. Constructs representing multiple parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail. The raw luminescence data obtained from these ELISA experiments informed the analysis of epitopes present on the surface of TNFR2 that bind antagonistic TNFR2 antibodies.

Peptide Synthesis

To reconstruct epitopes of the target molecule a library of peptides was synthesized. An amino functionalized polypropylene support was obtained by grafting a proprietary hydrophilic polymer formulation via reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS® liquid handling stations (Perkin Elmer). CLIPS technology allows one to structure peptides into single loops, double-loops, triple loops, sheet-like folds, helix-like folds and combinations thereof. CLIPS templates are coupled to cysteine residues. The side-chains of multiple cysteines in the peptides are coupled to one or two CLIPS templates. For example, a 0.5 mM solution of the CLIPS template (2,6-bis(bromomethyl)pyridine) is dissolved in ammonium bicarbonate (20 mM, pH 7.8)/acetonitrile (1:3 (v/v)). This solution is added to a surface-bound peptide array. The CLIPS template will react with side-chains of two cysteines as present in the solid-phase bound peptides of the peptide-arrays (455 wells plate with 3 μl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes.

Analysis of Binding Affinities of Antagonistic TNFR2 Antibodies by Surface Plasmon Resonance The affinities of antagonistic TNFR2 antibodies for recombinant human TNFR2 were measured using BIACORE™ Analysis Services (Precision Antibody). Briefly, the antibody was biotinylated at a 5:1 stoichiometric ratio using biotinyl-LC-LC-NOSE (Thermo-Fisher) in PBS. Excess biotinylation reagent was removed by centrifugation chromatography and the biotinylated antibody was captured on 3000 RU of streptavidin surface to a level of 100 RU. Theoretical maximum of signal with TNFR2 with that level of antibody capture was 26 RU and that signal was reached with a preliminary experiment using 500 nM TNFR2 in the running buffer. Analysis of the kinetics of antigen binding was performed at a flow of 60 μL/min with 2 min injections. Antibodies were injected at a concentration of 1 mg/ml to the final capture of 100 RU. The instrument used was BIACORE™ 3000 with the BioCap chip (GE Healthcare). Double reference method was used for analysis. Reference channel contained the identical level of streptavidin.

ELISA Screening

The binding of antibody to each of the synthesized peptides was tested in an ELISA format. Surface-immobilized peptide arrays were incubated with primary antibody solution (overnight at 4° C.). After washing, the peptide arrays were incubated with a ¹⁄₁₀₀₀ dilution of an appropriate antibody peroxidase conjugate (SBA) for one hour at 25° C. After washing, the peroxidase substrate 2,2'-azino-di-3-eth-ylbenzthiazoline sulfonate (ABTS) and 2 µl/ml of 3 percent H₂O₂ were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader. The results are quantified and stored into the Peplab database. Occasionally a well contains an air-bubble resulting in a false-positive value, the cards are manually inspected and any values caused by an air-bubble are scored as 0.

To verify the quality of the synthesized peptides, a separate set of positive and negative control peptides was synthesized in parallel. These were screened with a negative control, antibody 57.9, which does not specifically bind TNFR2 (Posthumus et al. (J. Virology. 64:3304-3309, 1990)).

Epitope Mapping

ELISA was also used to determine linear epitopes present on the extracellular surface of TNFR2. Linear peptides corresponding to various regions within the TNFR2 primary sequence were purchased from GenScript (Piscataway, NJ), diluted in coating buffer and placed on Immulon 4HBX Flat Bottom Microtiter Plates (Thermo Scientific) at a concentration of 1 pg/well. Primary TNFR2 antagonistic antibodies (0.1 µg/well) were incubated with substrates. Secondary antibodies against rodent IgG were used to detect the primary antibodies. Absorbance was measured using the SPECTRAMAX® 190 Absorbance Plate Reader and analyzed with SoftMax Pro 6.3 (Molecular Devices).

Results of the epitope mapping analysis are shown in FIG. 1, which displays the primary structure of human TNFR2 highlighting the regions that are bound by exemplary antagonistic TNFR2 antibodies TNFRAB1, TNFRAB2, TNFRAB3, TNFRAB4, and TNFRAB5.

Example 2. Antagonistic TNFR2 Polypeptides of the Human IgG2-A Isoform Optimally Kill T-Reg Cells, Expand T Effector Cells, and Deplete TNFR2+ Cancer Cells Chimeric variants of monoclonal antibody TNFRAB2 containing the variable domain of TNFRAB2 and the constant domain of various human IgG antibody isotypes were manufactured. TNFRAB2 is a murine antibody having an IgG2 isotype, and is a dominant TNFR2 antagonist. The TNFR2-binding properties of TNFRAB2 are described above. TNFRAB2 contains the following CDRs:

```
TNFRAB2 CDR-H1:
                        (SEQ ID NO: 274)
GYTFTDYL

TNFRAB2 CDR-H2:
                        (SEQ ID NO: 258)
VDPEYGST

TNFRAB2 CDR-H3:
                        (SEQ ID NO: 259)
ARDDGSYSPFDYWG
```

```
-continued

TNFRAB2 CDR-L1:
                        (SEQ ID NO: 260)
QNINKY

TNFRAB2 CDR-L2:
TYS

TNFRAB2 CDR-L3:
                        (SEQ ID NO: 272)
CLQYVNLLT
```

The chimeric antibodies were generated using one of three different human IgG constant domain subtypes: IgG1, IgG2, and IgG3. To investigate the effects of the chimeric antibodies, nucleic acids encoding these antibodies were generated using molecular biology techniques, such as those described herein, and the encoded antibodies were subsequently expressed from host cells prior to evaluation in vitro.

Figure 3:
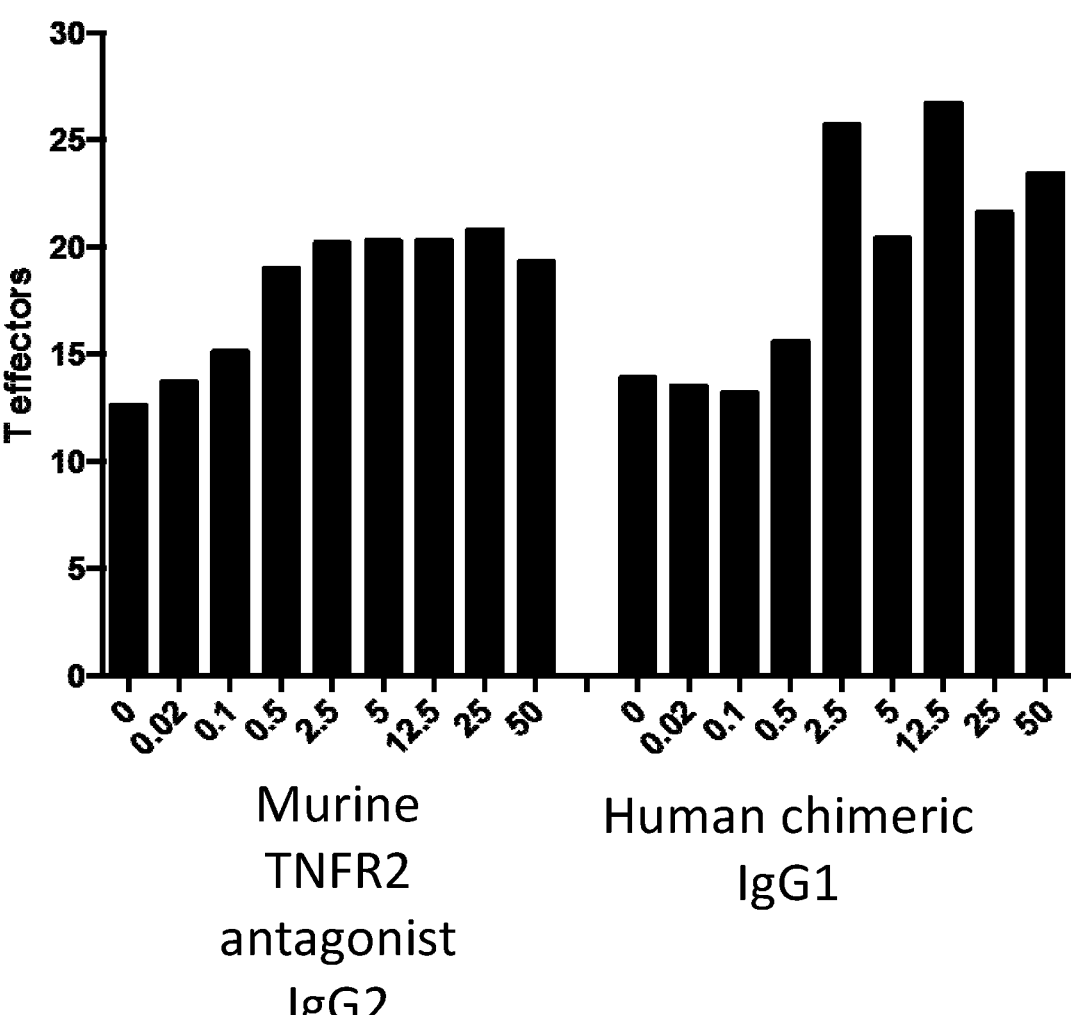
FIG. 3 is a graph contrasting the effects of murine monoclonal TNFR2 antagonist antibody TNFRAB2 on the quantity of effector T cells in an in vitro sample (left) with the effects of a human chimeric version of TNFRAB2 on the quantity of effector T cells in an in vitro sample under the same assay conditions (right). The human chimeric TNFR2 antagonist antibody is the same one described in FIG. 2. Values along the x-axis represent antibody concentration in units of pg/ml. Values along the y-axis represent the percentage of T effector cells present in an in vitro cell sample after the sample is incubated with the indicated concentration of TNFR2 antibody.
Figure 4:
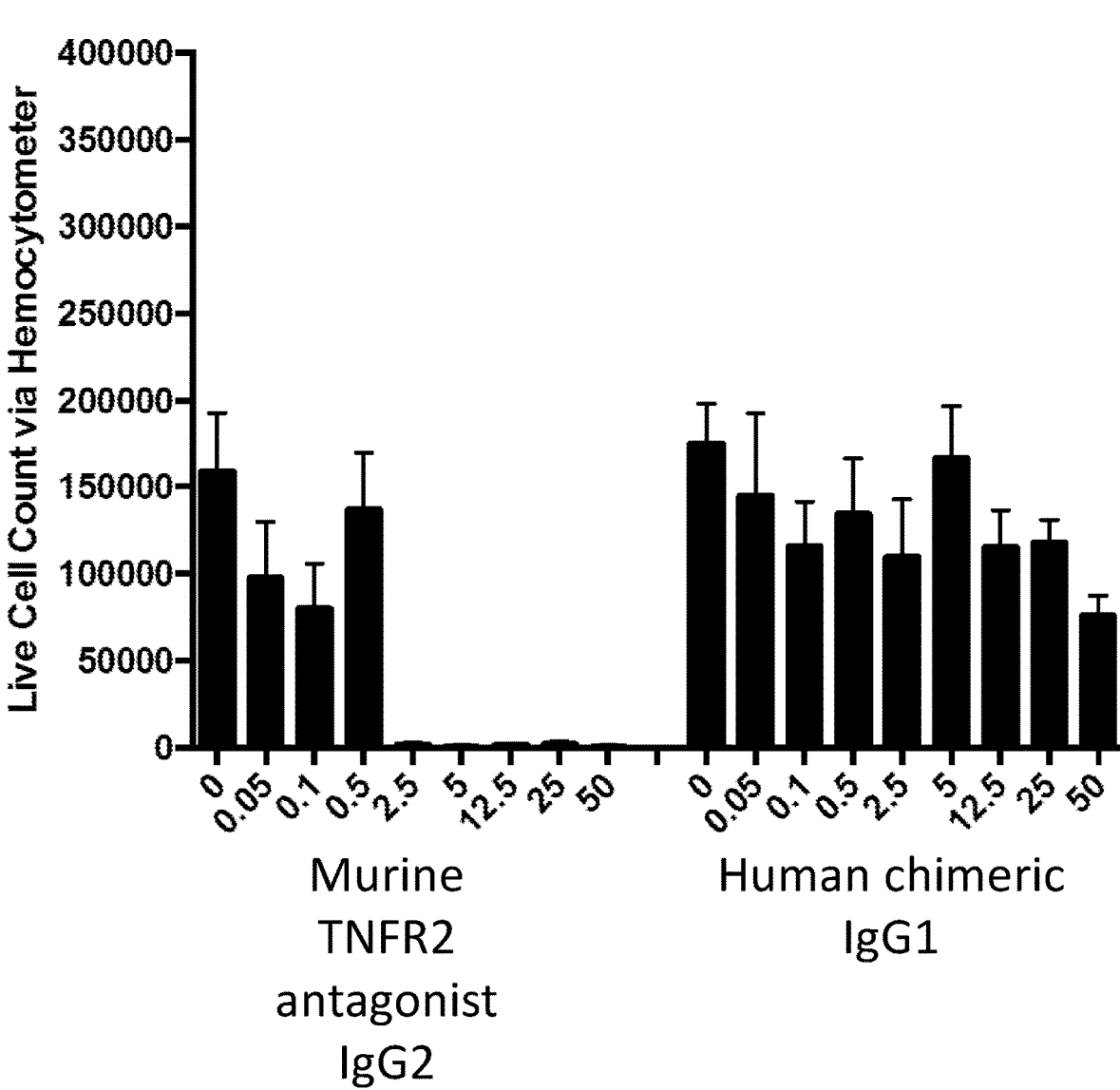
FIG. 4 is a graph contrasting the effects of murine monoclonal TNFR2 antagonist antibody TNFRAB2 on the quantity of TNFR2+SW480 colon cancer cells in an in vitro sample (left) with the effects of a human chimeric version of TNFRAB2 on the quantity of TNFR2+SW480 colon cancer cells in an in vitro sample under the same assay conditions (right). The human chimeric TNFR2 antagonist antibody is the same one described in FIG. 2. Values along the x-axis represent antibody concentration in units of pg/ml. Values along the y-axis represent the quantity of TNFR2+SW480 colon cancer cells present in an in vitro cell sample after the sample is incubated with the indicated concentration of TNFR2 antibody.
Figure 5:
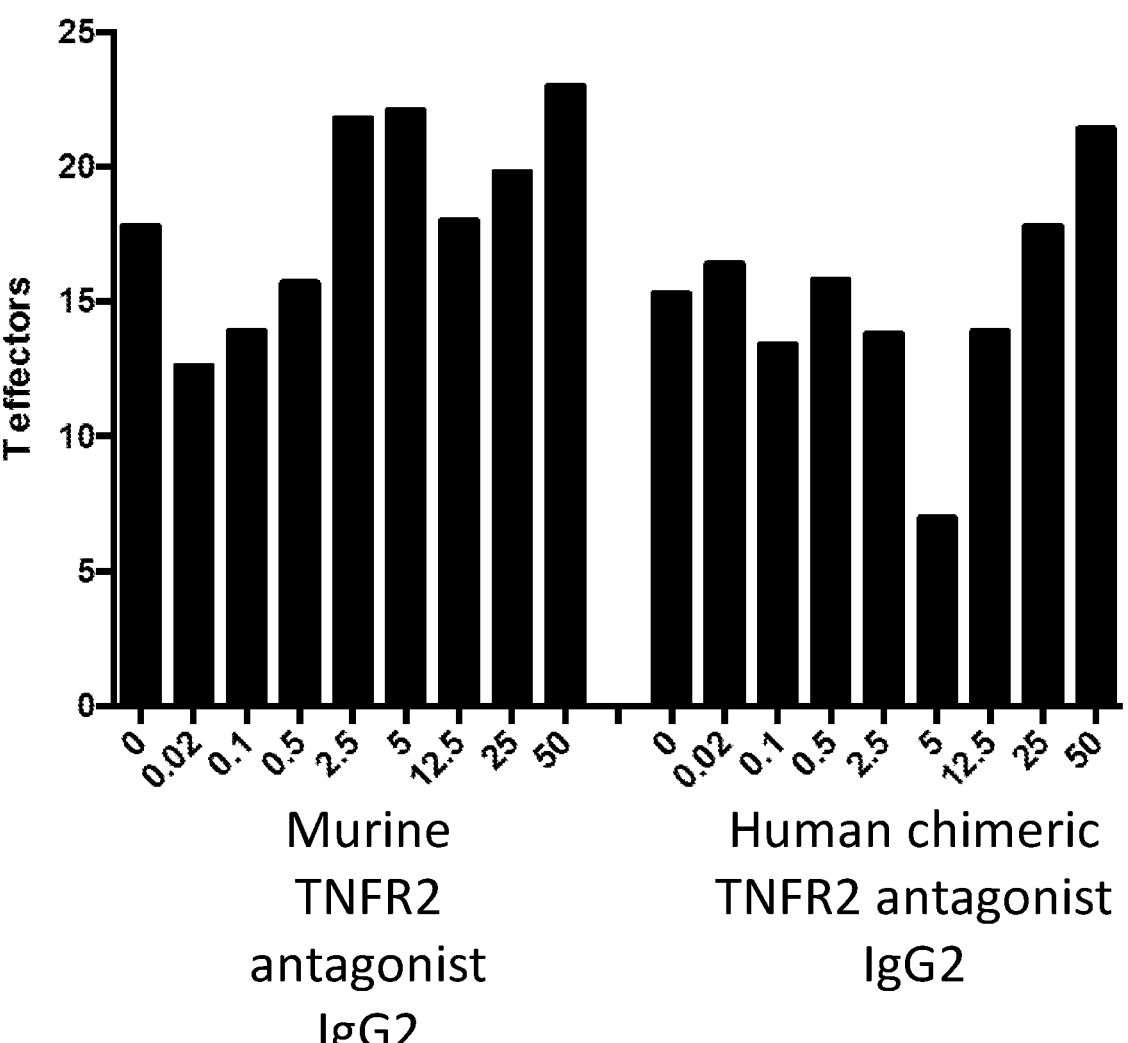
FIG. 5 is a graph contrasting the effects of murine monoclonal TNFR2 antagonist antibody TNFRAB2 on the quantity of effector T cells in an in vitro sample (left) with the effects of a human chimeric version of TNFRAB2 on the quantity of effector T cells in an in vitro sample under the same assay conditions (right). The human chimeric TNFR2 antagonist antibody is the same one described in FIG. 2. Values along the x-axis represent antibody concentration in units of pg/ml. Values along the y-axis represent the percentage of T effector cells present in an in vitro cell sample after the sample is incubated with the indicated concentration of TNFR2 antibody.
Figure 6:
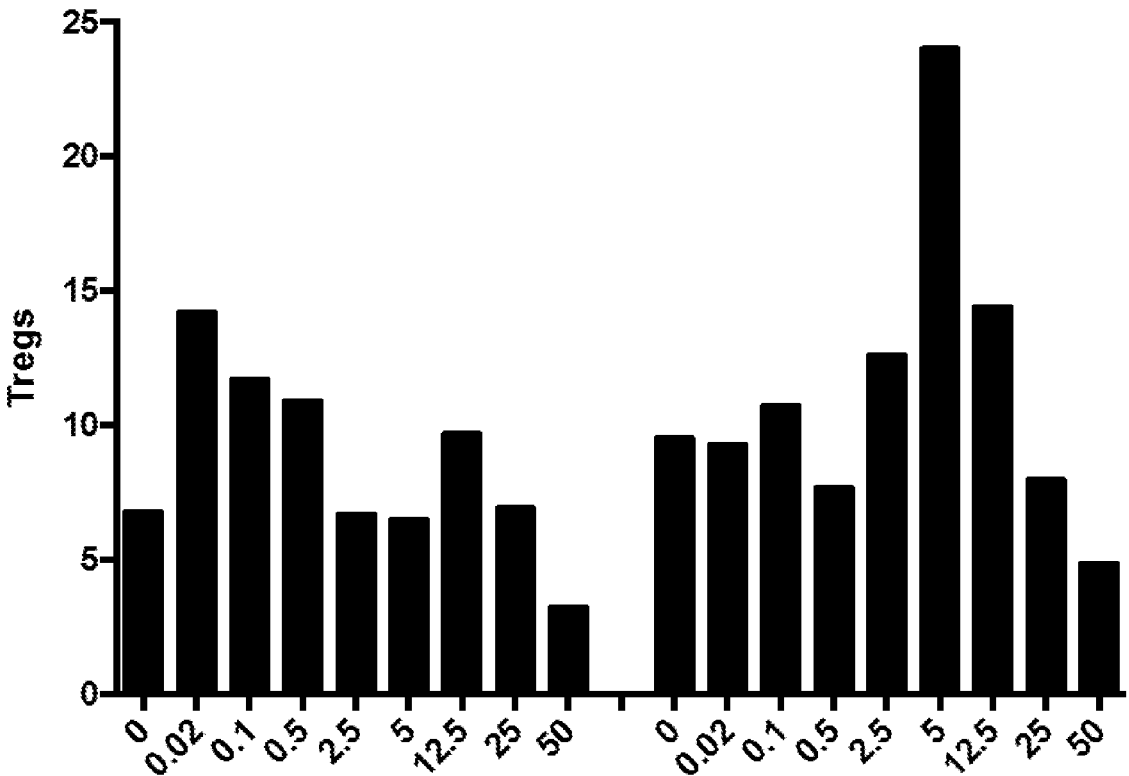
FIG. 6 is a graph contrasting the effects of murine monoclonal TNFR2 antagonist antibody TNFRAB2 on the viability of T-reg cells in vitro (left) with the effects of a human chimeric version of TNFRAB2 on the viability of T-reg cells under the same assay conditions (right). The human chimeric TNFR2 antagonist antibody is the same one described in FIG. 2. Values along the x-axis represent antibody concentration in units of pg/ml. Values along the y-axis represent the percentage of T-reg cells present in an in vitro cell sample after the sample is incubated with the indicated concentration of TNFR2 antibody.
Figure 7:
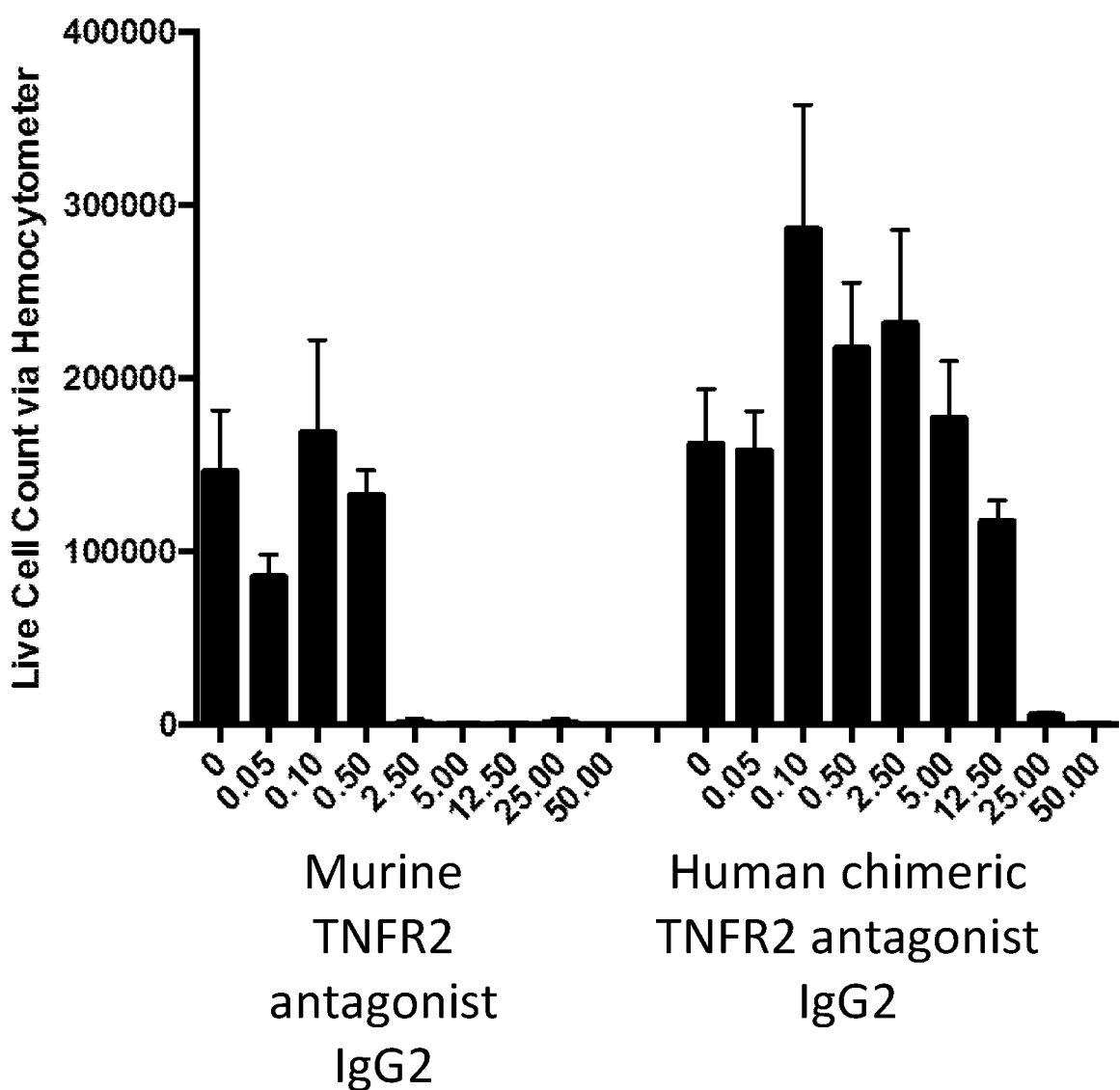
FIG. 7 is a graph contrasting the effects of murine monoclonal TNFR2 antagonist antibody TNFRAB2 on the quantity of TNFR2+SW480 colon cancer cells in an in vitro sample (left) with the effects of a human chimeric version of TNFRAB2 on the quantity of TNFR2+SW480 colon cancer cells in an in vitro sample under the same assay conditions (right). The human chimeric TNFR2 antagonist antibody is the same one described in FIG. 2. Values along the x-axis represent antibody concentration in units of pg/ml. Values along the y-axis represent the quantity of TNFR2+SW480 colon cancer cells present in an in vitro cell sample after the sample is incubated with the indicated concentration of TNFR2 antibody.

A series of experiments were conducted to assess the TNFR2 antagonistic properties of these chimeric antibodies, in particular, the ability to kill T-reg cells, induce T effector cell expansion, and to kill TNFR2+ SW480 colon cancer cells. FIGS. 2-4 demonstrate these properties for chimeric antibodies having a human IgG1 subtype, and FIGS. 5-7 demonstrate these properties for chimeric antibodies having a human IgG2 subtype. The effects of chimeric antibodies having a human IgG3 subtype are reported in Table 3, below, which also provides a summary of the characteristics observed for the IgG1 and IgG2 subtypes.

TABLE 3

| Effects of chimeric TNFR2 antagonist antibodies on T-reg cells and effector T cells | | |
|---|---|---|
| Antibody isotype and spacing between antigen-binding arms | T-reg cell killing observed? | Effector T cell proliferation observed? |
| Human IgG1 (117 Å) | No (0/5) | No (0/5) |
| Human IgG2 (134 Å) | Yes (4/5) | Yes (3/5) |
| Human IgG3 (125 Å) | Little (3/5) | Little (2/5) |

In Table 3, T-reg killing and T effector expansion properties are reported qualitatively. Values in parentheses indicate the number of instances a particular effect (e.g., T-reg cell killing or T effector expansion) was observed out of n-5 individual experiments.

As shown in FIGS. 2-7 and in Table 3, chimeric antibodies having a human IgG2 isotype were found to exhibit a superior ability to kill T-reg cells and TNFR2+ cancer cells and to expand T effector cells relative to chimeric antibodies having either a human IgG1 isotype constant domain or an IgG3 isotype constant domain. Table 3, above, correlates antibody isotype with the spacing between antigen-binding arms of the respective antibody. Collectively, these data demonstrate that a minimum spacing between antigen-binding arms is required for an optimal TNFR2 antagonist phenotype. For example, based on the results of these experiments, antibodies having optimal TNFR2 antagonist properties can be developed by matching the distance between antigen-binding arms to the distance between antigen-binding arms present in human IgG2 antibodies.

Despite the superior results of chimeric antibodies having the human IgG2 isotype constant domain, relative to those having the human IgG1 or IgG3 isotype constant domain, it was observed that chimeric antibodies having the human IgG2 subtype exhibited a bimodal effect on T-reg cells, T effector cells, and TNFR2+ cancer cells. Namely, as the concentration of the IgG2 antibody increased in these assays, the value being measured appears to vary in one direction and then change course. For example, in FIG. 5, the quantity of T effector cells appears to decrease at a lower concentration of the antibody and then to increase as the concentration of the antibody increases. Similarly, in FIGS. 6 and 7, the quantity of T-reg cells and TNFR2+ cancer cells, respectively, appears to increase with lower concentrations of the antibody and then to decrease with elevated concentrations of the antibody. This behavior inspired an investigation into the structure of the chimeric IgG2 antibody.

Figure 12:
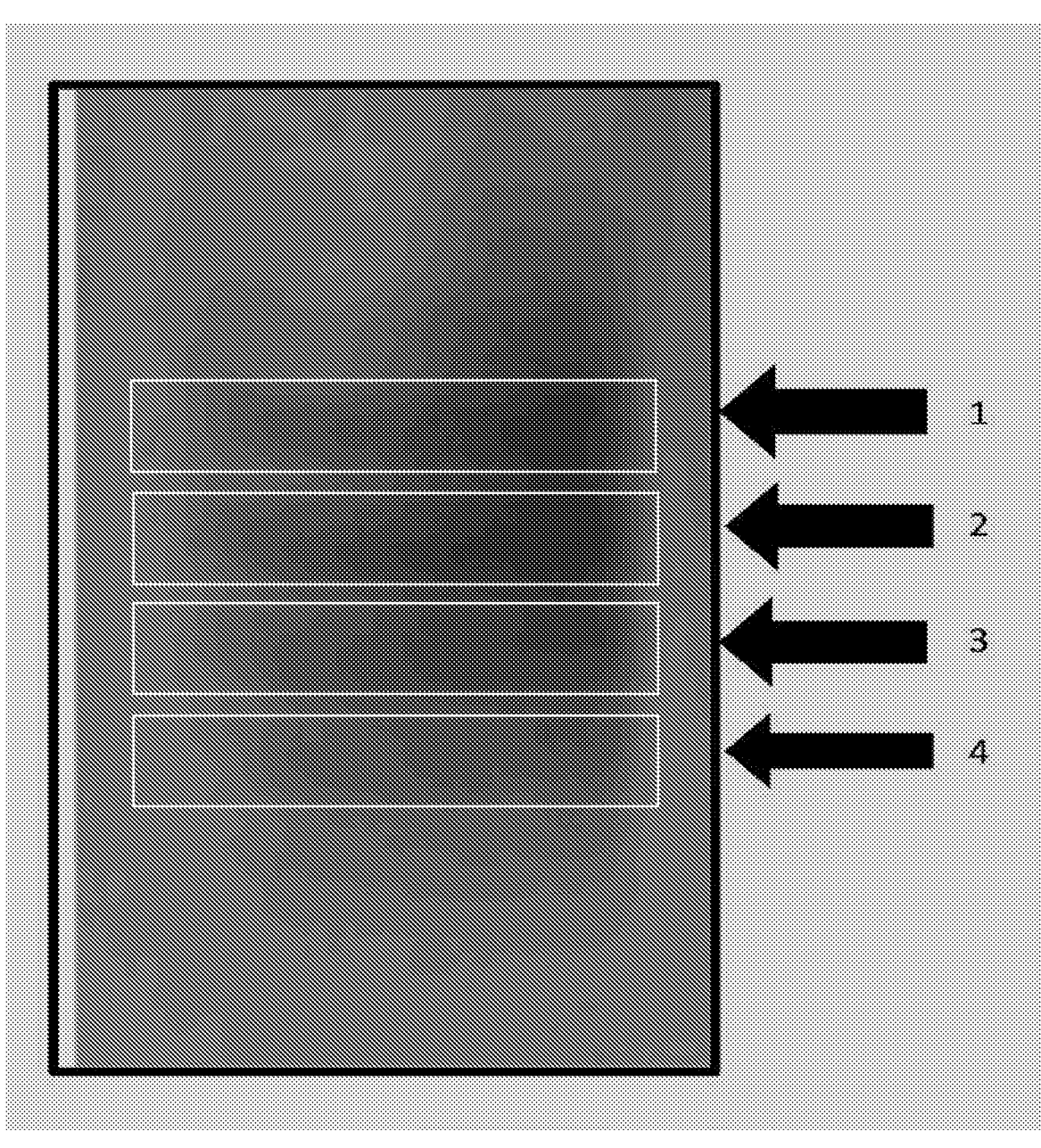
FIG. 12 is an image showing the results of a polyacrylamide gel electrophoresis separation of a chimeric TNFRAB2 variant antibody containing a human IgG2 constant domain, along with a wild-type human IgG2 hinge region, and the variable domain of the murine TNFRAB2 monoclonal antibody described herein. The gel electrophoresis separation shown in this figure was conducted under non-reducing conditions. Four unique bands were observed upon performing this separation, corresponding to the IgG2-A, IgG2-B, IgG2-A/B1, and IgG2-A/B2 disulfide-bonded isoforms of the human IgG2 isotype. For clarity, these bands are highlighted in white boxes.

Upon conducting a polyacrylamide gel electrophoresis separation of the chimeric IgG2 antibody under non-reducing conditions, four unique bands were observed. These results are shown in FIG. 12. These four bands correspond to four distinct disulfide-bonded isoforms of the human IgG2 isotype, which are illustrated in FIGS. 13A-13D. To assess the TNFR2 antagonist properties of these disulfide-bonded isoforms, the individual bands were purified and subjected to the T-reg killing, T effector expansion, and TNFR2+ cancer cell killing assays described above. The results of these experiments are shown in Table 4.

TABLE 4

| Effects of human IgG2 disulfide-bonded isoform on the ability of TNFR2 antagonist antibodies to kill T-reg cells and expand effector T cells | | |
| --- | --- | --- |
| Human IgG2 Disulfide-bonded isoform | T-reg cell killing observed? | Effector T cell proliferation observed? |
| Band 1 | Yes (5/5) | Yes (5/5) |
| Band 2 | Yes (3/5) | Yes (3/5) |
| Band 3 | No (1/5) | No (2/5) |
| Band 4 | No (0/5) | No (0/5) |

Surprisingly, as shown in Table 4, the disulfide-bonded isoform present in band 1 of the gel shown in FIG. 12 exhibited superior TNFR2 antagonist effects relative to the disulfide-bonded isoforms present in bands 3 and 4. The disulfide-bonded isoform present in band 2 exhibited greater antagonistic activity relative to bands 3 and 4 as well. It was determined that band 1 corresponded to the IgG2-A disulfide-bonded isoform and that band 2 corresponded to the IgG2-B disulfide-bonded isoform. The structures of these isoforms are shown in FIGS. 13A and 13B, respectively.

In order to stabilize the IgG2-A isoform, a series of mutations were introduced into the human IgG2 hinge region of the chimeric IgG2 antibodies based on TNFRAB2. These included the C232S and C233S amino acid substitutions, which preserve the steric and electronegativity properties of cysteine at positions 232 and 233 while prohibiting the formation of disulfide bonds that are not present in the IgG2-A isoform. The effects of these mutations on the TNFR2 antagonist properties of the chimeric IgG2 antibodies are shown in Table 5, below.

TABLE 5

| Effects of IgG2 hinge region amino acid substitutions on the ability of TNFR2 antagonist antibodies to kill T-reg cells and expand effector T cells | | |
| --- | --- | --- |
| Mutations introduced into human IgG2 hinge region | T-reg cell killing observed? | Effector T cell proliferation observed? |
| None (wild-type) | Yes (4/5) | Yes (3/5) |
| C232S and C233S | Yes (5/5) | Yes (5/5) |
| C232S | Yes (5/5) | Yes (4/5) |
| C233S | Yes (4/5) | Yes (4/5) |

Figure 8:
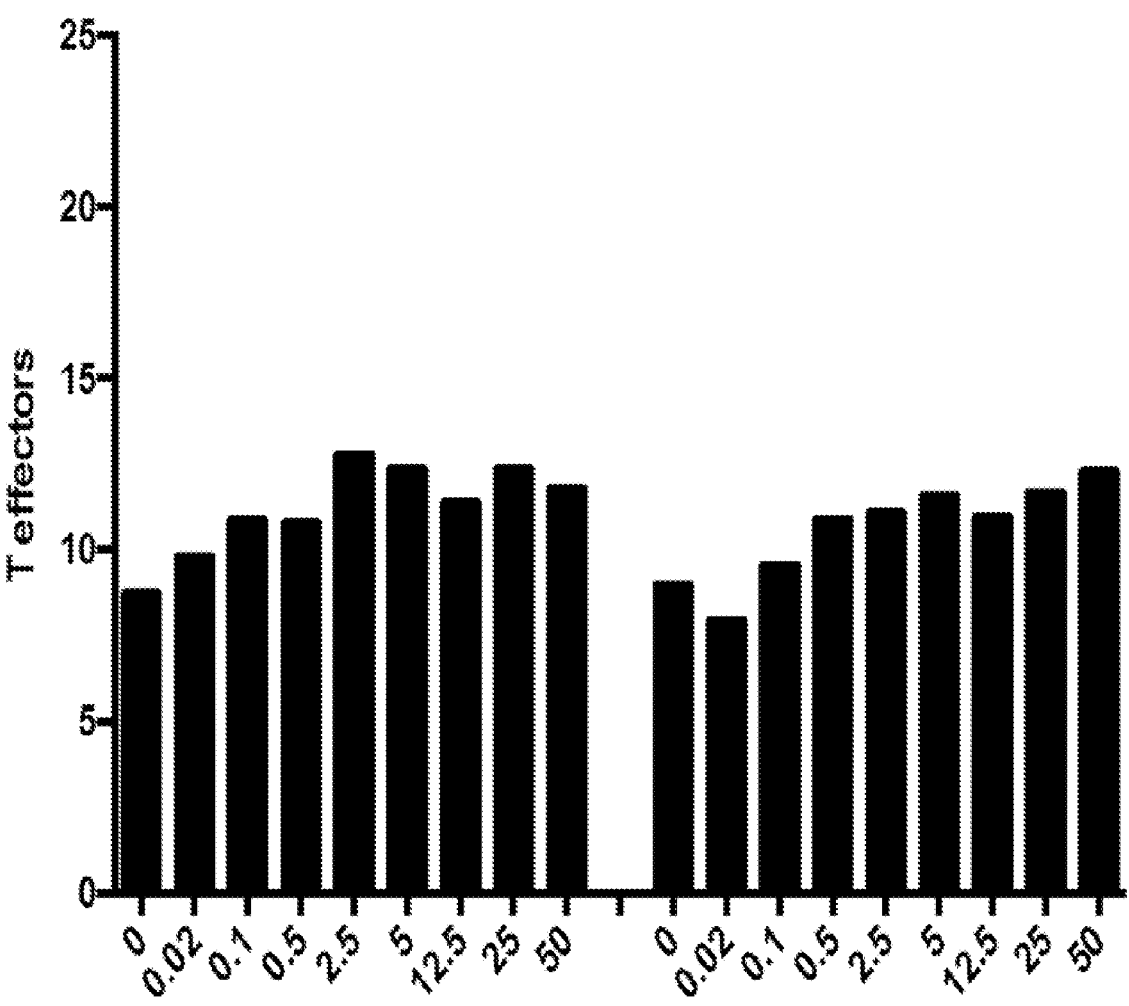
FIG. 8 is a graph contrasting the effects of murine monoclonal TNFR2 antagonist antibody TNFRAB2 on the quantity of effector T cells in an in vitro sample (left) with the effects of a human chimeric version of TNFRAB2 on the quantity of effector T cells in an in vitro sample under the same assay conditions (right). The human chimeric TNFR2 antagonist antibody tested in this example has a human IgG2 isotype and has a human IgG2 hinge region featuring C232S and C233S amino acid substitutions. Values along the x-axis represent antibody concentration in units of pg/ml. Values along the y-axis represent the percentage of T effector cells present in an in vitro cell sample after the sample is incubated with the indicated concentration of TNFR2 antibody.
Figure 9:
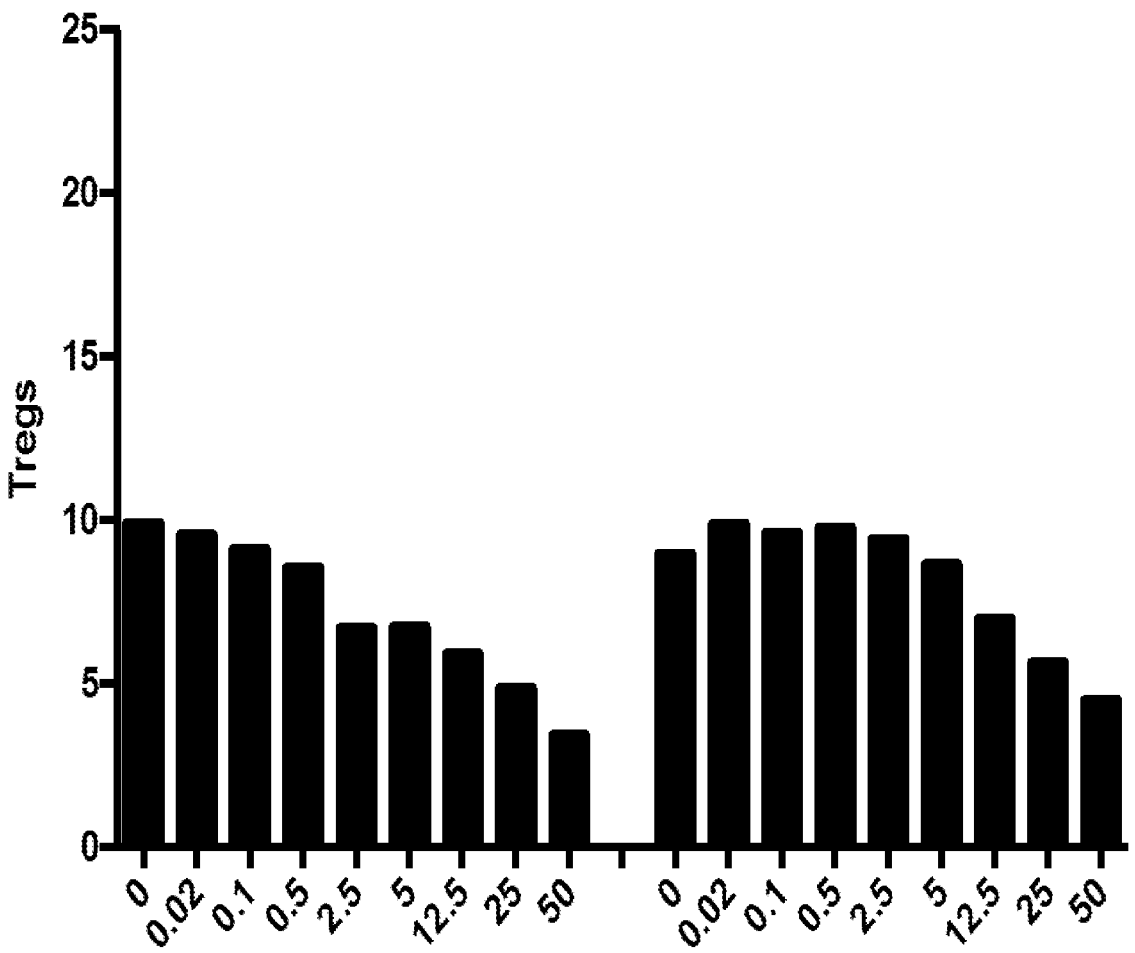
FIG. 9 is a graph contrasting the effects of murine monoclonal TNFR2 antagonist antibody TNFRAB2 on the viability of T-reg cells in vitro (left) with the effects of a human chimeric version of TNFRAB2 on the viability of T-reg cells under the same assay conditions (right). The human chimeric TNFR2 antagonist antibody tested in this example has a human IgG2 isotype and has a human IgG2 hinge region featuring C232S and C233S amino acid substitutions. Values along the x-axis represent antibody concentration in units of pg/ml. Values along the y-axis represent the percentage of T-reg cells present in an in vitro cell sample after the sample is incubated with the indicated concentration of TNFR2 antibody.
Figure 10:
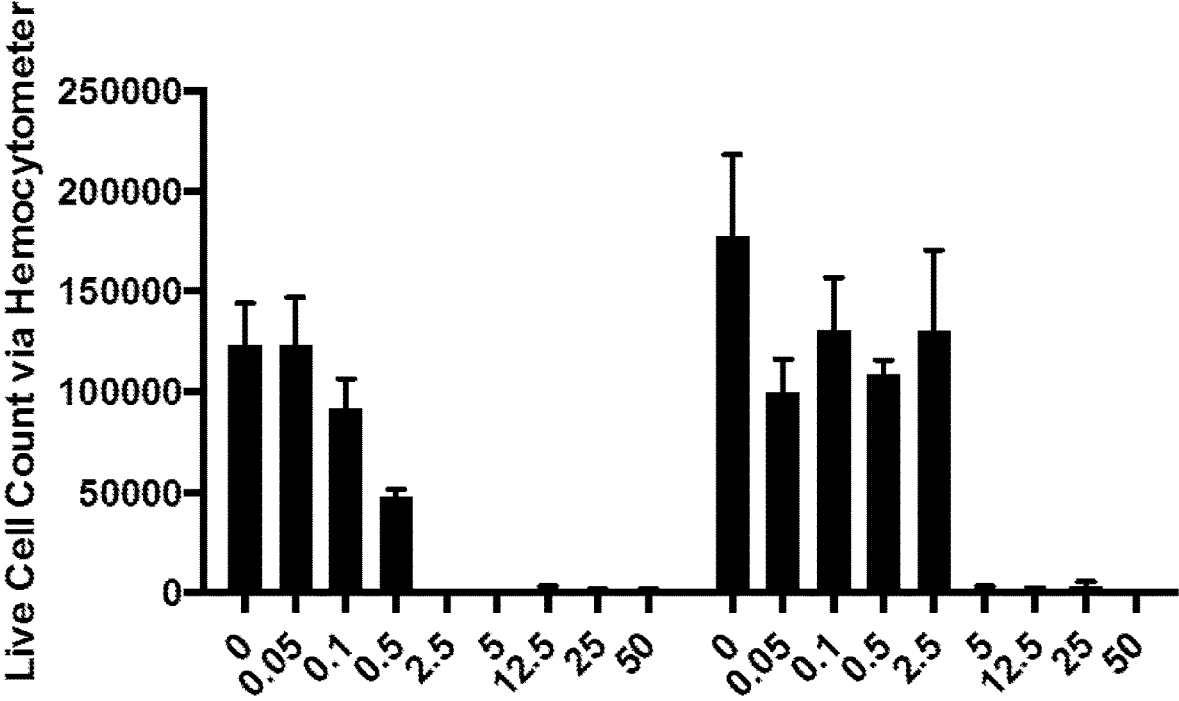
FIG. 10 is a graph contrasting the effects of murine monoclonal TNFR2 antagonist antibody TNFRAB2 on the quantity of TNFR2+SW480 colon cancer cells in an in vitro sample (left) with the effects of a human chimeric version of TNFRAB2 on the quantity of TNFR2+SW480 colon cancer cells in an in vitro sample under the same assay conditions (right). The human chimeric TNFR2 antagonist antibody tested in this example has a human IgG2 isotype and has a human IgG2 hinge region featuring C232S and C233S amino acid substitutions. Values along the x-axis represent antibody concentration in units of pg/ml. Values along the y-axis represent the quantity of TNFR2+SW480 colon cancer cells present in an in vitro cell sample after the sample is incubated with the indicated concentration of TNFR2 antibody.
Figure 11:
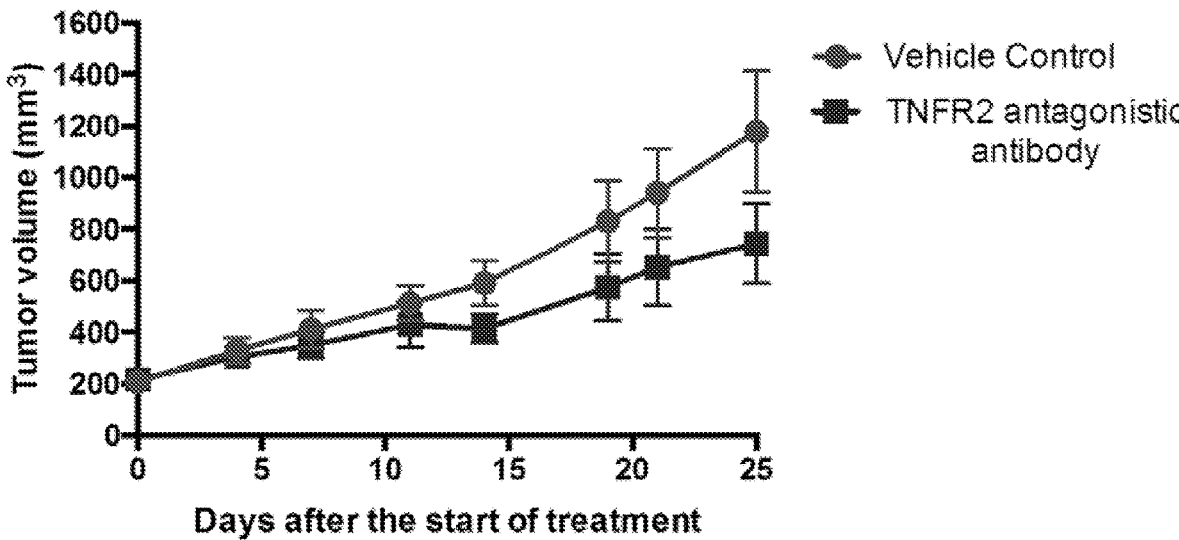
FIG. 11 is a graph demonstrating the TNFR2+ cancer cell-killing properties of a chimeric variant of monoclonal antibody TNFRAB2. The human chimeric TNFR2 antagonist antibody tested in this example has a human IgG2 isotype and has a human IgG2 hinge region featuring C232S and C233S amino acid substitutions. Values along the x-axis represent the number of days following the treatment of TNFR2+SW480 tumor cells with the chimeric TNFRAB2 variant antibody. Values along the y-axis represent SW480 tumor volume, in units of cubic millimeters, following treatment with the TNFRAB2 variant antibody. Tumor volume values observed following treatment with the TNFRAB2 variant antibody (squares) are compared to values observed following treatment with vehicle control (circles).

As shown in Table 5, the C232S and C233S mutations in the hinge region of human IgG2 result in antagonist TNFR2 antibodies that exhibit superior abilities to kill T-reg cells and to induce T effector cell expansion. As shown in FIGS. 8-10, introduction of the C232S and C233S mutations into the human IgG2 hinge region of chimeric antibodies based on TNFRAB2 no longer exhibit a bimodal effect in T-reg cell killing, T effector cell expansion, and TNFR2+ cancer cell killing assays. The ability of these mutations to impart IgG2 antibodies with optimal cancer cell killing properties is further evidenced by the data shown in FIG. 11, which demonstrates that chimeric antibodies containing a human IgG2 isotype featuring C232S and C233S amino acid substitutions exhibit a time-dependent ability to reduce tumor volume.

Taken together, these data demonstrate that TNFR2 antagonist antibodies having a human IgG2 isotype, and particularly the IgG2-A disulfide-bonded isoform, and to a lesser extent, the IgG2-B disulfide-bonded isoform, exhibit superior TNFR2 antagonist properties. Using the compositions and methods described herein, a variety of techniques can be employed to generate antibodies that adopt, in particular, the IgG2-A disulfide-bonding pattern.

Materials and Methods for T-Reg Killing Assay

Human T-reg Flow™ Kit (BIOLEGEND®, Cat. No. 320401)

Cocktail Anti-human CD4 PE-Cy5/CD25 PE (BIOLEGEND®, Part No. 78930)

ALEXA FLUOR® 488 Anti-human FOXP3, Clone 259D (BIOLEGEND®, Part No. 79467)

ALEXA FLUOR® 488 Mouse IgG1, k Isotype Ctrl (ICFC), Clone MOPC-21 (BIOLEGEND®, Part No. 79486)

FOXP3 Fix/Perm Buffer (4×) (BIOLEGEND®, Cat. No. 421401)

FOXP3 Perm Buffer (10×) (BIOLEGEND®, Cat. No. 421402)

PE anti-human CD25, Clone: BC96 (BIOLEGEND®, Cat. No. 302606)

ALEXA FLUORO 488 Anti-human FOXP3, Clone 259D (BIOLEGEND®, Cat. No. 320212)

PBS pH 7.4 (1×) (GIBCO® Cat. No. 10010-023)

HBSS (1×) (GIBCO® Cat. No. 14175-095)

FBS (heat inactivated)

15 ml tubes

Bench top centrifuge with swing bucket rotor for 15 ml tubes (set speed 1100 rpm or 200 g)

Cultured T-reg cells were treated with varying concentrations of TNFR2 antagonist antibodies for set periods of time. Following the incubation of T-reg cells under the conditions described above, the cell counts were determined using flow cytometry analysis. T-reg cells at a density of $0.2-1 \times 10^6$ cells/100 µl were distributed into a 15-ml conical tube and centrifuged for 5 minutes in order to pellet the cells. The supernatant was discarded and cells were resuspended in 100 µl of wash buffer (1×HBSS containing 2% FBS). 5 µl of PE anti-human CD25 fluorophore-antibody conjugate were added to this mixture, and the cells were subsequently vortexed and incubated in the dark for 25 minutes. The cells were then washed by adding 1 ml of wash buffer and subsequently centrifuging for 5 minutes. The supernatant was then discarded and 1 ml of FoxP3 fixation/permeabilization buffer (1:4 dilution of 4×FOXP3 Fix/Perm buffer in PBS) was added to the cells. The cells were then vortexed and incubated in the dark for 20 minutes. Cells were subsequently centrifuged for 5 minutes and supernatant was discarded. Cells were then resuspended in 1 ml of fresh wash buffer, vortexed, and centrifuged for 5 minutes. Cells were subsequently resuspended in 1 ml of 1×FOXP3 Perm Buffer (1:10 dilution of 10×FOXP3 Perm Buffer in PBS), vortexed, and incubated in the dark for 15 minutes. Following incubation, cells were centrifuged for 5 minutes and supernatant was subsequently discarded. The cell pellet was then resuspended in 100 µl of 1×FOXP3 Perm Buffer. At this point, 5 µl of either ALEXA FLUORO 488 anti-human FOXP3 or ALEXA FLUORO mouse IgG1, k isotype control were added to the cells. Cells were then vortexed and incubated in the dark for 35 minutes. Following incubation, cells were washed by adding 1 ml of fresh wash buffer to the cells, vortexing the cells and centrifuging for 5 minutes. The supernatant was then discarded and the cell pellet was resuspended in 0.2-0.5 ml of 1×HBSS free of FBS. Cell counts were then determined by flow cytometry analysis.

Materials and Methods for T Effector Induction Assay

T effector induction assays described in this example were performed as outlined in Torrey et al. (Science Signaling 10:462, 2017, the disclosure of which is incorporated herein by reference in its entirety).

Materials and Methods for Cancer Cell Killing Assay

SW480 colon cancer cells were cultured in 96-well flat-bottom plates at a concentration of $0.1 \times 10^6$ cells per well in 200 ml of media. Cells were treated directly with TNFR2 antagonistic antibodies and incubated for up to 21 days with half of the medium renewed every 2 to 3 days.

After incubation, cells were detached from the plate with 0.25% Trypsin-EDTA (GIBCO®), collected, and stained for FACS analysis or with trypan blue (Sigma-Aldrich) to count viable cells or with cell viability assays.

Example 3. Generating Antagonistic TNFR2 Antibodies by Phage Display

An exemplary method for in vitro protein evolution of antagonistic TNFR2 antibodies described herein is phage display, a technique which is well known in the art. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations can be introduced may be, e.g., a naive human germline sequence as described herein. These mutations can be performed using standard mutagenesis techniques described herein or known in the art. Each mutant sequence thus encodes an antibody corresponding in overall structure to the template except having one or more amino acid variations in the sequence of the template. Retroviral and phage display vectors can be engineered using standard vector construction techniques as described herein or known in the art. P3 phage display vectors along with compatible protein expression vectors, as is well known in the art, can be used to generate phage display vectors for antibody diversification as described herein.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its structure.

In a typical screen, a phage library is contacted with and allowed to bind a TNFR2-derived peptide (e.g., a peptide having the sequence of any one of SEQ ID NOs: 11, 19, 20, and 34-117), or a particular subcomponent thereof. To facilitate separation of binders and non-binders, it is convenient to immobilize the target on a solid support. Phage bearing a TNFR2-binding moiety can form a complex with the target on the solid support whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means. To isolate the binding phage, a protein elution can be performed.

The recovered phage can then be amplified through infection of bacterial cells and the screening process can be repeated with the new pool that is now depleted in non-binding antibodies and enriched for antibodies that bind the target peptide. The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof, typically 10-50 out of about $10^9$ to $10^{10}$ original candidates from each library. An increase in the number of phage recovered at each round of selection is a good indication that convergence of the library has occurred in a screen. After a set of binding polypeptides is identified, the sequence information can be used to design other secondary phage libraries, biased for members having additional desired properties (see, e.g., WO 2014/152660; the disclosure of which is incorporated herein by reference).

Example 4. Producing a Humanized Antagonistic TNFR2 Antibody

One method for producing humanized TNFR2 antibodies described herein is to import one or more, or all, of the CDRs of a non-human antagonistic TNFR2 antibody, such as TNFRAB1, TNFRAB2, TNFRAB3, TNFRAB4, or TNFRAB5, into a human antibody consensus sequence. Consensus human antibody heavy chain and light chain sequences are known in the art (see, e.g., the "VBASE" human germline sequence database; Kabat et al. (Sequences of Proteins of Immunological Interest, Fifth Edition, U.S. Department of Health and Human Services, NIH Publication No. 91-3242, 1991); Tomlinson et al. (J. Mol. Biol. 227:

776-798, 1992); and Cox et al. (Eur. J. Immunol. 24:827-836, 1994); the disclosures of each of which are incorporated herein by reference). Using established procedures, one can identify the variable domain framework residues and CDRs of a consensus antibody sequence (e.g., by sequence alignment (see Kabat, supra)). One can substitute, e.g., one or more, or all, of the CDR-H1, CDR-H2, CDR-H3, CDR-L1, CDR-L2, and CDR-L3 sequences of the consensus antibody with the corresponding CDR sequence(s) of a non-human antagonistic TNFR2 antibody described herein in order to produce a humanized, antagonistic TNFR2 antibody described herein. Polynucleotides encoding the above-described CDRs sequences can be produced synthetically or recombinantly, e.g., using the techniques described herein or known in the art.

One example of a variable domain of a consensus human antibody includes the heavy chain variable domain EVQLVESGGGLVQPGGSLRLSCAASGFTFSDYAM-SWVRQAPGKGLEWVAVISENGSDTYYADSVKGR FTISRDDSKNTLYLQMNSLRAEDTAVYYCARDRG-GAVSYFDVWGQGTLVTVSS (SEQ ID NO: 32) and the light chain variable domain DIQMTQSPSSL-SASVGDRVTITCRASODVSSY-LAWYQQKPGKAPKLLIYAASSLESGVPSRFSGSGSGT DFTLTISSLQPEDFATYYCQQYNSLPY-TFGQGTKVEIKRT (SEQ ID NO: 33), identified in U.S. Pat. No. 6,054,297; the disclosure of which is incorporated herein by reference (CDRs are shown in bold). In order to produce a humanized, antagonistic TNFR2 antibody of the present disclosure, one can recombinantly express a polynucleotide encoding the variable domains of the above consensus sequences in which one or more, or all, of the CDR-H1, CDR-H2, CDR-H3, CDR-L1, CDR-L2, and CDR-L3 sequences are replaced with the corresponding CDR sequences of a non-human antagonistic TNFR2 antibody described herein, such as TNFRAB1, TNFRAB2, TNFRAB3, TNFRAB4, or TNFRAB5, such as a CDR-H1 having the amino acid sequence of any one of SEQ ID NOs: 23, 257, 274, 275, 293, 294, or 295.

A polynucleotide encoding the above heavy chain and light chain variable domains operatively linked to one another can be incorporated into an expression vector (e.g., an expression vector optimized for protein expression in prokaryotic or eukaryotic cells as described herein or known in the art). For example, the polynucleotide may contain a region that encodes the CDR-H1 of TNFRAB1, TNFRAB2, TNFRAB3, TNFRAB4, or TNFRAB5, such as a CDR-H1 having the amino acid sequence of any one of SEQ ID NOs: 23, 257, 274, 275, 293, 294, or 295. The humanized antibody can be expressed in a host cell and subsequently purified from the host cell medium or the host cell using established techniques, such as size-exclusion chromatography and/or affinity chromatography as described herein.

Example 5. Humanized TNFR2 Antibodies Containing C232S and C233S Amino Acid Substitutions Using humanization techniques described herein, a series of 25 humanized TNFR2 antibodies were developed by humanization of monoclonal murine antibody TNFRAB2. These humanized TNFR2 antibodies have an IgG2 isotype and contain C232S and C233S amino acid substitutions within the IgG2 hinge region. As described herein, these substitutions confer beneficial properties to TNFR2 antibodies, including a heightened ability to kill Treg cells and proliferate CD8+ effector T cells. To investigate the effects of C232S and C233S amino acid substitutions on humanized, antagonistic TNFR2 antibodies having an IgG2 subtype, all 25 humanized antibodies were tested for antagonistic activity in at least three functional assays. First, all humanized antibodies were tested for their ability to kill Treg cells obtained from human blood donors in a dose-dependent manner. All humanized antibodies were then tested for their ability to proliferate T effector cells from human blood donors. The humanized antibodies were additionally tested for their ability to kill at least one TNFR2-expressing tumor cell line, such as the SW480 or MOTN-1 cell line.

All of the 25 humanized TNFR2 antibodies containing the C232S and C233S substitutions within the IgG2 hinge region exhibited the ability to kill Treg cells, expand CD8+ effector T cells, and kill TNFR2-expressing cancer cells. These results are summarized in Table 6, below.

TABLE 6

Ability of Humanized TNFR2 Antibodies Containing C232S and C233S Substitutions in the IgG2 Hinge Region to Deplete Treg Cells, Expand CD8+ T Effector Cells, and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| 1 | MVSSAQFLGLLLLCFQ GTRCDIQMTQSPSSLS ASVGDRVTVTCQASQ NINKYIAWYQQKPGKA PKLLIHYTSTLESGVPS RFSGSGSGTDFTLTISS LQAEDVATYYCLQYVN LITFGGGTKVEIKRTVA APSVFIFPPSDEQLKSG TASVVCLLNNFYPREA KVQWKVDNALQSGNS QESVTEQDSKDSTYSL SSTLTLSKADYEKHKV YACEVTHQGLSSPVTK SFNRGEC (SEQ ID NO: 297) | MGWTLVFLFLLSVTAGVH SQVQLVQSGAEVKKPGA SVKVSCKASGYTFTDYLM HWVRQAPGQG LEWIGWVDPEYGSTDYAE KFKK WVTVTRDTSISTAYMELS RLTSDDTAVYYCARDDGS YSPFDYWGQGTMVTVSS ASTKGPSVFPLAPCSRST SESTAALGCLVKDYFPEP VTVSWNSGALTSGVHTFP AVLQSSGLYSLSSVVTVP SSNFGTQTYTCNVDHKPS NTKVDKTVERKSSVECPP CPAPPVAGPSVFLFPPKP KDTLMISRTPEVTCVVVDV | Yes | Yes | Yes; SW480 and MOTN-1 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | SHEDPEVQFNWYVDGVE VHNAKTKPREEQFNSTFR VVSVLTVVHQDWLNGKEY KCKVSNKGLPAPIE KTISKTKGQPREPQVYTLP PSREEMTKNQVSLTCLVK GFYPSDIAVEWESNGQPE NNYKTTPPMLDSDGSFFL YSKLTVDKSRWQQGN VFSCSVMHEALHNHYTQK SLSLSPGK (SEQ ID NO: 302) | | | |
| 2 | MVSSAQFLGLLLLCFQ GTRCDIQMTQSPSSLS ASVGDRVTVTCQASQ NINKYIAWYQQKPGKA PKLLIHYTSTLESGVPS RFSGSGSGTDFTLTISS LQAEDVATYYCLQYVN LITFGGGTKVEIKRTVA APSVFIFPPSDEQLKSG TASVVCLLNNFYPREA KVQWKVDNALQSGNS QESVTEQDSKDSTYSL SSTLTLSKADYEKHKV YACEVTHQGLSSPVTK SFNRGEC (SEQ ID NO: 297) | MGWTLVFLFLLSVTAGVH SEVQLVQSGAEVKKPGAS VKVSCKASGYTFTDYLMH WVRQAPGQGLEWMGWV DPEYGSTDYAEKFK KRVTMTRDTSTSTFYMEL SSLRSDDT AVYFCARDDGSYSPFDY WGQGTLVTVSSASTKGP SVFPLAPCSRSTSESTAAL GCLVKDYFPEPVTVSWNS GALTSGVHTFPAVLQSSG LYSLSSVVTVPSSNFGTQ TYTCNVDHKPSNTKVDKT VERKSSVECPPCPAPPVA GPSVFLFPPKPKDTLMISR TPEVTCVVVDVSHEDPEV QFNWYVDGVEVHNAKTK PREEQFNSTFRVVSVLTV VHQDWLNGKEYKCKVSN KGLPAPIEKTISKTKGQPR EPQVYTLPPSREEMTKNQ VSLTCLVKGFYPSDIAVE WESNGQPENNYKTTPPM LDSDGSFFLYSKLTVDKS RWQQGNVFSCSVMHEAL HNHYTQKSLSLSPGK (SEQ ID NO: 303) | Yes | Yes | Yes; SW480 and MOTN-1 |
| 3 | MVSSAQFLGLLLLCFQ GTRCDIQMTQSPSSLS ASVGDRVTVTCQASQ NINKYIAWYQQKPGKA PKLLIHYTSTLESGVPS RFSGSGSGTDFTLTISS LQAEDVATYYCLQYVN LITFGGGTKVEIKRTVA APSVFIFPPSDEQLKSG TASVVCLLNNFYPREA KVQWKVDNALQSGNS QESVTEQDSKDSTYSL SSTLTLSKADYEKHKV YACEVTHQGLSSPVTK SFNRGEC (SEQ ID NO: 297) | MGWTLVFLFLLSVTAGVH SEVQLVESGAEVKKPGAS VKVSCKASGYTFTDYLMH WVRQAPGQGLEWMGWV DPEYGSTDYAEKFKK RVTMTRDTSISTAYMELN RLTSDDTAVYFCARDDGS YSPFDYWGQGTLVTVSSA STKGPSVFPLAPCSRSTS ESTAALGCLVKDYFPEPV TVSWNSGALTSGVHTFPA VLQSSGLYSLSSVVTVPS SNFGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEK TISKTKGQPREPQVYTLPP SREEMTKNQVSLTCLVKG FYPSDIAVEWESNGQPEN NYKTTPPMLDSDGSFFLY | Yes | Yes | Yes; SW480 and MOTN-1 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | SKLTVDKSRWQQGNV FSCSVMHEALHNHYTQKS LSLSPGK (SEQ ID NO: 304) | | | |
| 4 | MVSSAQFLGLLLLCFQ GTRCDIQMTQSPSSLS ASVGDRVTVTCQASQ NINKYIAWYQQKPGKA PKLLIHYTSTLESGVPS RFSGSGSGTDFTLTISS LQAEDVATYYCLQYVN LITFGGGTKVEIKRTVA APSVFIFPPSDEQLKSG TASVVCLLNNFYPREA KVQWKVDNALQSGNS QESVTEQDSKDSTYSL SSTLTLSKADYEKHKV YACEVTHQGLSSPVTK SFNRGEC (SEQ ID NO: 297) | MGWTLVFLFLLSVTAGVH SQVQLVQSGTEVTKPGAS VKVSCKASGYTFTDYLMH WVRQAPGQGLEWLGWV DPEYGSTDYAEKFKKRVT MTRDTSTNTVYMELTSLR SEDTAIYYCARDDGSYSP FDYWGQGTLVTVSSASTK GPSVFPLAPCSRSTSEST AALGCLVKDYFPEPVTVS WNSGALTSGVHTFPAVLQ SSGLYSLSSVVTVPSSNF GTQTYTCNVDHKPSNTKV DKTVERKSSVECPPCPAP PVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREE MTKNQVSLTCLVKGFYPS DIAVEWESNGQPENNYKT TPPMLDSDGSFFLYSKLT VDKSRWQQGNVFSCSVM HEALHNHYTQKSLSLSPG K (SEQ ID NO: 305) | Yes | Yes | Yes; SW480 and MOTN-1 |
| 5 | MVSSAQFLGLLLLCFQ GTRCDIQMTQSPSSLS ASVGDRVTVTCQASQ NINKYIAWYQQKPGKA PKLLIHYTSTLESGVPS RFSGSGSGTDFTLTISS LQAEDVATYYCLQYVN LITFGGGTKVEIKRTVA APSVFIFPPSDEQLKSG TASVVCLLNNFYPREA KVQWKVDNALQSGNS QESVTEQDSKDSTYSL SSTLTLSKADYEKHKV YACEVTHQGLSSPVTK SFNRGEC (SEQ ID NO: 297) | MGWTLVFLFLLSVTAGVH SEVQLVQSGAEVKKPGAT VKISCKVSGYTFTDYLMH WVQQAPGKGLEWMGWV DPEYGSTDYAEKFKKRVTI TADTSTDTAYMELSSLRS EDTAVYYCARDDGSYSPF DYWGQGVMVTVSSASTK GPSVFPLAPCSRSTSEST AALGCLVKDYFPEPVTVS WNSGALTSGVHTFPAVLQ SSGLYSLSSVVTVPSSN FGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEKTI SKTKGQPREPQVYTLPPS REEMTKNQVSLTCLVKGF YPSDIAVEWESNGQPENN YKTTPPMLDSDGSFFLYS KLTVDKSRWQQGNVFSC SVMHEALHNHYTQKSLSL SPGK (SEQ ID NO: 306) | Yes | Yes | Yes; SW480 and MOTN-1 |
| 6 | MVSSAQFLGLLLLCFQ GTRCDIQMTQSPSSLS ASVGDRVTITCQASQNI NKYIAWYQQKPGKAPK LLLYYTSTLESGVPSRF SGSGSGTDYTLTISSLQ | MGWTLVFLFLLSVTAGVH SQVQLVQSGAEVKKPGA SVKVSCKASGYTFTDYLM HWVRQAPGQG LEWIGWVDPEYGSTDYAE KFKK | Yes | Yes | Yes; MOTN-1 |

TABLE 6-continued

Ability of Humanized TNFR2 Antibodies Containing C232S and C233S Substitutions in the IgG2 Hinge Region to Deplete Treg Cells, Expand CD8+ T Effector Cells, and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | PEDFATYYCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 298) | WVTVTRDTSISTAYMELS RLTSDDTAVYYCARDDGS YSPFDYWGQGTMVTVSS ASTKGPSVFPLAPCSRST SESTAALGCLVKDYFPEP VTVSWNSGALTSGVHTFP AVLQSSGLYSLSSVVTVP SSNFGTQTYTCNVDHKPS NTKVDKTVERKSSVECPP CPAPPVAGPSVFLFPPKP KDTLMISRTPEVTCVVVDV SHEDPEVQFNWYVDGVE VHNAKTKPREEQFNSTFR VVSVLTVVHQDWLNGKEY KCKVSNKGLPAPIE KTISKTKGQPREPQVYTLP PSREEMTKNQVSLTCLVK GFYPSDIAVEWESNGQPE NNYKTTPPMLDSDGSFFL YSKLTVDKSRWQQGN VFSCSVMHEALHNHYTQK SLSLSPGK (SEQ ID NO: 302) | | | |
| 7 | MVSSAQFLGLLLLCFQ GTRCDIQMTQSPSSLS ASVGDRVTITCQASQNI NKYIAWYQQKPGKAPK LLLYYTSTLESGVPSRF SGSGSGTDYTLTISSLQ PEDFATYYCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 298) | MGWTLVFLFLLSVTAGVH SEVQLVQSGAEVKKPGAS VKVSCKASGYTFTDYLMH WVRQAPGQGLEWMGWV DPEYGSTDYAEKFK KRVTMTRDTSTSTFYMEL SSLRSDDT AVYFCARDDGSYSPFDY WGQGTLVTVSSASTKGP SVFPLAPCSRSTSESTAAL GCLVKDYFPEPVTVSWNS GALTSGVHTFPAVLQSSG LYSLSSVVTVPSSNFGTQ TYTCNVDHKPSNTKVDKT VERKSSVECPPCPAPPVA GPSVFLFPPKPKDTLMISR TPEVTCVVVDVSHEDPEV QFNWYVDGVEVHNAKTK PREEQFNSTFRVVSVLTV VHQDWLNGKEYKCKVSN KGLPAPIEKTISKTKGQPR EPQVYTLPPSREEMTKNQ VSLTCLVKGFYPSDIAVE WESNGQPENNYKTTPPM LDSDGSFFLYSKLTVDKS RWQQGNVFSCSVMHEAL HNHYTQKSLSLSPGK (SEQ ID NO: 303) | Yes | Yes | Yes; SW480 and MOTN-1 |
| 8 | MVSSAQFLGLLLLCFQ GTRCDIQMTQSPSSLS ASVGDRVTITCQASQNI NKYIAWYQQKPGKAPK LLLYYTSTLESGVPSRF SGSGSGTDYTLTISSLQ PEDFATYYCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 298) | MGWTLVFLFLLSVTAGVH SEVQLVESGAEVKKPGAS VKVSCKASGYTFTDYLMH WVRQAPGQGLEWMGWV DPEYGSTDYAEKFKK RVTMTRDTSISTAYMELN RLTSDDTAVYFCARDDGS YSPFDYWGQGTLVTVSSA STKGPSVFPLAPCSRSTS ESTAALGCLVKDYFPEPV TVSWNSGALTSGVHTFPA VLQSSGLYSLSSVVTVPS SNFGTQTYTCNVDH KPSNTKVDKTVER KSSVECPPCPAPPVAGPS VFLFPP KPKDTLMISRTPEVTCVVV | Yes | Yes | Yes; SW480 |

TABLE 6-continued

Ability of Humanized TNFR2 Antibodies Containing C232S and C233S Substitutions in the IgG2 Hinge Region to Deplete Treg Cells, Expand CD8+ T Effector Cells, and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | DVSHEDPEVQFNWYVDG VEVHNAKTKPREEQFNST FRVVSVLTVVHQDWLNGK EYKCKVSNKGLPAPIEK TISKTKGQPREPQVYTLPP SREEMTKNQVSLTCLVKG FYPSDIAVEWESNGQPEN NYKTTPPMLDSDGSFFLY SKLTVDKSRWQQGNV FSCSVMHEALHNHYTQKS LSLSPGK (SEQ ID NO: 304) | | | |
| 9 | MVSSAQFLGLLLLCFQ GTRCDIQMTQSPSSLS ASVGDRVTITCQASQNI NKYIAWYQQKPGKAPK LLLYYTSTLESGVPSRF SGSGSGTDYTLTISSLQ PEDFATYYCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 298) | MGWTLVFLFLLSVTAGVH SQVQLVQSGTEVTKPGAS VKVSCKASGYTFTDYLMH WVRQAPGQGLEWLGWV DPEYGSTDYAEKFKKRVT MTRDTSTNTVYMELTSLR SEDTAIYYCARDDGSYSP FDYWGQGTLVTVSSASTK GPSVFPLAPCSRSTSEST AALGCLVKDYFPEPVTVS WNSGALTSGVHTFPAVLQ SSGLYSLSSVVTVPSSNF GTQTYTCNVDHKPSNTKV DKTVERKSSVECPPCPAP PVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREE MTKNQVSLTCLVKGFYPS DIAVEWESNGQPENNYKT TPPMLDSDGSFFLYSKLT VDKSRWQQGNVFSCSVM HEALHNHYTQKSLSLSPG K (SEQ ID NO: 305) | Yes | Yes | Yes; SW480 |
| 10 | MVSSAQFLGLLLLCFQ GTRCDIQMTQSPSSLS ASVGDRVTITCQASQNI NKYIAWYQQKPGKAPK LLLYYTSTLESGVPSRF SGSGSGTDYTLTISSLQ PEDFATYYCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 298) | MGWTLVFLFLLSVTAGVH SEVQLVQSGAEVKKPGAT VKISCKVSGYTFTDYLMH WVQQAPGKGLEWMGWV DPEYGSTDYAEKFKKRVTI TADTSTDTAYMELSSLRS EDTAVYYCARDDGSYSPF DYWGQGVMVTVSSASTK GPSVFPLAPCSRSTSEST AALGCLVKDYFPEPVTVS WNSGALTSGVHTFPAVLQ SSGLYSLSSVVTVPSSN FGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEKTI SKTKGQPREPQVYTLPPS REEMTKNQVSLTCLVKGF YPSDIAVEWESNGQPENN YKTTPPMLDSDGSFFLYS | Yes | Yes | Yes; SW480 and MOTN-1 |

TABLE 6-continued

Ability of Humanized TNFR2 Antibodies Containing C232S and C233S Substitutions in the IgG2 Hinge Region to Deplete Treg Cells, Expand CD8+ T Effector Cells, and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | KLTVDKSRWQQGNVFSC SVMHEALHNHYTQKSLSL SPGK (SEQ ID NO: 306) | | | |
| 11 | MVSSAQFLGLLLLCFQ GTRCDIQMTQSPSSLS ASVGDRVTITCQASQNI NKYIAWYQQKPGKVPT LLIFYTSTLESGVPSRF SGSGSGTDFTLTISSLQ SEDVATYFCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 299) | MGWTLVFLFLLSVTAGVH SQVQLVQSGAEVKKPGA SVKVSCKASGYTFTDYLM HWVRQAPGQG LEWIGWVDPEYGSTDYAE KFKK WVTVTRDTSISTAYMELS RLTSDDTAVYYCARDDGS YSPFDYWQGTMVTVSS ASTKGPSVFPLAPCSRST SESTAALGCLVKDYFPEP VTVSWNSGALTSGVHTFP AVLQSSGLYSLSSVVTVP SSNFGTQTYTCNVDHKPS NTKVDKTVERKSSVECPP CPAPPVAGPSVFLFPPKP KDTLMISRTPEVTCVVVDV SHEDPEVQFNWYVDGVE VHNAKTKPREEQFNSTFR VVSVLTVVHQDWLNGKEY KCKVSNKGLPAPIE KTISKTKGQPREPQVYTLP PSREEMTKNQVSLTCLVK GFYPSDIAVEWESNGQPE NNYKTTPPMLDSDGSFFL YSKLTVDKSRWQQGN VFSCSVMHEALHNHYTQK SLSLSPGK (SEQ ID NO: 302) | Yes | Yes | Yes; SW480 |
| 12 | MVSSAQFLGLLLLCFQ GTRCDIQMTQSPSSLS ASVGDRVTITCQASQNI NKYIAWYQQKPGKVPT LLIFYTSTLESGVPSRF SGSGSGTDFTLTISSLQ SEDVATYFCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 299) | MGWTLVFLFLLSVTAGVH SEVQLVQSGAEVKKPGAS VKVSCKASGYTFTDYLMH WVRQAPGQGLEWMGWV DPEYGSTDYAEKFK KRVTMTRDTSTSTFYMEL SSLRSDDT AVYFCARDDGSYSPFDY WGQGTLVTVSSASTKGP SVFPLAPCSRSTSESTAAL GCLVKDYFPEPVTVSWNS GALTSGVHTFPAVLQSSG LYSLSSVVTVPSSNFGTQ TYTCNVDHKPSNTKVDKT VERKSSVECPPCPAPPVA GPSVFLFPPKPKDTLMISR TPEVTCVVVDVSHEDPEV QFNWYVDGVEVHNAKTK PREEQFNSTFRVVSVLTV VHQDWLNGKEYKCKVSN KGLPAPIEKTISKTKGQPR EPQVYTLPPSREEMTKNQ VSLTCLVKGFYPSDIAVE WESNGQPENNYKTTPPM LDSDGSFFLYSKLTVDKS RWQQGNVFSCSVMHEAL HNHYTQKSLSLSPGK (SEQ ID NO: 303) | Yes | Yes | Yes; SW480 and MOTN-1 |
| 13 | MVSSAQFLGLLLLCFQ GTRCDIQMTQSPSSLS ASVGDRVTITCQASQNI NKYIAWYQQKPGKVPT LLIFYTSTLESGVPSRF SGSGSGTDFTLTISSLQ | MGWTLVFLFLLSVTAGVH SEVQLVESGAEVKKPGAS VKVSCKASGYTFTDYLMH WVRQAPGQGLEWMGWV DPEYGSTDYAEKFKK RVTMTRDTSISTAYMELN | Yes | Yes | Yes; SW480 and MOTN-1 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | SEDVATYFCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 299) | RLTSDDTAVYFCARDDGS YSPFDYWGQGTLVTVSSA STKGPSVFPLAPCSRSTS ESTAALGCLVKDYFPEPV TVSWNSGALTSGVHTFPA VLQSSGLYSLSSVVTVPS SNFGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEK TISKTKGQPREPQVYTLPP SREEMTKNQVSLTCLVKG FYPSDIAVEWESNGQPEN NYKTTPPMLDSDGSFFLY SKLTVDKSRWQQGNV FSCSVMHEALHNHYTQKS LSLSPGK (SEQ ID NO: 304) | | | |
| 14 | MVSSAQFLGLLLLCFQ GTRCDIQMTQSPSSLS ASVGDRVTITCQASQNI NKYIAWYQQKPGKVPT LLIFYTSTLESGVPSRF SGSGSGTDFTLTISSLQ SEDVATYFCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 299) | MGWTLVFLFLLSVTAGVH SQVQLVQSGTEVTKPGAS VKVSCKASGYTFTDYLMH WVRQAPGQGLEWLGWV DPEYGSTDYAEKFKKRVT MTRDTSTNTVYMELTSLR SEDTAIYYCARDDGSYSP FDYWGQGTLVTVSSASTK GPSVFPLAPCSRSTSEST AALGCLVKDYFPEPVTVS WNSGALTSGVHTFPAVLQ SSGLYSLSSVVTVPSSNF GTQTYTCNVDHKPSNTKV DKTVERKSSVECPPCPAP PVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREE MTKNQVSLTCLVKGFYPS DIAVEWESNGQPENNYKT TPPMLDSDGSFFLYSKLT VDKSRWQQGNVFSCSVM HEALHNHYTQKSLSLSPG K (SEQ ID NO: 305) | Yes | Yes | Yes; SW480 |
| 15 | MVSSAQFLGLLLLCFQ GTRCDIQMTQSPSSLS ASVGDRVTITCQASQNI NKYIAWYQQKPGKVPT LLIFYTSTLESGVPSRF SGSGSGTDFTLTISSLQ SEDVATYFCLQYVNLIT FGGGTKVEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 299) | MGWTLVFLFLLSVTAGVH SEVQLVQSGAEVKKPGAT VKISCKVSGYTFTDYLMH WVQQAPGKGLEWMGWV DPEYGSTDYAEKFKKRVTI TADTSTDTAYMELSSLRS EDTAVYYCARDDGSYSPF DYWGQGVMVTVSSASTK GPSVFPLAPCSRSTSEST AALGCLVKDYFPEPVTVS WNSGALTSGVHTFPAVLQ SSGLYSLSSVVTVPSSN FGTQTYTCNVDH KPSNTKVDKTVER KSSVECPPCPAPPVAGPS VFLFPP KPKDTLMISRTPEVTCVVV | Yes | Yes | Yes; SW480 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | DVSHEDPEVQFNWYVDG VEVHNAKTKPREEQFNST FRVVSVLTVVHQDWLNGK EYKCKVSNKGLPAPIEKTI SKTKGQPREPQVYTLPPS REEMTKNQVSLTCLVKGF YPSDIAVEWESNGQPENN YKTTPPMLDSDGSFFLYS KLTVDKSRWQQGNVFSC SVMHEALHNHYTQKSLSL SPGK (SEQ ID NO: 306) | | | |
| 16 | MVSSAQFLGLLLLCFQ GTRCDIQMTQSPSSLS ASIGDRVTITCQASQNI NKYIAWYQQKPGKAPK LLIYYTSTLESGVPSRF SGSGSGTDFTFTISSLQ PEDIGTYYCLQYVNLIT FGQGTRLEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 300) | MGWTLVFLFLLSVTAGVH SQVQLVQSGAEVKKPGA SVKVSCKASGYTFTDYLM HWVRQAPGQG LEWIGWVDPEYGSTDYAE KFKK WVTVTRDTSISTAYMELS RLTSDDTAVYYCARDDGS YSPFDYWGQGTMVTVSS ASTKGPSVFPLAPCSRST SESTAALGCLVKDYFPEP VTVSWNSGALTSGVHTFP AVLQSSGLYSLSSVVTVP SSNFGTQTYTCNVDHKPS NTKVDKTVERKSSVECPP CPAPPVAGPSVFLFPPKP KDTLMISRTPEVTCVVVDV SHEDPEVQFNWYVDGVE VHNAKTKPREEQFNSTFR VVSVLTVVHQDWLNGKEY KCKVSNKGLPAPIE KTISKTKGQPREPQVYTLP PSREEMTKNQVSLTCLVK GFYPSDIAVEWESNGQPE NNYKTTPPMLDSDGSFFL YSKLTVDKSRWQQGN VFSCSVMHEALHNHYTQK SLSLSPGK (SEQ ID NO: 302) | Yes | Yes | Yes; SW480 and MOTN-1 |
| 17 | MVSSAQFLGLLLLCFQ GTRCDIQMTQSPSSLS ASIGDRVTITCQASQNI NKYIAWYQQKPGKAPK LLIYYTSTLESGVPSRF SGSGSGTDFTFTISSLQ PEDIGTYYCLQYVNLIT FGQGTRLEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 300) | MGWTLVFLFLLSVTAGVH SEVQLVQSGAEVKKPGAS VKVSCKASGYTFTDYLMH WVRQAPGQGLEWMGWV DPEYGSTDYAEKFK KRVTMTRDTSTSTFYMEL SSLRSDDT AVYFCARDDGSYSPFDY WGQGTLVTVSSASTKGP SVFPLAPCSRSTSESTAAL GCLVKDYFPEPVTVSWNS GALTSGVHTFPAVLQSSG LYSLSSVVTVPSSNFGTQ TYTCNVDHKPSNTKVDKT VERKSSVECPPCPAPPVA GPSVFLFPPKPKDTLMISR TPEVTCVVVDVSHEDPEV QFNWYVDGVEVHNAKTK PREEQFNSTFRVVSVLTV VHQDWLNGKEYKCKVSN KGLPAPIEKTISKTKGQPR EPQVYTLPPSREEMTKNQ VSLTCLVKGFYPSDIAVE WESNGQPENNYKTTPPM | Yes | Yes | Yes; SW480 and MOTN-1 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | LDSDGSFFLYSKLTVDKS RWQQGNVFSCSVMHEAL HNHYTQKSLSLSPGK (SEQ ID NO: 303) | | | |
| 18 | MVSSAQFLGLLLLCFQ GTRCDIQMTQSPSSLS ASIGDRVTITCQASQNI NKYIAWYQQKPGKAPK LLIYYTSTLESGVPSRF SGSGSGTDFTFTISSLQ PEDIGTYYCLQYVNLIT FGQGTRLEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 300) | MGWTLVFLFLLSVTAGVH SEVQLVESGAEVKKPGAS VKVSCKASGYTFTDYLMH WVRQAPGQGLEWMGWV DPEYGSTDYAEKFKK RVTMTRDTSISTAYMELN RLTSDDTAVYFCARDDGS YSPFDYWGQGTLVTVSSA STKGPSVFPLAPCSRSTS ESTAALGCLVKDYFPEPV TVSWNSGALTSGVHTFPA VLQSSGLYSLSSVVTVPS SNFGTQTYTCNVDH KPSNTKVDKTVER KSSVECPPCPAPPVAGPS VFLFPPP KPKDTLMISRTPEVTCVVV DVSHEDPEVQFNWYVDG VEVHNAKTKPREEQFNST FRVVSVLTVVHQDWLNGK EYKCKVSNKGLPAPIEK TISKTKGQPREPQVYTLPP SREEMTKNQVSLTCLVKG FYPSDIAVEWESNGQPEN NYKTTPPMLDSDGSFFLY SKLTVDKSRWQQGNV FSCSVMHEALHNHYTQKS LSLSPGK (SEQ ID NO: 304) | Yes | Yes | Yes; SW480 |
| 19 | MVSSAQFLGLLLLCFQ GTRCDIQMTQSPSSLS ASIGDRVTITCQASQNI NKYIAWYQQKPGKAPK LLIYYTSTLESGVPSRF SGSGSGTDFTFTISSLQ PEDIGTYYCLQYVNLIT FGQGTRLEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 300) | MGWTLVFLFLLSVTAGVH SQVQLVQSGTEVTKPGAS VKVSCKASGYTFTDYLMH WVRQAPGQGLEWLGWV DPEYGSTDYAEKFKKRVT MTRDTSTNTVYMELTSLR SEDTAIYYCARDDGSYSP FDYWGQGTLVTVSSASTK GPSVFPLAPCSRSTSEST AALGCLVKDYFPEPVTVS WNSGALTSGVHTFPAVLQ SSGLYSLSSVVTVPSSNF GTQTYTCNVDHKPSNTK DKTVERKSSVECPPCPAP PVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREE MTKNQVSLTCLVKGFYPS DIAVEWESNGQPENNYKT TPPMLDSDGSFFLYSKLT VDKSRWQQGNVFSCSVM HEALHNHYTQKSLSLSPG K (SEQ ID NO: 305) | Yes | Yes | Yes; SW480 and MOTN-1 |
| 20 | MVSSAQFLGLLLLCFQ GTRCDIQMTQSPSSLS ASIGDRVTITCQASQNI NKYIAWYQQKPGKAPK LLIYYTSTLESGVPSRF SGSGSGTDFTFTISSLQ | MGWTLVFLFLLSVTAGVH SEVQLVQSGAEVKKPGAT VKISCKVSGYTFTDYLMH WVQQAPGKGLEWMGWV DPEYGSTDYAEKFKKRVTI TADTSTDTAYMELSSLRS | Yes | Yes | Yes; SW480 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | PEDIGTYYCLQYVNLIT FGQGTRLEIKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 300) | EDTAVYYARDDGSYSPF DYWGQGVMVTVSSASTK GPSVFPLAPCSRSTSEST AALGCLVKDYFPEPVTVS WNSGALTSGVHTFPAVLQ SSGLYSLSSVVTVPSSN FGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEKTI SKTKGQPREPQVYTLPPS REEMTKNQVSLTCLVKGF YPSDIAVEWESNGQPENN YKTTPPMLDSDGSFFLYS KLTVDKSRWQQGNVFSC SVMHEALHNHYTQKSLSL SPGK (SEQ ID NO: 306) | | | |
| 21 | MVSSAQFLGLLLLCFQ GTRCDIQMTQSPSSLS ASVGDRVTITCQASQNI NKYIAWYQQKPGKAPK LLIYYTSTLESGVPSRF SGSGSGTDFTFTISSLQ PEDIATYYCLQYVNLIT FGAGTKLELKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 301) | MGWTLVFLFLLSVTAGVH SQVQLVQSGAEVKKPGA SVKVSCKASGYTFTDYLM HWVRQAPGQG LEWIGWVDPEYGSTDYAE KFKK WVTVTRDTSISTAYMELS RLTSDDTAVYYCARDDGS YSPFDYWGQGTMVTVSS ASTKGPSVFPLAPCSRST SESTAALGCLVKDYFPEP VTVSWNSGALTSGVHTFP AVLQSSGLYSLSSVVTVP SSNFGTQTYTCNVDHKPS NTKVDKTVERKSSVECPP CPAPPVAGPSVFLFPPKP KDTLMISRTPEVTCVVVDV SHEDPEVQFNWYVDGVE VHNAKTKPREEQFNSTFR VVSVLTVVHQDWLNGKEY KCKVSNKGLPAPIE KTISKTKGQPREPQVYTLP PSREEMTKNQVSLTCLVK GFYPSDIAVEWESNGQPE NNYKTTPPMLDSDGSFFL YSKLTVDKSRWQQGN VFSCSVMHEALHNHYTQK SLSLSPGK (SEQ ID NO: 302) | Yes | Yes | Yes; SW480 and MOTN-1 |
| 22 | MVSSAQFLGLLLLCFQ GTRCDIQMTQSPSSLS ASVGDRVTITCQASQNI NKYIAWYQQKPGKAPK LLIYYTSTLESGVPSRF SGSGSGTDFTFTISSLQ PEDIATYYCLQYVNLIT FGAGTKLELKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 301) | MGWTLVFLFLLSVTAGVH SEVQLVQSGAEVKKPGAS VKVSCKASGYTFTDYLMH WVRQAPGQGLEWMGWV DPEYGSTDYAEKFK KRVTMTRDTSTSTFYMEL SSLRSDDT AVYFCARDDGSYSPFDY WGQGTLVTVSSASTKGP SVFPLAPCSRSTSESTAAL GCLVKDYFPEPVTVSWNS GALTSGVHTFPAVLQSSG LYSLSSVVTVPSSNFGTQ TYTCNVDHKPSNTKVDKT VERKSSVECPPCPAPPVA GPSVFLFPPKPKDTLMISR | Yes | Yes | Yes; SW480 and MOTN-1 |

TABLE 6-continued

Ability of Humanized TNFR2 Antibodies Containing C232S and C233S Substitutions in the IgG2 Hinge Region to Deplete Treg Cells, Expand CD8+ T Effector Cells, and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | TPEVTCVVVDVSHEDPEV QFNWYVDGVEVHNAKTK PREEQFNSTFRVVSVLTV VHQDWLNGKEYKCKVSN KGLPAPIEKTISKTKGQPR EPQVYTLPPSREEMTKNQ VSLTCLVKGFYPSDIAVE WESNGQPENNYKTTPPM LDSDGSFFLYSKLTVDKS RWQQGNVFSCSVMHEAL HNHYTQKSLSLSPGK (SEQ ID NO: 303) | | | |
| 23 | MVSSAQFLGLLLLCFQ GTRCDIQMTQSPSSLS ASVGDRVTITCQASQNI NKYIAWYQQKPGKAPK LLIYYTSTLESGVPSRF SGSGSGTDFTFTISSLQ PEDIATYYCLQYVNLIT FGAGTKLELKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 301) | MGWTLVFLFLLSVTAGVH SEVQLVESGAEVKKPGAS VKVSCKASGYTFTDYLMH WVRQAPGQGLEWMGWV DPEYGSTDYAEKFKK RVTMTRDTSISTAYMELN RLTSDDTAVYFCARDDGS YSPFDYWGQGTLVTVSSA STKGPSVFPLAPCSRSTS ESTAALGCLVKDYFPEPV TVSWNSGALTSGVHTFPA VLQSSGLYSLSSVVTVPS SNFGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEK TISKTKGQPREPQVYTLPP SREEMTKNQVSLTCLVKG FYPSDIAVEWESNGQPEN NYKTTPPMLDSDGSFFLY SKLTVDKSRWQQGNV FSCSVMHEALHNHYTQKS LSLSPGK (SEQ ID NO: 304) | Yes | Yes | Yes; SW480 and MOTN-1 |
| 24 | MVSSAQFLGLLLLCFQ GTRCDIQMTQSPSSLS ASVGDRVTITCQASQNI NKYIAWYQQKPGKAPK LLIYYTSTLESGVPSRF SGSGSGTDFTFTISSLQ PEDIATYYCLQYVNLIT FGAGTKLELKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 301) | MGWTLVFLFLLSVTAGVH SQVQLVQSGTEVTKPGAS VKVSCKASGYTFTDYLMH WVRQAPGQGLEWLGWV DPEYGSTDYAEKFKKRVT MTRDTSTNTVYMELTSLR SEDTAIYYCARDDGSYSP FDYWGQGTLVTVSSASTK GPSVFPLAPCSRSTSEST AALGCLVKDYFPEPVTVS WNSGALTSGVHTFPAVLQ SSGLYSLSSVVTVPSSNF GTQTYTCNVDHKPSNTKV DKTVERKSSVECPPCPAP PVAGPSVFLFPPKPKDTL MISRTPEVTCVVVDVSHE DPEVQFNWYVDGVEVHN AKTKPREEQFNSTFRVVS VLTVVHQDWLNGKEYKC KVSNKGLPAPIEKTISKTK GQPREPQVYTLPPSREE MTKNQVSLTCLVKGFYPS DIAVEWESNGQPENNYKT | Yes | Yes | Yes; SW480 and MOTN-1 |

TABLE 6-continued

Ability of Humanized TNFR2 Antibodies Containing C232S and C233S Substitutions
in the IgG2 Hinge Region to Deplete Treg Cells, Expand CD8+ T Effector Cells,
and Kill TNFR2-expressing Cancer Cells

| Antibody No. | Light Chain Amino Acid Sequence | Heavy Chain Amino Acid Sequence | Kills Treg Cells? | Induces CD8+ T Cell Growth? | Kills SW480 or MOTN-1 Cells? |
|---|---|---|---|---|---|
| | | TPPMLDSDGSFFLYSKLT VDKSRWQQGNVFSCSVM HEALHNHYTQKSLSLSPG K (SEQ ID NO: 305) | | | |
| 25 | MVSSAQFLGLLLLCFQ GTRCDIQMTQSPSSLS ASVGDRVTITCQASQNI NKYIAWYQQKPGKAPK LLIYYTSTLESGVPSRF SGSGSGTDFTFTISSLQ PEDIATYYCLQYVNLIT FGAGTKLELKRTVAAP SVFIFPPSDEQLKSGTA SVVCLLNNFYPREAKV QWKVDNALQSGNSQE SVTEQDSKDSTYSLSS TLTLSKADYEKHKVYA CEVTHQGLSSPVTKSF NRGEC (SEQ ID NO: 301) | MGWTLVFLFLLSVTAGVH SEVQLVQSGAEVKKPGAT VKISCKVSGYTFTDYLMH WVQQAPGKGLEWMGWV DPEYGSTDYAEKFKKRVTI TADTSTDTAYMELSSLRS EDTAVYYCARDDGSYSPF DYWGQGVMVTVSSASTK GPSVFPLAPCSRSTSEST AALGCLVKDYFPEPVTVS WNSGALTSGVHTFPAVLQ SSGLYSLSSVVTVPSSN FGTQTYTCNVDH KPSNTKVDKTVER KSSVECPPCPAPPVAGPS VFLFPP KPKDTLMISRTPEVTCVVV DVSHEDPEVQFNWYVDG VEVHNAKTKPREEQFNST FRVVSVLTVVHQDWLNGK EYKCKVSNKGLPAPIEKTI SKTKGQPREPQVYTLPPS REEMTKNQVSLTCLVKGF YPSDIAVEWESNGQPENN YKTTPPMLDSDGSFFLYS KLTVDKSRWQQGNVFSC SVMHEALHNHYTQKSLSL SPGK (SEQ ID NO: 306) | Yes | Yes | Yes; SW480 |

Example 6. Treatment of Cancer in a Human Patient by Administration of Antagonistic TNFR2 Polypeptides The antagonistic TNFR2 polypeptides (e.g., single-chain polypeptides, antibodies, antigen-binding fragments thereof, or constructs thereof) described herein can be administered to a human patient in order to treat a cell proliferation disorder, such as cancer. The antagonistic polypeptide may contain, for example, a CDR-H1 having the amino acid sequence of any one of SEQ ID NOs: 23, 257, 274, 275, 293, 294, or 295. Administration of these polypeptides may suppress the growth and proliferation of T-reg cells. Thus, antibodies described herein can be administered to a patient in order to suppress a T-reg-mediated immune response. For instance, a human patient suffering from cancer, e.g., a cancer described herein, can be treated by administering an antagonistic TNFR2 polypeptide described herein by an appropriate route (e.g., intravenously) at a particular dosage (e.g., between 0.001 and 100 mg/kg/day) over a course of days, weeks, months, or years. If desired, the antagonistic-TNFR2 polypeptide can be modified, e.g., by hyperglycosylation or by conjugation with PEG, so as to evade immune recognition and/or to improve the pharmacokinetic profile of the polypeptide.

The cancer may be, for instance, one that is characterized by cells that express TNFR2, such as, for instance, Hodg-kin's lymphoma, cutaneous non-Hodgkin's lymphoma, T cell lymphoma, ovarian cancer, colon cancer, multiple myeloma, renal cell carcinoma, skin cancer, lung cancer, liver cancer, endometrial cancer, a hematopoietic or lymphoid cancer, a central nervous system cancer (e.g., glioma, neuroblastoma, and other cancers of central nervous system cells described herein), breast cancer, pancreatic cancer, stomach cancer, esophageal cancer, and upper gastrointestinal cancer. In such instances, the antagonistic TNFR2 polypeptide may treat the cancer by one or more mechanisms. For example, the antagonistic TNFR2 polypeptide may bind TNFR2 on the surface of a T-reg cell, such as an activated T-reg cell expressing $CD25^{Hi}$ and $CD45RA^{Low}$, or a MDSC, thereby inhibiting the proliferation of, and/or directly killing, the T-reg cell or MDSC. The T-reg cells and/or MDSCs that are killed or for which proliferation is suppressed may be those that are located in the microenvironment of a tumor. The reduced population of T-reg cells and/or MDSCs effectuated by the antagonistic TNFR2 polypeptide may, in turn, enable the expansion of populations of tumor-reactive CD8+ cytotoxic T cells, which can mount an immune response against the cancerous cells. The antagonistic TNFR2 polypeptide may, additionally, or alternatively, induce the direct expansion of CD8+ effector T cells. Additionally, or alternatively, the antagonistic TNFR2 polypeptide may bind TNFR2 on the surface of a TNFR2+ cancer cell, thereby inhibiting the proliferation of, and/or directly killing, the cancer cell.

The progression of the cancer that is treated with an antagonistic TNFR2 polypeptide described herein can be monitored by any one or more of several established methods. A physician can monitor the patient by direct observation in order to evaluate how the symptoms exhibited by the patient have changed in response to treatment. A patient may also be subjected to MRI, CT scan, or PET analysis in order to determine if a tumor has metastasized or if the size of a tumor has changed, e.g., decreased in response to treatment with an anti-TNFR2 antibody described herein. Optionally, cells can be extracted from the patient and a quantitative biochemical analysis can be conducted in order to determine the relative cell-surface concentrations of various growth factor receptors, such as the epidermal growth factor receptor. Based on the results of these analyses, a physician may prescribe higher/lower dosages or more/less frequent dosing of the antagonistic TNFR2 polypeptide in subsequent rounds of treatment.

Example 7. Treatment of HIV in a Human Patient by Administration of Antagonistic TNFR2 Polypeptides The antagonistic TNFR2 polypeptides (e.g., single-chain polypeptides, antibodies, antigen-binding fragments thereof, and constructs thereof) described herein can be administered to a human patient in order to treat a viral infection, such as HIV. Administration of these polypeptides can, for instance, suppress the growth and proliferation of T-reg cells and MDSCs, which can enhance the immune response of a patient by allowing the expansion of cytotoxic T lymphocytes capable of mounting an attack on infected cells. For instance, a human patient suffering from HIV can be treated by administering an antagonistic TNFR2 polypeptide described herein by an appropriate route (e.g., intravenously) at a particular dosage (e.g., between 0.001 and 100 mg/kg/day) over a course of days, weeks, months, or years. The antagonistic polypeptide may contain, for example, a CDR-H1 having the amino acid sequence of any one of SEQ ID NOs: 23, 257, 274, 275, 293, 294, or 295. If desired, the polypeptide can be modified, e.g., by hyperglycosylation or by conjugation with PEG, so as to evade immune recognition and/or to improve the pharmacokinetic profile of the polypeptide.

The progression of HIV that is treated with an antagonistic TNFR2 polypeptide described herein can be monitored by any one or more of several established methods. A physician can monitor the patient by direct observation in order to evaluate how the symptoms exhibited by the patient have changed in response to treatment. A blood sample can also be withdrawn from the patient in order to analyze the cell count of one or more white blood cells in order to determine if the quantity of infected cells has changed (e.g., decreased) in response to treatment with an antagonistic TNFR2 polypeptide described herein. Based on the results of these analyses, a physician may prescribe higher/lower dosages or more/less frequent dosing of the antagonistic TNFR2 polypeptide in subsequent rounds of treatment.

Example 8. Treatment of *Mycobacterium tuberculosis* in a Non-Human Mammal by Administration of Antagonistic TNFR2 Polypeptides The antagonistic TNFR2 polypeptides (e.g., single-chain polypeptides, antibodies, antigen-binding fragments thereof, and constructs thereof) described herein can be administered to a non-human mammal (e.g., a bovine mammal, pig, bison, horse, sheep, goat, cow, cat, dog, rabbit, hamster, guinea pig, or other non-human mammal) in order to treat a bacterial infection, such as *Mycobacterium tuberculosis*. Administration of these polypeptides may, for instance, suppress the proliferation of, and/or directly kill, T-reg cells and/or MDSCs, which can enhance the immune response of a patient by allowing the expansion of cytotoxic T lymphocytes capable of mounting an attack on the pathogenic organism. For instance, a non-human mammal suffering from *Mycobacterium tuberculosis* can be treated by administering an antagonistic TNFR2 polypeptide described herein by an appropriate route (e.g., intravenously) at a particular dosage (e.g., between 0.001 and 100 mg/kg/day) over a course of days, weeks, months, or years. The antagonistic polypeptide may contain, for example, a CDR-H1 having the amino acid sequence of any one of SEQ ID NOs: 23, 257, 274, 275, 293, 294, or 295. If desired, the antagonistic TNFR2 polypeptide can be modified, e.g., by hyperglycosylation or by conjugation with PEG, so as to evade immune recognition and/or to improve the pharmacokinetic profile of the polypeptide.

The progression of the *Mycobacterium tuberculosis* infection that is treated with an antagonistic TNFR2 polypeptide described herein can be monitored by any one or more of several established methods. A physician can monitor the patient by direct observation in order to evaluate how the symptoms exhibited by the patient have changed in response to treatment. A blood sample can also be withdrawn from the patient in order to analyze the cell count of one or more white blood cells in order to determine if the immune response has changed (e.g., increased) in response to treatment with an antagonistic TNFR2 polypeptide described herein. Based on the results of these analyses, a physician may prescribe higher/lower dosages or more/less frequent dosing of the antagonistic TNFR2 polypeptide in subsequent rounds of treatment.

Example 9. Treatment of Cancer or an Infectious Disease in a Human Patient by Administration of Antagonistic TNFR2 Polypeptides in Combination with an Immunotherapy Agent The antagonistic TNFR2 antibodies, antigen-binding fragments, single-chain polypeptides, and constructs described herein can be administered to a human patient in combination with (for instance, admixed with, co-administered with, or administered separately from) an immunotherapy agent in order to treat a cell proliferation disorder, such as cancer, or an infectious disease, such as a viral, bacterial, fungal, or parasitic infection. Administration of the antibody, antigen-binding fragment, single-chain polypeptide, or construct can suppress the growth and proliferation of T-reg cells and/or cancer cells that express TNFR2. Immunotherapy agents, such as anti-CTLA-4 agents (e.g., an anti-CTLA-4 antibody or antigen-binding fragment thereof, such as ipilimumab and tremelimumab), anti-PD-1 agents (e.g., an anti-PD-1 antibody or antigen-binding fragment thereof, such as nivolumab, pembrolizumab, avelumab, durvalumab, and atezolizumab), anti-PD-L1 agents (e.g., atezolizumab and avelumab), anti-PD-L2 agents, TNF-α cross-linking agents, TRAIL cross-linking agents, anti-CD27 agents, anti-CD30 agents, anti-CD40 agents, anti-4-1BB agent, anti-GITR agents, anti-OX40 agents, anti-TRAILR1 agents, anti-TRAILR2 agent, and anti-TWEAKR agents can function in tandem with antagonist TNFR2 antibodies, antigen-binding fragments thereof, single-chain polypeptides, or constructs, as immunotherapy agents are capable of downregulating the signal transduction of immune checkpoint proteins (e.g., immune checkpoint receptors and/or ligands) that would otherwise lead to tolerance toward tumor-associated antigens and downregulation of the cytotoxic T cell response. Additional examples of immunotherapy agents that may be used in conjunction with an antagonistic TNFR2 antibody, antigen-binding fragment thereof, single-chain polypeptide, or construct include Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and/or small molecular therapies like Vorinostat.

A physician of skill in the art may administer a polypeptide described herein that specifically binds to TNFR2 as an antagonist (e.g., an antibody, antigen-binding fragment thereof, single-chain polypeptide, or construct thereof) to a human patient suffering from a cancer or infectious disease in combination with an immunotherapy agent. The antagonistic polypeptide may contain, for example, a CDR-H1 having the amino acid sequence of any one of SEQ ID NOs: 23, 257, 274, 275, 293, 294, or 295. The polypeptide and the immunotherapy agent may be administered to the patient by an appropriate route of administration (for example, intravenously, intramuscularly, or subcutaneously, among others) at a particular dosage (for example, between 0.001 and 100 mg/kg/day, among other ranges) over a course of days, weeks, months, or years. If desired, the anti-TNFR2 antibody, antigen-binding fragment, single-chain polypeptide, or construct can be modified, for instance, by hyperglycosylation or by conjugation with PEG, so as to evade immune recognition and/or to improve the pharmacokinetic profile of the antibody, antigen-binding fragment, single-chain polypeptide, or construct.

The progression of the cancer or infectious disease that is treated in this fashion can be monitored by any one or more of several established methods. A physician can monitor the patient by direct observation in order to evaluate how the symptoms exhibited by the patient have changed in response to treatment. A patient may also be subjected to MRI, CT scan, or PET analysis in order to determine if a tumor has metastasized or if the size of a tumor has changed, for example, decreased in response to treatment with an anti-TNFR2 antibody, antigen-binding fragment, single-chain polypeptide, or construct and an immunotherapy agent. Optionally, cells can be extracted from the patient and a quantitative biochemical analysis can be conducted in order to determine the relative cell-surface concentrations of various growth factor receptors, such as the epidermal growth factor receptor. Based on the results of these analyses, a physician may prescribe higher/lower dosages or more/less frequent dosing of the antagonistic TNFR2 antibody, antigen-binding fragment, single-chain polypeptide, or construct and immunotherapy agent in subsequent rounds of treatment.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations described herein following, in general, the principles described herein and including such departures from the invention that come within known or customary practice within the art to which the invention pertains and may be applied to the essential features hereinbefore set forth, and follows in the scope of the claims.

Other embodiments are within the claims.

The invention claimed is:

1. A humanized antibody or antigen-binding fragment thereof that specifically binds human TNFR2, wherein the antibody or antigen-binding fragment thereof comprises:

(a) a human IgG2 hinge region that lacks a cysteine residue at positions 232 and 233 of the amino acid sequence of the IgG2 hinge region, numbering according to Kabat;

(b) a heavy chain comprising an amino acid sequence with at least 85% sequence identity to the amino acid sequence of any one of SEQ ID NOs: 302-306, wherein the heavy chain comprises the following CDRs: a CDR-H1 having the amino acid sequence of SEQ ID NO: 274, a CDR-H2 having the amino acid sequence of SEQ ID NO: 258, and a CDR-H3 having the amino acid sequence of SEQ ID NO: 259; and (c) a light chain comprising an amino acid sequence with at least 85% sequence identity to the amino acid sequence of any one of SEQ ID NOs: 297-301, wherein the light chain comprises the following CDRs: a CDR- L1 having the amino acid sequence of SEQ ID NO: 260, a CDR-L2 having the amino acid sequence YTS, and a CDR-L3 having the amino acid sequence of SEQ ID NO: 273.

2. An antibody or antigen-binding fragment thereof that specifically binds human TNFR2, wherein the antibody or antigen-binding fragment thereof comprises:

(a) a heavy chain comprising the amino acid sequence of SEQ ID NO: 302 and a light chain comprising the amino acid sequence of SEQ ID NO: 297;

(b) a heavy chain comprising the amino acid sequence of SEQ ID NO: 302 and a light chain comprising the amino acid sequence of SEQ ID NO: 298;

(c) a heavy chain comprising the amino acid sequence of SEQ ID NO: 302 and a light chain comprising the amino acid sequence of SEQ ID NO: 299;

(d) a heavy chain comprising the amino acid sequence of SEQ ID NO: 302 and a light chain comprising the amino acid sequence of SEQ ID NO: 300;

(e) a heavy chain comprising the amino acid sequence of SEQ ID NO: 302 and a light chain comprising the amino acid sequence of SEQ ID NO: 301;

(f) a heavy chain comprising the amino acid sequence of SEQ ID NO: 303 and a light chain comprising the amino acid sequence of SEQ ID NO: 297;

(g) a heavy chain comprising the amino acid sequence of SEQ ID NO: 303 and a light chain comprising the amino acid sequence of SEQ ID NO: 298;

(h) a heavy chain comprising the amino acid sequence of SEQ ID NO: 303 and a light chain comprising the amino acid sequence of SEQ ID NO: 299;

(i) a heavy chain comprising the amino acid sequence of SEQ ID NO: 303 and a light chain comprising the amino acid sequence of SEQ ID NO: 300;

(j) a heavy chain comprising the amino acid sequence of SEQ ID NO: 303 and a light chain comprising the amino acid sequence of SEQ ID NO: 301;

(k) a heavy chain comprising the amino acid sequence of SEQ ID NO: 304 and a light chain comprising the amino acid sequence of SEQ ID NO: 297;

(l) a heavy chain comprising the amino acid sequence of SEQ ID NO: 304 and a light chain comprising the amino acid sequence of SEQ ID NO: 298;

(m) a heavy chain comprising the amino acid sequence of SEQ ID NO: 304 and a light chain comprising the amino acid sequence of SEQ ID NO: 299;

(n) a heavy chain comprising the amino acid sequence of SEQ ID NO: 304 and a light chain comprising the amino acid sequence of SEQ ID NO: 300;

(o) a heavy chain comprising the amino acid sequence of SEQ ID NO: 304 and a light chain comprising the amino acid sequence of SEQ ID NO: 301;

(p) a heavy chain comprising the amino acid sequence of SEQ ID NO: 305 and a light chain comprising the amino acid sequence of SEQ ID NO: 297;

(q) a heavy chain comprising the amino acid sequence of SEQ ID NO: 305 and a light chain comprising the amino acid sequence of SEQ ID NO: 298;

(r) a heavy chain comprising the amino acid sequence of SEQ ID NO: 305 and a light chain comprising the amino acid sequence of SEQ ID NO: 299;

(s) a heavy chain comprising the amino acid sequence of SEQ ID NO: 305 and a light chain comprising the amino acid sequence of SEQ ID NO: 300;

(t) a heavy chain comprising the amino acid sequence of SEQ ID NO: 305 and a light chain comprising the amino acid sequence of SEQ ID NO: 301;

(u) a heavy chain comprising the amino acid sequence of SEQ ID NO: 306 and a light chain comprising the amino acid sequence of SEQ ID NO: 297;

(v) a heavy chain comprising the amino acid sequence of SEQ ID NO: 306 and a light chain comprising the amino acid sequence of SEQ ID NO: 298;

(w) a heavy chain comprising the amino acid sequence of SEQ ID NO: 306 and a light chain comprising the amino acid sequence of SEQ ID NO: 299;

(x) a heavy chain comprising the amino acid sequence of SEQ ID NO: 306 and a light chain comprising the amino acid sequence of SEQ ID NO: 300; or (y) a heavy chain comprising the amino acid sequence of SEQ ID NO: 306 and a light chain comprising the amino acid sequence of SEQ ID NO: 301.

3. The humanized antibody or antigen-binding fragment thereof of claim 1, wherein the heavy chain comprises SEQ ID NO: 302 and the light chain comprises SEQ ID NO: 297.

4. The humanized antibody or antigen-binding fragment thereof of claim 1, wherein the heavy chain comprises SEQ ID NO: 302 and the light chain comprises SEQ ID NO: 298.

5. The humanized antibody or antigen-binding fragment thereof of claim 1, wherein the heavy chain comprises SEQ ID NO: 302 and the light chain comprises SEQ ID NO: 299.

6. The humanized antibody or antigen-binding fragment thereof of claim 1, wherein the heavy chain comprises SEQ ID NO: 302 and the light chain comprises SEQ ID NO: 300.

7. The humanized antibody or antigen-binding fragment thereof of claim 1, wherein the heavy chain comprises SEQ ID NO: 302 and the light chain comprises SEQ ID NO: 301.

8. The humanized antibody or antigen-binding fragment thereof of claim 1, wherein the heavy chain comprises SEQ ID NO: 303 and the light chain comprises SEQ ID NO: 297.

9. The humanized antibody or antigen-binding fragment thereof of claim 1, wherein the heavy chain comprises SEQ ID NO: 303 and the light chain comprises SEQ ID NO: 298.

10. The humanized antibody or antigen-binding fragment thereof of claim 1, wherein the heavy chain comprises SEQ ID NO: 303 and the light chain comprises SEQ ID NO: 299.

11. The humanized antibody or antigen-binding fragment thereof of claim 1, wherein the heavy chain comprises SEQ ID NO: 303 and the light chain comprises SEQ ID NO: 300.

12. The humanized antibody or antigen-binding fragment thereof of claim 1, wherein the heavy chain comprises SEQ ID NO: 303 and the light chain comprises SEQ ID NO: 301.

13. The humanized antibody or antigen-binding fragment thereof of claim 1, wherein the heavy chain comprises SEQ ID NO: 304 and the light chain comprises SEQ ID NO: 297.

14. The humanized antibody or antigen-binding fragment thereof of claim 1, wherein the heavy chain comprises SEQ ID NO: 304 and the light chain comprises SEQ ID NO: 298.

15. The humanized antibody or antigen-binding fragment thereof of claim 1, wherein the heavy chain comprises SEQ ID NO: 304 and the light chain comprises SEQ ID NO: 299.

16. The humanized antibody or antigen-binding fragment thereof of claim 1, wherein the heavy chain comprises SEQ ID NO: 304 and the light chain comprises SEQ ID NO: 300.

17. The humanized antibody or antigen-binding fragment thereof of claim 1, wherein the heavy chain comprises SEQ ID NO: 304 and the light chain comprises SEQ ID NO: 301.

18. The humanized antibody or antigen-binding fragment thereof of claim 1, wherein the heavy chain comprises SEQ ID NO: 305 and the light chain comprises SEQ ID NO: 297.

19. The humanized antibody or antigen-binding fragment thereof of claim 1, wherein the heavy chain comprises SEQ ID NO: 305 and the light chain comprises SEQ ID NO: 298.

20. The humanized antibody or antigen-binding fragment thereof of claim 1, wherein the heavy chain comprises SEQ ID NO: 305 and the light chain comprises SEQ ID NO: 299.

21. The humanized antibody or antigen-binding fragment thereof of claim 1, wherein the heavy chain comprises SEQ ID NO: 305 and the light chain comprises SEQ ID NO: 300.

22. The humanized antibody or antigen-binding fragment thereof of claim 1, wherein the heavy chain comprises SEQ ID NO: 305 and the light chain comprises SEQ ID NO: 301.

23. The humanized antibody or antigen-binding fragment thereof of claim 1, wherein the heavy chain comprises SEQ ID NO: 306 and the light chain comprises SEQ ID NO: 297.

24. The humanized antibody or antigen-binding fragment thereof of claim 1, wherein the heavy chain comprises SEQ ID NO: 306 and the light chain comprises SEQ ID NO: 298.

25. The humanized antibody or antigen-binding fragment thereof of claim 1, wherein the heavy chain comprises SEQ ID NO: 306 and the light chain comprises SEQ ID NO: 299.

26. The humanized antibody or antigen-binding fragment thereof of claim 1, wherein the heavy chain comprises SEQ ID NO: 306 and the light chain comprises SEQ ID NO: 300.

27. The humanized antibody or antigen-binding fragment thereof of claim 1, wherein the heavy chain comprises SEQ ID NO: 306 and the light chain comprises SEQ ID NO: 301.

28. The antibody or antigen-binding fragment thereof of claim 1, wherein the amino acid sequence of the heavy chain of the antibody or antigen-binding fragment thereof has at least 90%, 91%, 92%, 93%, or 94% identity to the amino acid sequence of any one of SEQ ID NOs: 302-306 and the amino acid sequence of the light chain of the antibody or antigen-binding fragment thereof has at least 90%, 91%, 92%, 93%, or 94% identity to the amino acid sequence of any one of SEQ ID NOs: 297-301.

29. The antibody or antigen-binding fragment thereof of claim 1, wherein the amino acid sequence of the heavy chain of the antibody or antigen-binding fragment thereof has at least 95%, 96%, 97%, 98% or 99% identity to the amino acid sequence of any one of SEQ ID NOs: 302-306 and the amino acid sequence of the light chain of the antibody or antigen-binding fragment thereof has at least 95%, 96%, 97%, 98%, or 99% identity to the amino acid sequence of any one of SEQ ID NOs: 297-301.

30. A humanized antibody or antigen-binding fragment thereof that specifically binds human TNFR2, wherein the antibody or antigen-binding fragment thereof comprises:

(a) a human IgG2 hinge region that lacks a cysteine residue at positions 232 and 233 of the amino acid sequence of the IgG2 hinge region, numbering according to Kabat;

(b) a heavy chain comprising an amino acid sequence with at least 90% sequence identity to the amino acid sequence of SEQ ID NO: 303, wherein the heavy chain comprises the following CDRs: a CDR-H1 having the amino acid sequence of SEQ ID NO: 274, a CDR-H2 having the amino acid sequence of SEQ ID NO: 258, and a CDR-H3 having the amino acid sequence of SEQ ID NO: 259; and (c) a light chain comprising an amino acid sequence with at least 90% sequence identity to the amino acid sequence of SEQ ID NO: 299, wherein the light chain comprises the following CDRs: a CDR-L1 having the amino acid sequence of SEQ ID NO: 260, a CDR-L2 having the amino acid sequence YTS, and a CDR-L3 having the amino acid sequence of SEQ ID NO: 273.

31. The antibody or antigen-binding fragment thereof of claim 30, wherein the amino acid sequence of the heavy chain of the antibody or antigen-binding fragment thereof has at least 91%, 92%, 93%, or 94% identity to the amino acid sequence of SEQ ID NO: 303 and the amino acid sequence of the light chain of the antibody or antigen-binding fragment thereof has at least 91%, 92%, 93%, or 94% identity to the amino acid sequence of SEQ ID NO: 299.

32. The antibody or antigen-binding fragment thereof of claim 30, wherein the amino acid sequence of the heavy chain of the antibody or antigen-binding fragment thereof has at least 95%, 96%, 97%, 98% or 99% identity to the amino acid sequence of SEQ ID NO: 303 and the amino acid sequence of the light chain of the antibody or antigen-binding fragment thereof has at least 95%, 96%, 97%, 98%, or 99% identity to the amino acid sequence of SEQ ID NOs: 299.

33. The antibody or antigen-binding fragment thereof of claim 1, wherein the human IgG2 hinge region of the antibody or antigen-binding fragment thereof has a serine residue at positions 232 and/or 233.

34. The antibody or antigen-binding fragment thereof of claim 1, wherein the human IgG2 hinge region of the antibody or antigen-binding fragment thereof has a serine residue at positions 232 and 233.

35. The antibody or antigen-binding fragment thereof of claim 30, wherein the human IgG2 hinge region of the antibody or antigen-binding fragment thereof has a serine residue at positions 232 and/or 233.

36. The antibody or antigen-binding fragment thereof of claim 30, wherein the human IgG2 hinge region of the antibody or antigen-binding fragment thereof has a serine residue at positions 232 and 233.

37. The antibody or antigen-binding fragment thereof of claim 31, wherein the human IgG2 hinge region of the antibody or antigen-binding fragment thereof has a serine residue at positions 232 and 233.

38. The antibody or antigen-binding fragment thereof of claim 32, wherein the human IgG2 hinge region of the antibody or antigen-binding fragment thereof has a serine residue at positions 232 and 233.

39. A construct comprising a first polypeptide domain and a second polypeptide domain, wherein said first polypeptide domain and said second polypeptide domain are each, independently, an antigen-binding fragment of claim 1.

40. A construct comprising a first polypeptide domain and a second polypeptide domain, wherein said first polypeptide domain and said second polypeptide domain are each, independently, an antigen-binding fragment of claim 2.

41. A construct comprising a first polypeptide domain and a second polypeptide domain, wherein said first polypeptide domain and said second polypeptide domain are each, independently, an antigen-binding fragment of claim 30.

42. A composition comprising the construct of claim 39 and a pharmaceutically acceptable carrier.

43. A composition comprising the construct of claim 40 and a pharmaceutically acceptable carrier.

44. A composition comprising the construct of claim 41 and a pharmaceutically acceptable carrier.

45. A composition comprising the antibody or antigen-binding fragment thereof of claim 1 and a pharmaceutically acceptable carrier.

46. A composition comprising the antibody or antigen-binding fragment thereof of claim 2 and a pharmaceutically acceptable carrier.

47. A composition comprising the antibody or antigen-binding fragment thereof of claim 30 and a pharmaceutically acceptable carrier.

48. A composition comprising the antibody or antigen-binding fragment thereof of claim 31 and a pharmaceutically acceptable carrier.

49. A composition comprising the antibody or antigen-binding fragment thereof of claim 32 and a pharmaceutically acceptable carrier.

50. A composition comprising the antibody or antigen-binding fragment thereof of claim 33 and a pharmaceutically acceptable carrier.

51. A composition comprising the antibody or antigen-binding fragment thereof of claim 34 and a pharmaceutically acceptable carrier.

52. A composition comprising the antibody or antigen-binding fragment thereof of claim 35 and a pharmaceutically acceptable carrier.

53. A composition comprising the antibody or antigen-binding fragment thereof of claim 36 and a pharmaceutically acceptable carrier.

54. A composition comprising the antibody or antigen-binding fragment thereof of claim 37 and a pharmaceutically acceptable carrier.

55. A composition comprising the antibody or antigen-binding fragment thereof of claim 38 and a pharmaceutically acceptable carrier.

* * * * *